(12) United States Patent
Yao et al.

(10) Patent No.: US 12,188,096 B2
(45) Date of Patent: Jan. 7, 2025

(54) CLEAR CELL RENAL CELL CARCINOMA BIOMARKERS

(71) Applicants: AGENCY FOR SCIENCE, TECHNOLOGY AND RESEARCH, Singapore (SG); Singapore Health Services Pte Ltd, Singapore (SG)

(72) Inventors: Xiaosai Yao, Singapore (SG); Patrick Tan, Singapore (SG); Bin Tean Teh, Singapore (SG); Jing Tan, Singapore (SG); Huilin Shao, Singapore (SG); Joanna Koh, Singapore (SG)

(73) Assignees: AGENCY FOR SCIENCE, TECHNOLOGY AND RESEARCH, Singapore (SG); Singapore Health Services Pte Ltd, Singapore (SG)

( * ) Notice: Subject to any disclaimer, the term of this patent is extended or adjusted under 35 U.S.C. 154(b) by 17 days.

(21) Appl. No.: 17/820,925

(22) Filed: Aug. 19, 2022

(65) Prior Publication Data
US 2023/0279496 A1    Sep. 7, 2023

Related U.S. Application Data

(62) Division of application No. 16/642,430, filed as application No. PCT/SG2018/050450 on Sep. 5, 2018, now abandoned.

(30) Foreign Application Priority Data

Sep. 5, 2017 (SG) .......................... 10201707218R

(51) Int. Cl.
   C12Q 1/6886    (2018.01)
   G01N 33/574    (2006.01)

(52) U.S. Cl.
   CPC ..... *C12Q 1/6886* (2013.01); *G01N 33/57438* (2013.01); *C12Q 2600/106* (2013.01); *C12Q 2600/112* (2013.01); *C12Q 2600/158* (2013.01)

(58) Field of Classification Search
   CPC ............ C12Q 1/6886; C12Q 2600/112; G01N 33/57438
   See application file for complete search history.

(56) References Cited

U.S. PATENT DOCUMENTS

| | | |
|---|---|---|
| 2005/0037389 A1 | 2/2005 | Santin |
| 2009/0175827 A1 | 7/2009 | Byrom et al. |
| 2011/0281263 A1 | 11/2011 | Matthiesen et al. |

FOREIGN PATENT DOCUMENTS

| | | |
|---|---|---|
| WO | WO-2014/089055 A1 | 6/2014 |
| WO | WO-2015/179773 A1 | 11/2015 |
| WO | WO-2016/004387 A1 | 1/2016 |
| WO | WO-2016/156230 A1 | 10/2016 |
| WO | WO-2017/009084 A1 | 1/2017 |
| WO | WO-2017/053192 A1 | 3/2017 |

OTHER PUBLICATIONS

Allantaz et al. PLoS One. 2012. 7(1):e29979. (Year: 2012).*
Kumar et al. Nature Communications. 2015. 6:7971. (Year: 2015).*
Min et al. BMC Genomics. 2010. 11:96. (Year: 2010).*
Palmer et al. BMC Genomics. 2006. 7:115. (Year: 2006).*
Saito-Hisaminato et al. DNA Research. 2002. 9:35-45. (Year: 2002).*
Whitehead et al. Genome Biology. 2005. 6: R13. (Year: 2005).*
Pascal et al. BMC Genomics. 2008. 9:246. (Year: 2008).*
Chan et al. Drug Discovery & Development. 2006. 4 pages. (Year: 2006).*
Maier et al. FEBS Letters. 2009. 583:3966-3973. (Year: 2009).*
Kendrick. "A gene's mRNA level does not usually predict its protein level" Kendrick Labs, Inc. Sep. 25, 2014. (Year: 2014).*
Greenbaum et al. Genome Biology. 2003. 4:117. (Year: 2003).*
Chen et al. Molecular & Cellular Proteomics. 2002. 1:304-313. (Year: 2002).*
Communication Pursuant to Rules 70(2) and 70a(2) EPC in EP Application No. 18854714.5 dated May 21, 2021, 1 page.
Couvé et al., "Genetic Evidence of a Precisely Tuned Dysregulation in the Hypoxia Signaling Pathway During Oncogenesis", Cancer Res, vol. 74, No. 22, Nov. 4, 2014, pp. 6554-6564.
Extended European Search Report in EP Application No. 18854714.5 dated May 4, 2021, 13 pages.
Invitation to Respond to Written Opinion in SG Application No. 11202002043Y dated Oct. 19, 2020, 1 page.
Schrödter et al., "Identification of the Dopamine Transporter SLC6A3 as a Biomarker for Patients With Renal Cell Carcinoma", Mol Cancer, vol. 15, Feb. 2, 2016, pp. 1-10.
Search Report and Written Opinion in International Application No. PCT/SG2018/050450 dated Dec. 13, 2018, 13 pages.
Traini et al., "Sphingomyelin Phosphodiesterase Acid-like 3A (SMPDL3A) is a Novel Nucleotide Phosphodiesterase Regulated by Cholesterol in Human Macrophages", Journal of Biological Chemistry, vol. 289, No. 47, Oct. 6, 2014, pp. 32895-32913.
Tóth et al., Constitutive Expression of HIF-α Plays a Major Role in Generation of Clear Cell Phenotype in Human Primary and Metastatic Renal Carcinoma, Appl Immunohistochem Mol Morphol, vol. 22, No. 9, Oct. 2014, pp. 642-647.
Winter et al., "Methylomes of Renal Cell Lines and Tumors or Metastases Differ Significantly With Impact on Pharmacogenes", Scientific Reports, vol. 6, Jul. 20, 2016, pp. 1-15.

(Continued)

*Primary Examiner* — Joseph G. Dauner
(74) *Attorney, Agent, or Firm* — MARSHALL, GERSTEIN & BORUN LLP

(57) ABSTRACT

Disclosed herein is a clear cell renal cell carcinoma (ccRCC) biomarker set. Also disclosed herein is a detection system using the biomarker set disclosed herein, methods of determining whether a subject has or shows recurrence of clear cell renal cell carcinoma, method of determining whether a renal mass sample is benign or malignant, method of detecting response of a subject to systemic treatment, and a kit for carrying out the same.

18 Claims, 74 Drawing Sheets

Specification includes a Sequence Listing.

(56) References Cited

OTHER PUBLICATIONS

Written Opinion in SG Application No. 11202002043Y dated Apr. 27, 2022, 9 pages.
Written Opinion in SG Application No. 11202002043Y dated Oct. 15, 2020, 8 pages.
Yao et al., "VHL Deficiency Drives Enhancer Activation of Oncogenes in Clear Cell Renal Cell Carcinoma", Cancer Discovery, vol. 7, No. 11, Sep. 11, 2017, pp. 1284-1305.
Zhang et al., Metastatic Clear Cell Renal Cell Carcinoma: Circulating Biomarkers to Guide Antiangiogenic and Immune Therapies, Urol Oncol, vol. 34, No. 11, Aug. 4, 2016, pp. 510-518.
Second Office Action issued in counterpart Chinese Patent Application No. 201880071330.6 dated Jan. 4, 2024, 6 pages.
First Office Action issued in counterpart Chinese Patent Application No. 2018800713306 on Feb. 20, 2023.

* cited by examiner

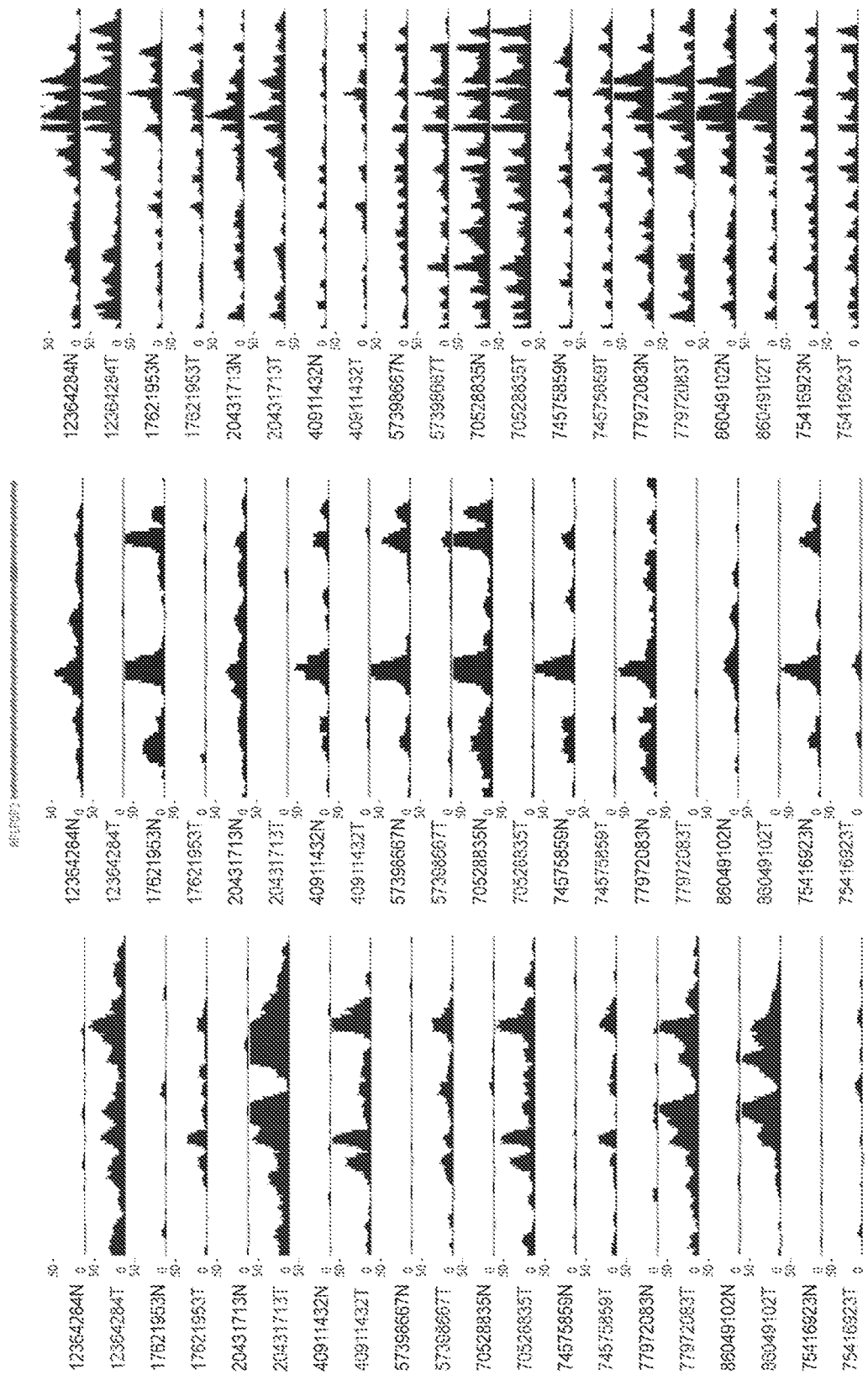
Fig. 1K(ii)

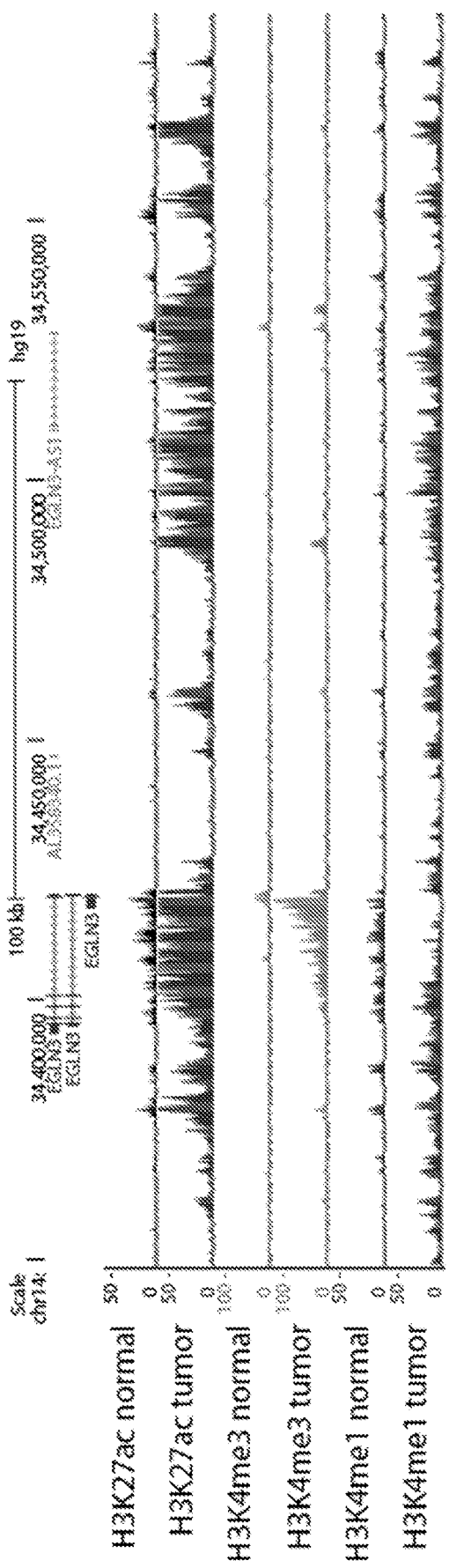
Fig. 3K(ii)

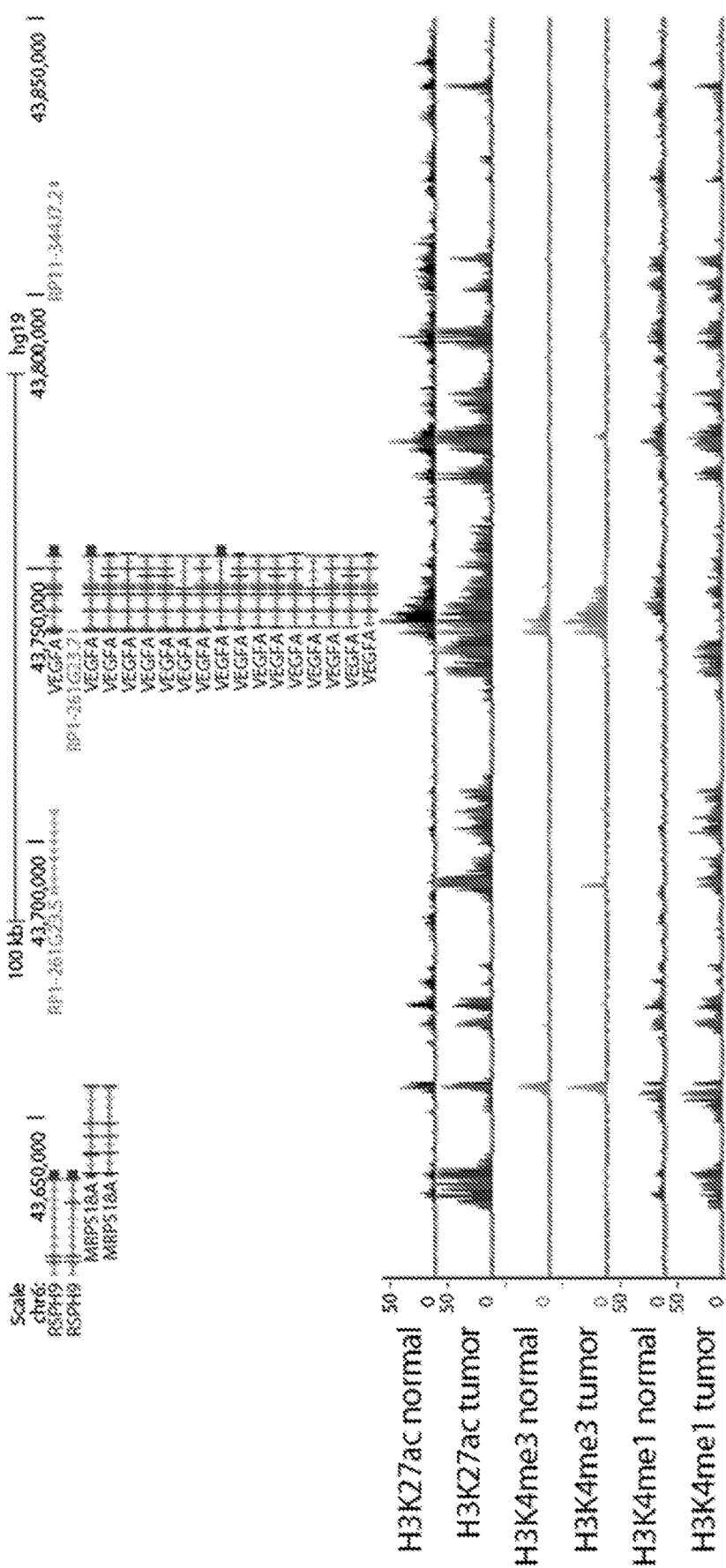
Fig. 3K(iii)

Fig. 4J  Fig. 4K

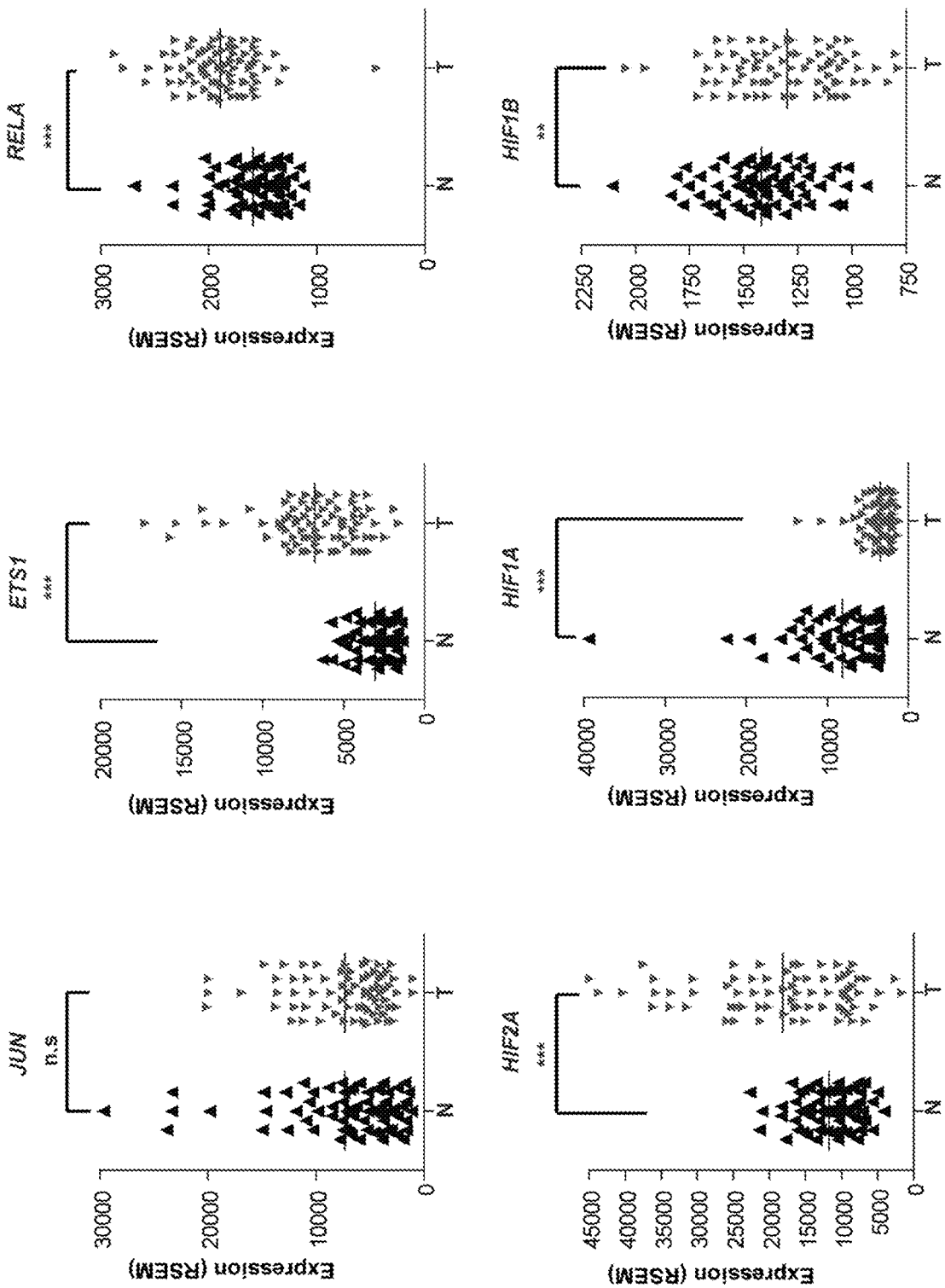

G

HIF1α (786-O)

- Promoter (<=1kb) (69.24%)
- Promoter (1-2kb) (1.71%)
- Promoter (2-3kb) (0.76%)
- 5' UTR (0.62%)
- 3' UTR (1.63%)
- 1st Exon (0.91%)
- Other Exon (2.12%)
- 1st Intron (2.12%)
- Other Intron (6.84%)
- Downstream (<=3kb) (0.62%)
- Distal Intergenic (13.43%)

HIF2α (786-O)

- Promoter (<=1kb) (10.03%)
- Promoter (1-2kb) (3.55%)
- Promoter (2-3kb) (1.33%)
- 5' UTR (0.31%)
- 3' UTR (1.37%)
- 1st Exon (0.59%)
- Other Exon (2.26%)
- 1st Intron (7.45%)
- Other Intron (29.03%)
- Downstream (<=3kb) (0.94%)
- Distal Intergenic (43.15%)

HIF1α (40911432)

- Promoter (<=1kb) (32.67%)
- Promoter (1-2kb) (9.55%)
- Promoter (2-3kb) (4.6%)
- 5' UTR (1.42%)
- 3' UTR (15.33%)
- 1st Exon (0.24%)
- Other Exon (6.96%)
- 1st Intron (3.07%)
- Other Intron (9.2%)
- Downstream (<=3kb) (0.83%)
- Distal Intergenic (16.16%)

HIF2α (40911432)

- Promoter (<=1kb) (24.34%)
- Promoter (1-2kb) (4%)
- Promoter (2-3kb) (1.26%)
- 5' UTR (0.43%)
- 3' UTR (1.58%)
- 1st Exon (0.36%)
- Other Exon (2.02%)
- 1st Intron (7.38%)
- Other Intron (25.53%)
- Downstream (<=3kb) (1.69%)
- Distal Intergenic (31.4%)

```
                        SEQUENCE LISTING

Sequence total quantity: 59
SEQ ID NO: 1                moltype = RNA   length = 19
FEATURE                     Location/Qualifiers
misc_feature                1..19
                            note = HIF2alpha (EPAS1) siRNA
source                      1..19
                            mol_type = other RNA
                            organism = synthetic construct
SEQUENCE: 1
ggcagcacct cacatttga                                                 19

SEQ ID NO: 2                moltype = RNA   length = 19
FEATURE                     Location/Qualifiers
misc_feature                1..19
                            note = HIF2alpha (EPAS1) siRNA
source                      1..19
                            mol_type = other RNA
                            organism = synthetic construct
SEQUENCE: 2
gagcgcaaat gtacccaat                                                 19

SEQ ID NO: 3                moltype = RNA   length = 19
FEATURE                     Location/Qualifiers
misc_feature                1..19
                            note = HIF2alpha (EPAS1) siRNA
source                      1..19
                            mol_type = other RNA
                            organism = synthetic construct
SEQUENCE: 3
gacaaggtct gcaaagggt                                                 19

SEQ ID NO: 4                moltype = RNA   length = 19
FEATURE                     Location/Qualifiers
misc_feature                1..19
                            note = HIF2alpha (EPAS1) siRNA
```

```
source                         1..19
                               mol_type = other RNA
                               organism = synthetic construct
SEQUENCE: 4
gcaaagacat gtccacaga                                                          19

SEQ ID NO: 5                   moltype = RNA   length = 19
FEATURE                        Location/Qualifiers
misc_feature                   1..19
                               note = SMDPL3A siRNA
source                         1..19
                               mol_type = other RNA
                               organism = synthetic construct
SEQUENCE: 5
cagtatgatc ctcgtgatt                                                          19

SEQ ID NO: 6                   moltype = RNA   length = 19
FEATURE                        Location/Qualifiers
misc_feature                   1..19
                               note = SMDPL3A siRNA
source                         1..19
                               mol_type = other RNA
                               organism = synthetic construct
SEQUENCE: 6
gaagatttgc agccggaaa                                                          19

SEQ ID NO: 7                   moltype = RNA   length = 19
FEATURE                        Location/Qualifiers
misc_feature                   1..19
                               note = SMDPL3A siRNA
source                         1..19
                               mol_type = other RNA
                               organism = synthetic construct
SEQUENCE: 7
gacagtaagc agtttataa                                                          19

SEQ ID NO: 8                   moltype = RNA   length = 19
FEATURE                        Location/Qualifiers
misc_feature                   1..19
                               note = SMDPL3A siRNA
source                         1..19
                               mol_type = other RNA
                               organism = synthetic construct
SEQUENCE: 8
cggcccaaat ataatgaca                                                          19

SEQ ID NO: 9                   moltype = RNA   length = 19
FEATURE                        Location/Qualifiers
misc_feature                   1..19
                               note = ZNF395 siRNA
source                         1..19
                               mol_type = other RNA
                               organism = synthetic construct
SEQUENCE: 9
ccaaactgat catggcttt                                                          19

SEQ ID NO: 10                  moltype = RNA   length = 19
FEATURE                        Location/Qualifiers
misc_feature                   1..19
                               note = ZNF395 siRNA
source                         1..19
                               mol_type = other RNA
                               organism = synthetic construct
SEQUENCE: 10
tcaggcagat catgcatac                                                          19

SEQ ID NO: 11                  moltype = RNA   length = 19
FEATURE                        Location/Qualifiers
misc_feature                   1..19
                               note = ZNF395 siRNA
source                         1..19
                               mol_type = other RNA
                               organism = synthetic construct
SEQUENCE: 11
gttctgcgct ccattgtgg                                                          19

SEQ ID NO: 12                  moltype = RNA   length = 19
FEATURE                        Location/Qualifiers
misc_feature                   1..19
```

```
                        note = ZNF395 siRNA
source                  1..19
                        mol_type = other RNA
                        organism = synthetic construct
SEQUENCE: 12
ggacgaacca gctccacga                                                        19

SEQ ID NO: 13           moltype = DNA   length = 58
FEATURE                 Location/Qualifiers
misc_feature            1..58
                        note = TRCN0000233231
source                  1..58
                        mol_type = other DNA
                        organism = synthetic construct
SEQUENCE: 13
ccgggcatca aacgacacgt caaagctcga gctttgacgt gtcgtttgat gcttttg              58

SEQ ID NO: 14           moltype = DNA   length = 58
FEATURE                 Location/Qualifiers
misc_feature            1..58
                        note = TRCN0000233234
source                  1..58
                        mol_type = other DNA
                        organism = synthetic construct
SEQUENCE: 14
ccggcagaag cctttactga ttaaactcga gtttaatcag taaaggcttc tgttttg              58

SEQ ID NO: 15           moltype = DNA   length = 20
FEATURE                 Location/Qualifiers
misc_feature            1..20
                        note = ZNF395-E1-F primer
source                  1..20
                        mol_type = other DNA
                        organism = synthetic construct
SEQUENCE: 15
gcaaccttcc aggcctgccg                                                       20

SEQ ID NO: 16           moltype = DNA   length = 22
FEATURE                 Location/Qualifiers
misc_feature            1..22
                        note = ZNF395-E1-R primer
source                  1..22
                        mol_type = other DNA
                        organism = synthetic construct
SEQUENCE: 16
aggagaaagg ggacaggagg gc                                                    22

SEQ ID NO: 17           moltype = DNA   length = 20
FEATURE                 Location/Qualifiers
misc_feature            1..20
                        note = ZNF395-E2-F primer
source                  1..20
                        mol_type = other DNA
                        organism = synthetic construct
SEQUENCE: 17
tgggccgccc gtgacttttc                                                       20

SEQ ID NO: 18           moltype = DNA   length = 20
FEATURE                 Location/Qualifiers
misc_feature            1..20
                        note = ZNF395-E2-R primer
source                  1..20
                        mol_type = other DNA
                        organism = synthetic construct
SEQUENCE: 18
ggttggaagg aggccaccgc                                                       20

SEQ ID NO: 19           moltype = DNA   length = 24
FEATURE                 Location/Qualifiers
misc_feature            1..24
                        note = ZNF395-E3-F primer
source                  1..24
                        mol_type = other DNA
                        organism = synthetic construct
SEQUENCE: 19
tcgtgctgaa ggcttctcag gaaa                                                  24

SEQ ID NO: 20           moltype = DNA   length = 20
FEATURE                 Location/Qualifiers
```

```
                            -continued misc_feature            1..20
                        note = ZNF395-E3-R primer
source                  1..20
                        mol_type = other DNA
                        organism = synthetic construct
SEQUENCE: 20
ccctcctgt tggtgacggc                                                20

SEQ ID NO: 21           moltype = DNA   length = 20
FEATURE                 Location/Qualifiers
misc_feature            1..20
                        note = ZNF395-E4-F primer
source                  1..20
                        mol_type = other DNA
                        organism = synthetic construct
SEQUENCE: 21
aagcggcggg aggaggttga                                               20

SEQ ID NO: 22           moltype = DNA   length = 20
FEATURE                 Location/Qualifiers
misc_feature            1..20
                        note = ZNF395-E4-R primer
source                  1..20
                        mol_type = other DNA
                        organism = synthetic construct
SEQUENCE: 22
gggctgcgtc acctgcagaa                                               20

SEQ ID NO: 23           moltype = DNA   length = 42
FEATURE                 Location/Qualifiers
misc_feature            1..42
                        note = Forward primer
source                  1..42
                        mol_type = other DNA
                        organism = synthetic construct
SEQUENCE: 23
gtagctgcat agatctgcgc gccacccctc tggcgccacc gt                      42

SEQ ID NO: 24           moltype = DNA   length = 39
FEATURE                 Location/Qualifiers
misc_feature            1..39
                        note = Reverse primer
source                  1..39
                        mol_type = other DNA
                        organism = synthetic construct
SEQUENCE: 24
gtagctgcat caagcttgcc ggctcagtct tggcttctc                          39

SEQ ID NO: 25           moltype = DNA   length = 32
FEATURE                 Location/Qualifiers
misc_feature            1..32
                        note = VEGFA-E1-F_MluI primer
source                  1..32
                        mol_type = other DNA
                        organism = synthetic construct
SEQUENCE: 25
gctcttacgc gttggggggtg cctctcccac tg                                32

SEQ ID NO: 26           moltype = DNA   length = 33
FEATURE                 Location/Qualifiers
misc_feature            1..33
                        note = VEGFA-E1-R_NheI primer
source                  1..33
                        mol_type = other DNA
                        organism = synthetic construct
SEQUENCE: 26
gcccgggcta gcgggtgggg gtccaacagg aca                                33

SEQ ID NO: 27           moltype = DNA   length = 32
FEATURE                 Location/Qualifiers
misc_feature            1..32
                        note = VEGFA-E2-F_MluI primer
source                  1..32
                        mol_type = other DNA
                        organism = synthetic construct
SEQUENCE: 27
gctcttacgc gtcccatccc ctgcctcctg ct                                 32

SEQ ID NO: 28           moltype = DNA   length = 32
```

```
FEATURE                 Location/Qualifiers
misc_feature            1..32
                        note = VEGFA-E2-R_NheI primer
source                  1..32
                        mol_type = other DNA
                        organism = synthetic construct
SEQUENCE: 28
gcccgggcta gctgggctgg ctgcaaagtg gc                              32

SEQ ID NO: 29           moltype = DNA  length = 33
FEATURE                 Location/Qualifiers
misc_feature            1..33
                        note = SLC2A1-E1_F_MluI primer
source                  1..33
                        mol_type = other DNA
                        organism = synthetic construct
SEQUENCE: 29
gctcttacgc gttggtgacc gtgttggggg tga                             33

SEQ ID NO: 30           moltype = DNA  length = 32
FEATURE                 Location/Qualifiers
misc_feature            1..32
                        note = SLC2A1-E1_R_NheI primer
source                  1..32
                        mol_type = other DNA
                        organism = synthetic construct
SEQUENCE: 30
gcccgggcta gctccccgcc cctctgttgc at                              32

SEQ ID NO: 31           moltype = DNA  length = 32
FEATURE                 Location/Qualifiers
misc_feature            1..32
                        note = ZNF395-E1-F_MluI primer
source                  1..32
                        mol_type = other DNA
                        organism = synthetic construct
SEQUENCE: 31
gctcttacgc gtacaggtgt gcgctaccac gc                              32

SEQ ID NO: 32           moltype = DNA  length = 39
FEATURE                 Location/Qualifiers
misc_feature            1..39
                        note = ZNF395-E1-R_NheI primer
source                  1..39
                        mol_type = other DNA
                        organism = synthetic construct
SEQUENCE: 32
gcccgggcta gctggtgtgg aattctggcc agttaaagg                       39

SEQ ID NO: 33           moltype = DNA  length = 34
FEATURE                 Location/Qualifiers
misc_feature            1..34
                        note = ZNF395-E2-F_MluI primer
source                  1..34
                        mol_type = other DNA
                        organism = synthetic construct
SEQUENCE: 33
gctcttacgc gttcgggagg ttcaagacca gcct                            34

SEQ ID NO: 34           moltype = DNA  length = 38
FEATURE                 Location/Qualifiers
misc_feature            1..38
                        note = ZNF395-E2-R_NheI primer
source                  1..38
                        mol_type = other DNA
                        organism = synthetic construct
SEQUENCE: 34
gcccgggcta gcgctcccaa gaaagaactt accagagg                        38

SEQ ID NO: 35           moltype = DNA  length = 34
FEATURE                 Location/Qualifiers
misc_feature            1..34
                        note = ZNF395-E3-F_MluI primer
source                  1..34
                        mol_type = other DNA
                        organism = synthetic construct
SEQUENCE: 35
gctcttacgc gtaccagcca tccctagtt tgcc                             34
```

```
SEQ ID NO: 36            moltype = DNA  length = 37
FEATURE                  Location/Qualifiers
misc_feature             1..37
                         note = ZNF395-E3-R_NheI primer
source                   1..37
                         mol_type = other DNA
                         organism = synthetic construct
SEQUENCE: 36
gcccgggcta gcggcatttg tcagcagaga tgttggc                                    37

SEQ ID NO: 37            moltype = DNA  length = 25
FEATURE                  Location/Qualifiers
misc_feature             1..25
                         note = ZNF395_E3_L_F_gRNA
source                   1..25
                         mol_type = other DNA
                         organism = synthetic construct
SEQUENCE: 37
caccgtccct actgccgtca ccaac                                                 25

SEQ ID NO: 38            moltype = DNA  length = 25
FEATURE                  Location/Qualifiers
misc_feature             1..25
                         note = ZNF395_E3_L_R_gRNA
source                   1..25
                         mol_type = other DNA
                         organism = synthetic construct
SEQUENCE: 38
aaacgttggt gacggcagta gggac                                                 25

SEQ ID NO: 39            moltype = DNA  length = 25
FEATURE                  Location/Qualifiers
misc_feature             1..25
                         note = ZNF395_E3_R_F_gRNA
source                   1..25
                         mol_type = other DNA
                         organism = synthetic construct
SEQUENCE: 39
caccgaaata tgtttatggt cctcc                                                 25

SEQ ID NO: 40            moltype = DNA  length = 25
FEATURE                  Location/Qualifiers
misc_feature             1..25
                         note = ZNF395_E3_R_R_gRNA
source                   1..25
                         mol_type = other DNA
                         organism = synthetic construct
SEQUENCE: 40
aaacggagga ccataaacat atttc                                                 25

SEQ ID NO: 41            moltype = DNA  length = 23
FEATURE                  Location/Qualifiers
misc_feature             1..23
                         note = ZNF395-E3-F
source                   1..23
                         mol_type = other DNA
                         organism = synthetic construct
SEQUENCE: 41
accagccatc ccctagtttg cca                                                   23

SEQ ID NO: 42            moltype = DNA  length = 21
FEATURE                  Location/Qualifiers
misc_feature             1..21
                         note = ZNF395-E3-R
source                   1..21
                         mol_type = other DNA
                         organism = synthetic construct
SEQUENCE: 42
gccaccaggt agcagttggg t                                                     21

SEQ ID NO: 43            moltype = DNA  length = 4807
FEATURE                  Location/Qualifiers
misc_feature             1..4807
                         note = ZNF395 mRNA (NM_018660.2)
source                   1..4807
                         mol_type = other DNA
                         organism = synthetic construct
SEQUENCE: 43
aagtgcgcat gtgcgcgagg agtcgctcgg gcacttattg agcgccgact gtctacgggc           60
```

```
ggccggggqt gatgggcaga ggcttcaqtg tccccttcqc ctccgcagga gaggagaggc    120
aqcaqcatgg cqaqtgtcct gtcccgacgc cttggaaagc ggtccctcct gqgaqcccgg    180
gtgttgggac ccagtgcctc ggaggggccc tcgqctgccc caccctcgga gccactgcta    240
gaaggggccg ctccccagcc tttcaccacc tctgatgaca ccccctgcca ggagcagccc    300
aaggaagtcc ttaaggctcc cagcacctcg ggccttcagc ggtggcctt tcagcctggg    360
cagaaggttt atgtgtggta cggggqtcaa gagtgcacag gactggtgga gcagcacagc    420
tggatggagg tcaggtgac cgtctggctg ctggagcaga agctgcaggt ctgctgcagg    480
gtggaggagg tgtggctggc agagctgcag ggccctgtc cccaggcacc accctggag    540
cccggagccc aggcctggc ctacaggccc gtctccagga acatcgatgt cccaaagagg    600
aagtcggacg cagtggaaat ggatgagatg atgcgcagcca tggtgctgac gtccctgtcc    660
tgcagccctg ttgtacagag tcctcccggg accgaggcca acttctctgc ttcccgtgcg    720
gcctgcgacc catggaagga gagtggtgac atctcggaca cgcagcag cactaccagc    780
ggtcactgga gtgggaqcag tggtgtctcc acccctcqc ccccaccc caggccagc    840
cccaagtatt tggggactgc ttttggttct cccccaaacctg atcatggctt tgagaccgat    900
cctgaccctt tcctgctgga cgaaccagct ccacgaaaaa gaaagaactc tgtgaaggtg    960
atgtacaagt gcctgtggcc aaactgtggc aagttctgc gctccattgt gggcatcaaa   1020
cgacacgtca aagccctcca tctggggac acagtggact ctgatcagtt caagcgggag   1080
gaggattcct actacacaga ggtgcagctg aaggaggaa ctgctgctgc tgctgctgct   1140
gctgccgcag gcaccccagt ccctgggact cccacctccg agccagctcc caccccagc   1200
atgactggcc tgcctctgtc tgctcttcca ccacctctgc acaaagccca gtcctccggc   1260
ccagaacatc ctggccggga gtcctccctg ccctcagggg ctctcagcaa gtcagctcct   1320
gggtccttct ggcacattca ggcagatcat gcataccagg gtctgccatc cttccagatc   1380
ccagtctcac cacacatcta caccagtgtc agctgggctg ctgcccctc cgccgcctgc   1440
tctctctctc cgqtccggag ccggtcgcta agcttcagcg agcccagca gccagcacct   1500
gcgatgaaat ctcatctgat cgtcacttct ccaccccggg ccagagtgg tgccaggaaa   1560
gcccqgqgqg aggctaagaa gtgccgcaag gtgtatgqca tcgagcaccg gaccagtgg   1620
tgcacgqcct gccggtgaa gaaggcctgc caqccgcttttc tggactgagc tgtgctqcag   1680
gttctactct gttcctggcc ctgccggcag ccactgacaa gaggcagtg tgtcaccagc   1740
cctcagcaga aaccgaaaga gaaagaacgg aaacacgag tttgggctct gttggctaag   1800
gtgtaaact taaagcaatt ttctcccatt gtgcgaacat tttatttttt aaaaaaaaga   1860
aacaaaaata tttttcccc taaaatagga gagagccaaa actgaccaag gctattcagc   1920
agtgaaccag tgaccaaaga attaattacc ctccgtttcc cacatcccca ctctctaggg   1980
gattaggcttg tgcgtgtcaa aagaaggaac agctcgttct gcttcctgct gagtcggtga   2040
attctttgct ttctaaactc ttccagaaag gactgtgagc aagatgaatt tacttttctt   2100
aaaaaaaaaa aaaaaaaaaa aaaaaaagag tttctggctg atgggtgact cagagtgcag   2160
gactgcctgg cgtggggca gagggggttttg cccttctcgg agggtacctc ctgttccctg   2220
tctgagcatc ctgcatqgaa gtcaaaggaa atccctttct tgggtgacgac ttaaatctgg   2280
gttccctcag acattggqtt gcaccccaac aaatattaaa tggcttcttc ttaaagccca   2340
gagaaagagg tttttaaaa gactgtcgcc aaatagctga gccaaaagqc tgatcagaat   2400
tcactttttg gaatgtggca gttaaacact accttgatca ttctctcctc tttcctcgag   2460
gaactcctgg aggggtttgag cgtctggaaa ctctctgctc tgacccgagg aagcaccctc   2520
ctgacgccgc cttcctccgg ttattgaaag gacgcctcag aaatgctttg ttttcttta   2580
cgatgtattc agaagccttt actgattaaa gttttctttt atttgggtgg ccgggagaga   2640
cccaqgqqgq ttctgqaggt tccttttctgt ctcctggccc caccaggat ttccccattt   2700
ctgtttgctg cctgaaaqca gggatgaqgaa ggccaaqgaq agtccttgca cccgtqaqcg   2760
tcaggatgag gaaatgacaq gaggaagacg tgggtttggg ttagtggctg ctggcgtttt   2820
ggcccttggt gtttctggaq cctccaqgga tctagggaq gtgcctgctgc gtgcatgtcg   2880
ataagcagag ctgttcttgg ggagaaggag ggaggtctcg ggaqtgtaqc accatgccaa   2940
ccagcccctqc gcgaagacag agtgagccac gcccggatgg cagggcatgt ttctgttttg   3000
gtgtctcact ttcctcccag cgtgacttat ttggggattc ctcagggcct actggaatgt   3060
gactgcccac tgcccagctg cctcgggtac aagtcctggc cctatgtcc agctgtcag   3120
ggctcaggga atcctaccca gccaccttgtc ctgggatgga gtgtcagcat ccacccttg   3180
gttgtcatcg aggccgccct cccagtcctg ggtgaagata tttgggccac cagggctccc   3240
ttggccctt cacgtaggaa atagacacgt gcttttaat gcaggacact tgagtgtta   3300
caaaatctgt agacctggca gtagggtcat gatgttgaga agggtgtagt gccctaggtt   3360
ggtgacagaa gggacagaca cttgtgcaca ggtgtctttg gtgatggggt tttttttt   3420
ataacttagt aaaaaaaaaa aaatgtatgt ggaattctgt ctcttggtaa agctcaaagc   3480
caqqctagcc tgaggtgqcg caqqgctctc cttcctgtcc cttcgatctc cttgagaatt   3540
aagagctggc agctgctgat ggtgtttccc aaccccctc acttcccaag acaaccccca   3600
gcttcaggtc ctcatgggga ggggaqggca cgttcttgac acatgggaac ttcgctcagg   3660
agggcctccc cttccctct ccctcagagt tttcactgcc gtctcgtctt tagaaagctg   3720
tttgaattcc ccccgcccc agtttggacc gtgtagatat aactggatat acggattttt   3780
ctctttgtgc aggcttctta tgccgttggt atacagggca ggaagagaga gaataaaggg   3840
agagagcagt gtggaaacca cggtggtttt gctttgttct tactaggttt tggtgccacc   3900
ttccctgcct gcgcttgtgc cccctctcct ccttggcact ggcggcctcc ttgcctcct   3960
tccaccgtg ctgccatccc gtgcctgctg tgttggttct tcacgcgtqc tctgttctcg   4020
gggttgttcc attcatgcct tcttggaggg tgagggtggc ttgggaaccg acccagtgat   4080
catgcctact ttcttctttg tatctcccctc cttcccagcc caccgggca gcagactctg   4140
atggaaggaa ggtgccgtag gtgggctttt agaaactaac gggactggtt tcaaagcag   4200
ttatcttggg aaactgttta ttccagcgat gtgactttt tcagaatatt tcttggaatc   4260
atattcagag tctgggcgtg tgtgttgaqc agccttaagg atgctagaca ctcatttagt   4320
gcccaggag tccagcgaat gacgtctgtg gccaagcgag gtctcaggtg caaagcaaaa   4380
ggaccattta aagtaaaata gcttggattc aatcatgtga ctttttaatt ggctcagaaa   4440
gcaattttgt aattcagag agtgtttga gccatggcca cgttgtcatt gtgagtctat   4500
agcttgactc cttggagaac aatattcatt tggttgtgga gactgatttg ctgggagaaa   4560
tctgtcctgt tactttctgg tcatcccagg ttctgacttt taccaqgggc aaaaaaaaaa   4620
aaagcaagag ggagataaat cccatctgtg agtttgtctt ttggcgcct ttttcctcag   4680
ctgtcttcca agtattattt ttactgttaa aaaatttttt aaaatgtgag aatgtaatgt   4740
ttttacaqca acaatatgaa atatatttta taaggaataa aatggtacct tgtctgattt   4800
```

```
                                                       aaaaaaa                                               4807

SEQ ID NO: 44           moltype = AA  length = 513
FEATURE                 Location/Qualifiers
REGION                  1..513
                        note = ZNF395 protein (NP_061130.1)
source                  1..513
                        mol_type = protein
                        organism = synthetic construct
SEQUENCE: 44
MASVLSRRLG KRSLLGARVL GPSASEGPSA APPSEPLLEG AAPQPFTTSD DTPCQEQPKE    60
VLKAPSTSGL QQVAFQPGQK VYVWYGGQEC TGLVEQHSWM EGQVTWLLE QKLQVCCRVE   120
EVWLAELQGP CPQAPPLEPG AQALAYRPVS RNIDVPKRKS DAVEMDEMMA AMVLTSLSCS   180
PVVQSPPGTE ANFSASRAAC DPWKESGDIS DSGSSTTSGH WSGSSGVSTP SPPHPQASPK   240
YLGDAFGSPQ TDHGFETDPD PFLLDEPAPR KRKNSVKVMY KCLWPNCGKV LRSIVGIKRH   300
VKALHLGDTV DSDQFKREED FYYTEVQLKE ESAAAAAAAA AGTPVPGTPT SEPAPTPSMT   360
GLPLSALPPP LHKAQSSGPE HPGPESSLPS GALSKSAPGS FWHIQADHAY QALPSFQIPV   420
SPHIYTSVSW AAAPSAACSL SPVRSRSLSF SEPQQPAPAM KSHLIVTSPP RAQSGARKAR   480
GEAKKCRKVY GIEHRDQWCT ACRWKKACQR FLD                                513

SEQ ID NO: 45           moltype = DNA  length = 1773
FEATURE                 Location/Qualifiers
misc_feature            1..1773
                        note = SMPDL3A mRNA (isoform b)(NM_001286138.1)
source                  1..1773
                        mol_type = other DNA
                        organism = synthetic construct
SEQUENCE: 45
accagtatgt cagtgtttga catcaactgc accactgata cacgagtcgg aatttgagct    60
tctacaagta cattccttcc taggccaaac actgacgcta agaaatacga gaacagatca   120
tcgctaaaca gcagctgaag gtcaggcgaa ctgactcgct gcggaatctg cctttgcacg   180
tgatcagtcg gacgtctaca cccgcagccg tcttctgtct ccgcctcacc ctcaggcctg   240
acggtccgag tggagctgcg ggacagcccg aacctccagg tcagcccgc ggccctccat   300
ggcgctggtg cgcgcactcg tctgctgcct gctgactgcc tggcactgcc gctccggcct   360
cgggctgccc gtggcgcccg caggcgggag gaatcctcct ccggcgatag ggatagccca   420
cctcatgttc ctgtacctga actcctcaaca gacactgtta taaatgtgat cactaatatg   480
acaaccacca tccagagtct ctttccaaat ctccaggttt ccctgcgct gggtaatcat   540
gactattggc cacaggatca actgcctgta gtcaccagta aagtgtacaa tgcagtagca   600
aacctcttgg aaccatggct agatgaagaa gctattagta cttaaggaa aggtggttt   660
tattcacaga aagttacaac taatccaaac cttaggatca tcagtctaaa cacaaacttg   720
tactacggcc caaatataat gacactgaac aagactgacc cagccaacca gtttgaatgg   780
ctagaaagta cattgaacaa ctctcagcag aataaggaga aggtgtatat catagcacat   840
gttccagtgg ggtatctgcc atcttcacag aacatcacag tagatgaaga tactatata   900
gagaaattga tagatatttt tcaaaaatac agtgatgtca ttgcaggaca attttatgga   960
cacactcaca gagacagcat tatggttctt tcagataaaa aaggaagtcc agtaaattct  1020
ttgtttgtgt ctcctgctgt tacaccagtg aagagtgttt tagaaaaaca gaccaacaat  1080
cctggtatca gactgtttca gtatgatcct cgtgattata aattattgga tatgttgcag  1140
tattacttga atctgacaga ggcgaatcta aagggagagt ccatctggaa gctggagtat  1200
atcctgaccc agacctacga cattgaagat ttgcagccgg aaagtttata tggattagct  1260
aaaacaattta caatcctaga cagtaagcag tttataaaat actacaatta cttctttgtg  1320
agttatgaca gcagtgtaac atgtgataag acatgtaagg cctttcagat ttgtgcagat  1380
atgaatcttg ataatatttc ctatgcagat tgcctcaaac agcttatat aaagcacaat  1440
tactagtatt tcacagtttt tgctaataga aaatgctgat tctgattctg agatcaattt  1500
gtgggaattt tacataaatc tttgttaatt actgagtggg caagtagact tcctgtcttt  1560
gcttttcttt tattttttctt tttgatgcct taatgtagat atctttatca ttctgaattg  1620
tattatatat ttaaagtgct cattaataga atgatggatg taaattggat gtaaatattc  1680
agttatatata attatatcta atttgtaccc ttgttgaaat tgtcatttat acaataaagc  1740
gaattctttta tctctaaaaa aaaaaaaaaa aaa                              1773

SEQ ID NO: 46           moltype = AA  length = 322
FEATURE                 Location/Qualifiers
REGION                  1..322
                        note = SMPDL3A protein (isoform b)(NP_001273067.1)
source                  1..322
                        mol_type = protein
                        organism = synthetic construct
SEQUENCE: 46
MTTTIQSLFP NLQVFPPALGN HDYWPQDQLP VVTSKVYNAV ANLWKPWLDE EAISTLRKGG    60
FYSQKVTTNP NLRIISLNTN LYYGPNIMTL NKTDPANQFE WLESTLNNSQ QNKEKVYIIA   120
HVPVGYLPSS QNITAMREYY NEKLIDIFQK YSDVIAGQFY GHTHRDSIMV LSDKKGSPVN   180
SLFVAPAVTP VKSVLEKQTN NPGIRLFQYD PRDYKLLDML QYYLNLTEAN LKGESIWKLE   240
YILTQTYDIE DLQPESLYGL AKQFTILDSK QFIKYYNYFF VSYDSSVTCD KTCKAFQICA   300
IMNLDNISYA DCLKQLYIKH NY                                            322

SEQ ID NO: 47           moltype = DNA  length = 1987
FEATURE                 Location/Qualifiers
misc_feature            1..1987
                        note = SMPDL3A mRNA (isoform a)(NM_006714.4)
source                  1..1987
```

|  |  |  |  |  |  |
|---|---|---|---|---|---|
|  |  | mol_type = other DNA | | | |
|  |  | organism = synthetic construct | | | |
| SEQUENCE: 47 | | | | | |
| accagtatgt | cagtgtttga | catcaactgc | accactgata | cacgagtcgg | aatttgagct | 60 |
| tctacaagta | cattccttcc | taggccaaac | actgacgtca | agaaatacga | gaacagatca | 120 |
| tcgctaaaca | gcagctgaag | gtcaggcgaa | ctgactcgct | gcggaatctg | cctttgcacg | 180 |
| tgatcagtcg | gacgtctaca | cccgcagccg | tcttctgtct | ccgcctcacc | ctcaggcctg | 240 |
| acggtccgag | tggagctgcg | ggacagcccg | aacctccagg | tcagcccgc | ggccctccat | 300 |
| ggcgctggtg | cgcgcactcg | tctgctgcct | gctgactgcc | tggcactgcc | gctccggcct | 360 |
| cgggctgccc | gtggcgcccg | caggcggcag | gaatcctcct | ccggccgatag | gacagtttg | 420 |
| gcatgtgact | gacttacact | tagaccctac | ttaccacatc | acagatgacc | acacaaaagt | 480 |
| gtgtgcttca | tctaaaggtg | caaatgcctc | caaccctggc | cctttggag | atgttctgtg | 540 |
| tgattctcca | tatcaactta | ttttgtcagc | atttgatttt | attaaaaatt | ctggacaaga | 600 |
| agcatctttc | atgatatgga | cagggatg | cccacctcat | gttcctgtac | ctgaactctc | 660 |
| aacagacact | gttataaatg | tgatcactaa | tatgacaacc | accatccaga | gtctctttcc | 720 |
| aaatctccag | gttttccctg | cgctgggtaa | tcatgactat | tggccacagg | atcaactgcc | 780 |
| tgtagtcacc | agtaaagtgt | acaatgcagt | agcaaacctc | tggaaaccat | ggctagatga | 840 |
| agaagctatt | agtactttaa | ggaaagtgt | ttttattca | cagaaagtta | caactaatcc | 900 |
| aaaccttagg | atcatcagtc | taaacacaaa | cttgtactac | ggcccaaata | atgacact | 960 |
| gaacaagact | gacccagcca | accagtttga | atggctagaa | agtacattga | caactctca | 1020 |
| gcagaataag | gagaaggtgt | atatcatagc | acatgttcca | gtggggtatc | tgccatcttc | 1080 |
| acagaacatc | acagcaatga | gagaatacta | taatgaaaa | ttgatagata | tttttcaaaa | 1140 |
| atacagtgat | gtcattgcag | gacaattta | tggacacact | cacagagaca | gcattatggt | 1200 |
| tctttcagat | aaaaaaggaa | gtccagtaaa | ttctttgttt | gtggctcctg | ctgttacacc | 1260 |
| agtgaagagt | gttttagaaa | aacagaccaa | caatcctggt | atcagactgt | ttcagtatga | 1320 |
| tcctcgtgat | tataaattat | tggatatgtt | gcagtattac | ttgaatctga | cagaggcgaa | 1380 |
| tctaaaggga | gagtccatct | ggaagctgga | gtatatcctg | acccagacct | acgacattga | 1440 |
| agatttgcag | ccggaaagtt | tatatggatt | agctaaacaa | tttacaatcc | tagacagtaa | 1500 |
| gcagtttata | aaatactaca | attacttctt | tgtgagttat | gacagcagtg | taacatgtga | 1560 |
| taagacatgt | aaggcctttc | agatttgtgc | aattatgaac | cttgataata | tttcctatgc | 1620 |
| agattgcctc | aaacagcttt | atataaagca | caattactag | tatttcacag | ttttttgctaa | 1680 |
| tagaaaatgc | tgattctgat | tctgagatca | atttgtggga | attttacata | aatctttgtt | 1740 |
| aattactgag | tgggcaagta | gacttcctgt | ctttgctttc | ttttttttt | tctttttgat | 1800 |
| gccttaatgt | agatatcttt | atcattctga | attgtattat | atatttaaag | tgctcattaa | 1860 |
| tagaatgatg | gatgtaaatt | ggatgtaaat | attcagttta | tataattata | tctaatttgt | 1920 |
| accttgttg | aaaattgtcat | ttatacaata | aagcgaattc | tttatctcta | aaaaaaaaaa | 1980 |
| aaaaaaa | | | | | | 1987 |

| SEQ ID NO: 48 | | moltype = AA length = 453 |
|---|---|---|
| FEATURE | | Location/Qualifiers |
| REGION | | 1..453 |
| | | note = SMPDL3A protein (isoform a)(NP_006705.1) |
| source | | 1..453 |
| | | mol_type = protein |
| | | organism = synthetic construct |
| SEQUENCE: 48 | | |

| | | | | | |
|---|---|---|---|---|---|
| MALVRALVCC | LLTAWHCRSG | LGLPVAPAGG | RNPPPAIGQF | WHVTDLHLDP | TYHITDDHTK | 60 |
| VCASSKGANA | SNPGPFGDVL | CDSPYQLILS | AFDFIKNSGQ | EASFMIWTGD | SPPHVPVPEL | 120 |
| STDTVINVIT | NMTTTIQSLF | PNLQVFPALG | NHDYWPQDQL | PVVTSKVYNA | VANLWKPWLD | 180 |
| EEAISTLRKG | GFYSQKVTTN | PNLRIISLNT | NLYYGPNIMT | LNKTDPANQF | EWLESTLNNS | 240 |
| QQNKEKVYII | AHVPVGYLPS | SQNITAMREY | YNEKLIDIFQ | KYSDVIAGQF | YGHTHRDSIM | 300 |
| VLSDKKGSPV | NSLFVAPAVT | PVKSVLEKQT | NNPGIRLFQY | DPRDYKLLDM | LQYYLNLTEA | 360 |
| NLKGESIWKL | EYILTQTYDI | EDLQPESLYG | LAKQFTILDS | KQFIKYYNYF | FVSYDSSVTC | 420 |
| DKTCKAFQIC | AIMNLDNISY | ADCLKQLYIK | HNY | | | 453 |

| SEQ ID NO: 49 | | moltype = DNA length = 2155 |
|---|---|---|
| FEATURE | | Location/Qualifiers |
| misc_feature | | 1..2155 |
| | | note = SLC28A1 mRNA (NM_001287761.1) |
| source | | 1..2155 |
| | | mol_type = other DNA |
| | | organism = synthetic construct |
| SEQUENCE: 49 | | |

| | | | | | |
|---|---|---|---|---|---|
| acaacgatgt | gaaggttata | agctgcactg | catggttgct | gctggatgtg | ttgtgttcct | 60 |
| ggcttccctc | tggatgctga | cagaaacaag | gctggaaggt | ctgggacatg | agaacgacc | 120 |
| cctcgagacg | aagagagtcc | atctctctca | cacctgtggc | caagggtctg | agaacatgg | 180 |
| gggctgattt | cttggaaagc | ctggaggaag | gccagctccc | taggagtgac | ttgagccccg | 240 |
| cagagatcag | gagcagctgg | agcgaggcgg | cgccgaagcc | cttctccaga | tggaggaacc | 300 |
| tgcagccagc | cctgagaqcc | agaagcttct | gcagggagca | catgcagctg | tttcgatgga | 360 |
| tcggcacagg | cctgctctgc | actgggtct | ctgccttcct | gctggtggcc | tgcctcctga | 420 |
| atttccagag | ggccctggct | ctgtttgtcc | tcacctgtgt | ggtcctcacc | ttcctgggcc | 480 |
| accgcctgct | gaaacggctt | ctgggggcaa | agctgaggag | gttctcaag | cctcaggcc | 540 |
| atccccgcct | gctgctctgg | tttaagaggg | gtctagctct | tgctgctttc | ctgggcctgg | 600 |
| tcctggtgt | gtcctggac | acctcccagc | caggtgacga | actggttcc | cttggcaggaa | 660 |
| tctgcgtgtt | cgtcgctctc | ctctttgcct | gctcaaagca | tcattgcgca | gtgtcctgga | 720 |
| gggccgtgtc | ttggggactt | ggactgcagt | ttgtacttgg | actcctgtc | atcagaacag | 780 |
| aaccaggatt | cattgcgttc | gagtggctgg | gcgagcagat | ccggatcttc | ctgagctaca | 840 |
| cgaaggctgc | ctccagcttc | gtgttgggg | aggcgctggt | caaggatgtc | tttgcctttc | 900 |
| aggttctgcc | catcattgtc | tttttcagct | gtgtcatatc | cgttctctac | cacgtgggcc | 960 |

```
tcatgcagtg ggtgatcctg aagattgcct ggctgatgca agtcaccatg ggcaccacag    1020
ccactgagac cctgagtgtg gctgaaaaca tctttgtgag ccagaccgag gctccattac    1080
tgatccggcc ctacttggca gacatgacac tctctgaagt ccacgttgtc atgaccggag    1140
gttacgccac cattgctggc agcctgctgg gtgcctacat ctccttgg gtcagagctg      1200
aagtcctcac gacgttgcc tctctgtgat ttgccaattt cagctccatt gggatcatgc     1260
tgggaggctt gacctccatg gtcccccaac ggaagagcga cttctcccag atagtgctcc    1320
gggcgctctt cacgggagcc tgtgtgtccc tggtgaacgc ctgtatggca gggatcctct    1380
acatgcccag gggggctgaa gttgactgca tgtcccctctt gaacacgacc ctcagcagca   1440
gtagctttga gatttaccag tgctgccgtg aggcttcca gagcgtcaat ccagagttca    1500
gcccagaggc cctggacaac tgctgtcggt tttacaacca cacgatctgt gcacagtgag    1560
gacagaacat gcttgtgctt ctgcgcttct gagggctgtt ctccccccggg aaccatctgt   1620
ccccaccttc cctttcccag agccctcttc agggaagcca caggactag acccagctca    1680
atcccacaat tgggaagggt tcatggagtg agtgtgcaga gagtgagtga ggacataagg    1740
aaggacatgt cccactccat ccccccttcct gctccccat ttcctaactc cccagtgttg    1800
aattctcagg gtcacttctg cctcctcccg tttcccctcc acatccaaac agcaccctg    1860
tcctctctat ccccccctc ctggggtccc tcacatgccc cttcccttct gttgtgggct     1920
gcacaccaaa gcctcctccc ctcccactt cctaggcact aggatctctc tgtggcttcc    1980
cctgctgggt ggtgtcacct cttctctgc tttcagagaa acccttcccg cctttcctca    2040
gagtgcttcc caaactgagg tcccatggca cactgtcctg ggaggcgttc agagggttcc    2100
atgatggact aggtttggaa ccactgggtt aaataaactt agagagggct gttta         2155

SEQ ID NO: 50          moltype = AA  length = 483
FEATURE                Location/Qualifiers
REGION                 1..483
                       note = SLC28A1 protein (NP_001274690.1)
source                 1..483
                       mol_type = protein
                       organism = synthetic construct
SEQUENCE: 50
MENDPSRRRE SISLTPVAKG LENMGADFLE SLEEGQLPRS DLSPAEIRSS WSEAAPKPFS      60
RWRNLQPALR ARSFCREHMQ LFRWIGTGLL CTGLSAFLLV ACLLDFQRAL ALFVLTCVVL    120
TFLGHRLLKR LLGPKLRRFL KPQGHPRLLL WFKRGLALAA FLGLVLWLSL DTSQRPEQLV    180
SFAGICVFVA LLFACSKHHC AVSWRAVSWG LGLQFVLGLL VIRTEPGFIA FEWLGEQIRI    240
FLSYTKAGSS FVFGEALVKD VFAFQVLPII VFFSCVISVL YHVGLMQWVI LKIAWLMQVT    300
MGTTATETLS VAGNIFVSQT EAPLLIRPYL ADMTLSEVHV VMTGGYATIA GSLLGAYISF    360
GVRAEVLTTF ALCGFANFSS IGIMLGGLTS MVPQRKSDFS QIVLRALFTG ACVSLVNACM    420
AGILYMPRGA EVDCMSLLNT TLSSSSFEIY QCCREAFQSV NPEFSPEALD NCCRFYNHTI    480
CAQ                                                                  483

SEQ ID NO: 51          moltype = DNA  length = 3677
FEATURE                Location/Qualifiers
misc_feature           1..3677
                       note = VEGFA mRNA (NM_001025366.2)
source                 1..3677
                       mol_type = other DNA
                       organism = synthetic construct
SEQUENCE: 51
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg    120
ctcggtgctg gaatttgata ttcattgatc cgggttttat ccctcttctt ttttcttaaa    180
cattttttt taaaactgta ttgtttctcg ttttaatta ttttttgcttg ccattcccca     240
cttgaatcgg gccgacggct tggggagatt gctctacttc cccaaatcac tgtggatttt    300
ggaaccagc agaaagagga aagaggtagc aagagctcca gagagaagtc gaggaagaga    360
gagacgggt cagagagagc gcgcgggcgt gcgagcagcg aaagcgacag ggcaaagtg      420
agtgacctgc tttttgggggt gaccgccgga gcgcggcgtg agccctcccc cttgggatcc    480
cgcagctgac cagtcgcgct gacggacaga cagacagaca ccgccccag ccccagctac    540
cacctcctcc ccggccggcg gcggacagtg gacgcggcgg cgagccgcgg gcaggggccg    600
gagcccgcgc ccggaggcgg ggtggagggg gtcgggggctc gcggcgtcgc actgaaactt    660
ttcgtccaac ttctgggctg ttctcgcttc ggaggagccg tggtccgcgc gggggaagcc    720
gagccgagcg gagccgagag aagtgctagc tcggggcgga aggagccgca gccggaggag    780
ggggaggagg aagaagagaa ggaagaggag aggggggccgc agtggcgact cggcgctcgg    840
aagccgggct catggacggg tgaggcggcg gtgtgcgcag acagtgctcc agccgcgcgc    900
gctcccagg ccctggcccg gcctcggcc cggggaggaa gagtagctcg ccgaggcgcc    960
gaggagacg ggccgcccca cagcccgagc cggagagaga gcgcgagccg cgccggccca    1020
ggtcgggcct ccgaaaccat gaactttctg ctgtctttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag agagatgag cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccggtataa gtcctggagc gtgtacgttg tgcccgctg ctgtctaatg    1560
ccctgtgggc cttgctccc ccatccctgt gggccttcgt cagacgggaa aagcatttg    1620
tttgtacaag atccgcagac gtgtaaatgt tcctgcaaaa acacagactc gcgttgcaag    1680
gcgaggcagc ttgagttaaa cgaacgtact tgcagatgtg acaagccgag gcggtgagcc    1740
gggcaggagg aaggagcctc cctcagggtt tcgggaacca gatctctcac caggaaagac    1800
tgatacagaa cgatcgatac agaaaccacg ctgccgccac cacaccatca ccatcgcagg    1860
aacagtcctt aatccagaaa cctgaaatga aggaagagga gactctgcgc agagcacttt    1920
```

-continued

```
gggtccggag ggcgagactc cggcggaagc attcccgggc gggtgaccca gcacggtccc 1980
tcttggaatt ggattcgcca ttttatttt  cttgctgcta aatcaccgag cccggaagat 2040
tagagagttt tatttctggg attcctgtag acacacccac ccacatacat acatttatat 2100
atatatatat tatatatata taaaaataaa tatctctatt ttatatatat aaaatatata 2160
tattctttt  ttaaattaac agtgctaatg ttattggtgt cttcactgga tgtatttgac 2220
tgctgtggac ttgagttggg aggggaatgt tcccactcag atcctgacag ggaagaggag 2280
gagatgagag actctggcat gatctttttt ttgtcccact tggtggggcc agggtcctct 2340
ccctgccca  ggaatgtgca aggccagggc atggggcaa  atatgaccca gttttgggaa 2400
caccgacaaa cccagccctg cgcgctgagcc tctctacccc aggtcagacg gacagaaaga 2460
cagatcacag gtacagggat gaggacaccg gctctgacca ggagtttggg gagcttcagg 2520
acattgctgt gctttgggga ttccctccac atgctgcacg cgcatctcgc ccccagggggc 2580
actgcctgga agattcagga gcctgggcgg ccttcgctta ctctcacctg cttctgagtt 2640
gcccaggaga ccactggcag atgtcccggc aagagaaga  gacacattgt tggaagaagc 2700
agcccatgac agctccccctt cctgggactc gccctcatcc tcttcctgct ccccttcctg 2760
gggtgcagcc taaaaggacc tatgtcctca caccattgaa accactagtt ctgtcccccc 2820
aggagacctg gttgtgtgtg tgtgagtggt tgaccttcct ccatccctg  gtccttccct 2880
tcccttcccg aggcacagag agacagggca ggatccacgt gccccattgtg gaggcagaga 2940
aaagagaaag tgttttatat acggtactta tttaatatcc cttttttaatt agaaattaaa 3000
acagttaatt taattaaaga gtagggtttt ttttcagtat tcttggttaa tatttaattt 3060
caactatttta tgagatgtat cttttgctct ctcttgctct cttatttgta ccggttttg  3120
tatataaaat tcatgtttcc aatctctctc tccctgatcg gtgacagtca ctagcttatc 3180
ttgaacagat atttaatttt gctaaacactc agctctgccc tccccgatcc cctggctccc 3240
cagcacacat tcctttgaaa taaggtttca atatacatct acatactatcc tatatatttg 3300
gcaacttgta tttgtgtgta tatatatata tatgtttta  tgtatatatg tgattctgat 3360
aaaatagaca ttgctattct gtttttata  tgtaaaaaca aaacaagaaa aaatagaaa  3420
ttctacatac taaatctctc tccttttttta attttatcat ttgttatcat ttattttattg 3480
gtgctactgt ttatccgtaa taattgtggg gaaaagatat taacatcacg tctttgtctc 3540
tagtgcagtt tttcgagata ttccgtagta catatttatt tttaaacaac gacaaagaaa 3600
tacagatata tcttaaaaaa aaaaaagcat tttgtattaa agaatttaat tctgatctca 3660
aaaaaaaaaa aaaaaaa                                               3677

SEQ ID NO: 52           moltype = AA  length = 412
FEATURE                 Location/Qualifiers
REGION                  1..412
                        note = VEGFA protein (NP_001020537.2)
source                  1..412
                        mol_type = protein
                        organism = synthetic construct
SEQUENCE: 52
MTDRQTDTAP SPSYHLLPGR RRTVDAAASR GQGPEPAPGG GVEGVGARGV ALKLFVQLLG  60
CSRFGGAVVR AGEAEPSGAA RSASSGREEP QPEEGEEEEE KEEERGPQWR LGARKPGSWT 120
GEAAVCADSA PAARAPQALA RASGRGGRVA RRGAEESGPP HSPSRRGSAS RAGPGRASET 180
MNFLLSWVHW SLALLLYLHH AKWSQAAPMA EGGGQNHHEV VKFMDVYQRS YCHPIETLVD 240
IFQEYPDEIE YIFKPSCVPL MRCGGCCNDE GLECVPTEES NITMQIMRIK PHQGQHIGEM 300
SFLQHNKCEC RPKKDRARQE KKSVRGKGKG QKRKRKKSRY KSWSVYVGAR CCLMPWSLPG 360
PHPCGPCSER RKHLFVQDPQ TCKCSCKNTD SRCKARQLEL NERTCRCDKP RR         412

SEQ ID NO: 53           moltype = DNA  length = 2199
FEATURE                 Location/Qualifiers
misc_feature            1..2199
                        note = EGLN3 mRNA (isoform 1)(NM_001308103.1)
source                  1..2199
                        mol_type = other DNA
                        organism = synthetic construct
SEQUENCE: 53
ggcttcgcgc tcgtgtagat cgttccctct ctggttgcac gctggggatc ccggacctcg   60
attctgcggg cgagatgccc ctgggacaca tcatgaggct ggacctggag aaaattgccc  120
tggagtacat cgtgccctgt ctgcacgagg caatggtggc ttgctatccg ggaaatggaa  180
caggttatgt tcgccacgtg gacaacccca acggtgatgg tcgctgcatc acctgcatct  240
actatctgaa caagaattgg gatgccaagc tacatggtgg gatcctgcgg atatttccag  300
agggaaatc  attcatagca gatgtggagc ccatttttga cagactcctg ttcttctggt  360
cagatcgtag gaacccacac gaagtgcagc ctcttacgc  aaccagatat gctatgactg  420
tctggtactt tgatgctgaa gaagggcag  aagccaaaaa gaaattcagg aatttaacta  480
ggaaaactga atctgccctc actgaagact gaccgtgtca tgaaatctgc tggccttgtt  540
cattttagta acggttcctg aattctctta aattctttga gatccaaaga tggcctcttc  600
agtgacaaca atctccctgc tacttcttgc atccttcaca tccctgtctt gtgtgtggta  660
cttcatgttt tcttgccaag actgtgttga tcttcagata ctctctttgc cagatgaagt  720
tacttgctaa ctccagaaat tcctgcagac atcctactcg gccagcggtt tacctgatag  780
attcggtaat actatcaaga gaagagccta ggagcacagc aggggaatga accttacttg  840
cactttatgt atacttcctg atttgaaagg aggaggtttg aaaagaaaaa aatgagggtg  900
gtagatgcca cagagaggca tcacggaagc cttaacagca ggaaacagag aaatttgtgt  960
catctgaaca atttccagat gttcttaatc cagggctgtt ggggtttctg agaattatc  1020
acaacctaat gacattaata cctctagaaa gggctgctgt catagtgaac aatttataag 1080
tgtcccatgg ggcagacact cctttttttcc cagtcctgca acctggattt tctgcctcag 1140
cccccatttg ctgaaaataa tgactttctg aataaagatg gcaacacaat tttttctcca 1200
ttttcagttc ttacctggga acctaattcc ccagaagcta aaaaactaga cattagttgt 1260
tttggttgct ttgttggaat ggaatttaaa tttaaatgaa ggaaaaaata tatccctggt 1320
agttttgtgt taaccactga taactgtgga aagagctagg tctactgata tacaataaac 1380
atgtgtgcat cttgaacaat ttgagagggg aggtggagtt ggaaatgtgg gtgttcctgt 1440
```

```
ttttttttttt ttttttttttt tagttttcct ttttaatgag ctcacccttt aacacaaaaa  1500
aagcaaggtg atgtatttta aaaaggaag tggaaataaa aaaatctcaa agctatttga    1560
gttctcgtct gtcccctagca gtcttcttc agctcacttg gctctctaga tccactgtgg   1620
ttggcagtat gaccagaatc atggaatttg ctagaactgt ggaagcttct actcctgcag   1680
taagcacaga tcgcactgcc tcaataactt ggtattgac acgtattttg caaaagctac    1740
ttttcctagt tttcagtatt actttcatgt tttaaaaatc cctttaattt cttgcttgaa   1800
aatcccatga acattaaaga gccagaaata ttttcctttg ttatgtacgg atatatatat   1860
atatagtctt ccaagataga agtttactttt tcctcttct ggttttggaa aatttccaga   1920
taagacatgt caccattaat tctcaacgac tgctctatt tgttgtacgg taatagttat    1980
caccttctaa attactatgt aaattattca cttattatgt ttattgtctt gtatcctttc   2040
tctgagtgt aagcacaatg aagacaggaa ttttgtatat tttaaccaa tgcaacatac     2100
tctcagcacc taaaatagtg ccgggaacat agtaagggct cagtaaatac ttgttgaata   2160
aactcagtct cctacattag cattctaaaa aaaaaaaaa                          2199

SEQ ID NO: 54          moltype = AA   length = 145
FEATURE                Location/Qualifiers
REGION                 1..145
                       note = EGLN3 protein (isoform 1)(NP_001295032.1)
source                 1..145
                       mol_type = protein
                       organism = synthetic construct
SEQUENCE: 54
MPLGHIMRLD LEKIALEYIV PCLHEAMVAC YPGNGTGYVR HVDNPNGDGR CITCIYYLNK  60
NWDAKLHGGI LRIFPEGKSF IADVEPIFDR LLFFWSDRRN PHEVQPSYAT RYAMTVWYFD 120
AEERAEAKKK FRNLTRKTES ALTED                                       145

SEQ ID NO: 55          moltype = DNA   length = 2722
FEATURE                Location/Qualifiers
misc_feature           1..2722
                       note = EGLN3 mRNA (isoform 2)(NM_022073.3)
source                 1..2722
                       mol_type = other DNA
                       organism = synthetic construct
SEQUENCE: 55
gagtctggcc gcagtcgcgg cagtggtggc ttcccatccc caaaaggcgc cctccgactc   60
cttgcgccgc actgctcgcc gggccagtcc ggaaacgggt cgtggagctc cgcaccactc  120
ccgctggttc ccgaaggcag atcccttctc ccgagagttg cgagaaactt tcccttgtcc  180
ccgacgctgc agcggctcgg gtaccgtggc agccgcaggt ttctgaaccc cgggccacgc  240
tccccgccgc tcggcttcgc gctcgtgtag atcgttccct ctctggttgc acgctgggga  300
tcccggacct cgattctgcg ggcgagatgc ccctgggaca catcatgagg ctggacctgg  360
agaaaattgc cctggagtac atcgtgcccc gtctgcacga ggtgggcttc tgctacctgg  420
acaacttcct gggcgaggtg gtgggcgact gcgtcctgga gcgcgtcaag cagctgcact  480
gcaccgggtc cctgcgggac ggcaagctgg cgggccgcgg cgccgtc tccaagcgac    540
acctgcgggg cgaccagatc acgtggatcc ggggcaacga ggagggctgc gaggccatca  600
gcttcctcct gtcccctcatc gacaggctgg tcctctactg cgggagccgg ctgggcaaat  660
actacgtcaa ggagaggtct aaggcaatgg tggcttgcta tccgggaaat ggaacaggtt  720
atgttcgcca cgtggacaac cccaacggtg atggtcgctg catcacctgc atctactatc  780
tgaacaagaa ttgggatgcc aagctacatg gtgggatcct gcggatattt ccagagggga  840
aatcattcat agcagatgtg gagcccattt tgacagact cctgttcttc tggtcagatc   900
gtaggaaccc cacgaagtg cagccctctt acgcaaccag atatgctatg actgtctggt   960
actttgatgc tgaagaaagg gcagaagcca aaaagaaatt caggaattta actaggaaaa  1020
ctgaatctgc cctcactgaa gactgaccgt gctctgaaat ctgctggcct tgttcatttt  1080
agtaacggtt cctgaattct cttaaattct ttgagatcca aagatggcct cttcagtgac  1140
aacaatctcc ctgctacttc ttgcatcctt cacatccctg tcttgtgtgt ggtacttcat  1200
gttttcttgc caagactgtg ttgatcttca gatctctct ttgccagatg aagttacttg   1260
ctaactccag aaaattcctgc agacatccta ctcggccagc ggtttacctg atagattcgg  1320
taatactatc aagagaagag cctaggagca cagcgaggga atgaacctta cttgcacttt   1380
atgtatactt cctgatttga aggaggagg tttgaaaaga aaaaaatgga ggtggtagat    1440
gccacagaga ggcatcacgg aagccttaac agcaggaaac agagaaattt gtgtcatctg   1500
aacaatttcc agatgttctt aatccagggc tgttgggtt tctggagaat tatcacaacc    1560
taatgacatt aatacctcta gaaagggctg ctgtcatagt gaacaattta taagtgtccc   1620
atggggcaga cactccttt tcccagtcc tgcaacctgg atttttctgcc tcagccccat    1680
tttgctgaaa ataatgactt tctgaataaa gatggcaaca caattttttc tccattttca   1740
gttcttacct gggaacctaa ttccccagaa gctaaaaaac tagacattag ttgttttggt   1800
tgctttgttg gaatgaattt taaatttaaa tgaaagaaa aatatatccc tggtagtttt   1860
gtgttaacca ctgataactg tggaaagagc taggtctact gatatacaat aaacatgtgt   1920
gcatcttgaa caatttgaga ggggaggtgg agttggaaat gtgggtgttc ctgttttttt   1980
ttttttttt tttttagttt tccttttta tgagctcacc cttaacaca aaaaagcaa      2040
ggtgatgtat tttaaaaaag gaagtgaaa taaaaaaatc tcaaagctat ttgagttctc    2100
gtctgtccct agcagtcttt cttcagctca cttggctctc tagatccact gtggttggca   2160
gtatgaccag aatcatggaa tttgctagaa ctgtggaagc ttctactcct gcagtaagca   2220
cagatcgcac tgcctcaata acttggtatt gagcacgtat tttgcaaaag ctacttttcc   2280
tagttttcag tattactttc atgttttaaa aatcccttta atttcttgct tgaaaatccc   2340
atgaacatta aagagccaga aatattttcc tttgttgtgt acggatatat atatatatag   2400
tcttccaaga tagaagttta cttttcctc ttctggtttt ggaaaatttc cagataagac     2460
atgtcaccat taattctcaa cgactgctct attttgttgt acgtaatag ttatcacctt     2520
ctaaattact atgtaattta ttcacttatt atgtttattg tcttgtatcc tttctctgga   2580
gtgtaagcac aatgaagaca ggaattttgt atattttaa ccaatgcaac atactctcag    2640
cacctaaaat agtgccggga acatagtaag ggctcagtaa atacttgttg aataaactca   2700
```

```
gtctcctaca ttagcattct aa                                              2722
```

SEQ ID NO: 56         moltype = AA  length = 239
FEATURE              Location/Qualifiers
REGION               1..239
                     note = EGLN3 protein (isoform 2)(NP_071356.1)
source               1..239
                     mol_type = protein
                     organism = synthetic construct
SEQUENCE: 56
```
MPLGHIMRLD LEKIALEYIV PCLHEVGFCY LDNFLGEVVG DCVLERVKQL HCTGALRDGQ   60
LAGPRAGVSK RHLRGDQITW IGGNEEGCEA ISFLLSLIDR LVLYCGSRLG KYYVKERSKA  120
MVACYPGNGT GYVRHVDNPN GDGRCITCIY YLNKNWDAKL HGGILRIFPE GKSFIADVEP  180
IFDRLLFFWS DRRNPHEVQP SYATRYAMTV WYFDAEERAE AKKKFRNLTR KTESALTED   239
```

SEQ ID NO: 57         moltype = DNA  length = 3952
FEATURE              Location/Qualifiers
misc_feature       1..3952
                     note = SLC6A3 mRNA (NM_001044.4)
source               1..3952
                     mol_type = other DNA
                     organism = synthetic construct
SEQUENCE: 57
```
cgctgcggag cgggagggga ggcttcgcgg aacgctctcg gcgccaggac tcgcgtgcaa     60
agcccaggcc cgggcggcca gaccaagagg gaagaagcac agaattcctc aactcccagt    120
gtgccatga gtaagagcaa atgctccatg ggactcatgt cttccgtggt ggccccggct    180
aaggagccca atgccgtggg cccgaaggag gtggagctca tccttgtcaa ggagcagaac    240
ggagtgcagc tcaccagctc cacctcacc aacccgcggc agagcccgt ggaggcccag    300
gatcgggaga cctgggcaa aagatcgac tttctcctgt ccgtcattgg ctttgctgtg    360
gacctggcca agtctggcg gttcccctac ctgtgctaca aaaatggtgg cggtgcctc    420
ctggtcccct acctgctctt catggtcatt gctgggatgc cacttttcta catggagctg    480
gccctcggcc agttcaacag ggaaggggcc gctggtgtct ggaagatctg ccccatactg    540
aaaggtgtgg gcttcacggt catcctcatc tcactgtatg tcggcttctt ctacaacgtc    600
atcatcgcct gggcgctgca ctatctcttc cctccttca ccacgagct ccctggatc    660
cactgcaaca actcctggaa cagccccaac tgctcggatg cccatcctgg tgactccagt    720
ggagacagct cgggcctcaa cgacactttt gggaccacac ctgctgccga gtactttgaa    780
cgtggcgtgc tgcacctcca ccagagccat ggcatcgacg acctgggcc tccgcgtgtg    840
cagctcacag cctgcctggt gctggtcatc gtgctgctct acttcagcct ctggaagggc    900
gtgaagacct cagggaaggt ggtatggatc acagccacca tgccatacgt ggtcctcact    960
gccctgctcc tgcgtgggt caccctccct ggagcctatg acggcatcag agcatacctg   1020
agcgttgact tctaccggct ctgcgaggcg tctgtttgga ttgacgcggc cacccaggtg   1080
tgcttctccc tgggcgtggg gttcggggtg ctgatcgcct ctccagcta caacaagttc    1140
accaacaact gctacagga cgccgattgc caccctccct acgagctc                1200
tcctccggct tcgtcgtctt ctccttcctg gggtacatgg cacagaagca cagtgtgccc    1260
atcgggacg tggccaagga cgggccaggg ctgatcttca tcatctaccc ggaagccatc    1320
gccacgctcc ctctgtcctc agcctgggcc gtggtcttct tcatcatgct gctcacctg    1380
ggtatcgaca gcgccatggg tggtatggaa tcagtgataa ccgggctcat cgatgagttc    1440
cagctgctgc acagacaccg tgagctcttc acgctcttca tcgtcctggc gaccttcctc    1500
ctgtccctgt tctgcgtcac caacggtggc atctacgtct tcacgctcct ggaccatttt    1560
gcagccggca cgtccatcct ctttggagtg ctcatcgaag ccatcggagt ggcctggttc    1620
tatggtgttg ggcagttcag cgacgacatc cagcagatga ccgggcagcg gcccagcctg    1680
tactggcggc tgtgctggaa gctggtcagc cctgctttc tctgttcgt ggtcgtggtc    1740
agcattgtga ccttcagacc cccccactac ggagcctaca tcttccccga ctgggccaac    1800
gcgctgggct ggtcatcgc cacatcctcc atggccatgg tgcccatcta tgcggcctac    1860
aagttctgca gcctgcctgg gtcctttcga gagaaactgg cctacgccat tgcacccgag    1920
aaggaccgtg agctggtgga cagagggag gtgcgccagt tcacgctccg ccactggctc    1980
aaggtgtaga gggagcagag acgaagaccc aggaagtca tcctgcaatg ggagagacac    2040
gaacaaacca aggaaatcta agtttcgaga gaaaggaggg caacttctac tcttcaacct    2100
ctactgaaaa cacaaacaac aaagcagaag actcctctct tctgactgtt tacaccttc    2160
cgtgccggga gcgcacctcg ccgtgtcttg tgttgctgta ataacgacgt agatctgtgc    2220
agcgaggtcc accccgttgt tgtccctgca gggcagaaaa acgtctaact tcatgctgtc    2280
tgtgtgaggc tccctccctc cctgctccct gctcccggct ctgaggctgc ccaggggca    2340
ctgtgttctc aggcggggat cacgatcctt gtagacgcac tgctgagaa tccccgtgct    2400
cacagtagct tcctagacca tttacttttgc ccatattaaa aagccaagtg tcctgcttgg    2460
tttagctgtg cagaaggtga aatgaggaa accacaaatt catgcaaagt cctttccga    2520
tgcgtggctc ccagcagagg ccgtaaattg agcgttcagt tgacacattg cacacacagt    2580
ctgttcagag gcattggagg atgggggtcc tggtatgtct caccaggaaa ttctgtttat    2640
gttcttgcag cagagagaaa taaaactcct tgaaaccagc tcaggctact gccactcagg    2700
cagcctgtgg gtccttgcgg tgtagggaac ggcctgagag cgcgtgtcc tatcccgagg    2760
cgcatgcagg gccccacag gagcgtgtcc tatccctgga cgcatgcagg gccccacag    2820
gagcatgtcc tatccctgga cgcatgcagg gccccacag gagcgtgtac tacccagaa    2880
cgcatgcagg gccccacag gagcgtgtac taccccagga cgcatgcagg gccccactg    2940
gagcgtgtac taccccagga cgcatgcagg gccccacag gagcgtgtcc tatccccgga    3000
ccggacgcat gcagggcccc acaggagcg tgtactaccc caggatgcat gcagggccccc   3060
cacaggagcg tgtactaccc caggatgcat gcagggcccc cacaggagcg tgtactaccc   3120
caggacgcat gcagggcccc catgcaggca gcctgcagac cacactctgc ctggccttga   3180
gccgtgacct ccaggaaggg accccactgg aatttattt ctctcaggtg cgtgccacat    3240
caataacaac agttttatg tttgcgaatg cttttaaa atcatattta cctgtgaatc    3300
aaaacaaatt caagaatgca gtatccgcga ggcctgcttgc tgatattgca gttttgtttt    3360
```

```
acaagaataa ttagcaatac tgagtgaagg atgttggcca aaagctgctt tccatggcac    3420
actgccctct gccactgaca ggaaagtgga tgccatagtt tgaattcatg cctcaagtcg    3480
gtgggcctgc ctacgtgctg cccgagggca ggggccgtgc agggccagtc atggctgtcc    3540
cctgcaagtg gacgtgggct ccagggactg gagtgtaatg ctcggtggga gccgtcagcc    3600
tgtgaactgc caggcagctg cagttagcac agaggatggc ttccccattg ccttctgggg    3660
agggacacag aggacggctt ccccatcgcc ttctggccgc tgcagtcagc acagagagcg    3720
gcttccccat tgccttctgg ggagggacac agaggacagc ttccccatcg ccttctggct    3780
gctgcagtca gcacagagag cggcttcccc atcgccttct ggggaggggc tccgtgtagc    3840
aacccaggtg ttgtccgtgt ctgttgacca atctctattc agcatcgtgt gggtcccaa    3900
gcacaataaa agacatccac aatggaaaaa ctgcaaaaaa aaaaaaaaaa aa           3952

SEQ ID NO: 58           moltype = AA  length = 620
FEATURE                 Location/Qualifiers
REGION                  1..620
                        note = SLC6A3 protein (NP_001035.1)
source                  1..620
                        mol_type = protein
                        organism = synthetic construct
SEQUENCE: 58
MSKSKCSVGL MSSVVAPAKE PNAVGPKEVE LILVKEQNGV QLTSSTLTNP RQSPVEAQDR    60
ETWGKKIDFL LSVIGFAVDL ANVWRFPYLC YKNGGGAFLV PYLLFMVIAG MPLFYMELAL   120
GQFNREGAAG VWKICPILKG VGFTVILISL YVGFFYNVII AWALHYLFSS FTTELPWIHC   180
NNSWNSPNCS DAHPGDSSGD SSGLNDTFGT TPAAEYFERG VLHLHQSHGI DDLGPPRWQL   240
TACLVLVIVL LYFSLWKGVK TSGKVVWITA TMPYVVLTAL LLRGVTLPGA IDGIRAYLSV   300
DFYRLCEASV WIDAATQVCF SLGVGFGVLI AFSSYNKFTN NCYRDAIVTT SINSLTSFSS   360
GFVVFSPLGY MAQKHSVPIG DVAKDGPGLI FIIYPEAIAT LPLSSAWAVV FFIMLLTLGI   420
DSAMGGMESV ITGLIDEFQL LHRHRELFTL FIVLATFLLS LFCVTNGGIY VFTLLDHFAA   480
GTSILFGVLI EAIGVAWFYG VGQFSDDIQQ MTGQRPSLYW RLCWKLVSPC FLLFVVVSI    540
VTFRPPHYGA YIFPDWANAL GWVIATSSMA MVPIYAAYKF CSLPGSFREK LAYAIAPEKD   600
RELVDRGEVR QFTLRHWLKV                                               620

SEQ ID NO: 59           moltype = DNA  length = 12
FEATURE                 Location/Qualifiers
misc_feature            1..12
                        note = Reference sequence for VHL mutation in Sample ID
                          17621953
source                  1..12
                        mol_type = other DNA
                        organism = synthetic construct
SEQUENCE: 59
gtatggctca ac                                                        12
```

CLEAR CELL RENAL CELL CARCINOMA BIOMARKERS

CROSS-REFERENCE TO RELATED APPLICATIONS

This application is a divisional application of application Ser. No. 16/642,430 filed on Feb. 27, 2020, which claims the benefit of priority of Singapore application No. 10201707218R, filed 5 Sep. 2017, the contents of it being hereby incorporated by reference in its entirety for all purposes.

FIELD OF INVENTION

The present invention relates to molecular biology in particular biomarkers. In particular, the present invention relates to biomarkers associated with clear cell renal cell carcinoma (ccRCC) and methods and uses thereof.

BACKGROUND OF THE INVENTION

Renal cell carcinoma (RCC) is one of the most deadly cancers due to frequent late diagnosis and poor treatment options. Success in curing the disease relies on early detection of RCC and complete resection of the malignant cells. Since the kidney lies deeply in the retroperitoneal space, renal cell carcinoma is primarily asymptomatic in the early phase and upon diagnosis the tumour is large and/or metastasized. The three most common subtypes of renal cell carcinoma are clear cell renal cell carcinoma, papillary renal cell carcinoma and chromophobe renal cell carcinoma. Clear cell renal cell carcinoma is the most common subtype, accounting for 75-90% of all renal cell carcinomas and with 338,000 new cases in 2012 worldwide.

With most clear cell renal cell carcinomas being resistant to chemotherapy and radiotherapy, patients with metastatic clear cell renal cell carcinomas exhibit a dismal 8% five-year overall survival. Even early stage tumours remain at risk of metastatic progression after surgery, with 20-40% of patients having recurrence. Therefore, identification of this high-risk group of renal cell carcinoma patients remains a challenge. Furthermore, different subtypes of renal cell carcinoma have variable prognoses and treatment response rates. Therefore, it is crucial to be able to differentiate between different subtypes of renal cell carcinoma.

Previous methods for diagnosing patients with clear cell renal cell carcinoma involve invasive methods, including tumour biopsy, or imaging methods including ultrasound imaging or magnetic resonance imaging. However, based on known methods, it is difficult to determine whether a renal mass of less than 4 cm is a tumour, and/or whether the tumour is benign or malignant based on imaging studies alone. Around 50% to 60% of renal masses are less than 4 cm, of which 25% to 30% are benign tumours. The risk of overtreatment for small renal masses ranges from 40% for lesions less than 1 cm to 17% for masses 3 to 4 cm in diameter. In addition to initial diagnosis, the main tools for post-treatment follow up or active surveillance also include only imaging studies. Surgery or ablation would result in tissue change and scar formation, causing the detection of local recurrence to be challenging. Lastly, there is also a lack of methods to assess the efficiency of systemic treatments in advanced clear cell renal cell carcinoma patients. In view of the above, there is an unmet need for a method of identifying clear cell renal cell carcinoma, differentiation of benign lesions from malignant tumours, for detection of recurrence after local treatments, and for assessment of systemic treatments.

SUMMARY OF INVENTION

In one aspect, the present invention refers to a clear cell renal cell carcinoma (ccRCC) biomarker set, wherein the biomarker set comprises at least two biomarkers selected from the group consisting of ZNF395, SMPDL3A, SLC28A1, SLC6A3, VEGFA, EGLN3, wherein one of the at least two biomarkers is SMPDL3A or SLC28A1; wherein the biomarkers are proteins, or nucleic acids encoding the same, or variants thereof.

In another aspect, the present invention refers to a detection system comprising a) a receiving section to receive a sample from a subject suspected to suffer from clear cell renal cell carcinoma, and wherein the sample is suspected to comprise the biomarker set as disclosed herein; and b) a detection section comprising a substance or substances capable of detecting the biomarker set as disclosed herein.

In one aspect, the present invention refers to a method of determining whether a subject has or shows recurrence of clear cell renal cell carcinoma, wherein the method comprises obtaining a sample from the subject; detecting the presence of the biomarker set as disclosed herein in the sample using a detection system as disclosed herein, wherein the presence of the biomarker set determines that the subject has or shows recurrence of clear cell renal cell carcinoma.

In a further aspect, the present invention refers to a method of detecting response of a subject to systemic treatment, the method comprising a) obtaining a sample from the subject; and b) determining the levels of the biomarker set as defined herein in the sample; wherein a decrease in levels or an absence of the biomarker set indicates that the subject is responsive to treatment.

In yet another aspect, the present invention refers to a method of determining whether a renal mass sample is benign or malignant, the method comprising obtaining a sample from the renal mass of a subject; determining the levels or the presence or absence of the biomarker set as disclosed herein in the sample; wherein the increase in levels of the biomarker set compared to a benign sample indicates that the sample is malignant.

In another aspect, the present invention refers to a kit for carrying out the method as disclosed herein, wherein the kit comprises a detection buffer, a lysis buffer, and a substance or substances as defined herein suitable for the detection of the biomarker set as disclosed herein.

In a further aspect, the present invention refers to a kit as disclosed herein and a detection system as disclosed herein for detecting the biomarker set as defined herein.

BRIEF DESCRIPTION OF THE DRAWINGS

The invention will be better understood with reference to the detailed description when considered in conjunction with the non-limiting examples and the accompanying drawings, in which:

FIG. 1 illustrates that von Hippel-Lindau (VHL) deficient clear cell renal cell carcinoma tumours exhibit an aberrant cis-regulatory landscape.

FIG. 2 shows that enhancer aberration is a signature of clear cell renal cell carcinoma.

FIG. 3 illustrates the identification of key oncogenic drivers by tumour super-enhancers. FIG. 3L shows expression of SMPDL3A in a panel of cancers, with the highest expression being present in clear cell renal cell carcinoma (KIRC) (TCGA symbol for clear cell renal cell carcinoma) FIG. 3M shows expression of SLC28A1 in a panel of cancers, with the highest expression being present in clear cell renal cell carcinoma (KIRC). FIG. 3N shows expression of SLC6A3 in a panel of cancers, with the highest expression being present in clear cell renal cell carcinoma (KIRC). FIG. 3O shows expression of VEGFA in a panel of cancers, with the highest expression being present in clear cell renal cell carcinoma. FIG. 3P shows expression of EGLN3 in a panel of cancers, with the highest expression being present in clear cell renal cell carcinoma (KIRC).

FIG. 4 illustrates that VHL deficiency remodels clear cell renal cell carcinoma enhancers. FIG. 4J refers to a box plot that shows changes in expression of genes linked to VHL-responsive tumour enhancers after VHL restoration in 786-O cells. *p-value <0.05, two-sided t-test. FIG. 4K shows a box plot with changes of gene expression linked to VHL-responsive tumour enhancers in 12364284 cells. *p-value value <0.05, two-sided t-test.

FIG. 5 illustrates that HIF2α is enriched at enhancers of VHL-responsive tumour tumours. FIG. 5C shows scatter plots with gene expression of selected transcription factors in 73 pairs of normal kidney and clear cell renal cell carcinoma tumours of the The Cancer Genome Atlas (TCGA) cohort (RNA-Seq dataset). *p-value <0.001, p-value <0.01, n.s. (not significant), paired t-test.

FIG. 6 illustrates that HIF2α-HIF1β bound enhancers modulate gene expression.

FIG. 7 shows that VHL restoration reduces p300 recruitment but preserves promoter-enhancer interactions.

DETAILED DESCRIPTION OF THE PRESENT INVENTION

Figure 1A:
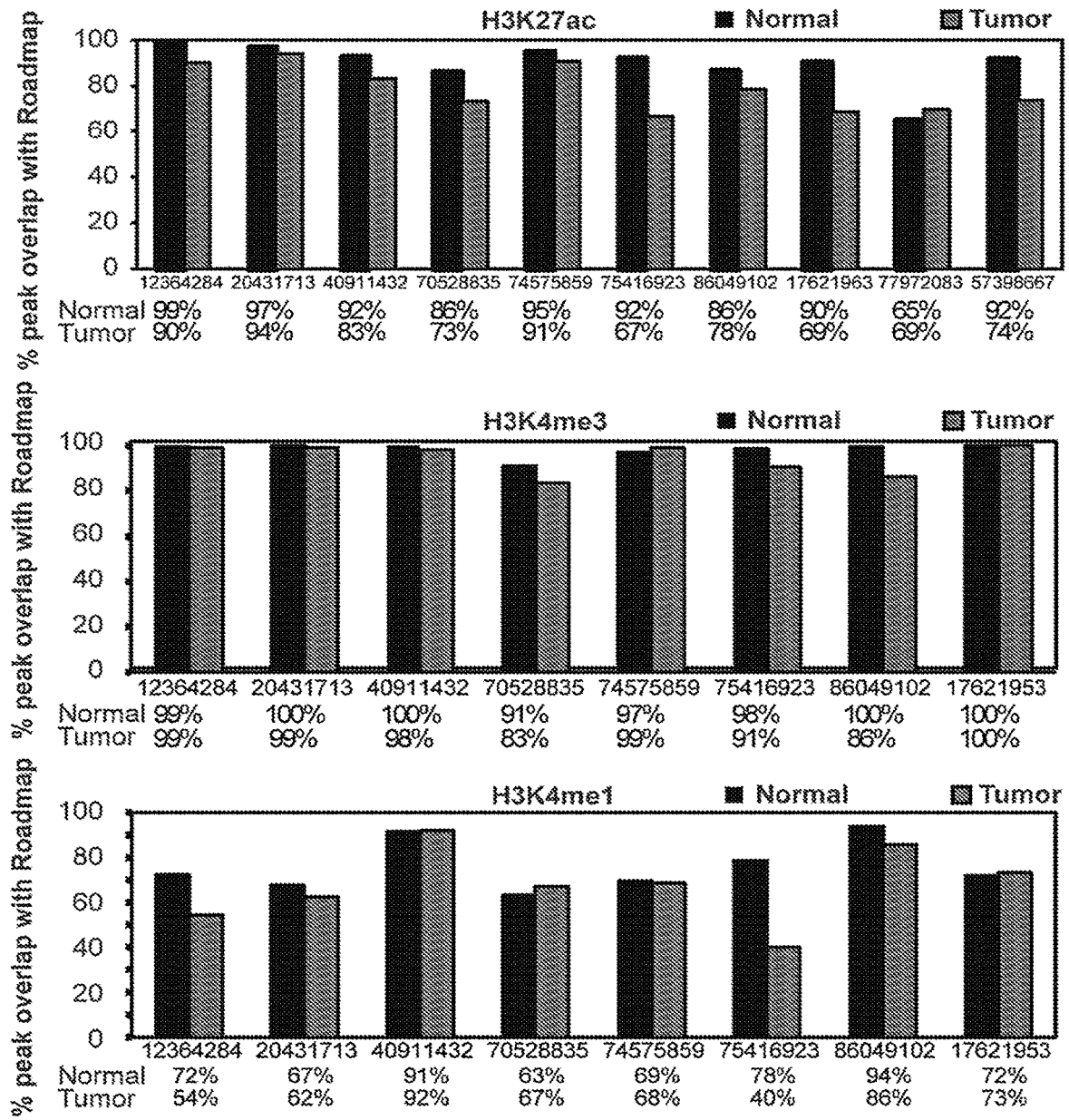
FIG. 1A shows a graph that illustrates the percentage of overlap of the histone chromatin immunoprecipitation sequencing (ChIP-seq) (H3K27ac, H3K4me3 and H3K4me1) peaks of normal kidney tissues with peaks from adult kidney tissues in the Epigenomics Roadmap dataset.

Renal cell carcinoma (RCC) is the most common type of kidney cancer in adults, with clear cell renal cell carcinoma (ccRCC) being one of the common subtypes of renal cell carcinoma. Other subtypes of renal cell carcinoma include, for example, papillary renal cell carcinoma (pRCC) and chromophobe renal cell carcinoma (crRCC). One particular challenge in the treatment of kidney tumours is the range of histologies and tumour phenotypes that a renal mass can represent. A kidney tumour range from benign to clinically indolent malignancy to aggressive disease. Examples of aggressive disease include, but are not limited to, clear cell renal cell carcinoma (ccRCC). Kidney cancers of various subtypes have diverse treatment response rates and variable prognoses. Therefore, the key to proper treatment is accurate diagnosis of the different subtypes of renal cell carcinomas.

Current methods of diagnosis include, but are not limited to, invasive methods involving histologies from tumour biopsies, such as, staining of glycogens by special stains, contrast-enhanced computed tomography (CT) scan (which demonstrates high vascularity of the tumours), ultrasound imaging or magnetic resonance imaging (MRI). However, invasive procedures causes patient discomfort, require local or general anaesthesia and can be, relatively expensive. Histologies from biopsies and imaging methods including CT scan, MRI and ultrasound imaging, are also unable to detect tumour stages accurately, resulting in frequent misdiagnosis. Another option to identify clear cell renal cell carcinoma patients is through detection of biomarkers. However, there is currently no clinically validated biomarker for diagnosis of clear cell renal cell carcinoma.

In view of the above problems, the inventors of the present disclosure have provided biomarker(s) for identifying clear cell renal cell carcinoma. Accordingly, in one example, there is disclosed one or more clear cell renal cell carcinoma biomarkers.

As used herein, the term "clear cell renal cell carcinoma" or "ccRCC" refers to the most common subtype of a kidney cancer, namely renal cell carcinoma (RCC). Kidney cancer refers to cancer that forms in tissues of the kidney, which is the organ that filters waste products from the blood. Kidney is also involved in regulating blood pressure, electrolyte balance and red blood cell production in the body. Each kidney is attached to a ureter, a tube that carries excreted urine to the bladder. Renal cell carcinoma is a kidney cancer that originates in the lining of the proximal convoluted tubule, a part of the very small tubes in the kidney that transport primary urine. Renal cell carcinoma is classified as an adenocarcinoma. The symptoms and implications accompanying renal cell carcinoma are well known in the art, for example hematuria (blood in the urine), low back pain or pain in the flank and/or noticeable lump in the flank. Clear cell renal cell carcinoma, which is the most common subtype of renal cell carcinoma, accounts for 75% to 85% of all renal cell carcinoma, and is also the most aggressive type of renal cell carcinoma. Clear cell renal cell carcinoma is associated with genetic lesions in chromosome 3p, encompassing the von Hippel-Lindau gene. On gross examination, clear cell renal cell carcinomas are typically golden yellow and often develop hemorrhage and infarction with formation of cysts within the tumour. Clear cell renal cell carcinoma is typically characterized by malignant epithelial cells with clear cytoplasm and a compact alveolar or acinar growth pattern interspersed with intricate, arborizing vasculature.

As used herein, the term "tumour" refers to a group of abnormal cells that form lumps or growth. A tumour can be cancerous (malignant), non-cancerous (benign) or pre-cancerous. Benign tumour usually consists of angiomyolipoma and oncocytoma. Angiomyolipoma is easy to differentiate based on imaging, while being difficult to differentiate oncocytoma with imaging studies.

As used herein, the term "carcinoma" refers to a type of cancer that starts in cells that make up the skin (also known as epithelial cells) of the tissue lining organs, for example, but not limited to, the liver or kidneys. Common types of carcinoma include, but are not limited to, basal cell carcinoma, squamous cell carcinoma and renal cell carcinoma. In one example, clear cell renal cell carcinoma refers to malignant tumours, while oncocytoma is or represents benign tumours. In another example, benign oncytomas are low in SLC28A1, VEGFA, ZNF395, EGLN3 and SLC6A3.

When confronted with a renal mass, it is difficult to differentiate between malignant or benign tumour. Benign tumours usually consist of angiomyolipoma and oncocytoma. Differentiation of angiomyolipoma can be performed with imaging studies, as performed in the art. However, it is difficult to differentiate oncocytoma based on imaging studies alone. Thus, in one example, there is disclosed a method for determining whether a renal mass sample is benign or malignant. In another example, the method method of determining whether a renal mass sample is benign or malignant, the method comprising obtaining a sample from the renal mass of a subject;

determining the levels or the presence or absence of the biomarker set as disclosed herein in the sample. In another example, the increase in levels of the biomarker set in such a renal mass sample, compared to a benign sample, indicates that the sample is malignant. In yet another example, the method of determining whether a renal mass sample is benign or malignant comprises obtaining a sample from the renal mass of a subject; determining the levels or the presence or absence of the biomarker set as disclosed herein in the sample; wherein the increase in levels of the biomarker set compared to a benign sample indicates that the sample is malignant.

As used herein, the term "biomarker" refers to molecular indicators of a specific biological property, a biochemical feature or facet that can be used to determine the presence or absence and/or severity of a particular disease or condition. In the present disclosure, the term "biomarker" refers to a polypeptide or a nucleic acid sequence encoding the polypeptide, a fragment or variant of a polypeptide being associated with clear cell renal cell carcinoma. In addition to a polypeptide or a nucleic acid sequence encoding the polypeptide, a fragment or variant of such a polypeptide being associated with clear cell renal cell carcinoma peptides as disclosed herein, the biomarker also refers to metabolites or metabolized fragments of the expressed polypeptide. A person skilled in the art would understand that a metabolite of one of the biomarkers referred to herein can still retain the capability of being used as biomarker for the methods described herein. It is also noted that some of the biomarkers in the biomarker set can be present in their variant form or metabolized form while others are still intact. The term "variant" as used herein includes a reference to substantially similar sequences. Generally, nucleic acid sequence variants of the invention encode a polypeptide which retains qualitative biological activity in common with the polypeptide encoded by the "non-variant" nucleic acid sequence. Variants of said polypeptide include polypeptides that differ in their amino acid sequence due to the presence of conservative amino acid substitutions. For example, such variants have an amino acid sequence being at least 80%, at least 90%, at least 95%, at least 98%, or at least 99% identical over the entire sequence region to the amino acid sequences of the "non-variant" polypeptides. Variants can be allelic variants, splice variants or any other species-specific homologs, paralogs, or orthologs. In one example, the percentage of identity can be determined by known in the art algorithms. The sequence identity values recited above in percent (%) are to be determined, preferably, using programs known in the art, for example, BLASTp and the like.

Variants can be made using, for example, the methods of protein engineering and site-directed mutagenesis as is well known in the art.

Conservative amino acid substitution tables providing functionally similar amino acids are well known to one of ordinary skill in the art. The following six groups are examples of amino acids that are considered to be conservative substitutions for one another: i) Alanine (A), Serine (S), Threonine (T); ii) Aspartic acid (D), Glutamic acid (E); iii) Asparagine (N), Glutamine (Q); iv) Arginine (R), Lysine (K); v) Isoleucine (I), Leucine (L), Methionine (M), Valine (V); and vi) Phenylalanine (F), Tyrosine (Y), Tryptophan (W).

A non-conservative amino acid substitution can result from changes in: i) the structure of the amino acid backbone in the area of the substitution; ii) the charge or hydrophobicity of the amino acid; or iii) the bulk of an amino acid side chain. Substitutions generally expected to produce the greatest change in protein properties are those in which i) a hydrophilic residue is substituted for (or by) a hydrophobic residue ii) a proline is substituted for (or by) any other residue; iii) a residue having a bulky side chain, for example, phenylalanine, is substituted for (or by) one not having a side chain, for example, glycine; or iv) a residue having an electropositive side chain, for example, lysyl, arginyl, or histadyl, is substituted for (or by) an electronegative residue, for example, glutamyl or aspartyl.

As defined herein, the terms "peptide", "protein", "polypeptide", and "amino acid sequence" are used interchangeably herein to refer to polymers of amino acid residues of any length. The polymer can be linear or branched, it can comprise modified amino acids or amino acid analogues, and it can be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labelling or bioactive component. The term peptide encompasses two or more naturally occurring or synthetic amino acids linked by a covalent bond (for example, an amide bond). The amino acid residues are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but is not be limited to, modified sequences such as glycoproteins. The term polypeptide is specifically intended to cover naturally occurring proteins, as well as those that are recombinantly or synthetically produced.

In one example, the clear cell renal cell carcinoma protein biomarker set includes at least two selected from the group consisting of ZNF395, SMPDL3A, SLC28A1, SLC6A3, VEGFA, EGLN3, and variants thereof, wherein one of the at least two biomarkers is SMPDL3A or SLC28A1. In another example, the clear cell renal cell carcinoma (ccRCC) biomarker set comprises at least two biomarkers selected from the group consisting of ZNF395, SMPDL3A, SLC28A1, SLC6A3, VEGFA, and EGLN3. In another example, one of the at least two biomarkers is SMPDL3A or SLC28A1. In yet another example, the biomarkers are proteins, or nucleic acids encoding the same, or variants thereof.

Also disclosed herein is a composition comprising the biomarker set as disclosed herein.

As used herein, the term "ZNF395", also known as HDBP-2, HDRF-2, PBF or PRF-1, refers to both a gene and the expressed polypeptide thereof, both of which are associated with Huntington Disease. This gene is a hypoxia-inducible transcription factor that is controlled by $I_KB$ signalling and activates genes involved in innate immune response and cancer. It has been found to be overexpressed in various human cancers, particularly in response to hypoxia. ZNF395 has also been shown to play a role in papillomavirus gene transcription.

As used herein "SMPDL3A", also known as sphingomyelin phosphodiesterase acid like 3A, or ASML3a, refers to a gene and the expressed polypeptide thereof, both of which has in vitro nucleotide phosphodiesterase activity with nucleoside triphosphates, such as for example, ATP. This protein has no activity with nucleoside diphosphates, and no activity with nucleoside monophosphates. SMPDL3A has in vitro activity with CDP-choline and CDP-ethanolamine, with no spingomyelin phosphodiesterase activity. As mentioned in the experimental section below, SMPDL3A is a target of a master regulator of cholesterol metabolism.

As used herein, the term "SLC28A1", also known as concentrative nucleoside transporter 1 (CNT1), HCNT1 or solute carrier family 28 member 1, refers to a gene and the expressed polypeptide thereof, both of which is sodium dependent and pyrimidine selective. SLC28A1 exhibits transport characteristics of the nucleoside transport system cit or N2 subtype (N2/cit). SLC28A1 also transports the antiviral pyrimidine nucleoside 3'-azido-3'-deoxythymidine (AZT) and 2',3'-dideoxycytidine (ddC). SLC28A1 is involved in the uptake of nucleoside-derived drugs using antiviral and chemical therapies.

As used herein, the term "SLC6A3", also known as solute carrier family 6 member 3, DAT, dopamine transporter, sodium dependent dopamine transporter, or PKDYS, refers to a gene or the expressed polypeptide thereof, both of which encodes a dopamine transporter, which is a member of the sodium and chloride dependent neurotransmitter transporter family. SLC6A3 terminates the action of dopamine by its high affinity sodium-dependent re-uptake into presynaptic terminals. Variation of the number of repeats of this gene or the expressed polypeptide thereof is associated with idiopathic epilepsy, attention-deficit hyperactivity disorder, dependence on alcohol and cocaine, susceptibility to Parkinson disease and protection against nicotine dependence.

As used herein, the term "VEGFA", also known as vascular endothelial growth factor A, vascular permeability factor, VEGF, VPF or MVCD1, refers to a gene or the expressed polypeptide thereof that is a member of the PDGF/VEGF growth factor family. VEGFA encodes a heparin-binding protein. It is a growth factor that induces proliferation and migration of vascular endothelial cells and is essential for both physiological and pathological angiogenesis. Disruption of this gene in mice resulted in abnormal embryonic blood vessel formation. This gene is up-regulated in many known tumours and its expression is correlated with tumour stage and progression. Variants of this gene has been reported, including, but not limited to, allelic variants associated with microvascular complications of diabetes 1 (MVCD1) and atherosclerosis, alternatively spliced transcript variants encoding different isoforms, alternative translation initiation from upstream non-AUG (CUG) codons (resulting in additional isoforms), and C-terminally extended isoforms produced by use of an alternative in-frame translation termination codon via a stop codon readthrough mechanism (with this isoform being antiangiogenic).

As used herein, the term "EGLN3", also known as Egl-9 family hypoxia inducible factor 3, prolyl hydroxylase domain-containing protein 3, hypoxia-inducible factor prolyl hydrolase 3, HIF-prolyl hydroxylase 3, HIF-PH3, HPH-1, HPH-3, PHD3, HIFP4H3, Egl Nine-like protein 3 isoform, refers to a gene or the expressed polypeptide thereof associated with diseases including hypoxia and chronic mountain sickness. Related pathways of this protein include HIF-1 signaling pathway and HIF repressor pathways. EGLN3 functions as a cellular oxygen sensor that catalyzes the post-translational formation of 4-hydroxyproline in hypoxia-inducible factor (HIF) alpha proteins under normoxic conditions.

The clear cell renal cell carcinoma (ccRCC) biomarker set disclosed herein can be used in combination with two or more further biomarkers, wherein one of the at least two biomarkers is SMPDL3A or SLC28A1. Thus, in one example, the clear cell renal cell carcinoma protein biomarker set comprises any two, three, four, five or all six biomarkers. In another example, the biomarker set as disclosed herein comprises at least three biomarkers. In another example, the biomarker set as disclosed herein comprises at least four biomarkers. In another example, the biomarker set as disclosed herein comprises at least five biomarkers. In another example, the biomarker set as disclosed herein comprises at least six biomarkers.

In another example, the biomarker set or the biomarkers are, but are not limited to, ZNF395, SMPDL3A, SLC28A1, SLC6A3, VEGFA and EGLN3, and combinations thereof. In one example, the clear cell renal cell carcinoma biomarker set or biomarkers comprise or consist of SMPDL3A and SLC28A1. In another example, the clear cell renal cell carcinoma biomarker set or biomarkers comprise or consist of SMPDL3A and ZNF395. In yet another example, the clear cell renal cell carcinoma biomarker set or biomarkers comprise or consist of SMPDL3A and SLC6A3. In still another example, the clear cell renal cell carcinoma biomarker set or biomarkers comprise or consist of SMPDL3A and VEGFA. In yet another example, the clear cell renal cell carcinoma biomarker set or biomarkers comprise or consist of SMPDL3A and EGLN3. In one example, the clear cell renal cell carcinoma biomarker set or biomarkers comprise or consist of SLC28A1 and ZNF395. In yet another example, the clear cell renal cell carcinoma biomarker set or biomarkers comprise or consist of SLC28A1 and SLC6A3. In still another example, the clear cell renal cell carcinoma biomarker set or biomarkers comprise or consist of SLC28A1 and VEGFA. In yet another example, the clear cell renal cell carcinoma biomarker set or biomarkers comprise or consist of SLC28A1 and EGLN3. In one example, the clear cell renal cell carcinoma biomarker set or biomarkers comprise or consist of SMPL3A, SLC28A1 and ZNF395. In yet another example, the clear cell renal cell carcinoma biomarker set or biomarkers comprise or consist of SMPL3A, SLC28A1 and SLC6A3. In still another example, the clear cell renal cell carcinoma biomarker set or biomarkers comprise or consist of SMPL3A, SLC28A1 and VEGFA. In yet another example, the clear cell renal cell carcinoma biomarker set or biomarkers comprise or consist of SMPL3A, SLC28A1 and EGLN3. In one example, the clear cell renal cell carcinoma biomarker set or biomarkers comprise or consist of SMPDL3A, ZNF395 and SLC6A3. In another example, the clear cell renal cell carcinoma biomarker set or biomarkers comprise or consist of SMPDL3A, ZNF395 and VEGFA. In yet another example, the clear cell renal cell carcinoma biomarker set or biomarkers comprise or consist of SMPDL3A, ZNF395 and EGLN3. In still another example, the clear cell renal cell carcinoma biomarker set or biomarkers comprise or consist of SMPDL3A, SLC6A3 and VEGFA. In yet another example, the clear cell renal cell carcinoma biomarker set or biomarkers comprise or consist of SMPDL3A, SLC6A3 and EGLN3. In another example, the clear cell renal cell carcinoma biomarker set or biomarkers comprise or consist of SMPDL3A, VEGFA and EGLN3. In still another example, the clear cell renal cell carcinoma biomarker set or biomarkers comprise or consist of SLC28A1, ZNF395 and SLC6A3. In another example, the clear cell renal cell carcinoma biomarker set or biomarkers comprise or consist of SLC28A1, ZNF395 and VEGFA. In another example, the clear cell renal cell carcinoma biomarker set or biomarkers comprise or consist of SLC28A1, ZNF395 and EGLN3. In one example, the clear cell renal cell carcinoma biomarker set or biomarkers comprise or consist of SLC28A1, SLC6A3 and VEGFA. In another example, the clear cell renal cell carcinoma biomarker set or biomarkers comprise or consist of SLC28A1, SLC6A3 and EGLN3. In yet another example, the clear cell renal cell carcinoma biomarker set or biomarkers comprise or consist of SLC28A1, VEGFA and EGLN3. In one example, the clear cell renal cell carcinoma biomarker set or biomarkers comprise or consist of SMPDL3A, SLC28A1, ZNF395 and SLC6A3. In another example, the clear cell renal cell carcinoma biomarker set or biomarkers comprise or consist of SMPDL3A, SLC28A1, ZNF395 and VEGFA. In yet another example, the clear cell renal cell carcinoma biomarker set or biomarkers comprise or consist of SMPDL3A, SLC28A1, ZNF395 and EGLN3. In still another example, the clear cell renal cell carcinoma biomarker set or biomarkers comprise or consist of SMPDL3A, ZNF395, VEGFA and EGLN3. In yet another example, the clear cell renal cell carcinoma biomarker set or biomarkers comprise or consist of SMPDL3A, ZNF395, SLC6A3 and VEGFA. In another example, the clear cell renal cell carcinoma biomarker set or biomarkers comprise or consist of SMPDL3A, ZNF395, SLC6A3 and EGLN3. In yet another example, the clear cell renal cell carcinoma biomarker set or biomarkers comprise or consist of SMPDL3A, SLC6A3, VEGFA and EGLN3. In one example, the clear cell renal cell carcinoma biomarker set or biomarkers comprise or consist of SLC28A1, ZNF395, SLC6A3 and VEGFA. In yet another example, the clear cell renal cell carcinoma biomarker set or biomarkers comprise or consist of SLC28A1, ZNF395, SLC6A3 and EGLN3. In still another example, the clear cell renal cell carcinoma biomarker set or biomarkers comprise or consist of SLC28A1, ZNF395, VEGFA and EGLN3. In one example, the clear cell renal cell carcinoma biomarker set or biomarkers comprise or consist of SMPDL3A, SLC28A1, ZNF395, SLC6A3 and VEGFA. In another example, the clear cell renal cell carcinoma biomarker set or biomarkers comprise or consist of SMPDL3A, SLC28A1, ZNF395, SLC6A3 and EGLN3. In yet another example, the clear cell renal cell carcinoma biomarker set or biomarkers comprise or consist of SMPDL3A, SLC28A1, ZNF395, VEGFA and EGLN3. In still another example, the clear cell renal cell carcinoma biomarker set or biomarkers comprise or consist of SMPDL3A, ZNF395, SLC6A3, VEGFA and EGLN3. In a further example, the clear cell renal cell carcinoma biomarker set biomarkers comprise or consist of SLC28A1, SLC6A3, VEGFA and EGLN3. In yet another example, the clear cell renal cell carcinoma biomarker set or biomarkers comprise or consist of SLC28A1, ZNF395, SLC6A3, VEGFA and EGLN3. In one example, the clear cell renal cell carcinoma biomarker set or biomarkers comprise or consist of ZNF395, SMPDL3A, SLC28A1, SLC6A3, VEGFA and EGLN3.

The biomarkers of the present invention can be combined with one another, for example, as a biomarker set, thereby providing sensitive and specific determination of clear cell renal cell carcinoma subjects thought to suffer from clear cell renal cell carcinoma. The option of combining the biomarkers of the present disclosure provides a statistically reliable detection of clear cell renal cell carcinomas. In one example, the presence of the two or more biomarkers in a sample is indicative of the presence of clear cell renal cell carcinoma. In another example, the presence of the biomarker set as disclosed herein is indicative of the presence of clear cell renal cell carcinoma. In another example, the upregulation of the biomarker set in a sample is indicative of the presence of clear cell renal cell carcinoma. This can be seen from the data provided in FIG. 3D, where statistical relevance based on a p-value is provided for a list of markers.

As used herein, the term "upregulation" refers to an increased level of expression of a nucleic acid or a protein in a sample obtained from a disease subject, whereby the increase is compared to expression of the same nucleic acid or protein in a control sample. In one example, the subject is suffering from clear cell renal cell carcinoma. As disclosed herein, this upregulation can be depicted as, for example, but not limited to, high tumour-normal ratios, low p-values or high levels of mRNA expression. In one example, the expression levels of nucleic acids can be measured, for example, by polymerase chain reaction (PCR). In one example, the polymerase chain reaction (PCR) is reverse transcription polymerase chain reaction (RT-PCR), or real-time polymerase chain reaction (qPCR) or combinations thereof. It is noted that RT-PCR is used to qualitatively detect gene expression through the creation of complementary DNA (cDNA) transcripts from RNA, while qPCR is used to quantitatively measure the amplification of DNA using fluorescent dyes. qPCR is also referred to in the art as quantitative PCR, quantitative real-time PCR, and real-time quantitative PCR.

Figure 3A:
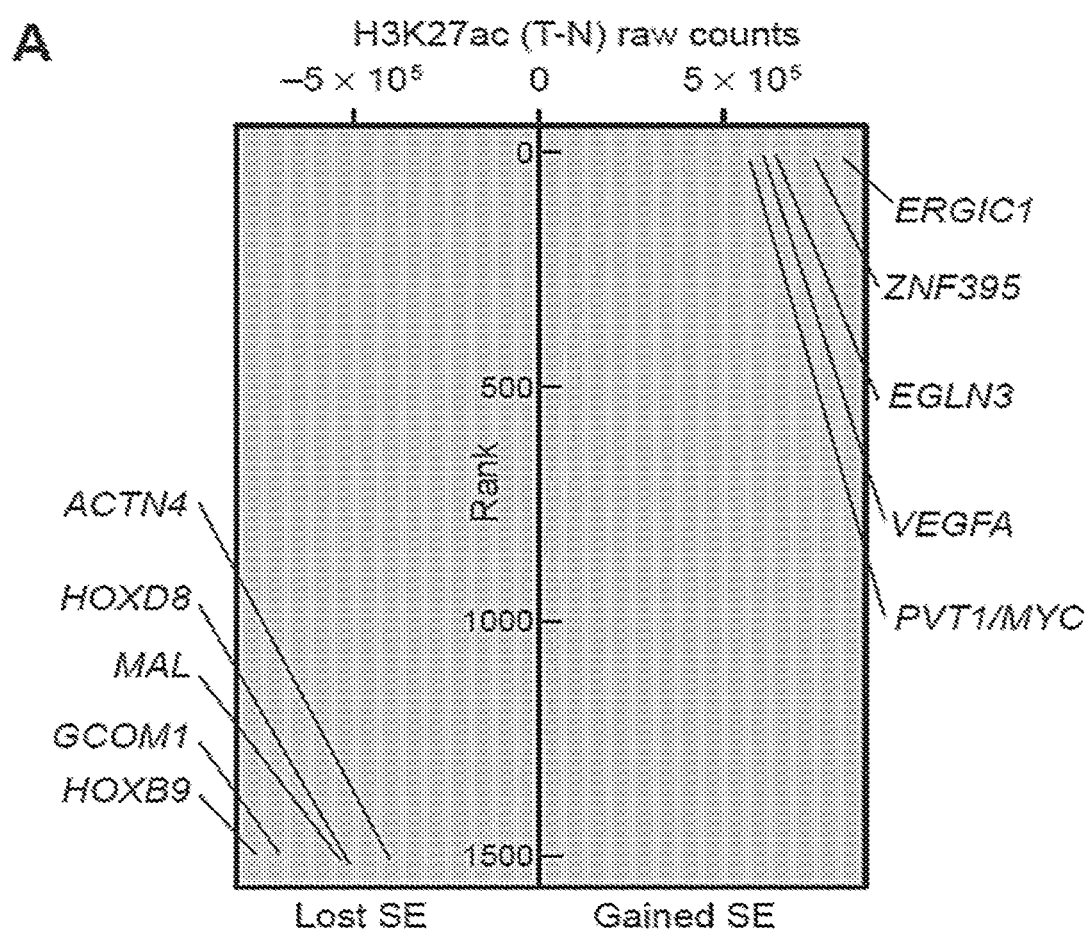
FIG. 3A shows a graph referring to a total of 1,451 super-enhancers that are identified by ROSE and ranked by their differential H3K27ac intensity between normal and tumour tissues. Genes associated with the top gained and lost super-enhancers are listed.
Figure 3B:
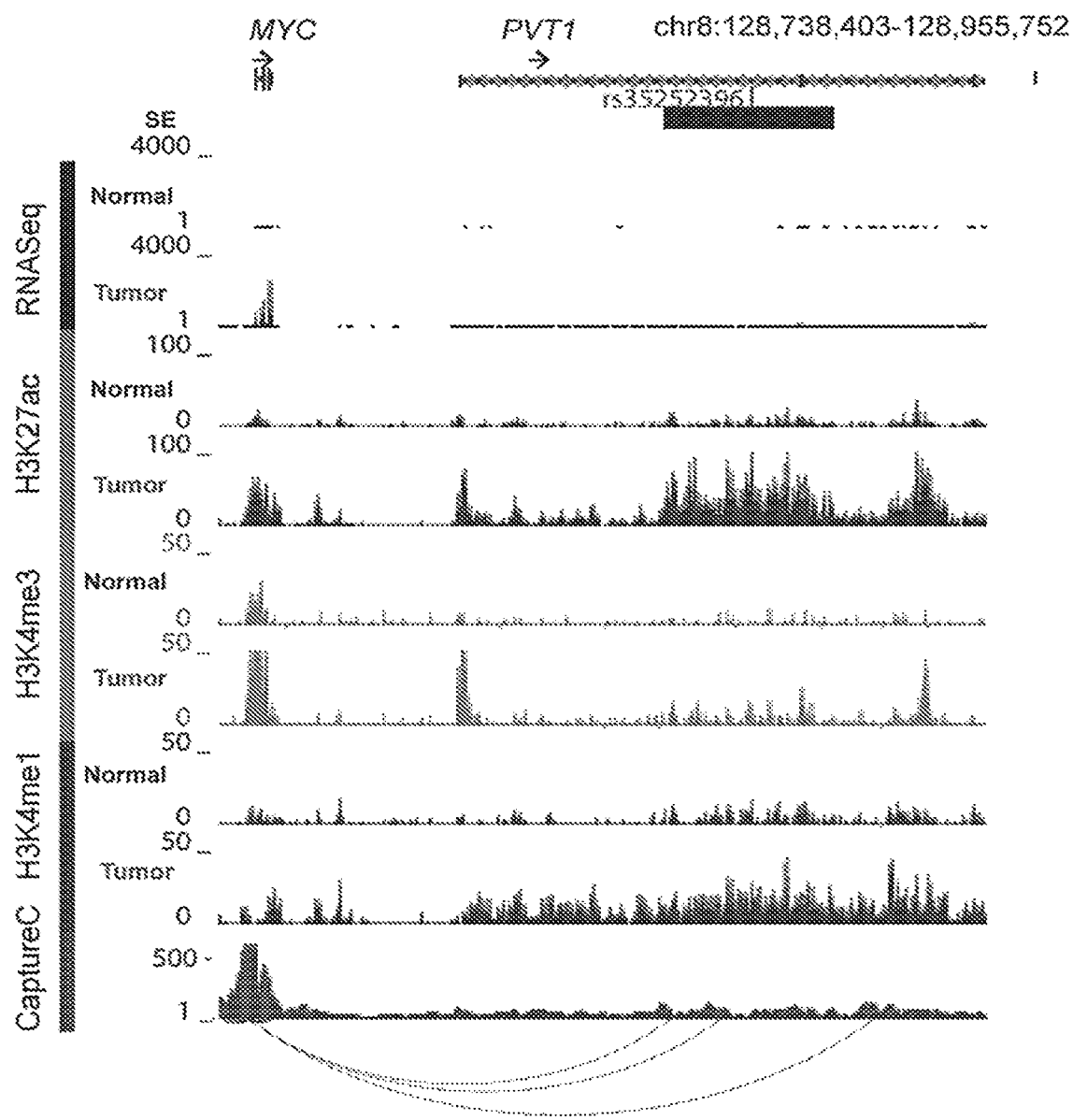
FIG. 3B shows a plot that refers to RNA sequencing (RNA seq), histone chromatin immunoprecipitation sequencing (ChIP-seq) and Capture C profiles of PVT1/MYC gene. Capture C shows chromosomal interactions between the c-Myc promoter and the super-enhancer.
Figure 3C:
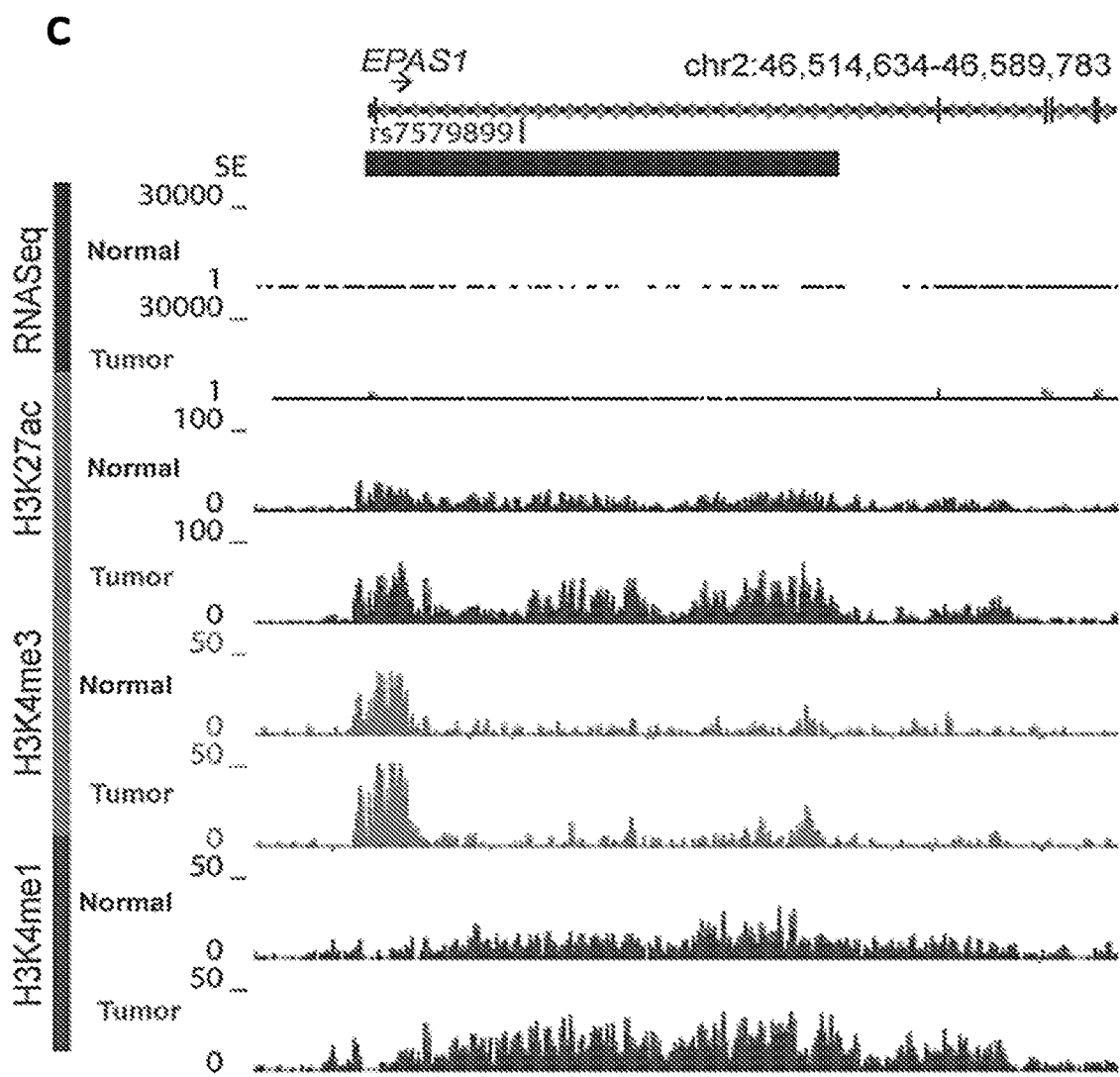
FIG. 3C shows a plot that refers to RNA seq and histone ChIP-seq of EPAS1 gene. Histone ChIP-Seq validated gained super-enhancers at PVT1/MYC (FIG. 3B) and EPAS1 (FIG. 3C) loci overlapping with a renal cell carcinoma risk allele respectively.
Figure 3D:
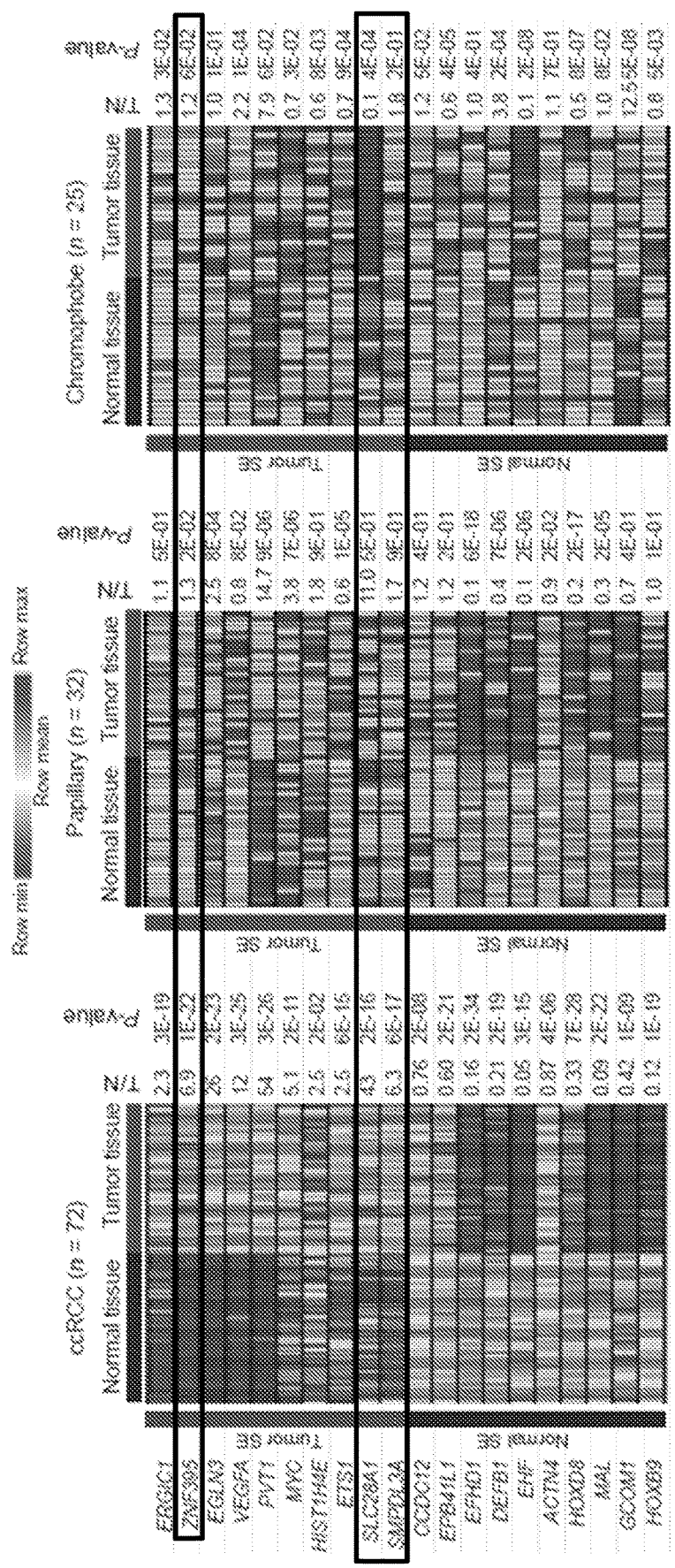
FIG. 3D shows a heatmap of The Cancer Genome Atlas (TCGA) RNA-seq data indicating that genes associated with top 10 gained enhancers are upregulated in tumours while genes associated with top 10 lost enhancers are downregulated. This tumour-specificity is restricted to clear cell renal cell carcinoma, but not the other two renal cell carcinoma subtypes, papillary and chromophobe. Without being bound by theory, it is thought that ZNF395, SLC28A1, SMPLD3A, VEGFA and EGLN3 are able to distinguish clear cell renal cell carcinoma from other major renal cell carcinoma subtypes, based on p-value and tumour/normal ratio (T/N) shown.
Figure 3E:
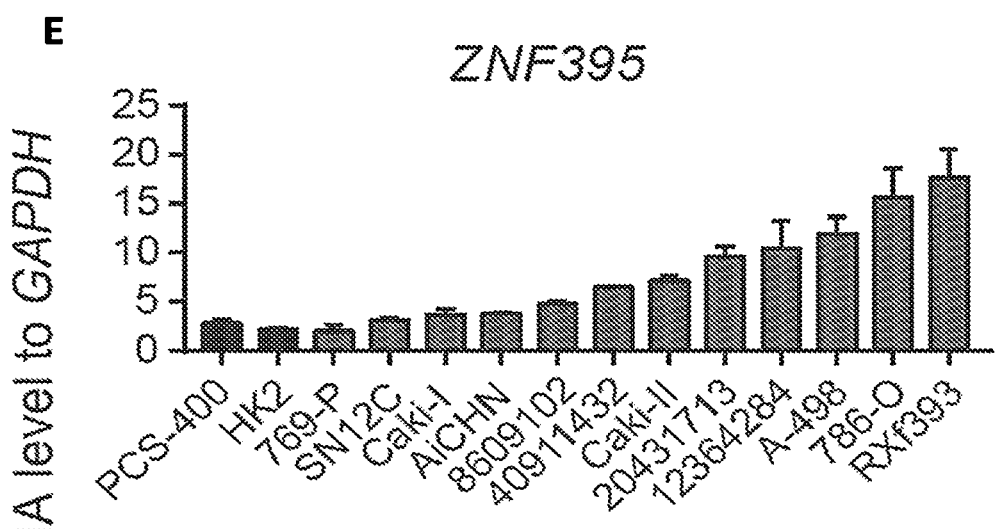
FIG. 3E refers to a graph with expression of ZNF395 and SMPLD3A measured in a panel of normal kidney cell lines and clear cell renal cell carcinoma cell lines by real time PCR (RT-qPCR).
Figure 3F:
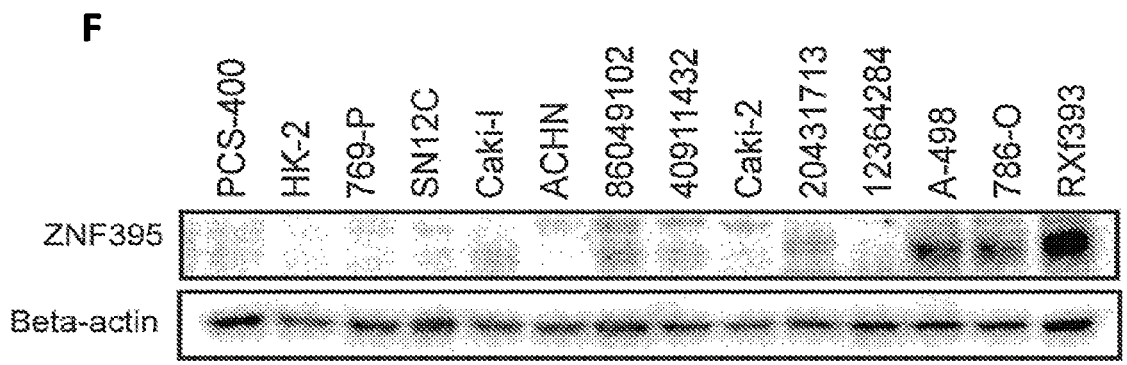
FIG. 3F shows an immunoblot comparing protein expression of ZNF395 in a panel of clear cell renal cell carcinoma cell lines.

As illustrated in the experimental section, the biomarkers of the present disclosure in particular ZNF395, SMPL3A and SLC28A1, have been shown to be specific to clear cell renal cell carcinoma, and were shown to not be overexpressed in papillary and chromophobe renal cell carcinomas, two other distinct renal cell carcinoma subtypes (FIG. 3D). ZNF395 exhibited tumour-normal ratio of about 7 in clear cell renal cell carcinoma with p-value of $1\times10^{-22}$, while showing little overexpression in papillary and chromophobe renal cell carcinomas with tumour-normal ratio of 1.2 (p=0.02) and 1.3 (p=0.06) respectively.

Furthermore, the experimental section, and for example, FIG. 3, also show that among the 12 types of cancer profiled by The Cancer Genome Atlas (TCGA), ZNF395, SMPL3A, SLC28A1, SLC6A3, VEGFA and EGFA were exclusively overexpressed in clear cell renal cell carcinoma tumours (KIRC). ZNF395 depletion in vivo further validates that ZNF395 plays an important role in clear cell renal cell carcinoma tumourigenesis. ZNF395 depletion significantly slowed in vivo tumour growth of 786-O clear cell renal cell carcinoma cells. In addition, SMPDL3A and SLC28A1 are shown to be associated with clear cell renal cell carcinoma-specific super-enhancer.

As described in the experimental section of the present disclosure, analysis of exosomes in culture medium of cell cultures can be performed, for example, by measuring levels of gene expression. This data can be found, for example, in FIG. 8. In one example, this can be done by qPCR, which was performed on clear cell renal cell carcinoma cell line (A498) and normal kidney cell lines (HK2). Results from exosome analysis in the present disclosure shows higher expression of ZNF395, SMPL3A, VEGFA and EGLN3 in clear cell renal cell carcinoma cell lines compared to normal kidney cell lines.

As used herein, the term "exosome" refers to a type of small extracellular vesicle (EV), ranging from 30 to 200 nm in diameter. These exosomes can be isolated from cell culture media, as well as an array of eukaryotic fluids. These fluids include, but are not limited to, blood, urine and sputum samples. Therefore, exosomes can be used to identify biomarkers from liquid samples using non-invasive methods. Exosomes are either released from the cell when multi-vesicular bodies fuse with the plasma membrane, or are released directly from the plasma membrane. These vesicles carry nucleic acid (for example, RNA and DNA) and proteins from, for example, the tumour in tumour-bearing subjects. Exosomes have been implicated in driving malignant cell behaviour including, but not limited to stimulation of tumour cell growth and suppression of a host immune response. Therefore, exosomes are a viable source for identifying biomarkers for cancer. Isolating exosomes from specific tissues also allows identification of tissue-specific or disease-specific biomarkers. Briefly, in one example, exosome analysis can be performed by ultracentrifugation from cells. After tryptic digestion, proteomic analysis can be performed, and candidate biomarkers are validated by, for example, methods known in the art, including but not limited to, western blotting and immunohistochemistry. In one example, the exosomes are detected using the detection system and/or the methods disclosed herein. In another example, the exosomes are detected and/or analysed using quantitative polymerase chain reaction (qPCR).

The terms "isolated" or "isolating" as used herein relates to a biological component (such as a nucleic acid molecule, protein or organelle) that has been substantially separated or purified away from other biological components in the cell of the organism in which the component naturally occurs, i.e., other chromosomal and extra-chromosomal DNA and RNA, proteins and organelles. Nucleic acids that have been "isolated" include nucleic acids purified by standard purification methods.

As illustrated in the experimental section of the present disclosure, the inventors of the present disclosure found that the biomarkers of the present disclosure can be detected in various sample types as described herein. The term "sample", as used herein, refers to single cells, multiple cells, fragments of cells, tissue, or body fluid, which has been obtained from, removed from, or isolated from a subject. An example of a sample includes, but is not limited to, blood, stool, serum, saliva, urine, sputum, cerebrospinal fluid, bone marrow fluid, frozen fresh tissue of a tumour sample, or frozen fresh tissue of a non-diseased tissue harvested from sites distant from the tumour. For example, the biomarkers were clearly detected in solid samples, which include, but are not limited to, solid tumour biopsy from suitable organs, such as the kidney. Fresh-frozen normal-tumour tissues were obtained from nephrectomy cases and normal tissues were harvested from sites distant from the tumour. Normal-tumour tissues as described herein or normal-tumour pair as described in the experimental section in other words means a tumour sample and a non-diseased sample that is obtained from the same subject. The sample can include, but is not limited to, tissue obtained from the lung, the muscle, brain, liver, skin, pancreas, stomach, bladder, and other organs. In another example, the sample includes, but is not limited to, fluid samples derived from or comprising bodily fluids, such as whole blood, serum, plasma, tears, saliva, nasal fluid, sputum, gastrointestinal fluid, exudate, transudate, fluid harvested from a site of an immune response, fluid harvested from a pooled collection site, bronchial lavage, a nucleated cell sample, a fluid associated with a mucosal surface, hair, or skin, and urine. In one example, the fluid sample is liquid tumour biopsy, urine sample, blood sample, sputum sample or cell culture medium. In another example, the fluid sample contains exosomes suspected to comprise the biomarkers or biomarker set as disclosed herein. In one example, the detection of the biomarkers in urine sample, blood sample or sputum sample is desirable as it allows for non-invasive detection of clear cell renal cell carcinoma in subjects.

In another example, there is provided a detection system for detecting the biomarker as disclosed herein. In one example, the detection system of the present disclosure comprises a receiving section to receive a sample from a patient suspected to suffer from clear cell renal cell carcinoma. In another example, the sample is suspected to comprise the two or more biomarkers of the present disclosure. In yet another example, the detection system comprises a substance or substances capable of detecting the two or more biomarkers of the present disclosure. In a further example, one of the at least two biomarkers is SMPDL3A or SLC28A1. In one example, the detection system of the present disclosure comprises a) a receiving section to receive a sample from a patient suspected to suffer from clear cell renal cell carcinoma, and wherein the sample is suspected to comprise the two or more biomarkers of the present disclosure, and b) a detection section comprising a substance or substances capable of detecting the two or more biomarkers, or the biomarker set, of the present disclosure, wherein one of the at least two biomarkers is SMPDL3A or SLC28A1.

In one example, the detection system comprises a receiving section to receive a sample from a patient suspected to suffer from clear cell renal cell carcinoma, and wherein the sample is suspected to comprise two, three, four, five or all six biomarkers, or a biomarker set, of the present disclosure. In one example, the receiving section can be a biochip, test strip, a real time polymerase chain reaction (qPCR) apparatus or microtiter plate. In one example, the sample can be fluid samples, as described herein.

In one example, the detection system or method of the present disclosure can require a fluid sample volume, such as, but not limited to, a sample volume of between about 1 µl to about 30 ml, 1 µl to 5 µl, 4 µl to 10 µl, 9 µl to 15 µl, 14 µl to 20 µl, 19 µl to 25 µl, 24 µl to 30 µl, 29 µl to 35 µl, 34 µl to 40 µl, 39 µl to 45 µl, 44 µl to 50 µl, 49 µl to 60 µl, 59 µl to 80 µl, 79 µl to 100 µl, 99 µl to 150 µl, 149 µl to 200 µl, 199 µl to 250 µl, 249 µl to 300 µl, 299 µl to 500 µl, 499 µl to 1 ml, 999 µl to 5 ml, 4.99 ml to 10 ml, 9.99 ml to 20 ml and 19.99 ml to 30 ml. In one example, the fluid or sample volume can be about 1 µl, about 5 µl, about 10 µl, about 15 µl, about 20 µl, about 25 µl, about 30 µl, about 35 µl, about 40 µl, about 45 µl, about 50 µl, about 100 µl, about 150 µl, about 200 µl, about 250 µl, about 300 µl, about 350 µl, about 400 µl, about 450 µl, about 500 µl, about 550 µl, about 600 µl, about 650 µl, about 700 µl, about 750 µl, about 800 µl, about 850 µl, about 900 µl, about 950 µl, about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml, about 20 ml, about 21 ml, about 22 ml, about 23 ml, about 24 ml, about 25 ml, about 26 ml, about 27 ml, about 28 ml, about 29 ml, to about 30 ml, or any values there between.

To assist in detecting the biomarkers of the present disclosure, the detection system of the present disclosure can comprise a substance capable of binding or specifically binding to two, three, four, five or all six biomarkers of the present disclosure. In one example, the substance is a biospecific capture reagent, such as, but not limited to, antibodies (or antigen-binding fragments thereof), interacting fusion proteins, aptamers or affibodies (which are non-immunoglobulin-derived affinity proteins based on a three-helical bundle protein domain), all of which can be chosen for their ability to recognize the biomarker and/or variants thereof. Antibodies can include, but are not limited to primary antibodies, secondary antibodies or horseradish peroxidase (HRP)-tagged secondary antibodies and the like. In one example, the substance includes antibodies known in the art to specifically recognise ZNF395, SMPDL3A, SLC28A1, SLC6A3, VEGFA or EGLN3.

In one example, the substance can be bound to a solid phase, wherein the biomarkers can then be detected by mass spectrometry, or by eluting the biomarkers from the biospecific capture reagents and detecting the eluted biomarkers by traditional matrix-assisted laser desorption/ionisation (MALDI) or by surface-enhanced laser desorption/ionization (SELDI). In another example, the detection system can be a biochip, test strip, qPCR apparatus, or microtiter plate.

In another example, the detection system comprising a receiving section and a detection section can be configured to detect one, two, three, four, five or all six biomarkers, or the biomarker set, as described herein, individually, or in combination with one another. The detection system, as disclosed herein, can also be configured to detect the one or more biomarkers simultaneously or in any given sequence (in other words, one at time).

In another example, there is disclosed a method of determining whether a subject has or shows recurrence of clear cell renal cell carcinoma (ccRCC). In one example, the method comprises obtaining a sample from a subject. In another example, the method comprises detecting the presence of the biomarker set of the present invention using a detection system of the present invention, wherein the presence of the biomarker set determines that a subject has or shows recurrence of clear cell renal cell carcinoma. In yet another example, the method comprises a) obtaining a sample from a subject; and b) detecting the presence of the biomarker set of the present invention using a detection system of the present invention, wherein the presence of the biomarker set determines that a subject has or shows recurrence of clear cell renal cell carcinoma.

In yet another example, the method comprises detecting the presence of the biomarker set of the present invention obtained from a sample from a subject, using a detection system of the present invention, wherein the presence of the biomarker set determines that a subject has or shows recurrence of clear cell renal cell carcinoma.

As used herein, the term "patient" or "subject" or "individual", which can be used interchangeably, relates to animals, for example mammals, including but not limited to, cows, horses, non-human primates, dogs, cats and humans. The subject or the patient of the present disclosure can be suspected of suffering from, or have previously suffered from, clear cell renal cell carcinoma. In one example, the method of the present invention can be applied to a subject suspected of suffering from clear cell renal cell carcinoma. In another example, the method of the present disclosure can be applied to a subject suspected of having a recurrence of clear cell renal cell carcinoma. The term "recurrence" as used herein refers to the return of or re-detection of clear cell renal cell carcinoma in a patient who has been deemed to be free of renal carcinomas or, specifically, free of clear cell renal carcinoma.

The biomarkers, or the biomarker set, disclosed herein can be detected in samples using methods known in the art. It is appreciated that the person skilled in the art would understand which assays known in the art would be suitable in detecting the biomarkers of the present disclosure. For example, detection of the biomarkers of the present disclosure relates to the observance of presence or absence of the biomarkers.

Detection can be done directly or indirectly. Direct detection relates to detection of the polypeptide based on a signal which is obtained from the polypeptide itself and the intensity of which directly correlates with the number of molecules of the polypeptide present in the sample. Such a signal—sometimes referred to as intensity signal, can be obtained, for example, by measuring an intensity value of a specific physical or chemical property of the polypeptide. Indirect measuring includes measuring of a signal obtained from a secondary component (i.e. a component not being the polypeptide itself) or a biological read out system, for example, measurable cellular responses, ligands, labels, or enzymatic reaction products. The concept outlined above can also be applied to genes, whereby the determination of the level of the gene can be determined by measuring gene expression, either global or targeted gene expression, using methods known in the art. For example, the detection can be carried out using molecular biological methods.

The molecular biological methods can include, but are not limited to, polymerase chain reaction (PCR), such as reverse transcription polymerase chain reaction (RT-PCR), or real-time polymerase chain reaction (qPCR, also known as quantitative PCR); Western Blot, Dot Blot; mass spectrometry; nucleic acid sequencing; immunological methods, such as enzyme-linked immunosorbent assay (ELISA) using antibodies; and the like. For example, in the experimental section of the present disclosure, Western Blot, real-time quantitative PCR (qPCR) and nucleic acid sequencing are used.

In one example, the detection system detects exosomes using quantitative polymerase chain reaction.

In one example, the indication as to whether the two or more biomarkers, or the biomarker set as disclosed herein, are present in a sample obtained from the patient or whether the subject has or shows recurrence of clear cell renal cell carcinoma can be made based on comparison of the two or more biomarkers, or the biomarker set as disclosed herein, with the same biomarkers in a control group. As use herein, a control group includes disease-free subjects and/or samples from non-diseased areas of the same or different subjects suffering from clear cell renal cell carcinoma. Control samples from the same or different subjects can also be known as matched or unmatched pairs, respectively. The control group can also be a non-cancerous sample obtained from a different subject with clear cell renal cell carcinoma; a subject that has a different renal cell carcinoma subtype; a subject with another type of cancer; or a sample obtained from non-cancerous kidney cell lines. A non-cancerous kidney cell line is, but is not limited to, HK-2 and PCS-400 cell lines. In one example, the clear cell renal cell carcinoma (ccRCC) sample and control sample are obtained from the same subject (normal-tumour pair or tumour-normal pair, as described herein). Therefore, the method also includes differentiation of clear cell renal cell carcinoma from other types of renal cell carcinoma or from another type of cancer.

In one example, there is disclosed a kit comprising a detection system as described herein, and substances needed to carry out the method as described herein. In one example, the kit comprises a detection buffer, a lysis buffer, and substance or substances as described herein.

In one example, the biomarkers, methods, detection system or kit of the present disclosure are used to identify clear cell renal cell carcinoma in patients. The biomarkers, methods, detection system or kit of the present disclosure can be used for detecting or predicting recurrence in clear cell renal cell carcinoma patients who may or may not be undergoing treatment or had received treatment for clear cell renal cell carcinoma.

In another example, there is disclosed a method of treating clear cell renal cell carcinoma in a subject, wherein the method comprises detecting the biomarker set as described herein, and treating the subject determined to suffer from clear cell renal cell carcinoma with an anti-clear cell renal cell carcinoma compound and/or treatment.

It will be appreciated that the biomarker set as disclosed herein can be used to detect whether a treatment being performed or which had been performed on a subject was successful or not. This is because there is a difference in biomarker expression level and/or presence or absence of the biomarker in diseased tissue when compared to non-diseased tissue. Thus, in one example, there is a method of detecting response of a subject to systemic treatment, the method comprising obtaining a sample from the subject; and determining the levels of the biomarker set as defined herein, wherein a decrease in levels or an absence of the biomarker set indicates that the subject is responsive to treatment.

Also disclosed herein is a method for detecting susceptibility of a subject to an anti-clear cell renal cell carcinoma treatment. This method comprises determining the response of a sample from a diseases subject when subjected to one or more anti-clear cell renal cell carcinoma treatments based on the expression and/or presence or absence of the biomarker set as disclosed herein. In one example, the anti-clear cell renal cell carcinoma treatment comprises anti-cancer treatment, antibodies and the like.

The data shown herein examines somatically altered super-enhancers, which enabled the identification of a master regulator thought to play a key role in the pathogenesis of clear cell renal cell carcinoma, ZNF395. This disclosure describes specific von Hippel-Lindau-dependent enhancer required for ZNF395 expression and shows the role of ZNF395 in clear cell renal cell carcinoma tumourigenesis in vitro and in vivo.

Epigenetic maps of this study reveal targets that contribute to clear cell renal cell carcinoma tumourigenesis. Extensive enhancer gains were found around well-characterized hypoxia-related targets (VEGFA, CXCR4, HK2), SLC-mediated membrane transporters (SLC2A1, SLC2A2, SLC38A1), SLC16A family, and adipogenesis (PLIN2). Targets revealed in this study include SMPDL3A, SLC28A1, SLC6A3, VECFA and EGLN3. SMPDL3A is a clear cell renal cell carcinoma-specific oncogene with a role in lipid and cholesterol metabolism. One finding from this epigenomic study is the tumourigenic requirement of ZNF395 in clear cell renal cell carcinoma. ZNF395 is also known as HDBP2 or papillomavirus binding factor (PBF). ZNF395 is required for the differentiation of mesenchymal stem cells to adipocytes, by partnering with PPARγ2 to promote adipogenesis. ZNF395 has been shown to bind to the promoters of Huntington gene and interferon-induced genes, and to cause upregulation of cancer-related genes (MACC1, PEG10, CALCOCO1, and MEF2C) and proangiogenic chemokines including IL6 and IL8 under hypoxia.

The invention illustratively described herein can suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed can be resorted to by those skilled in the art, and that such modifications and variations are considered to be within the scope of this invention.

As used in this application, the singular form "a," "an," and "the" include plural references unless the context clearly dictates otherwise. For example, the term "a genetic marker" includes a plurality of genetic markers, including mixtures and combinations thereof.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments can be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments can also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

The following examples illustrate methods by which aspects of the invention may be practiced or materials that may be prepared which is suitable for the practice of certain embodiments of the invention.

Example 1—Materials and Methods

Patient Information

Fresh-frozen normal-tumour tissues were obtained from nephrectomy cases under approvals from institutional research ethics review committees and patient consent. Normal tissues were harvested from sites distant from the tumour. Table 1 refers to detailed patient information of this study.

TABLE 1

| Patient information | | | | | |
|---|---|---|---|---|---|
| ID | Age at the time of diagnosis | Race | Sex | Histo Type | Fuhrman Nuclear Grade |
| 74575859 | 80 | Chinese | Female | Clear cell carcinoma | Grade II |
| 17621953 | 48 | Chinese | Male | Clear cell carcinoma | Grade II |
| 57398667 | 56 | Chinese | Male | Clear cell carcinoma | Grade III |
| 70528835 | 52 | Chinese | Male | Clear cell carcinoma | Grade III |
| 77972083 | 50 | Chinese | Male | Clear cell carcinoma | Grade IV |
| 75416923 | 49 | Unknown | Male | Clear cell carcinoma | Grade II |
| 20431713 | 65 | Indian | Male | Clear cell carcinoma with pappilary features | Grade IV |
| 40911432 | 56 | Chinese | Female | Clear cell carcinoma | Grade II |
| 12364284 | Unknown | Unknown | Unknown | Clear cell carcinoma | Grade III |
| 86049102 | 51 | Chinese | Male | Clear cell carcinoma | Grade II |

Cell Lines

Commercial cell lines (786-O, A-498, HK2, and PCS-400) were purchased from ATCC. Cell lines were maintained in RPMI (Invitrogen) with 10% FBS with the exception of primary renal proximal tubule epithelial cells, PCS-400, which were maintained in Renal Epithelial Cell Basal Medium (ATCC). Cell line authentication was performed by short tandem repeat (STR) analysis against publicly available STR profiles. *Mycoplasma* testing was performed using the MycoSensor PCR assay kit (Stratagene).

Establishment of Tumour-Derived Cell Lines from Primary Tumours

Tumour cells were disassociated from primary tumours by collagenase, seeded, and maintained in RPMI with 10% FBS. At 80% to 90% confluency, the cells were passaged at a ratio of 1:3. Cultured cells were considered to be successfully immortalized after 60 passages. Correct pairing of tumour tissues and cell lines was achieved by comparing the percentage identity of single nucleotide polymorphisms (SNP) based on targeted sequencing. All tumour-cell line pairs showed identities of >90% whereas shuffling of pairing showed identities <80%. Tumours and cell lines from 12364284 and 40911432 showed the same von Hippel-Lindau (VHL) mutations, but tissue from 86049102 (86049102T) is VHL-mutant, whereas the cognate 86049102 cell line (86049102L) is VHL-wild-type.

Stable Von Hippel-Lindau Restoration in Clear Cell Renal Cell Carcinoma Lines

786-O cells (WT2, VHL+) and 786-O cells (RC3, VHL−) were used. Stable transduction of von Hippel-Lindau (VHL) was performed in A-498, 12364284, and 40911432 cells as follows: HA-VHL wt-pBabe-puro plasmid was transfected into PlatA cells (RV-102, Cell Biolabs) at 2 μg DNA/well of a 6-well plate using Lipofectamine 3000 (LifeTechnologies). A medium change was performed 10 to 16 hours after transfection. The supernatant from PlatA cells containing retroviruses was harvested 48 hours later and added to clear cell renal cell carcinoma cells, which were then selected with puromycin for 3 days after transduction.

Histone Nano-Chromatin Immunoprecipitation Sequencing (Nano-ChIP-Seq)

Nano-ChIP-seq was performed as previously described with slight modifications. Fresh-frozen cancer and normal tissues were dissected using a razor blade to obtain about 5 mg of tissue. The tissues were fixed in 1% formaldehyde for 10 minutes at room temperature. Fixation was stopped by addition of glycine to a final concentration of 125 nmol/L. Tissue pieces were washed three times with TBSE buffer. Pulverized tissues were lysed in 100 μL lysis buffer and sonicated for 16 cycles (30 s on, 30 s off) using a Bioruptor (Diagenode). The following antibodies were used: H3K27ac (ab4729, Abcam), H3K4me3 (07-473, Millipore), H3K4me1 (ab8895, Abcam), and H3K27me3 (07-449, Millipore). The total volume of immunoprecipitation was 1 mL and the amount of antibody used was 2 μg. The input DNA was precleared with protein G Dynabeads (Life Technologies) for 1 hour at 4° C. and then incubated with antibodies conjugated protein G beads overnight at 4° C. The beads were washed 3 times with cold wash buffer. After recovery of chromatin immunoprecipitation (ChIP) and input DNA, whole-genome amplification was performed using the WGA4 kit (Sigma-Aldrich) and BpmI-WGA primers. Amplified DNA was digested with BpmI [New England Biolabs (NEB)]. After that, 30 ng of the amplified DNA was used with the NEBNext ChIP-seq library prep reagent set (NEB). Chromatin immunoprecipitation sequencing (ChIP-seq) in cell lines was performed using the same Nano-ChIP-seq protocol described above but with $1 \times 10^6$ cells. Each library was sequenced to an average depth of 20 to 30 million raw reads on HiSeq2500 using 101-bp single end reads.

Histone Chromatin Immunoprecipitation Sequencing (ChIP-Seq) Analysis

Sequencing tags were mapped against the human reference genome (hg19) using Burrows-Wheeler Aligner (BWA-mem; version 0.7.10). Reads were trimmed 10 bp from the front and the back to produce 81 bp. Only reads with mapQ >10 and with duplicates removed by rmdup were used for subsequent analysis. Significant peaks were called using CCAT (P<0.05). The strength and quality of immunoprecipitation were assessed using CHANCE.

Transcription Factor Chromatin Immunoprecipitation Sequencing (ChIP-Seq)

For each transcription factor, $3 \times 10^7$ cells were cross-linked with 1% formaldehyde for 10 minutes at room temperature and stopped by adding glycine to a final concentration of 125 nmol/L. Chromatin was extracted and sonicated to about 500 bp (Vibra cell, SONICS). The following antibodies were used for chromatin immunoprecipitation: c-Jun (sc-1694, Santa Cruz Biotechnology), NF-κB p65 (sc-372, Santa Cruz Biotechnology), ETS1 (sc-350, Santa Cruz Biotechnology), HIF1α (610959, BD Biosciences), HIF2α (NB100-122, Novus Bio), and p300 (sc-585, Santa Cruz Biotechnology). The total volume of immunoprecipitation was 1.5 mL and the amount of antibody used was 15 μg. Input DNAs were precleared with protein G Dynabeads (LifeTechnologies) for 2 hours at 4° C. and then incubated with antibody-conjugated protein G beads overnight at 4° C. The beads were washed 6 times with wash buffer at room temperature. At least 10 ng of the DNA was used with the NEBNext ChIP-seq library prep reagent set (NEB). Each library was sequenced to an average depth of 30 to 50 million reads on a HiSeq2500 using 101-bp single-end reads.

Transcription Factor Chromatin Immunoprecipitation Sequencing (Chip-Seq) Analysis Sequencing tags were mapped against the human reference genome (hg19) using Burrows-Wheeler Aligner (BWA-mem) (version 0.7.10). Only reads with mapQ >10 and with duplicates removed by rmdup were used in the subsequent analysis. Significant peaks were called using MACS2 (q-value <0.01). Fastq files of HIF2α ChIP-seq (GSM856790), HIF1β ChIP-seq (GSM856790) and HIF1α ChIP-Seq (GSM1642764) were downloaded from GEO database. Peaks were called using MACS2 using the same settings as above.

RNA-Seq

Ten pairs of normal-tumour tissue matching the chromatin immunoprecipitation sequencing (ChIP-seq) tissues were prepared for RNA-seq. Total RNA was extracted using the Qiagen RNeasy Mini kit. RNAseq libraries were prepared using the Illumina Tru-Seq RNA Sample Preparation v2 protocol, according to the manufacturer's instructions. Briefly, poly-A RNAs were recovered from 1 μg of input total RNA using poly-T oligo conjugated magnetic beads. The recovered poly-A RNA was chemically fragmented and converted to SuperScript II and random primers. The second strand was synthesized using the Second Strand Master Mix. Libraries were validated with an Agilent Bioanalyzer (Agilent Technologies, Palo Alto, CA), diluted to 11 pM and applied to an Illumina flow cell using the Illumina Cluster Station. Sequencing was performed on a HiSeq2000 with 74 bp or 76 base pair paired-end reads.

RNA-Seq Analysis

RNA-seq reads were aligned to the human genome (hg19) using TopHat2-2.0.12 (default parameter and—library-type fr-firststrand). Only uniquely mapped reads were analysed. Gene counts were obtained using HTSeq against the GENCODE v19 reference gene models and subsequent differential analysis was performed using DESeq2.

Capture-C

Capture-C was performed as previously described. Briefly, $1 \times 10^7$ cells were cross-linked by 2% formaldehyde, followed by lysis, homogenization, DpnII digestion, ligation, and de-cross-linking. DNA was sonicated using a Covaris to 150 to 200 bp to produce DNA suitable for oligo capture. A total of 3 pg of sheared DNA was used for sequencing library preparation (NEB). Enhancer sequences were double captured by hybridization to customized biotinylated oligos (IDT) and enriched with Dynabeads (Life Technologies). Captured DNA was sequenced to an average depth of 2 million reads per probe on the HiSeq Illumina platform using 150-bp paired-end reads.

Capture-C Analysis and Gene Assignment

Preprocessing of raw reads was performed to remove adaptor sequences (trim_galore), and overlapping reads were merged using FLASH. In order to achieve short read mapping to the hg19 reference genome, the resulting preprocessed reads were then in silico digested with DpnII and aligned using Bowtie (using p1, m2, best, and strata settings). Aligned reads were processed using Capture-C analyzer to (i) remove PCR duplicates; (ii) classify subfragments as "capture" if they were contained within the capture fragment, "proximity exclusion" if they were within 1 Kb on either side of the capture fragment, or "reporter" if they were outside of the "capture" and "proximity exclusion" regions; and (iii) normalize read counts per 100,000 interactions in bigwig format. r3Cseq package was used on the capture and reporter fragments to identify significant interactions of the viewpoint against a scaled background (q-value <0.05). Gene assignment is defined by the overlap of significant Capture-C peaks with genes with start and end defined by GENCODE v19. Interactions were plotted using Epigenome Gateway v40.0.

Identification of Differentially Enriched Regions

Significant H3K27ac peaks called by CCAT were merged across all normal-tumour samples. The same was performed with H3K4me1 and H3K4me3 chromatin immunoprecipitation sequencing (ChIP-seq) data. Transcription start sites (TSS) were based on GENCODE v19. Promoters were defined as regions of overlap between H3K27ac and H3K4me3 and also overlapping with ±2.0 Kb around the TSS. Enhancers were defined as regions of overlap between H3K27ac and H3K4me1 but not overlapping with promoters. To minimize stromal contamination, we performed further filtering using cell line data, where enhancers and promoters not overlapping with H3K27ac peaks in any of the cell lines were discarded. Wiggle files of window size 50 bp were generated using MEDIPs from bam files. The input subtracted signal for each promoter or enhancer region was computed using bigWigAverageOverBed to yield reads per kilobase per million (RPKM). The RPKM of H3K27ac, H3K4me1, and H3K4me3 chromatin immunoprecipitation sequencing (ChIP-seq) from promoters and enhancers were corrected for batch effects using Combat. Tumour-specific regions were defined as regions that have a fold difference of and a difference of 0.5 RPKM from patient matched normal tissue. Normal regions were defined as regions that have a fold difference of ≤0.5, and a difference of −0.5 RPKM from the corresponding regions in patient-matched tumours. Recurrently gained regions were defined as gain in ≥5/10 patients and no loss in any patients. Recurrently lost regions were defined as loss in ≥5/10 patients and no gain in any patients. Statistical testing for each cis regulatory region was performed using paired t tests with Benjamini-Hochberg correction. The differential regions were visualized using NGSplot.

Identification of Superenhancer Regions

Superenhancer regions were identified using ROSE (with promoter excluded), using H3K27ac peak regions merged from all patients (both normal and tumour tissue). Wiggle files of window size 50 bp were generated using MEDIPs from bam files. The input-subtracted signal for each superenhancer was computed using bigWigAverageOverBed (sum of reads over covered bases). The superenhancer regions were ranked by the average difference of normal-tumour H3K27ac chromatin immunoprecipitation sequencing (ChIP-seq) signals. Gained superenhancers were defined as regions that have average differential H3K27ac ChIPseq signals >0. Lost superenhancers were defined as regions that have average differential H3K27ac ChIP-seq signals <0.

Targeted Sequencing

Ten pairs of normal-tumour tissue matching the chromatin immunoprecipitation sequencing (ChIP-seq) tissues were prepared for targeted mutation sequencing. Genomic DNA was extracted using the QIAamp DNA Mini Kit. Genomic DNA libraries were prepared using KAPA Hyper Prep Kit, according to the manufacturer's instructions. Briefly, genomic DNA was fragmented to 150-200 bp by sonication using a Covaris E-220 Focused Ultrasonicator (Duty Factor: 10%, Cycles per Burst: 200, Treatment Time: 360; Covaris Inc.). After the fragmentation process, end-repair, A-tailing, adapter ligation, and PCR reactions before target enrichment was performed, following the manufacturer's recommended protocols. After each step, the purification step was performed with AMPure XP beads to remove short fragments such as adapter dimers. Enrichment was performed using SureSelect XT2 Xplora RNA Bait (Custom, 5.9 Mb). Sequencing was performed on a Hiseq2500 with the paired-end 100 bp option.

Principal Component Analysis (PCA)

RPKM values of H3K27ac intensities of all the cis-regulatory elements were first corrected for batch effects using COMBAT. PCA was performed on the entire 17,497 promoters or entire 66,448 enhancers. Variances and the cumulative proportion of each principal component were computed using R.

Saturation Analyses

Saturation analyses were performed independently for enhancers and promoters. Specifically, subsets of the H3K27ac profiles from 20 primary samples (consisting of 10 primary tumours and matched normal samples) were selected. All combinations in each subset size were tested except those subsets with >10,000 possible combinations (n=5-15 samples), in which case 10,000 randomly selected combinations were tested. Then, H3K27ac enriched regions from each subset were combined, and overlapping regions were merged. These unique regions were then further classified as promoters and enhancers using the definitions reported in "Identification of differentially enriched regions".

GREAT Analysis

Altered promoters were assigned using GREAT v3.0 by the nearest single gene. Altered enhancers were assigned to the genes with a proximal 5.0 Kb upstream, 1.0 Kb downstream extension and a distal extension up to 1000 Kb using default GREAT settings. The top pathways enriched in the MSigDB Pathways and Gene Ontology (GO) Molecular Functions were ranked by their hypergeometric q-values.

Epigenome Roadmap Datasets

The bed files from H3K27ac, H3K4me1 and H3K4me3 chromatin immunoprecipitation sequencing (ChIP-Seq) of two normal kidneys were generated by the Epigenome Road. Peaks were identified using COAT. Similarities between the Epigenome Roadmap and our ChIP-Seq data were computed by the percentage of overlap between peaks.

DNA Methylation Analysis

In total, 160 tumour-normal matched pairs were obtained from The Cancer Genome Atlas (TOGA) database. Quantile normalization was performed across all the samples. Probes were assigned to the nearest promoter or enhancer with a maximal cutoff of 10 kb.

Chromatin Accessibility Analysis

Bigwig-formatted files of 7 clear cell renal cell carcinoma matched normal-tumour FAIRE-Seq datasets obtained from EMBL-EBI ArrayExpress under accession number E-MTAB-1936. FAIRE-Seq signals for each promoter or enhancer region were computed using bigWigAverageOverBed with the promoters and enhancer regions as the input bed file. FAIRE-Seq data was normalized for batch effects using Combat.

lncRNA Analysis

A list of differentially expressed lncRNA in kidney cancer was downloaded from a previous study. RPKM values of each lncRNA were computed across the same ten pairs of normal-matched tissue where chromatin immunoprecipitation sequencing (ChIPseq) was performed, using bigWigAverageOverBed with chromosome positions defined by a previous study. These differentially expressed lncRNA were assigned to the nearest promoter and enhancer but with a maximum distance cut off of 10 Kb. In total, around 200 lncRNAs were assigned to a promoter or an enhancer.

Motif Analysis

Motif analysis was performed using HOMER using the gained promoters and enhancers as the input regions and lost promoters and enhancers as the background. The input regions covered the entire span of promoters and enhancers. For von Hippel-Lindau (VHL)-responsive regions, input regions were gained enhancers with H3K27ac depletion after VHL restoration and background regions were gained enhancers with H3K27ac enrichment after VHL restoration. Only known motifs were considered.

Histone Chromatin Immunoprecipitation Sequencing (ChIP-Seq) with Von Hippel-Lindau Restoration H3K27ac, H3K4me1 and H3K27me3 ChIP-seq were performed using histone ChIP-seq. Sonicated DNA was normalized for each pair of cells with and without wild-type von Hippel-Lindau (VHL) before immuno-precipitation. Differential analysis of H3K27ac was performed using Deseq2 using raw counts of H3K27ac ChIP-seq with p-value <0.05.

The Cancer Genome Atlas (TCGA) RNA-Seq

Preprocessed RNA-seq v2 data level 3 of clear cell renal cell carcinoma, papillary and chromophobe renal cell carcinoma was downloaded from TCGA. Only patients with matched normal-tumour pairs (72 clear cell renal cell carcinoma pairs, 32 papillary renal cell carcinoma pairs and 25 chromophobe renal cell carcinoma pairs) were considered. The overall tumour-normal ratio of a given gene was computed from averaging individual tumour-normal ratios, and p-values computed by paired t-test. Pan-cancer compilation of TCGA data was obtained from pancan12.

Immunoblotting

Cell lines were harvested with cold RIPA lysis buffer (50 mM Tris pH 8, 150 mM NaCl, 0.1% Triton X-100, 0.5% Sodium deoxycholate, 0.1% SDS) with protease inhibitors (Roche) on ice. Cells were mechanically lysed by passing through a 25 Gauge needle and centrifuged at 13,000 rpm for 15 min at 4° C. Protein concentrations were measured by the Pierce BCA protein assay (Life Technologies). Cell lysates were heated at 70° C. for 10 min in sample buffer. Per well, 15 pg of cell lysate was loaded and gel electrophoresis was run at 130V constant for 90 minutes. Proteins were transferred to nitrocellulose membranes by transferring at 100 V for 100 minutes in ice. Western blotting was performed by incubating membranes overnight at 4° C. with the following antibodies and dilutions: ZNF395 (1 pg/ml), von Hippel-Lindau (VHL) (1:250 dilution, Cell Signaling 2738), HIF1A (1:500 dilution, BD #610959), HIF1B (1:2000 dilution, Novus Bio NB100-110), HIF2A (1:1000 dilution, Novus Bio NB100-122), ETS1 (1:1000 dilution, Santa Cruz sc-350), c-Fos (1:500 dilution, Santa Cruz sc-7202), c-Jun (1:500 dilution, Santa Cruz sc-1694), NFκB p65 (ab7970, AbCAM) and β-actin (1:2000, Santa Cruz sc-47779). Membranes were incubated in secondary antibodies at 1:10,000 dilution for 1 hr at room temperature and developed with SuperSignal West Femto Maximum Sensitivity Substrate (Thermo Scientific).

siRNA Knockdown

ON-TARGETplus SMARTpool siRNA (Dharmacon, UK) were used with Non-Targeting Control Pool as negative control and GAPDH Control Pool as positive control. The sequences of the SMARTpool siRNAs were as follows:

```
HIF2α (EPAS1)
(SEQ ID NO: 1)
GGCAGCACCUCACAUUUGA,

SEQ ID NO: 2
GAGCGCAAAUGUACCCAAU,

SEQ ID NO: 3
GACAAGGUCUGCAAAGGGU,

SEQ ID NO: 4
GCAAAGACAUGUCCACAGA)
SMDPL3A
(SEQ ID NO: 5
CAGUAUGAUCCUCGUGAUU,

SEQ ID NO: 6
GAAGAUUUGCAGCCGGAAA,

SEQ ID NO: 7
GACAGUAAGCAGUUUAUAA,

SEQ ID NO: 8
CGGCCCAAAUAUAAUGACA)

ZNF395
(SEQ ID NO: 9)
CCAAACUGAUCAUGGCUUU,

SEQ ID NO: 10
UCAGGCAGAUCAUGCAUAC,

SEQ ID NO: 11
GUUCUGCGCUCCAUUGUGG,

SEQ ID NO: 12
GGACGAACCAGCUCCACGA)
```

A-498, 786-O and 12364284 and cells were trypsinized and diluted to appropriate concentrations. Lipofectamine RNAiMAX (Life Technologies) and SMARTpool siRNAs were diluted in Opti-MEM to a final siRNA concentration of 50 nM. The diluted Lipofectamine RNAiMAX was added to the diluted siRNA and incubated for 15 min at room temperature to allow complex formation to occur. The siRNA mixtures were aliquoted to wells in a 6-well plate. 48 hours after transfection, cells were re-seeded into 6-well plates for colony formation assays and 96-well plates for cell viability assay.

shRNA Knockdown

Lentiviral plasmids were transfected into HEK293T cells. MISSION shRNA clones against ZNF395 were purchased from Sigma Aldrich. The sequences of the clones are as follows:

TRCN0000233231
SEQ ID NO: 13
CCGGGCATCAAACGACACGTCAAAGCTCG

AGCTTTGACGTGTCGTTTGATGCTTTTTG

TRCN0000233234
SEQ ID NO: 14
CCGGCAGAAGCCTTTACTGATTAAACTCG

AGTTTAATCAGTAAAGGCTTCTGTTTTTG

Cells were transduced with lentiviral particles for 48 hours and selected with puromycin (2 pg/ml) for four days before being analyzed for gene and protein expression and other functional assays.

Quantitative PCR Analysis (qPCR)

Total RNA was extracted from cell lines using Trizol (ThermoFisher) and purified with the RNeasy Mini Kit (Qiagen). Reverse transcription was performed using iScript Reverse Transcription Supermix for RT-qPCR (Biorad). qPCR was performed using Taqman probes (ZNF395 Assay ID: Hs00608626_m1, SMPDL3A Assay ID: Hs00378308_m1) with TaqMan Gene Expression Master Mix (Thermo Fisher). Gene expression changes were normalized to GAPDH (Assay ID: Hs00699446_m1).

Chromatin Immunoprecipitation Quantitative Polymerase Chain Reaction (ChIP-qPCR)

ChIP DNA was probed with the following primers using the SYBR qPCR master mix (ThermoFisher).

ZNF395-E1 (hg19 chr8: 28221378-28221459)
ZNF395-E1-F:
(SEQ ID NO: 15)
GCAACCTTCCAGGCCTGCCG

ZNF395-E1-R:
(SEQ ID NO: 16)
AGGAGAAAGGGGACAGGAGGGC

ZNF395-E2 (hg19 chr8: 28222803-28222908)
ZNF395-E2-F:
(SEQ ID NO: 17)
TGGGCCGCCCGTGACTTTTC

ZNF395-E2-R:
(SEQ ID NO: 18)
GGTTGGAAGGAGGCCACCGC

ZNF395-E3 (hg19 chr8: 28223142-28223230)
ZNF395-E3-F:
(SEQ ID NO: 19)
TCGTGCTGAAGGCTTCTCAGGAAA

ZNF395-E3-R:
(SEQ ID NO: 20)
CCCCTCCTGTTGGTGACGGC

ZNF395-E4 (hg19 chr8: 28269095-28269211)
ZNF395-E4-F:
(SEQ ID NO: 21)
AAGCGGCGGGAGGAGGTTGA

ZNF395-E4-R:
(SEQ ID NO: 22)
GGGCTGCGTCACCTGCAGAA

Luciferase Assay

Genomic DNA from where 786-O cells were extracted using DNeasy Blood & Tissue Kit (Qiagen). Regions corresponding to putative enhancers were amplified using CloneAmp HiFi PCR Premix (Clonetech) and cloned into the pGL3 luciferase reporter vector with a minimal FOS promoter.

Forward primer:
(SEQ ID NO: 23)
GTAGCTGCATAGATCTGCGCGCCACCCCTCTGGCGCCACCGT

Reverse_primer:
(SEQ ID NO: 24)
GTAGCTGCATCAAGCTTGCCGGCTCAGTCTTGGCTTCTC

The day prior to transfection, $1\times10^4$ cells were seeded into each well of a 96-well plate. Cells were transfected with 100 ng of pGL3-Fos-enhancer and 20 ng of pRL-SV40 (Renilla luciferase vector, Promega). Cells were lysed and analyzed using the Dual-Luciferase Reporter System (Promega). Primer sequences used to amplify genomic regions for luciferase reporter assays are as follows:

VEGFA-E1 (hg19 chr6: 43635485-43636708)
VEGFA-E1-F_Mlul:
(SEQ ID NO: 25)
GCTCTTACGCGT TGGGGGTGCCTCTCCCACTG VEGFA-E1-R_Nhel:
(SEQ ID NO: 26)
GCCCGGGCTAGC GGGTGGGGGTCCAACAGGACA VEGFA-E2 (hg19 chr6: 43692413-43693560)
VEGFA-E2-F_Mlul:
(SEQ ID NO: 27)
GCTCTTACGCGT CCCATCCCCTGCCTCCTGCT VEGFA-E2-R_Nhel:
(SEQ ID NO: 28)
GCCCGGGCTAGC TGGGCTGGCTGCAAAGTGGC SLC2A1-E1 (hg19 chr1: 43523259-43525686)
SLC2A1-E1_F_Mlul:
(SEQ ID NO: 29)
GCTCTTACGCGT TGGTGACCGTGTTGGGGGTGA SLC2A1-E1_R_Nhel:
(SEQ ID NO: 30)
GCCCGGGCTAGC TCCCCGCCCCTCTGTTGCAT ZNF395-E1 (hg19 chr8: 28220788-28221483)
ZNF395-E1-F_Mlul:
(SEQ ID NO: 31)
GCTCTTACGCGT ACAGGTGTGCGCTACCACGC ZNF395-E1-R_Nhel:
(SEQ ID NO: 32)
GCCCGGGCTAGCTGGTGTGGAATTCTGGCCAGTTAAAGG ZNF395-E2 (hg19 chr8: 28221957-28222965)
ZNF395-E2-F_Mlul:
(SEQ ID NO: 33)
GCTCTTACGCGT TCGGGAGGTTCAAGACCAGCCT ZNF395-E2-R_Nhel:
(SEQ ID NO: 34)
GCCCGGGCTAGCGCTCCCAAGAAAGAACTTACCAGAGG ZNF395-E3 (hg19 chr8: 28222984-28224154)
ZNF395-E3-F_Mlul:
(SEQ ID NO: 35)
GCTCTTACGCGT ACCAGCCATCCCCTAGTTTGCC ZNF395-E3-R_Nhel:
(SEQ ID NO: 36)
GCCCGGGCTAGC GGCATTTGTCAGCAGAGATGTTGGC Colony Formation and Cell Viability Assays For colony formation assays, 5000 cells per condition were seeded into 6 well dishes and were allowed to grow for 12 days. Colonies were stained with 0.05% Crystal Violet. For cell viability assay, 1000 cells per condition were seeded into 96-well plate and the cell viability was measured by CellTiter-Glo Luminescent Cell Viability Assay (Promega) for 5 days.

Apoptosis Assay

For each condition, 1×10³ cells were seeded into each well of a 96-well plate. Caspase3/7 activity was measured with the cleavage of proluminescent caspase-3/7 substrate after 1 hour incubation using Caspase-Glo® 3/7 Assay (Promega). Alternatively, cells were stained with FITC Annexin V Apoptosis Detection Kit (BD Bioscences) and Calcein AM (ThermoFisher) and analyzed on a flow cytometer.

In Vivo Studies

All animal studies were conducted in compliance with animal protocols approved by Institutional Animal Care and Use Committee (IACUC) of Singapore. Female NOD/SCID mice (6-8 week old) were implanted with 1×10⁶ A-498 or 1×10⁶ 786-O cells transduced with either empty vector control or shRNA clones subcutaneously in the flank. Tumour volume was monitored every 2 to 3 days. Tumour volume was calculated as (length×width×width)×π/6. Animals were sacrificed when the tumour volume exceeded 1000 mm³.

CRISPR-Mediated Enhancer Deletion

To delete enhancer regions, 2 gRNAs (left and right) were used to cleave targeted regions as previously described. gRNAs were designed with ATUM gRNA Design Tool. Briefly, phosphorylated and annealed sense and antisense oligos were ligated into BpiI digested vectors. Left gRNAs were cloned into the BpiI digested pX330A-2A-GFP-1X2 backbone (Addgene #58766) whereas the right gRNAs into BpiI digested pX330S backbone (Addgene #58778). Golden gate assembly was performed to assemble the 2 gRNA protospacers into the pX330A-2A-GFP-1X2 plasmid backbone using a one-step digestion and ligation with slight modifications. After transfection using Lipofectamine 3000 (Life Technologies), GFP-positive single 786-O cells were sorted and cultured. Individual clones were validated for enhancer deletion by PCR of genomic DNA and the resulting gene expression was measured using qPCR and Taqman probes. Clones that were transfected with gRNAs but failed to have enhancer deletions were used as negative controls. The gRNAs used for deletion of enhancers are as follows:

```
ZNF395_E3 (hg19 chr8: 28223203-28224208)
ZNF395_E3_L_F_gRNA:
                                     (SEQ ID NO: 37)
CACCGTCCCTACTGCCGTCACCAAC ZNF395_E3_L_R_gRNA:
                                     (SEQ ID NO: 38)
AAACGTTGGTGACGGCAGTAGGGAC ZNF395_E3_R_F_gRNA:
                                     (SEQ ID NO: 39)
CACCGAAATATGTTTATGGTCCTCC ZNF395_E3_R_R_gRNA:
                                     (SEQ ID NO: 40)
AAACGGAGGACCATAAACATATTTC
```

Validation Primers for Deletion of Enhancers:

```
ZNF395-E3 (Product size after
deletion: 293bp; WT: 1299bp)
ZNF395-E3-F:
                                     (SEQ ID NO: 41)
ACCAGCCATCCCCTAGTTTGCCA ZNF395-E3-R:
                                     (SEQ ID NO: 42)
GCCACCAGGTAGCAGTTGGGT
```

Date Accession

Chromatin immunoprecipitation sequencing (ChIP-seq) and RNAseq data are available at Gene Expression Omnibus (GSE86095).

Example 2—Cis-Regulatory Landscapes in Clear Cell Renal Cell Carcinoma Tumours are Aberrant To explore whether clear cell renal cell carcinoma tumours display alterations in their cis-regulatory landscapes in vivo, histone chromatin immunoprecipitation sequencing (ChIP-seq) profiles (3 marks: H3K27ac, H3K4me3, and H3K4me1) were generated in 10 primary tumour/normal pairs, 5 patient-matched tumour-derived cell lines, 2 commercially available clear cell renal cell carcinoma lines (786-O and A-498), and 2 normal kidney cell lines (HK2 and PCS-400. Table 1 in example 1 shows patient clinical information. Of the original 87 samples, 79 samples passed pre-sequencing quality-control filters and were subjected to ChIP-seq processing and downstream analysis. In total, 2,363,904,778 uniquely mapped reads were generated. On average, 89% of H3K27ac peaks, 98% of H3K4me3 peaks, and 76% of H3K4me1 peaks obtained in our normal kidney tissues overlapped with peaks from adult kidney tissues in the Epigenomics Roadmap dataset (FIG. 1A). Among the 10 primary clear cell renal cell carcinomas, 9 harbored von Hippel-Lindau (VHL) mutations, detected by targeted sequencing and confirmed by Sanger sequencing (Table 2). Cell lines 786-O and A-498 also harbor VHL truncating mutations (Table 2). The VHL mutations co-occurred with somatic mutations of other chromatin modifiers commonly found in clear cell renal cell carcinoma, including PBRM1 (7/10), SETD2 (1/10), KDM5A (1/10), KDM5C (1/10), ARID1A (1/10), and KMT2C (1/10).

TABLE 2

Clear cell renal cell carcinoma tissue and cell lines von Hippel-Lindau (VHL) mutation confirmation by sequencing

| | Sample ID | Mutation | Chr | Position | Ref | Alt | amino acid change | % alt alleles |
|---|---|---|---|---|---|---|---|---|
| tissue | 12364284 | indel | chr3 | 10188261 | T | TAA | Phe136Asn-fsTer24 | 42.15 |
| tissue | 17621953 | indel | chr3 | 10183790 | GTATGGCTCAAC | G | Trp88Arg-fsTer41 | 14.29 |

TABLE 2-continued

Clear cell renal cell carcinoma tissue and
cell lines von Hippel-Lindau (VHL)
mutation confirmation by sequencing

|  | Sample ID | Mutation | Chr | Position | Ref | Alt | amino acid change | % alt alleles |
|---|---|---|---|---|---|---|---|---|
| tissue | 20431713 | indel | chr3 | 10191582 | AA | A | Asn193Met-fsTer201 | 49.09 |
| tissue | 40911432 | indel | chr3 | 10191500 | G | GT | Val125Cys-fsTer8 | 33.05 |
| tissue | 57398667 | indel | chr3 | 10183765 | TCGCAGTC | T | Ser80Ala-fsTer36 | 36.11 |
|  |  | missense | chr3 | 10183754 | A | G | Ile75Val | 32.86 |
| tissue | 70528835 | indel | chr3 | 10183699 | C | CG | Arg58Ala-fsTer75 | 77.27 |
| tissue | 74575859 | missense | chr3 | 10188320 | G | A | Val155Met | 37.9 |
| tissue | 77972083 | splice | chr3 | 10188195 | TAG | T | splice acceptor variant | 36.92 |
| tissue | 86049102 | missense | chr3 | 10183771 | T |  | Ser80Arg | 28.6 |
| tissue | 75416923 |  |  |  |  | wt |  |  |
| cell line | 786-O | indel | chr3 | 10183840 | GG | G | Gly104Ala-fsTer55 | 100 |
| cell line | A498 | indel | chr3 | 10188282 | TTGAC | T | Gly144Ser-fsTer14 | 93.87 |
| cell line | 40911432 | indel | chr3 | 10191500 | G | GT | Val125Cys-fsTer8 | 92.36 |
| cell line | 86049102 | missense | chr3 | 10191548 | G | A | Val140Ile | 2.61 |
| cell line | 12364284 | indel | chr3 | 10188261 | T | TAA | Phe136Asn-fsTer24 | 93.17 |

Figure 1B:
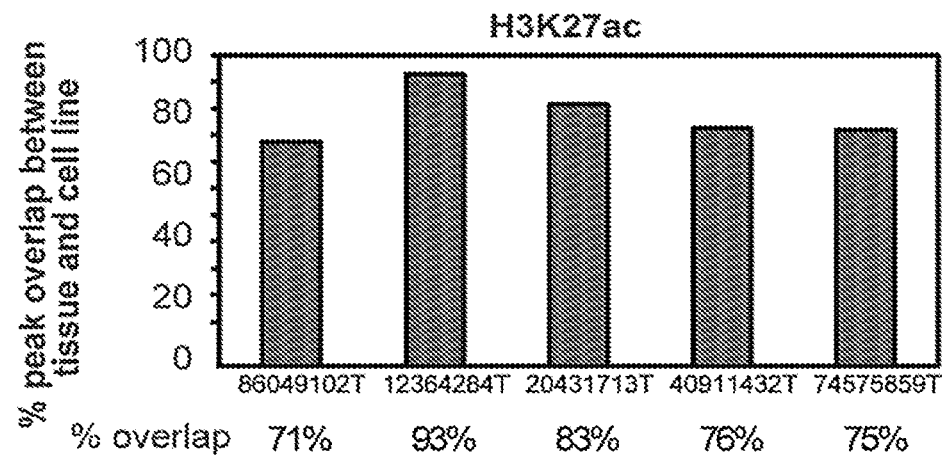
FIG. 1B shows a graph illustrating the percentage of overlap of histone ChIP-seq (H3K27ac, H3K4me3 and H3K4me1) peaks between five primary clear cell renal carcinoma tumours and cell lines derived from these tumours.
Figure 1B:
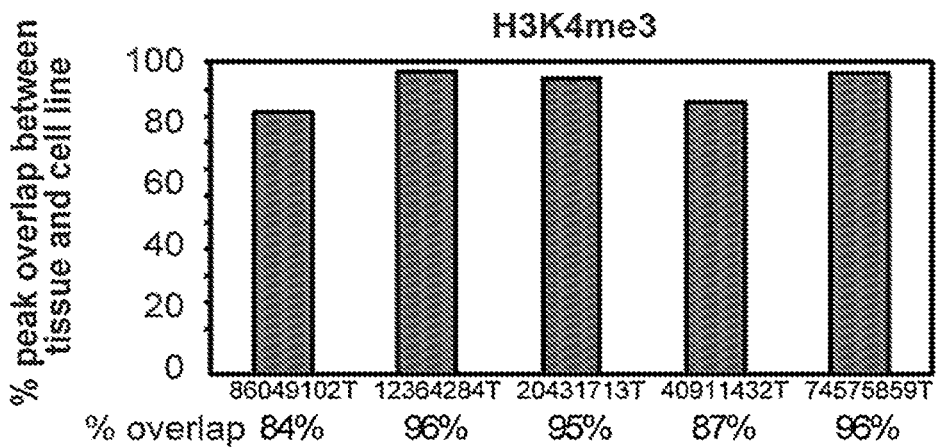
Figure 1B:
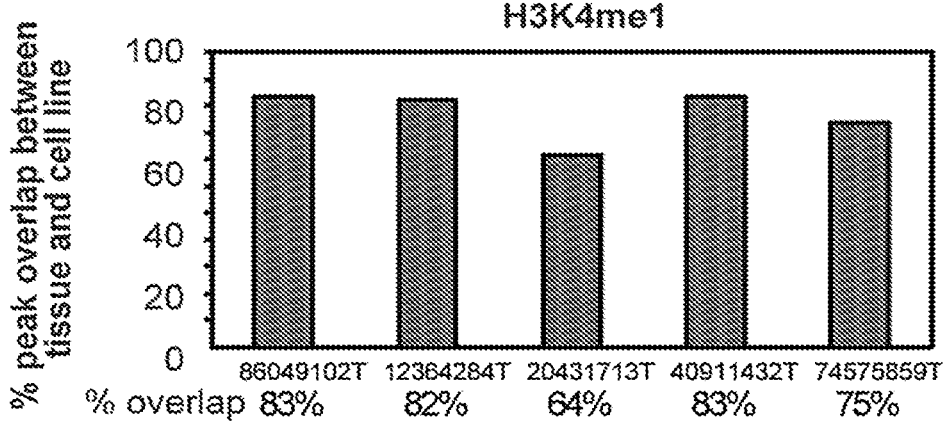
Figure 1C:
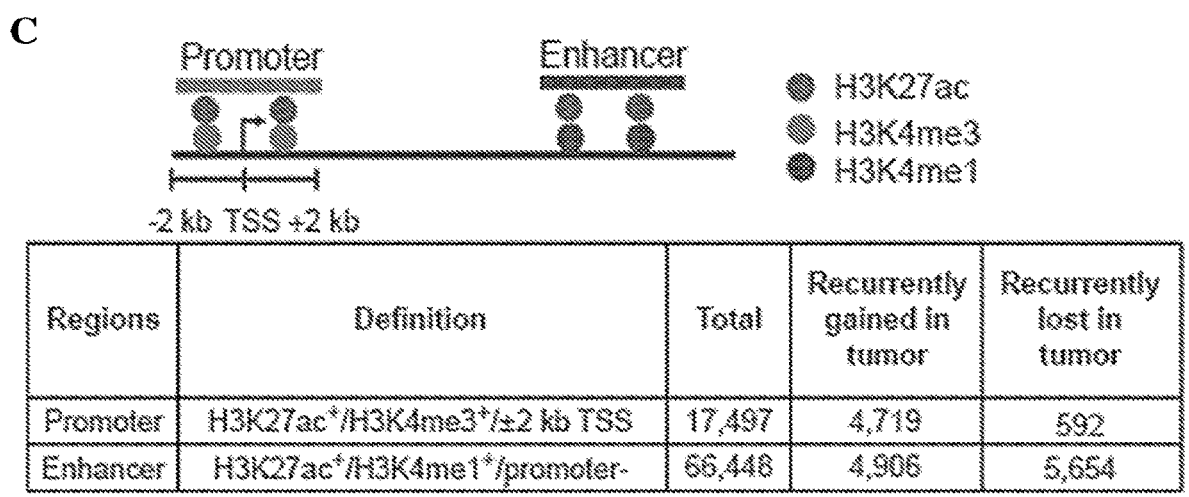
FIG. 1C shows a table and a diagram illustrating that the putative active promoters are defined by co-occurrence of H3K4me3, H3K27ac within 2 kilo bases (kb) proximity to transcription start sites (TSS); and putative active enhancers are defined by the presence of H3K4me1, H3K27ac and the exclusivity with promoters. The table further illustrates the total number of identified putative promoters and putative enhancers; and the total number of gained promoters, lost promoters, gained enhancers and lost enhancers identified in this study.
Figure 1D:
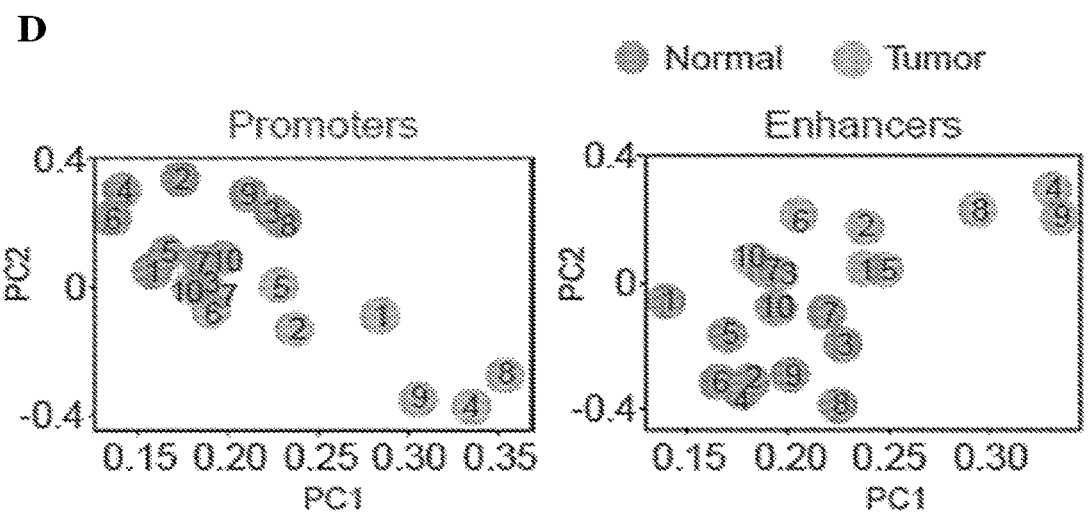
FIG. 1D shows a graph illustrating principal component analysis (PCA) using all 17,497 promoters and 66,448 enhancers to classify normal samples and tumour samples into distinct clusters. The numbers in the graph depicts patient IDs which are the following 1-12364284; 2-17621953; 3-20431713; 4-40911432; 5-57398667; 6-70528835; 7-74575859; 8-77972083; 9-86049102 and 10-75416923.
Figure 1E:
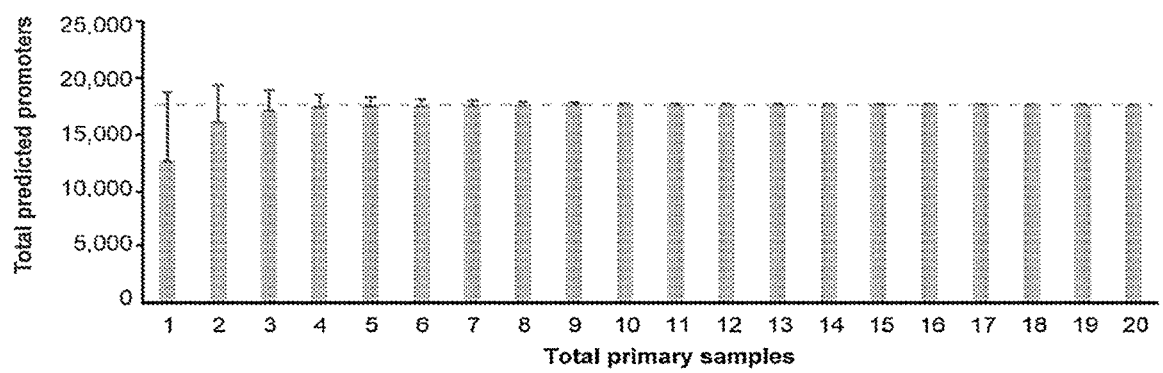
FIG. 1E shows graphs illustrating saturation analysis of the total number of predicted promoters or enhancers across increasing number of primary samples. The total number of predicted promoters saturates at 4 or more samples while the total number of predicted enhancers saturates at 16 or more samples. The dotted line indicates the total number of predicted regulatory elements by integrating all 10 normal-tumour pairs (n=20). The whiskers indicate standard deviations.
Figure 1E:
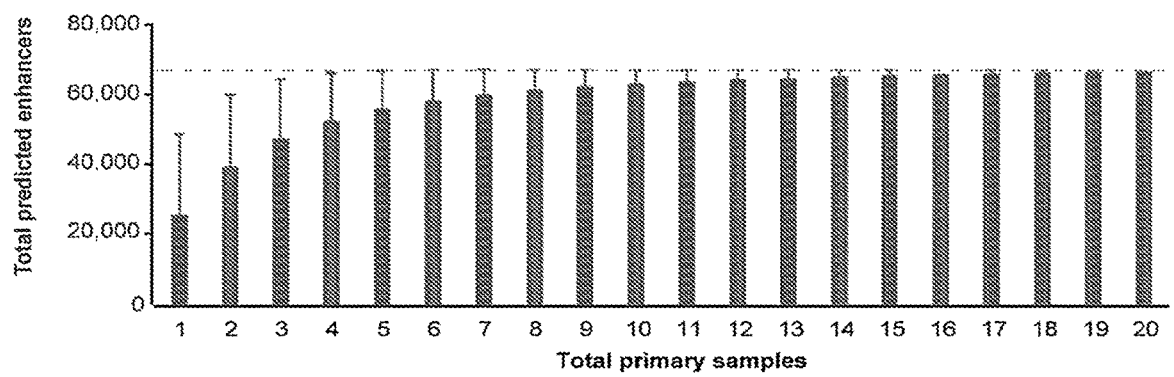
Figure 1F:
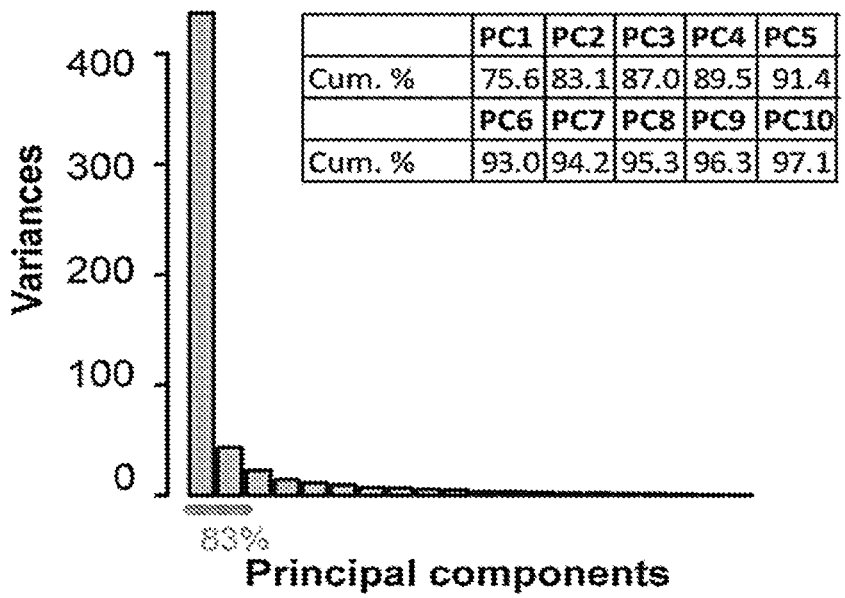
FIG. 1F shows graphs and tables describing the variances captured by each principle component from normalized H3K27ac signals at promoters or enhancers. The cumulative percentages of variance are indicated in the tables.
Figure 1F:
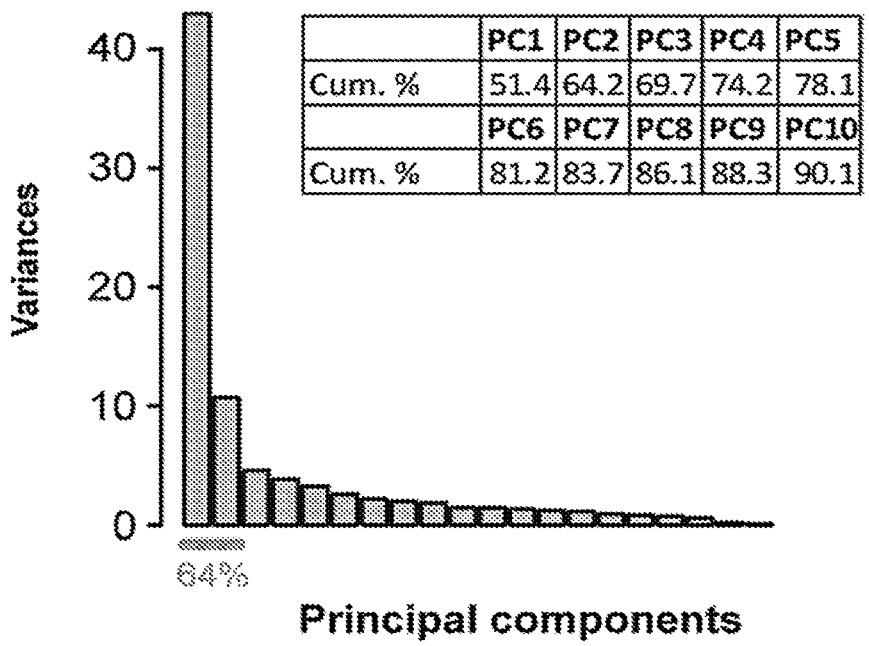

Specific histone modifications can distinguish different categories of functional regulatory elements—H3K4me3 is generally associated with promoters, H3K4me1 with enhancers, and H3K27ac with active elements. Integrating signals from three histone marks and GENCODE v19 annotated transcription start sites (TSS), active promoters were defined as H3K27ac$^+$/H3K4me3$^+$/±2.0 kb TSS regions, and distal enhancers as H3K27ac$^+$/H3K4me1$^+$ regions not overlapping with promoters. Focusing on epigenomic events specific to somatic cancer cells, cell lines were derived from five primary tumours and, combined with the commercial lines, excluded peaks not found in any of the cell lines to reduce confounding effects from stromal cells. On average, 80% overlap of chromatin immunoprecipitation sequencing (ChIP-seq) peaks was observed between primary tumours and matched lines (FIG. 1B). Using these criteria, 17,497 putative promoters and 66,448 putative enhancers (FIG. 1C) were identified, with numbers comparable with previous studies in other tumour types. The numbers of defined promoters and enhancers reached saturation after 4 and 16 samples, respectively, suggesting that a sample size of 20 (10 tumour/normal pairs) is sufficiently powered to discover the majority of cis-regulatory elements in clear cell renal cell carcinoma (FIG. 1E). Principal components analysis (PCA) using the first two components of global H3K27ac intensities at promoters or enhancers (representing 83% and 64% of total variance, respectively; FIG. 1F) successfully separated normal and tumour samples, indicating that genome-wide pervasive alterations in cis-regulatory elements are a salient feature of clear cell renal cell carcinoma (FIG. 1D).

Figure 1G:
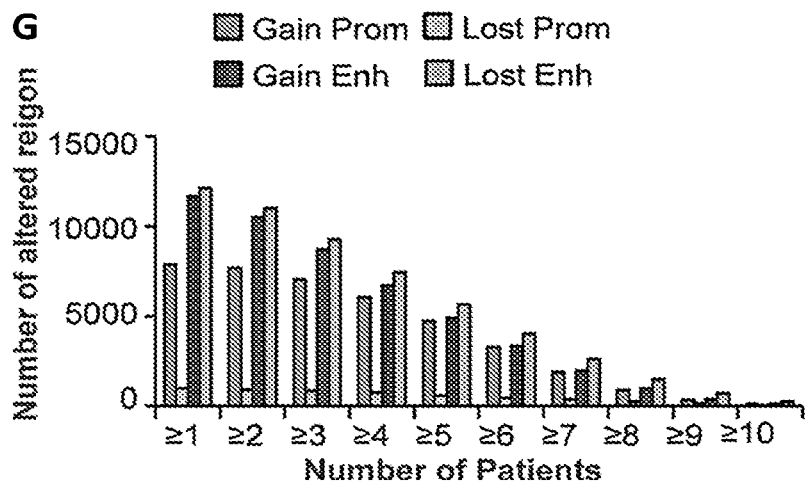
FIG. 1G shows a graph of the number of altered promoters and enhancers per patient.
Figure 1H:
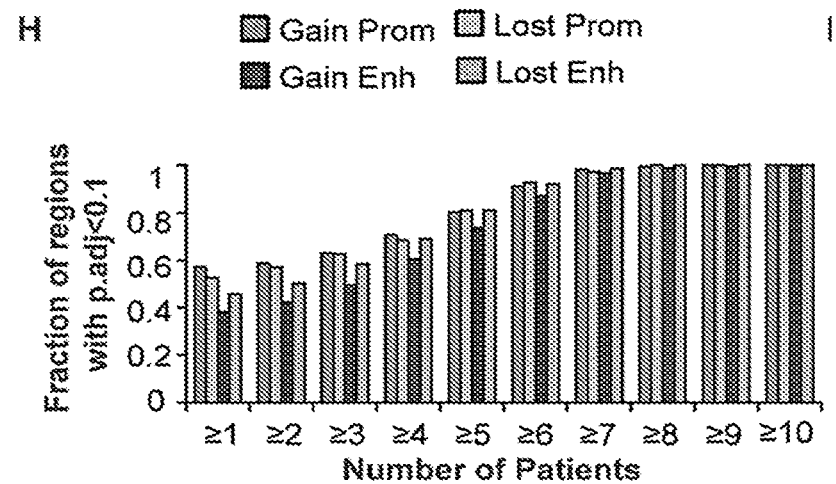
FIG. 1H shows a graph of the fraction of altered regions that meet statistical significance defined by paired t-tests with Benjamini-Hochberg correction (q value <0.10) at different cut-offs of recurrence.
Figure 1I:
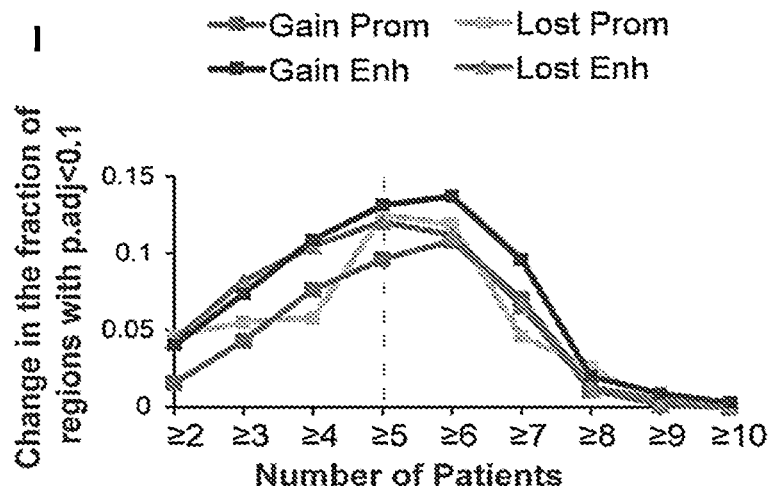
FIG. 1I shows a graph of the differences in the fractions of regions meeting statistical significance. Promoters reach saddle point at n 5 while enhancers reach saddle point at n 6.
Figure 1J:
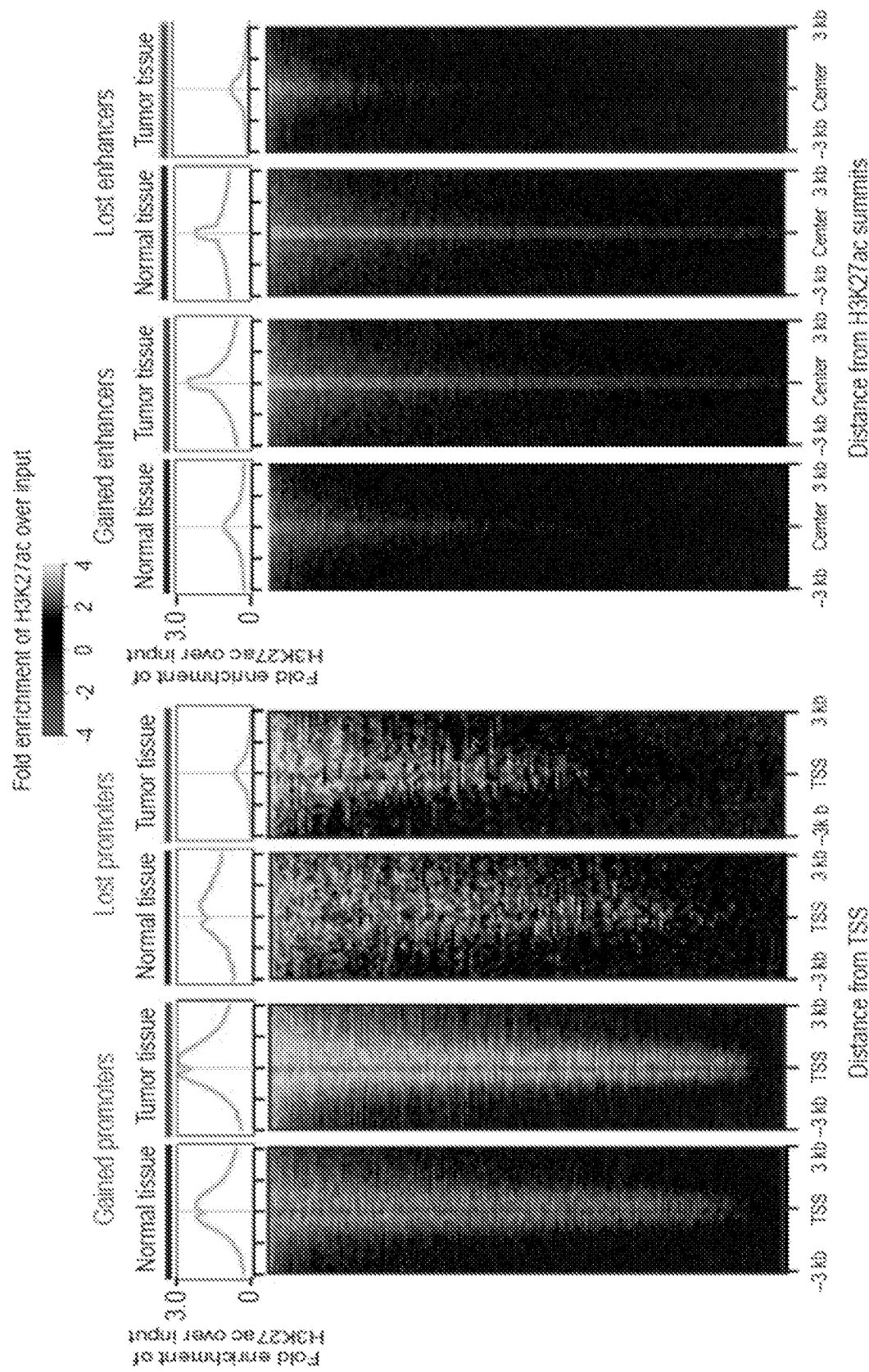
FIG. 1J shows a heatmap with H3K27ac levels of altered promoters and enhancers in a paired patient tissue (patient 40911432). High signal levels are reflected in white and low signal levels are reflected in black.
Figure 1K:
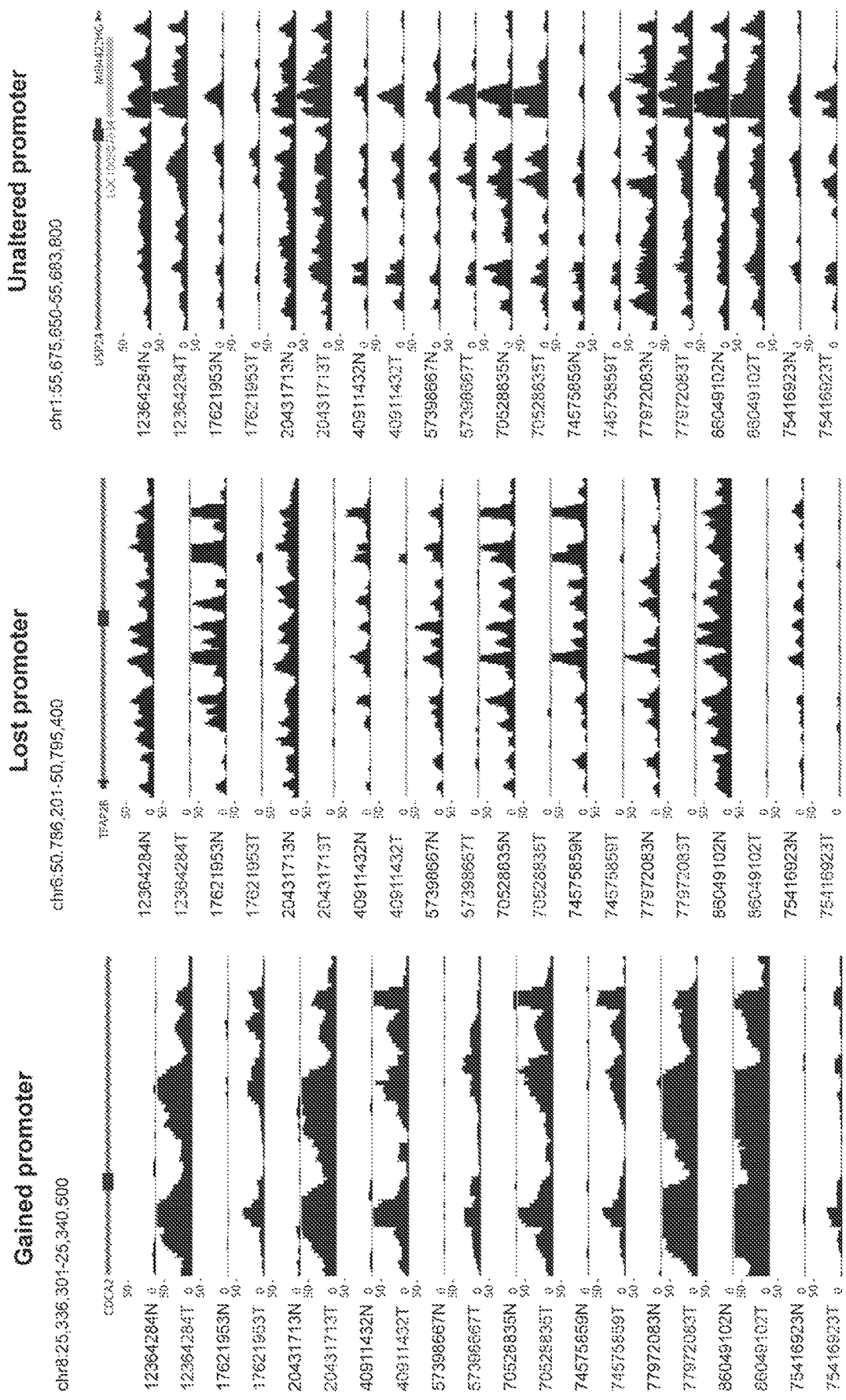
FIG. 1Ki and FIG. 1Kii shows a plot referring to examples of H3K27ac chromatin immunoprecipitation sequencing (ChIP-Seq) signals in 10 normal-tumour pairs shown for gained promoter, lost promoter, unaltered promoter, gained enhancer, lost enhancer and unaltered enhancer. N refers to signal from normal tissue and T refers to signal from tumour tissue.

Differential analysis was performed to identify altered promoters and enhancers. To define gained or lost regions, a fold difference of H3K27ac RPKM ≥2, an absolute difference 0.5, and for greater stringency no alterations in the reverse direction in the remaining tumour/normal pairs was applied (FIG. 1G). At the threshold of ≥5/10 patients, 80% of the altered regions achieved statistical significance (q-value <0.1, paired t test, with Benjamini-Hochberg correction; FIG. 1H), and at this same threshold, the increase in the fraction of samples meeting statistical significance reached a saddle point (FIG. 1I). Applying these criteria, a high-confidence and comprehensive set of 4,719 gained promoters, 592 lost promoters, 4,906 gained enhancers, and 5,654 lost enhancers was obtained (FIG. 10, FIG. 1J). Representative regions are presented in FIG. 1K (FIGS. 1Ki and 1Kii).

Figure 1L:
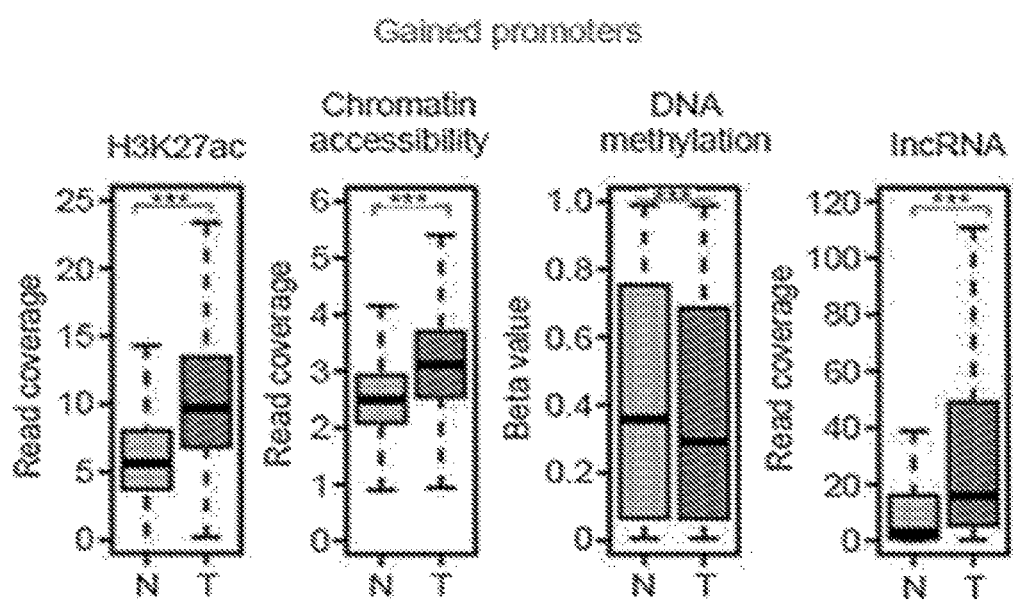
FIG. 1L shows box plots of H3K27ac levels, chromatin accessibility and DNA methylation of gained promoters and gained enhancers. Gene expression of the nearest clear cell renal cell carcinoma long coding RNA (lncRNA) is compared between normal and tumour tissues. ***p-value <0.001, two-sided t-test.
Figure 1L:
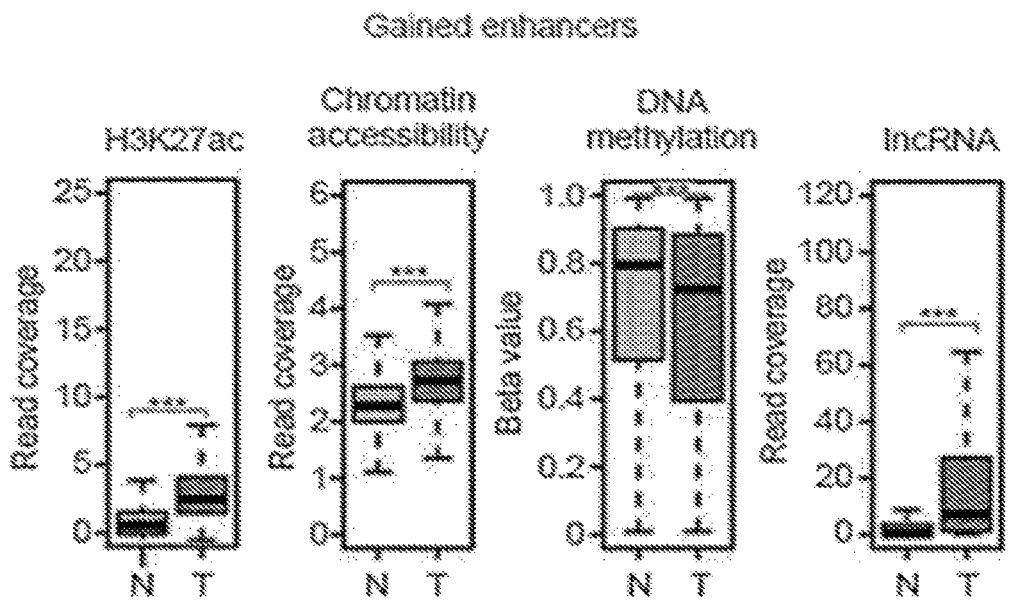
Figure 1M:
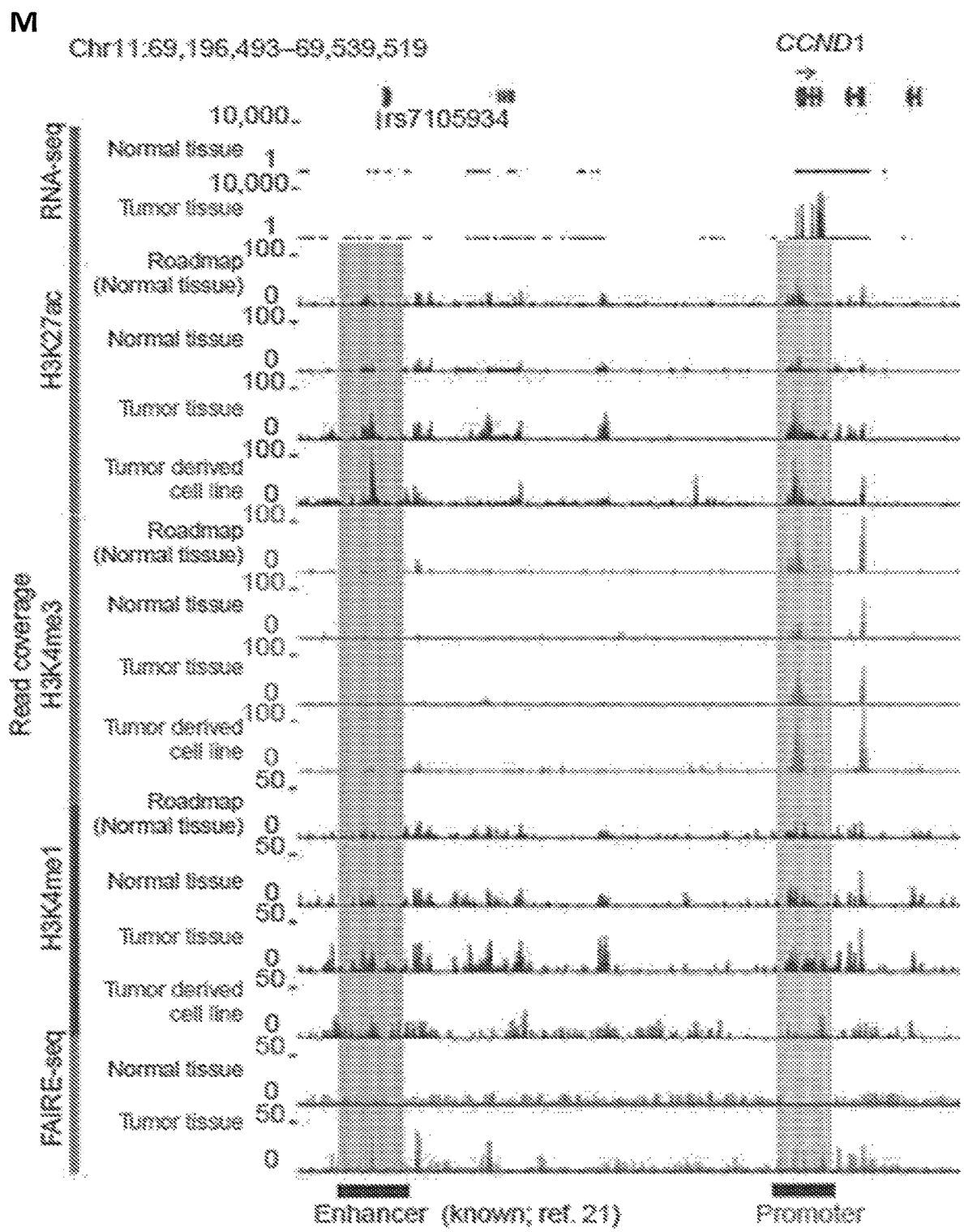
FIG. 1M shows a plot referring to histone ChIP-seq signals (H3K27ac, H3K4me1, H3K4me3), RNA-Seq signals and FAIRE-Seq signals at the CCND1 locus in a tumour-normal tissue sample pair of patient 40911432. For comparison, the histone ChIP-seq profiles of normal adult kidney tissue from the Epigenome Roadmap are displayed above the normal tissue profiles generated by Nano-ChIP-seq. The histone profile of a cell line derived from tumour tissue is displayed below the profile of the normal tissue.

Supporting these data, gained promoters and enhancers exhibited increased chromatin accessibility measured by higher FAIRE-seq signals in tumour tissues than normal tissues, respectively (P<0.0001) and also decreased DNA methylation based on data from The Cancer Genome Atlas (TCGA), consistent with reciprocal relationships between active regulatory regions and DNA methylation (FIG. 1L). Interestingly, elevated expression of long noncoding RNAs adjacent to gained promoters and enhancers was noted in tumour tissues compared with normal tissues (P<0.0001, respectively). Lastly, many of the cis-regulatory elements were confirmed to involve regions previously implicated in clear cell renal cell carcinoma; for example, gains of H3K27ac signals and enrichment of H3K4me1 at a distal enhancer of CCND1 overlapping with a renal cell carcinoma susceptibility locus (rs7105934; FIG. 1M) was observed. The ability to identify this previously known enhancer with unbiased profiling further supports the method of this study.

Figure 2A:
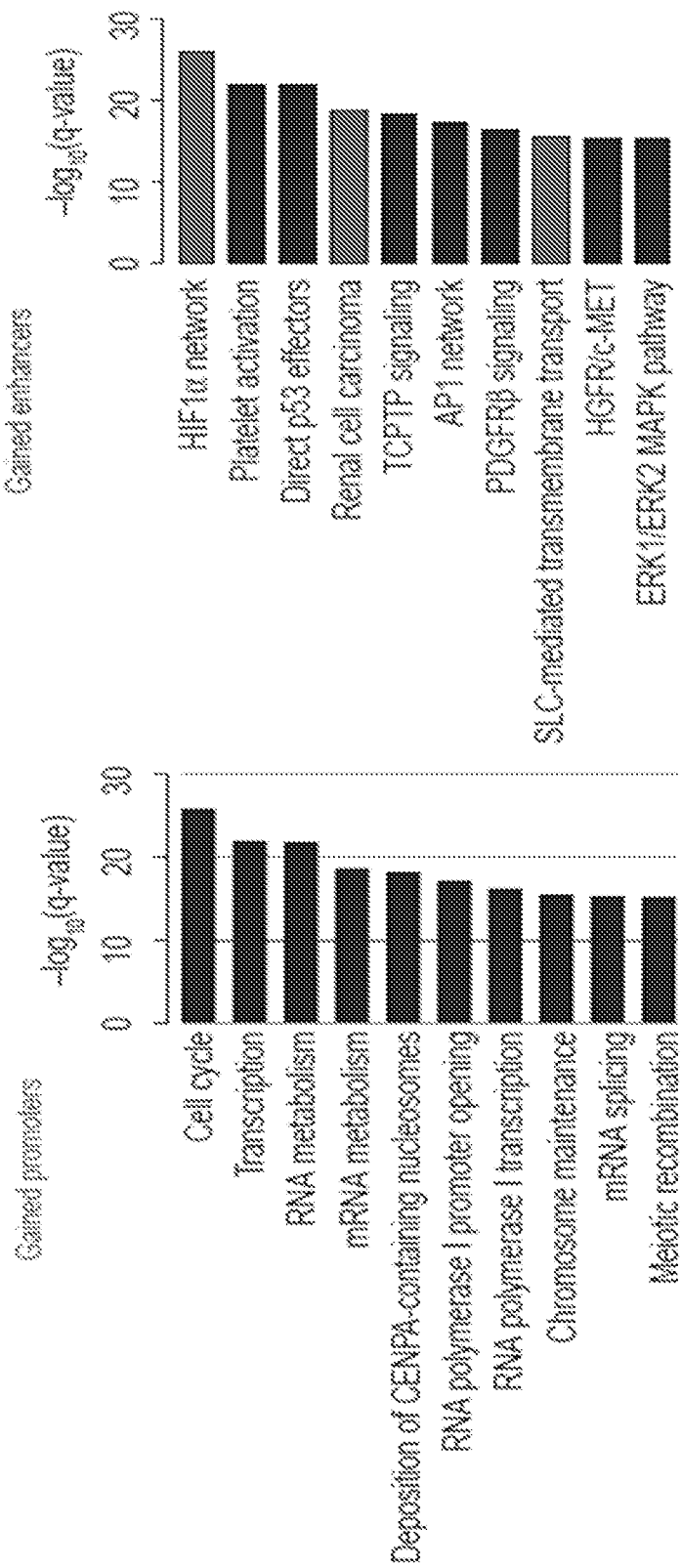
FIG. 2A shows bar graphs of enriched pathways associated with gained promoters and gained enhancers revealed by GREAT algorithm that is ranked by binomial FDR q-value.

Example 3—Tumour-Specific Enhancers are Associated with Hallmarks of Clear Cell Renal Cell Carcinoma To identify genes modulated by the tumour-specific regulatory elements, enhancers were assigned using three approaches. The first approach utilized predefined linear proximity rules involving a set of highly confident genes (GREAT algorithm). MSigDB pathway analysis using GREAT-assigned genes revealed that gained enhancers exhibit a highly significant renal cell carcinoma-specific signature compared with gained promoters (enhancer q-value=$3.2 \times 10^{-26}$; promoter q-value=$1.5 \times 10^{-1}$, binomial FDR; FIG. 2A). Although gained promoters were involved in general cancer processes (for example, cell cycle, transcription, and RNA metabolism) for a complete list of promoter pathways), gained enhancers were enriched in disease-specific features of clear cell renal cell carcinoma, including HIF1α network activity, proangiogenic pathways (platelet activation and PDGFRβ signaling), and SLC-mediated transmembrane transport (FIG. 2A) for a complete list of enhancer pathways). Notably, HIF1α network activity consistently emerged as one of the top five pathways, even with perturbations in the patient thresholds used to define gained enhancers (≥3-8 patients; Table 3).

TABLE 3

HIF pathway as the top pathway with patient thresholds.
FDR stand for false discovery rate.

| Cut-offs | Binomial FDR Rank | Binomial FDR |
|---|---|---|
| ≥3 | 1 | 2.50E−31 |
| ≥4 | 3 | 7.90E−28 |

TABLE 3-continued

HIF pathway as the top pathway with patient thresholds.
FDR stand for false discovery rate.

| Cut-offs | Binomial FDR Rank | Binomial FDR |
|---|---|---|
| ≥5 | 1 | 9.20E−30 |
| ≥6 | 1 | 1.50E−25 |
| ≥7 | 1 | 2.70E−18 |
| ≥8 | 4 | 3.30E−18 |

Figure 2B:
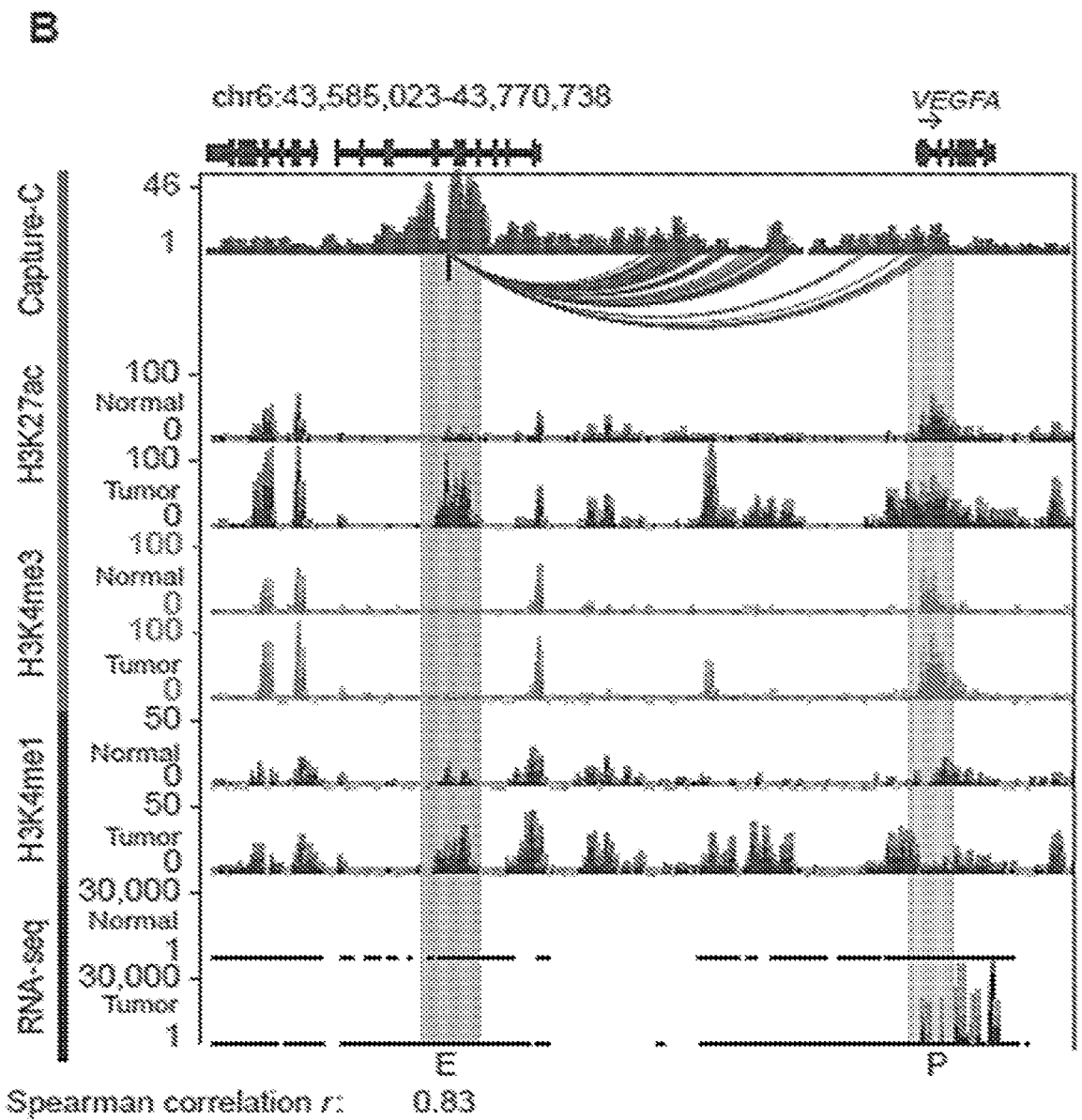
FIG. 2B illustrates a plot that refers to a histone chromatin immunoprecipitation sequencing (ChIP-Seq) profile of VEGFA. De novo enhancers are acquired in a clear cell renal cell carcinoma tumour tissue upstream of VEGFA. Capture-C confirmed interactions of this VEGFA enhancer (E) with its promoter (P) in 786-O cells. The arcs represent significant interactions detected by r3Cseq (q<0.05). The input-subtracted H3K27ac signals of this enhancer are highly correlated with VEGFA gene expression (Spearman's correlation).
Figure 2C:
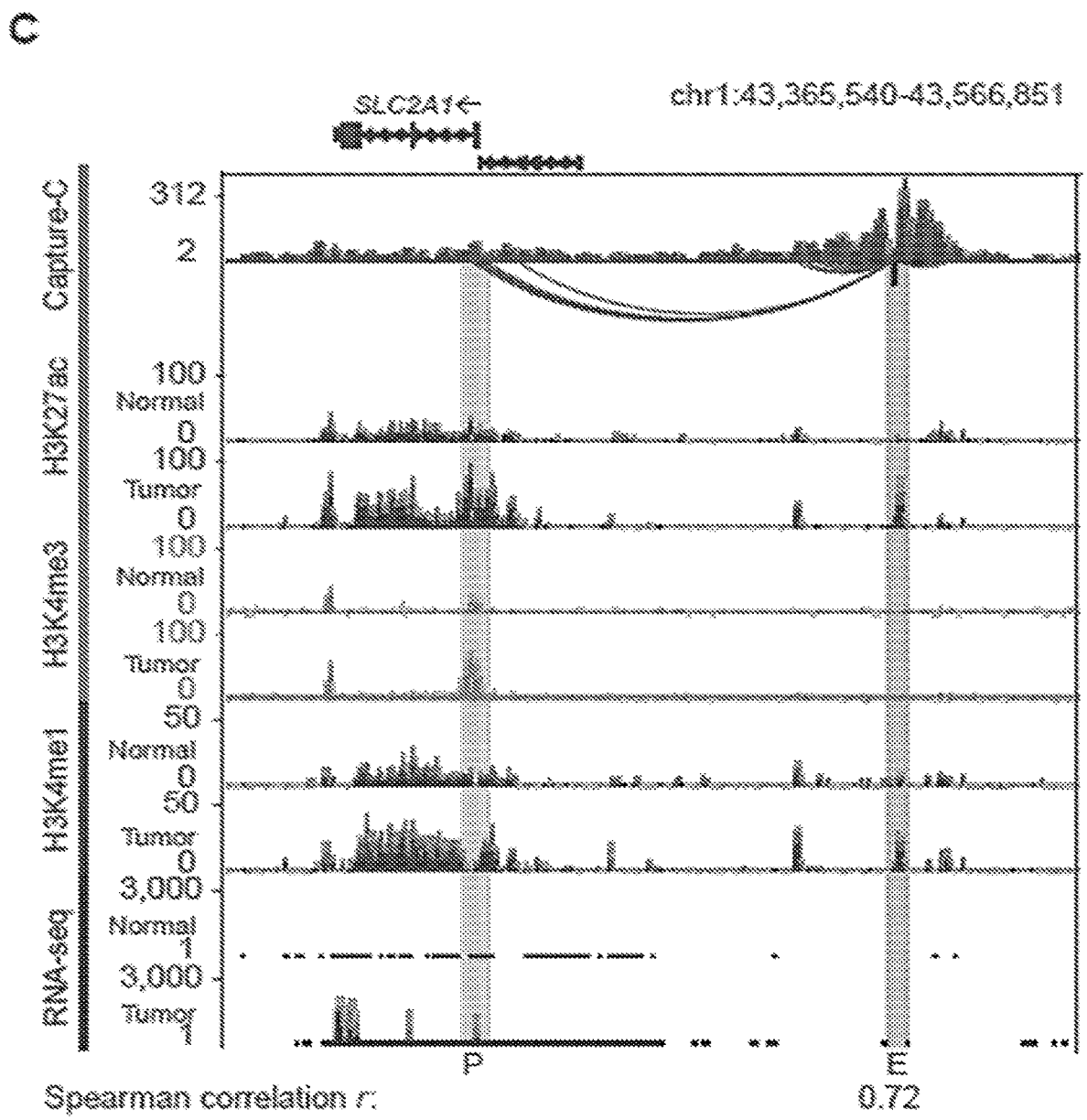
FIG. 2C illustrates a plot that refers to a histone ChIP-Seq profile of SLC2A1/GLUT1. A de novo tumour enhancer interacts with the SLC2A1/GLUT1 promoter.
Figure 2D:
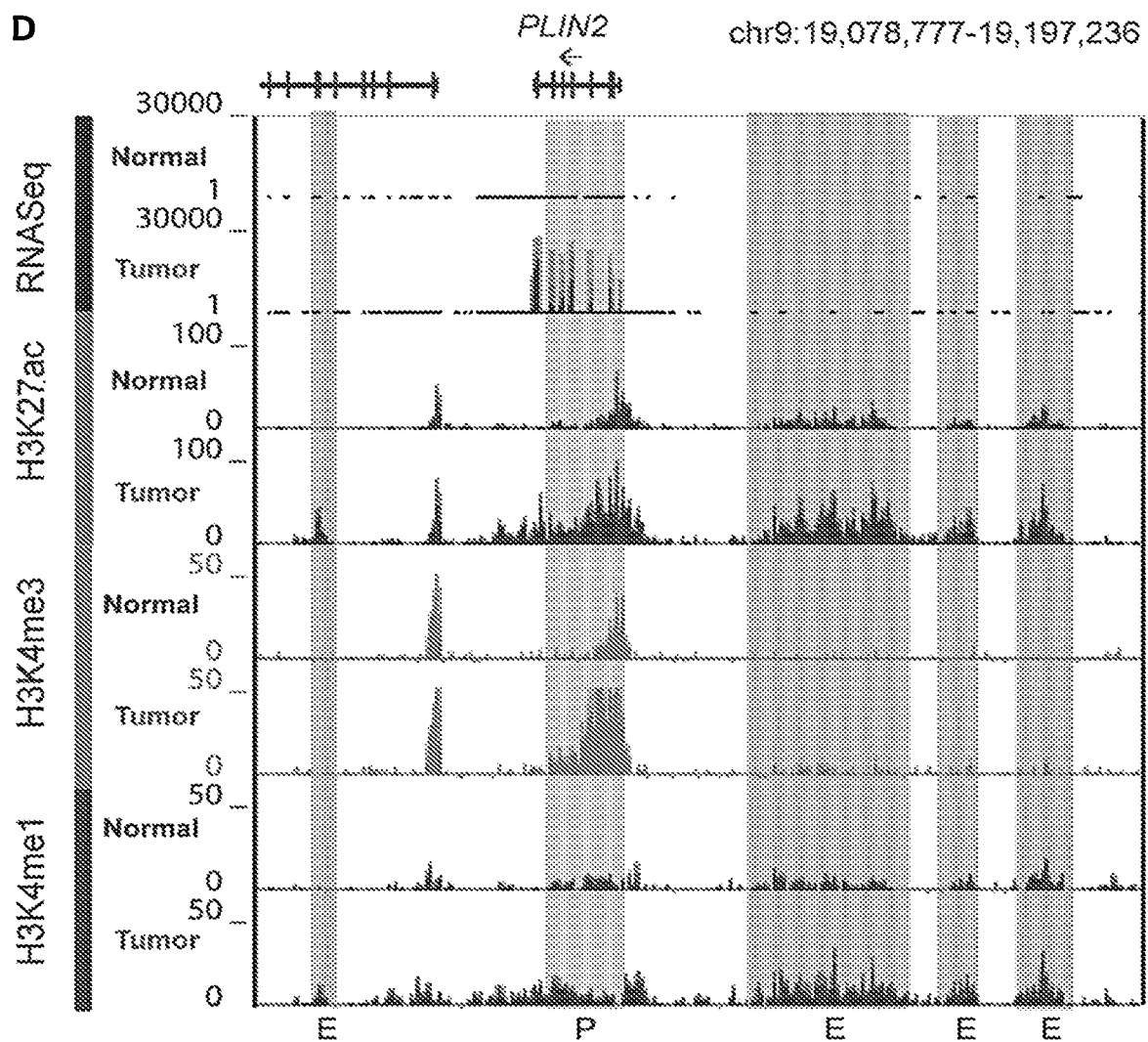
FIG. 2D and FIG. 2E illustrates a plot that refers to a histone ChIP-Seq profile of (D) PLIN2 and (E) SLC38A1, with gain of promoters and enhancers near overexpressed respective clear cell renal cell carcinoma oncogenes PLIN2 and SLC38A1.
Figure 2E:
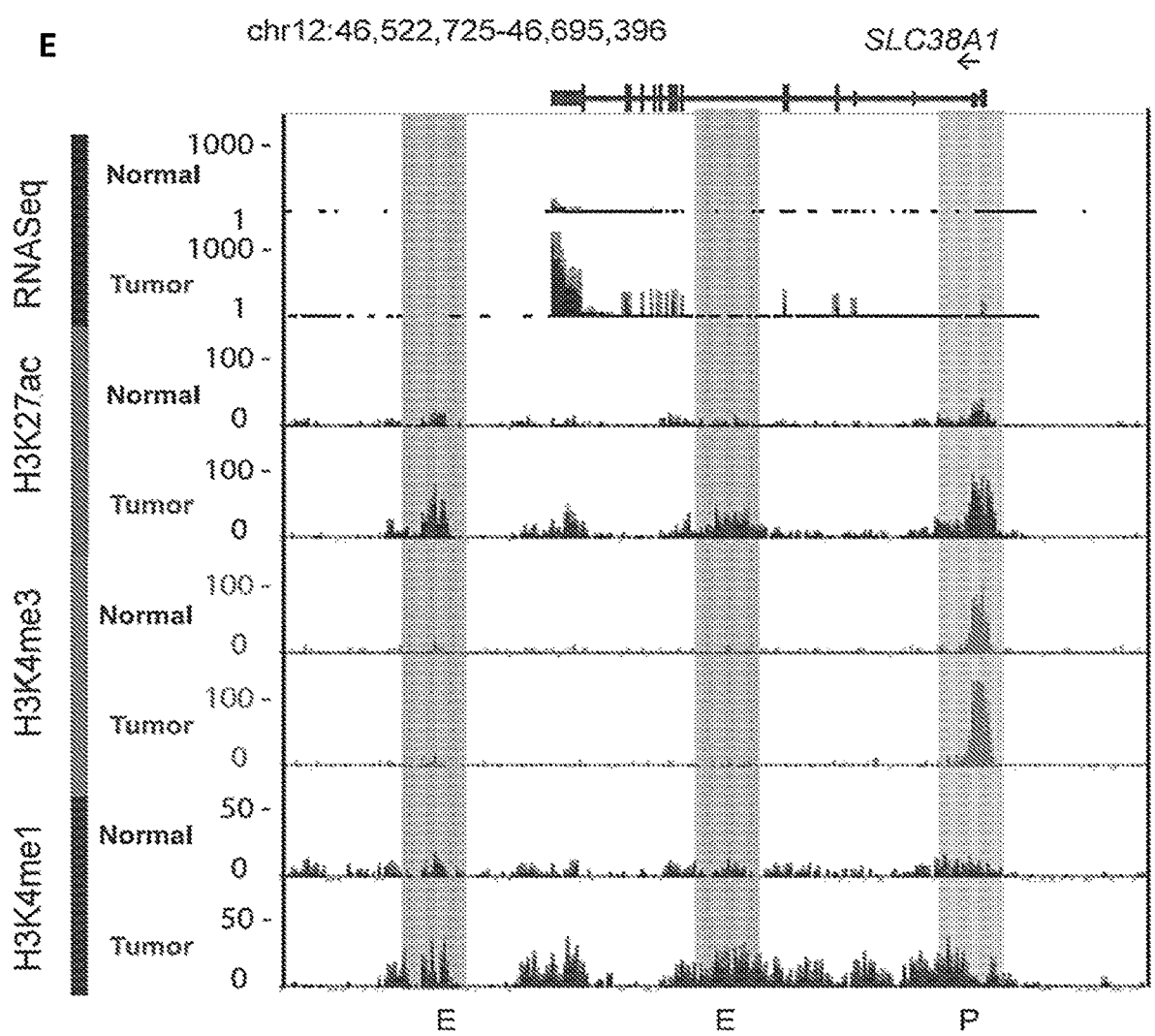
Figure 2F:
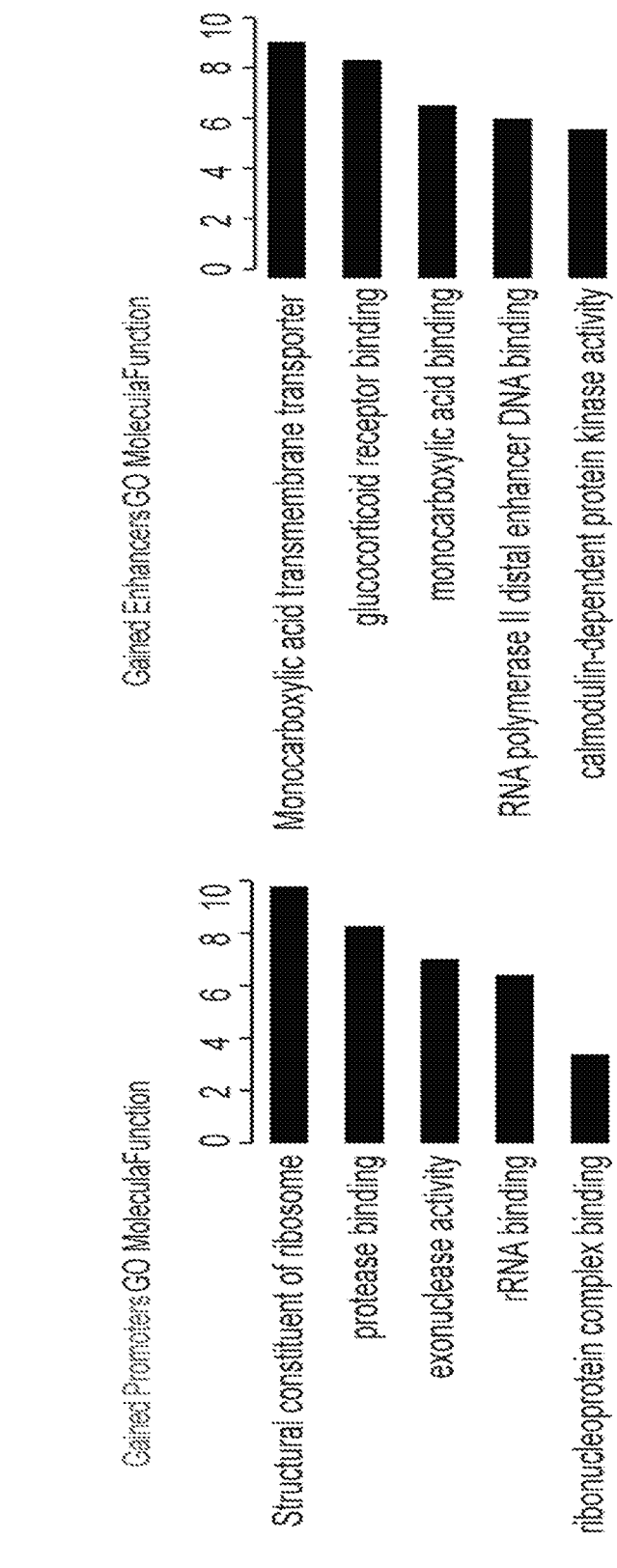
FIG. 2F shows a graph of the top 5 gene ontology Molecular Functions of tumour promoters and enhancers.

Individual genes associated with gained enhancers included well-known hypoxic targets (VEGFA, FIG. 2B; CXCR4) and metabolic genes involved in glycolysis, glutamine intake, and lipid storage (GLUT1/SLC2A1, FIG. 2C; HK2, PFKFB3, PLIN2, FIG. 2D) and SLC38A1 (FIG. 2E). The presence of enhancers around metabolic enzymes and transporters is largely consistent with the metabolic contexture of clear cell renal cell carcinoma, which involves increased glycolysis and glutaminolysis. Indeed, gene ontology (GO) analysis of gained enhancers strongly reflected hallmark metabolic changes associated with clear cell renal cell carcinoma, including monocarboxylic acid transmembrane transporter activity (binomial FDR q-value=$1.6 \times 10^{-10}$; FIG. 2F).

Figure 2G:
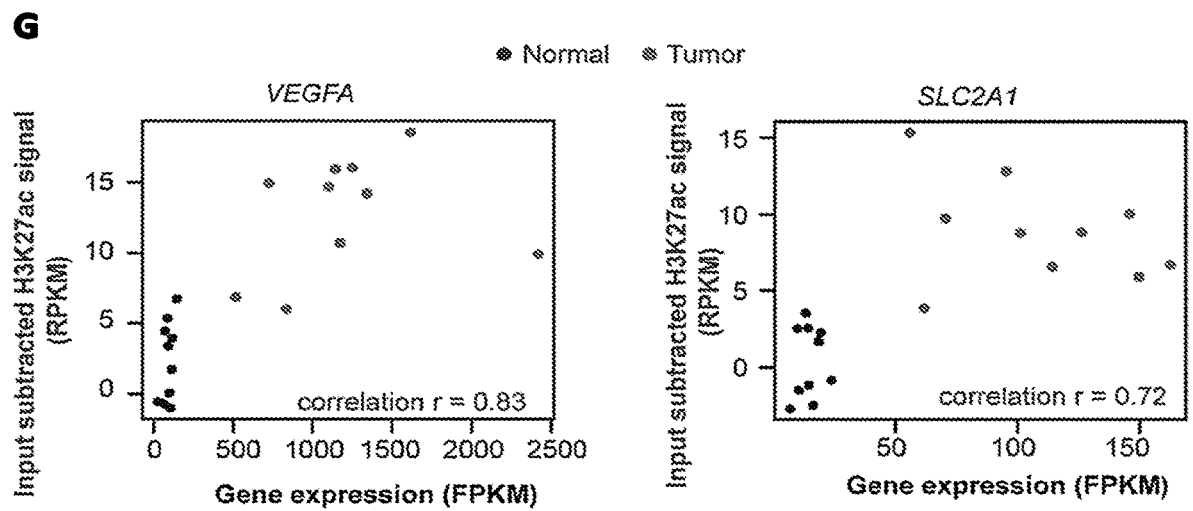
FIG. 2G shows a dot plot referring to Spearman's correlation between gene expression of VEGFA and SLC2A1 and the input subtracted H3K27ac levels of their predicted enhancers in 10 tumour samples and their matched normals.

A second method of enhancer-gene assignment based on correlations between H3K27ac signals and expression of genes within the same topologic associated domain (TAD). Using a q-value of <0.05 based on Spearman correlation, 2,311 gained enhancers were assigned to 2,186 protein-coding targets. H3K27ac signals of many gained enhancers were highly correlated with gene expression of their putative target genes. For example, H3K27ac levels of a VEGFA enhancer exhibited high correlation with VEGFA gene expression (r=0.83, Spearman correlation), whereas H3K27ac signals of an SLC2A1 enhancer were highly correlated with SLC2A1 gene expression (r=0.72, Spearman correlation; FIG. 2B; FIG. 2G). Similar to the GREAT approach, the TAD correlation approach also highlighted hypoxia (Krieg_Hypoxia_not_via_KDM3A, FDR q-value=$7 \times 10^{-120}$) and metabolism (Chen_Metabolic_Syndrome_Network, FDR q-value=$2 \times 10^{-91}$) as highly enriched pathways (Table 4).

TABLE 4

Highly enriched pathways of TAD correlation approach

| Gene Set Name | # Genes in Gene Set (K) | Description |
|---|---|---|
| KRIEG_HYPOXIA_NOT_VIA_KDM3A | 770 | Genes induced under hypoxia independently of KDM3A [GeneID = 55818] in RCC4 cells (renal carcinoma) expressing VHL [GeneID = 7428]. |
| PILON_KLF1_TARGETS_DN | 1972 | Genes down-regulated in erythroid progenitor cells from fetal livers of E13.5 embryos with KLF1 [GeneID = 10661] knockout compared to those from the wild type embryos. |
| PUJANA_ATM_PCC_NETWORK | 1442 | Genes constituting the ATM-PCC network of transcripts whose expression positively correlated (Pearson correlation coefficient, PCC >= 0.4) with that of ATM [GeneID = 472] across a compendium of normal tissues. |

TABLE 4-continued

Highly enriched pathways of TAD correlation approach

| Gene Set Name | # Genes in Gene Set (K) | Description |
| --- | --- | --- |
| CHEN_METABOLIC_SYNDROM_NETWORK | 1210 | Genes forming the macrophage-enriched metabolic network (MEMN) claimed to have a causal relationship with the metabolic syndrom traits. |
| BLALOCK_ALZHEIMERS_DISEASE_UP | 1691 | Genes up-regulated in brain from patients with Alzheimer's disease. |
| RODWELL_AGING_KIDNEY_UP | 487 | Genes whose expression increases with age in normal kidney. |
| PUJANA_BRCA1_PCC_NETWORK | 1652 | Genes constituting the BRCA1-PCC network of transcripts whose expression positively correlated (Pearson correlation coefficient, PCC >= 0.4) with that of BRCA1 [GeneID = 672] across a compendium of normal tissues. |
| DODD_NASOPHARYNGEAL_CARCINOMA_DN | 1375 | Genes down-regulated in nasopharyngeal carcinoma (NPC) compared to the normal tissue. |
| MARSON_BOUND_BY_E2F4_UNSTIMULATED | 728 | Genes with promoters bound by E2F4 [GeneID = 1874] in unstimulated hybridoma cells. |
| NUYTTEN_EZH2_TARGETS_UP | 1037 | Genes up-regulated in PC3 cells (prostate cancer) after knockdown of EZH2 [GeneID = 2146] by RNAi. |

Figure 2H:
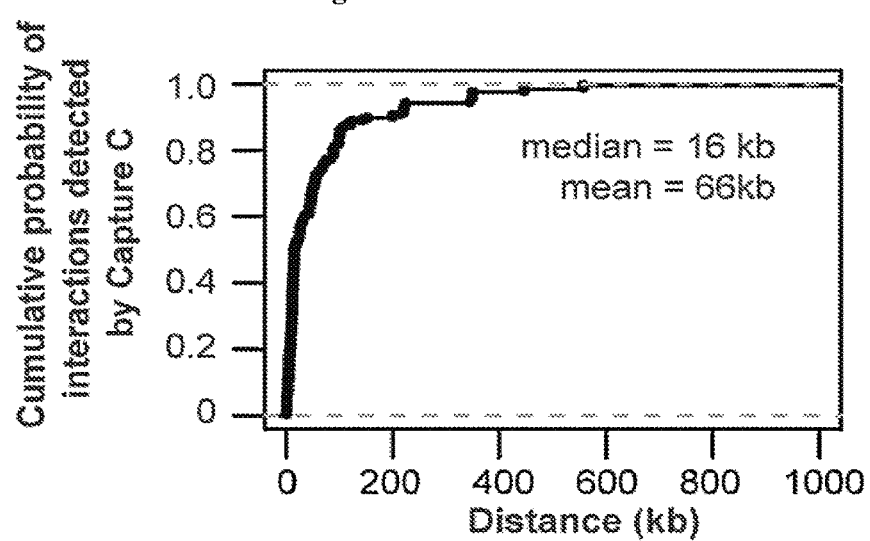
FIG. 2H shows a graph referring to the cumulative distribution of distance spanned by significant Capture C interactions.

Third, to independently validate the GREAT and TAD approaches in the specific context of clear cell renal cell carcinoma, the interactome of clear cell renal cell carcinoma tumour-specific enhancers was studied by performing Capture-C assays. Compared with other chromatin capture techniques, Capture-C offers both high-resolution (down to single Kb resolution) and high-throughput interrogation of user-defined regions (a usual working range of 10-500 regions). Probes were designed against a subset of 56 gained enhancers and examined their interactions with protein-coding genes in 786-O cells. Each gene-enhancer pair revealed by Capture-C was further filtered by correlations between gene expression and H3K27ac levels (q-value <0.05). The 56 gained enhancers were paired with 36 protein-coding genes. 58% of these were predicted by GREAT, and 80% by gene correlations within TADs. The median distance of interactions detected by Capture-C was 16 kb, and 83% of the interactions fell within a 100-kb window (FIG. 2H). As a visual example, Capture-C confirmed interactions between VEGFA enhancer and the VEGFA TSS, spanning a distance of about 100 kb (FIG. 2B), and interactions between the SLC2A1 enhancer and its promoter (FIG. 2C). Taken collectively, these findings highlight the disease-specific nature of enhancer elements and an important role for enhancer malfunction in modulating clear cell renal cell carcinoma pathology.

Example 4—Tumour Super-Enhancers Identify ZNF395 as a Master Regulator of Clear Cell Renal Cell Carcinoma Tumourigenesis The importance of enhancers in clear cell renal cell carcinoma led to this study to examine the landscape of "superenhancers" or "stretch-enhancers"—dense clusters of enhancers located near master regulators of cell identity and disease. Using ROSE, 1,451 superenhancers were identified in the clear cell renal cell carcinoma cohort, of which 1,157 were gained in tumours and 294 were lost in tumours.

Putative targets of top gained superenhancers validated well-known oncogenes including MYC/PVT1, VEGFA, and HIF2A (FIGS. 3A, 3B and 3C). In addition, several less-known genes were found including ERG/C1, ZNF395, SLC28A1, and SMPDL3A (FIG. 3D). These genes were highly overexpressed in tumours compared with their matched normal tissues (FIG. 3D). Furthermore, they were unique to clear cell renal cell carcinoma and were not overexpressed in papillary and chromophobe renal cell carcinomas, two other distinct clear cell renal cell carcinoma subtypes (FIG. 3D). For instance, ZNF395 exhibited a tumour-normal ratio of about 7 in clear cell renal cell carcinoma ($P=1\times10^{-22}$, paired t test) but experienced little overexpression in papillary and chromophobe renal cell carcinoma with tumour-normal ratios of 1.2 and 1.3, respectively ($P=0.02$ in papillary and $P=0.06$ in chromophobe, paired t test).

Conversely, genes associated with lost super-enhancers were recurrently suppressed in clear cell renal cell carcinoma and included EFHD1, EHF, MAL, GCOM1, and HOXB9 (FIG. 3D). In contrast to the lineage-specific nature of tumour super-enhancers, genes associated with lost super-enhancers were common between clear cell renal cell carcinoma and papillary renal cell carcinoma, implying a more universal function of tumour suppressor genes. For example, EHF/ESE2, a tumour suppressor previously found in prostate cancer, exhibited reduced expression across all three renal cell carcinoma subtypes (clear cell renal cell carcinoma tumour/normal=0.05, $P=3\times10^{-15}$; papillary tumour/normal=0.1, $P2\times10^{-6}$; chromophobe tumour/normal=0.1, $P=2\times10^{-6}$)

Since current therapeutic targets in kidney cancer are limited to angiogenesis and mTOR pathways, less-understood genes uncovered by superenhancer profiling were examined. ZNF395 and SMPDL3A were chosen for their differential tumour expression (6-7 tumour-normal ratio; FIG. 3D) and high abundance (average RPKM of ZNF395 about 112; average RPKM of SMPDL3A about 58). Even though ZNF395 was previously identified as a potential clear cell renal cell carcinoma biomarker, its functional role in clear cell renal cell carcinoma malignancy remains unexplored. SMPDL3A shares 31% amino acid identity with the acid sphingomyelinase SMPD1 and is a target of a master regulator of cholesterol metabolism, liver X receptors (LXR).

Figure 3G:
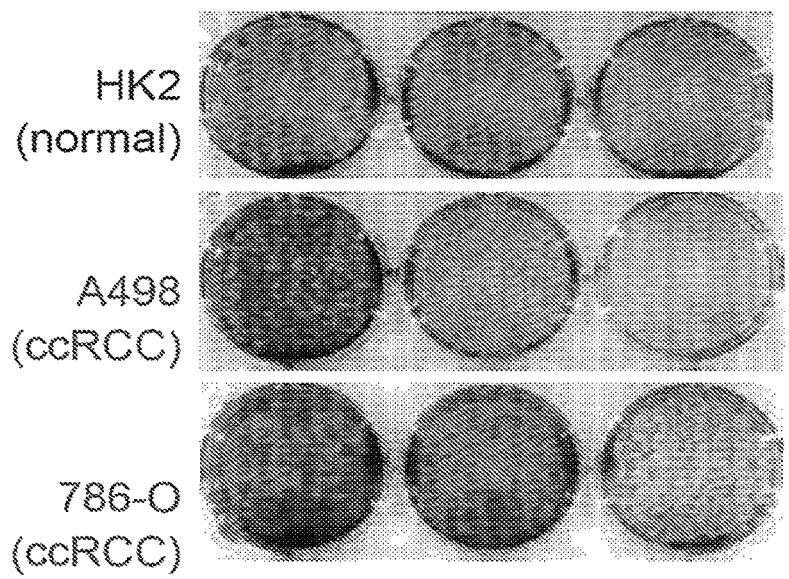
FIG. 3G refers to images that indicate pooled siRNA against ZNF395 inhibits colony formation of clear cell renal cell carcinoma cell lines A-498 and 786-O but not HK-2 normal immortalized kidney cells. Pooled siRNA against SMPDL3A inhibits colony formation of A-498 but not 786-O.
Figure 3H:
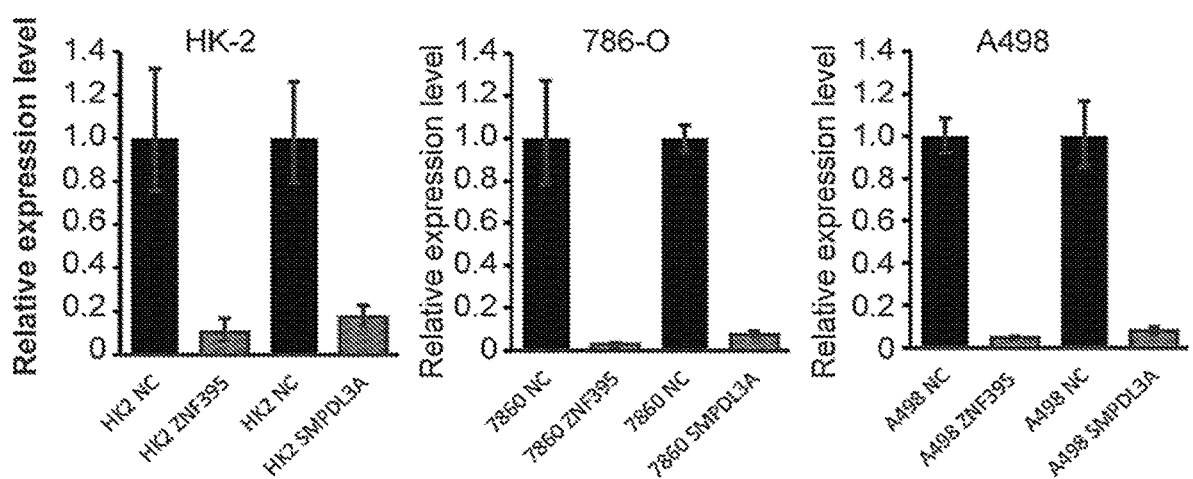
FIG. 3H shows a graph of siRNA knockdown efficiency of SMPDL3A and ZNF395 as measured by real time PCR (RT-qPCR) in HK-2, 786-O and A498 cells.
Figure 3I:
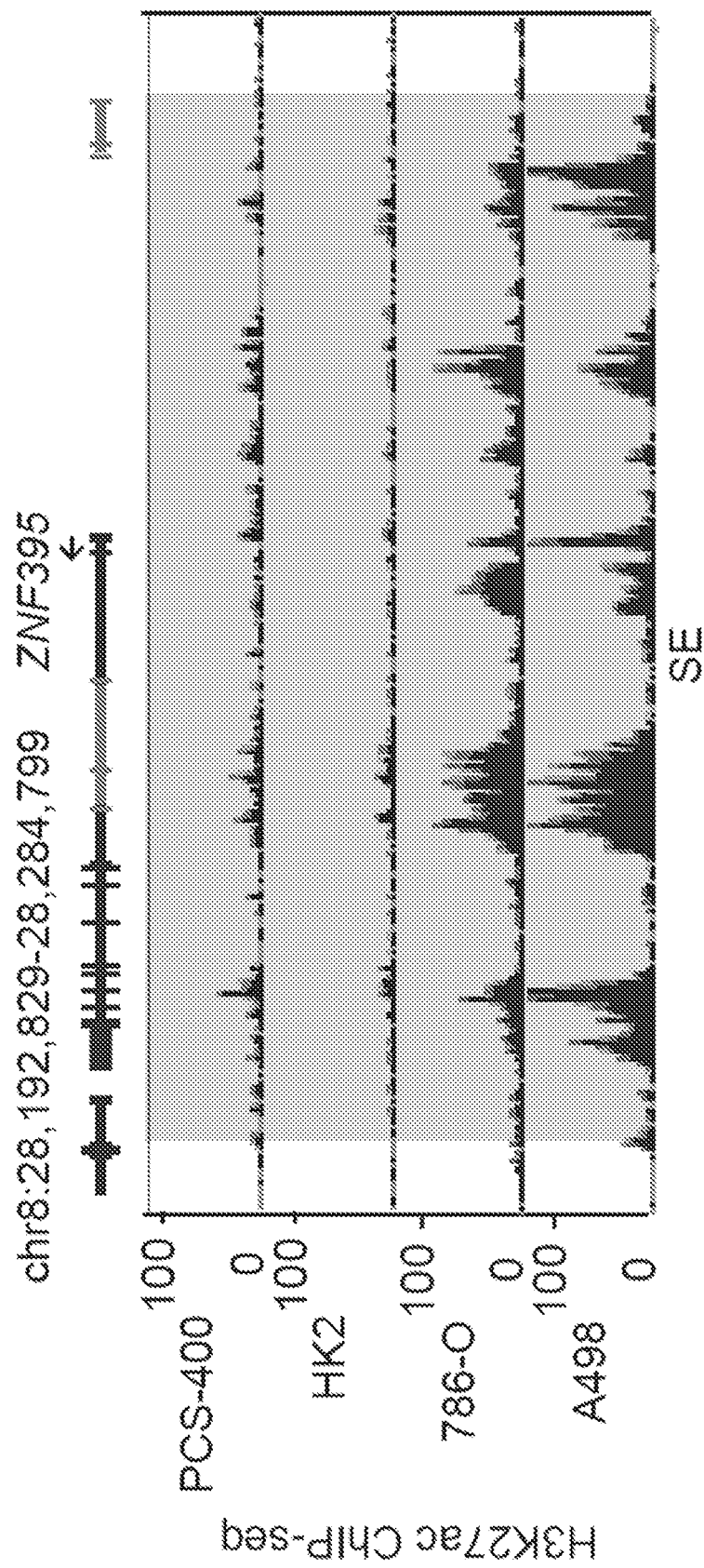
FIG. 3I refers to a plot of histone ChIP profile with H3K27ac ChIP-seq showing an active ZNF395 super-enhancer only in clear cell renal cell carcinoma cells (A-498 and 786-O) but not normal kidney cells (PCS-400, HK-2).
Figure 3J:
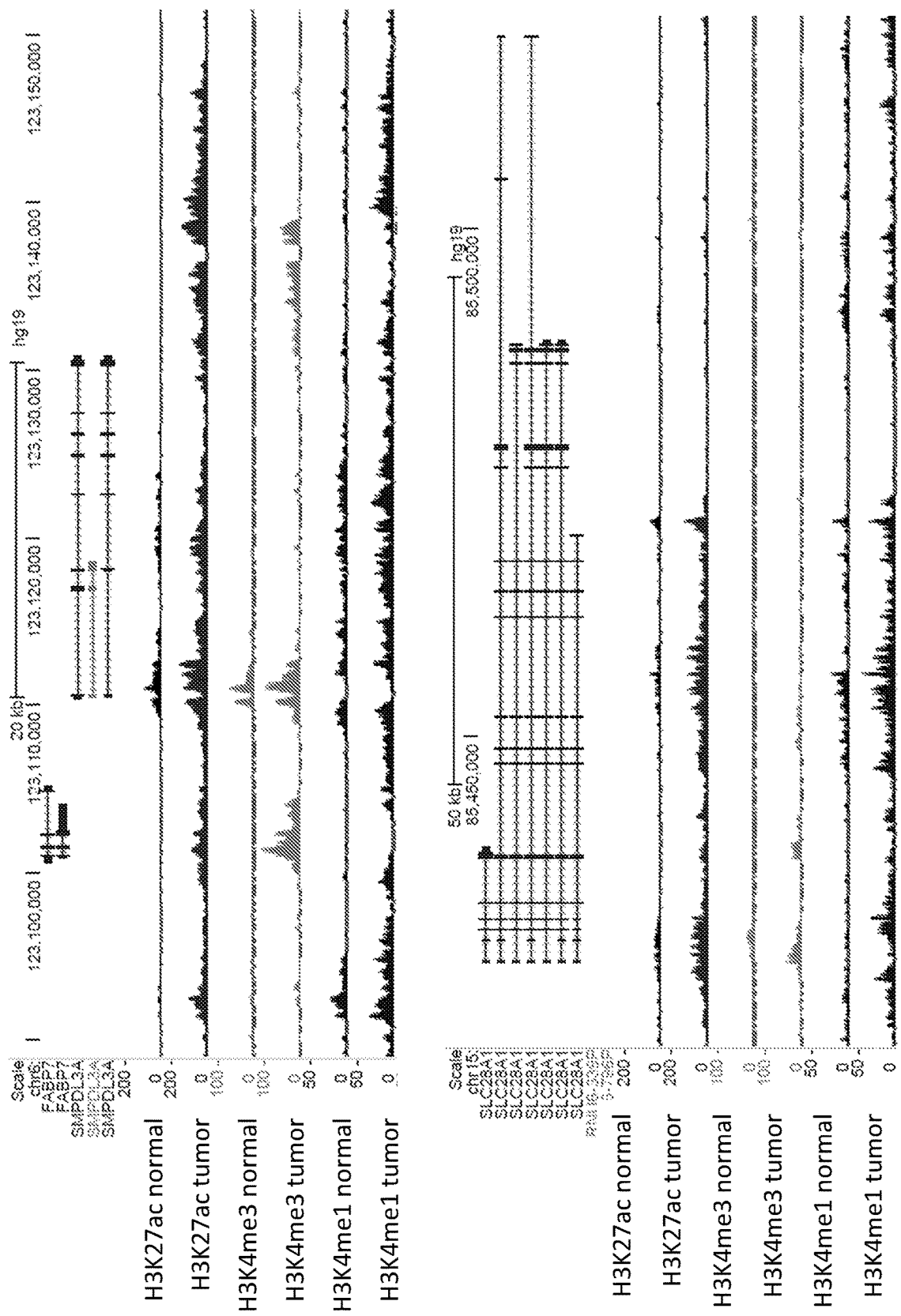
FIG. 3J refers to plots of histone ChIP profile with H3K27ac and H3K4me3 ChIP-seq of tumour/normal pair showing that SMPLD3A or SLC28A1 is associated with a clear cell renal cell carcinoma specific super enhancer.
Figure 3K:
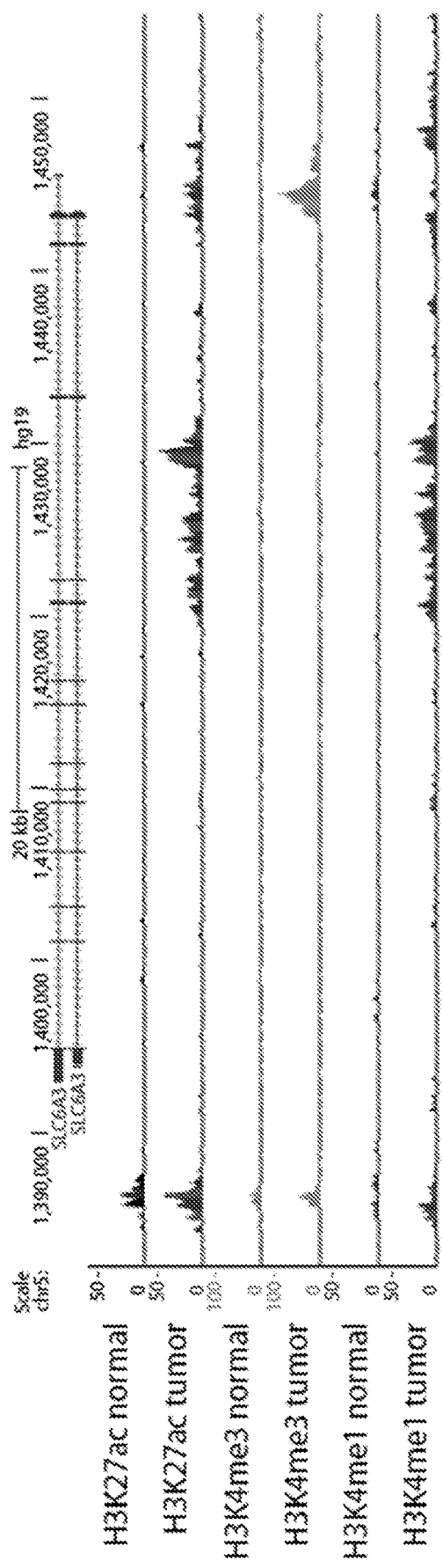
FIG. 3K (FIGS. 3Ki, 3Kii and 3Kiii) refers to a plot of histone ChIP-seq profile with H3K27ac, H3K4me3 and H3K4me1 ChIP-seq of tumour/normal pair showing the gain of promoters and enhancers in tumours for genes SLC6A3, EGLN3 or VEGFA.
Figure 3L:
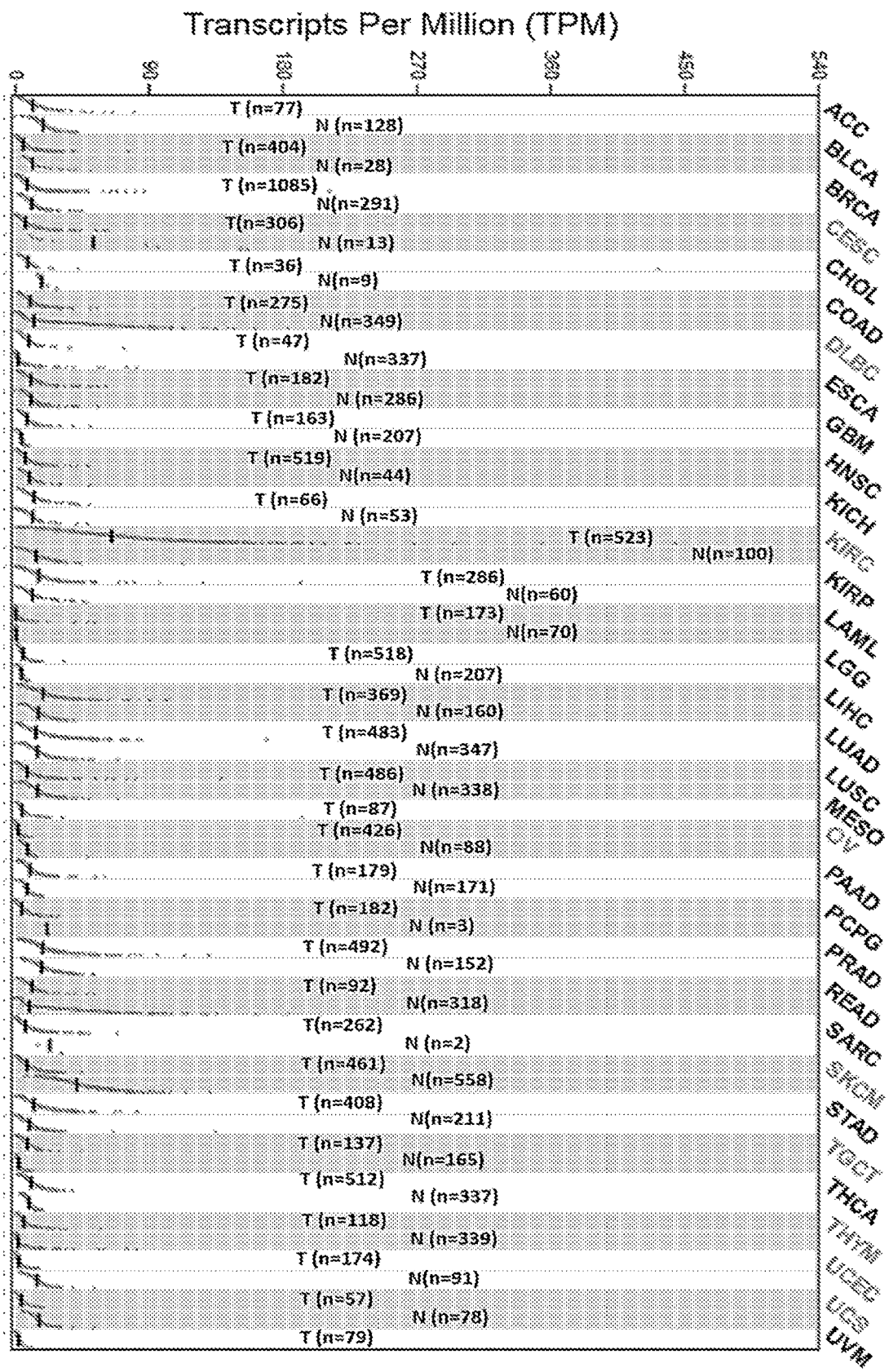
FIG. 3L to FIG. 3P refers to graphs showing expression data obtained from The Cancer Genome Atlas (TCGA).
Figure 3M:
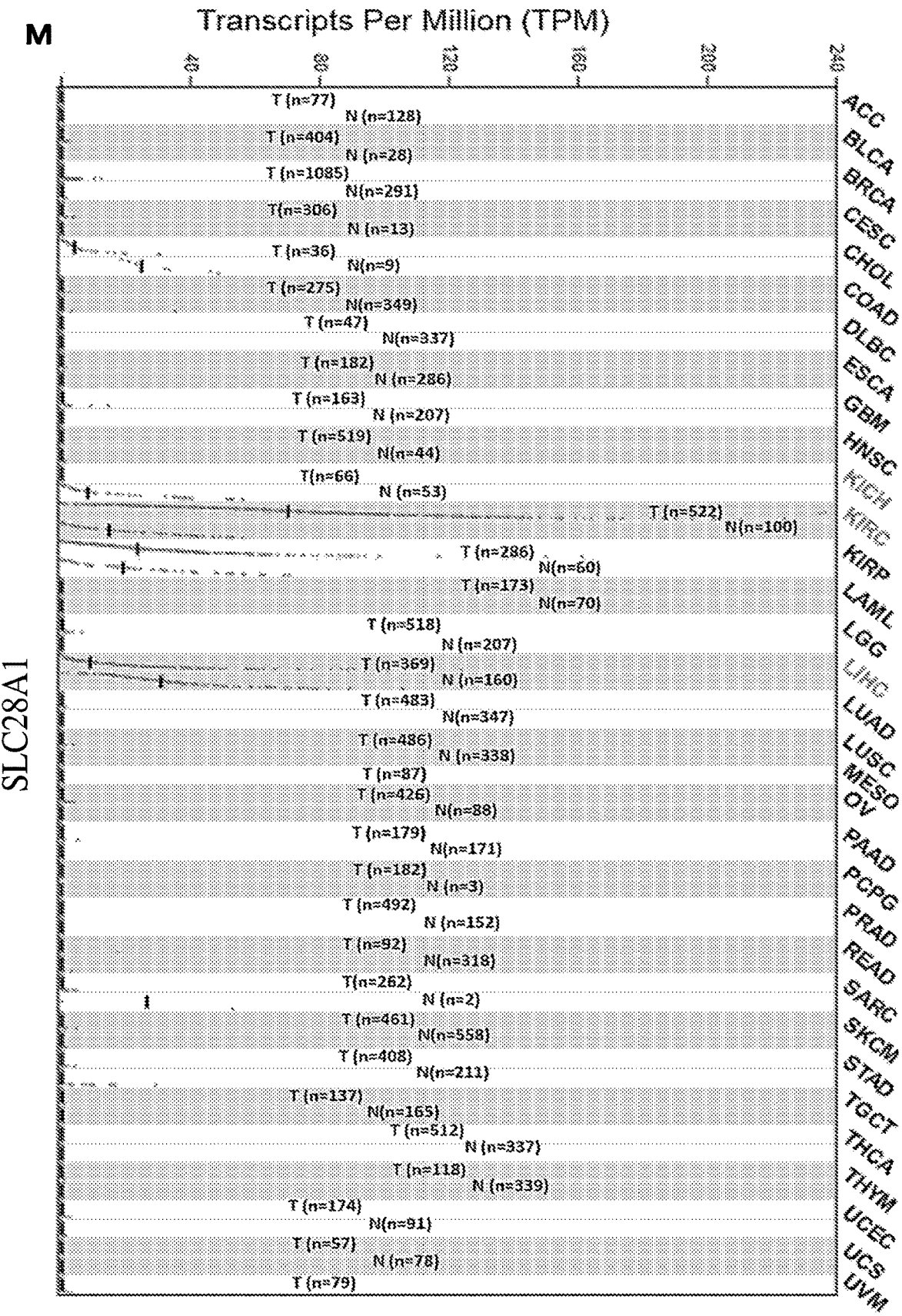
Figure 3N:
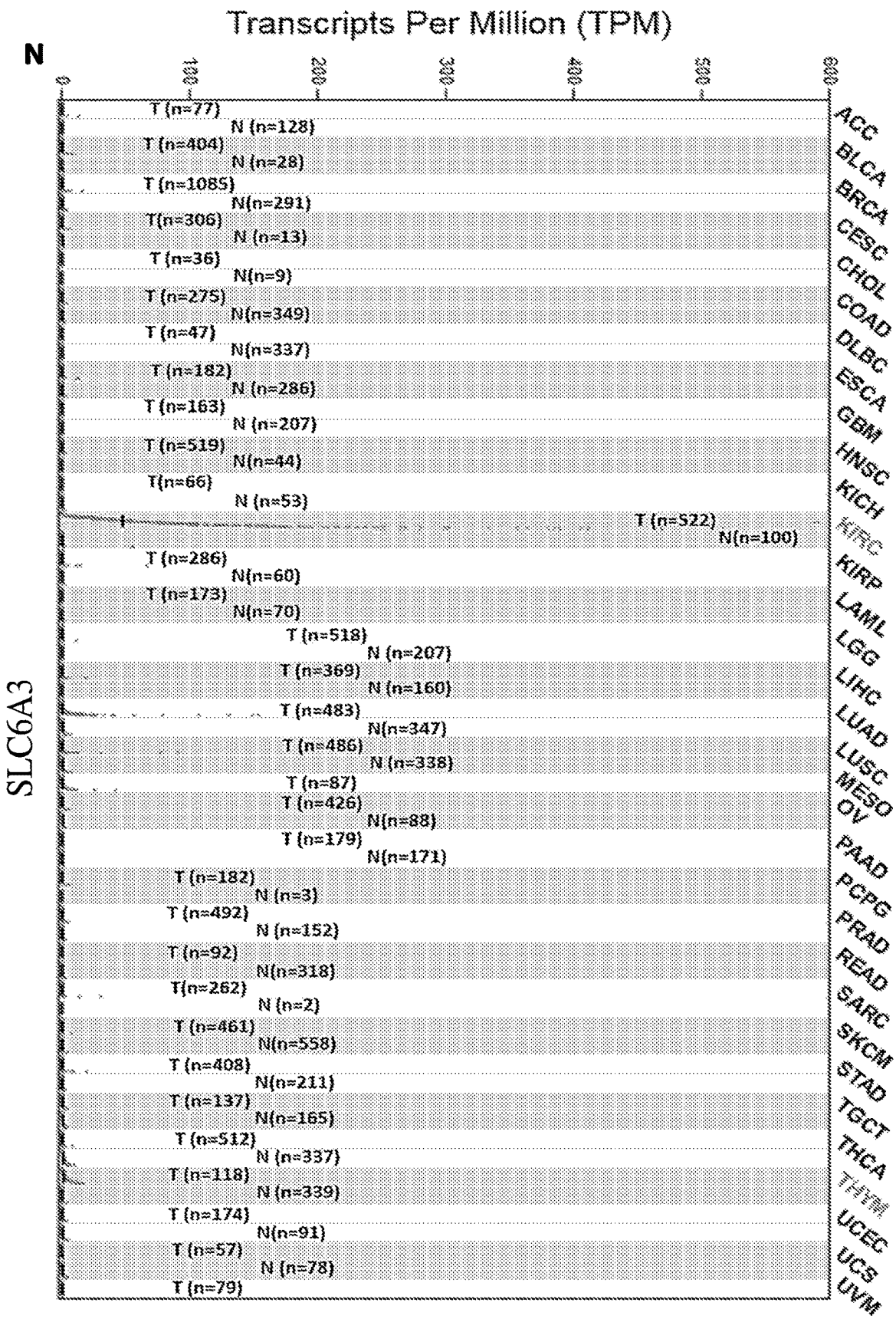
Figure 3O:
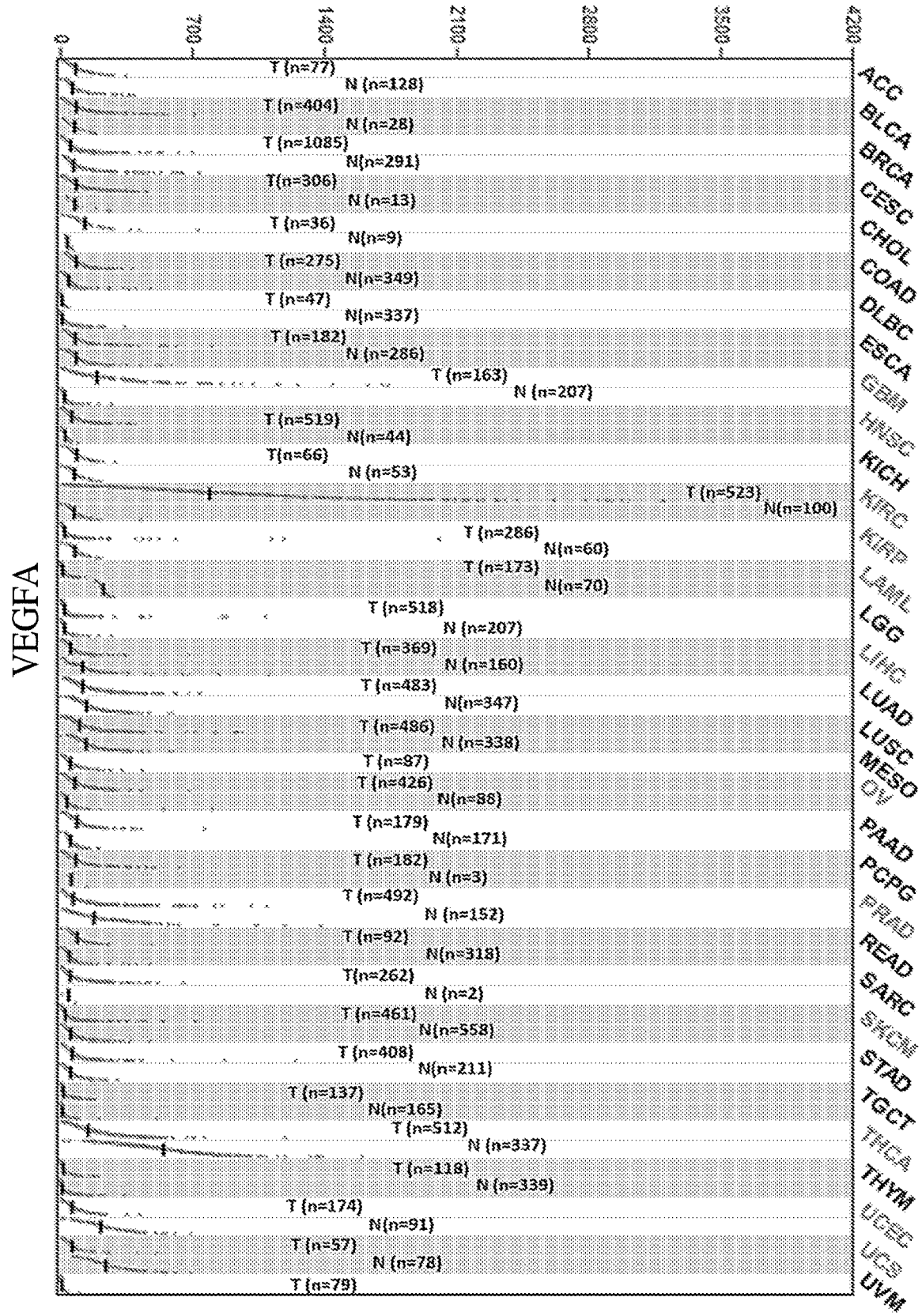
Figure 3P:
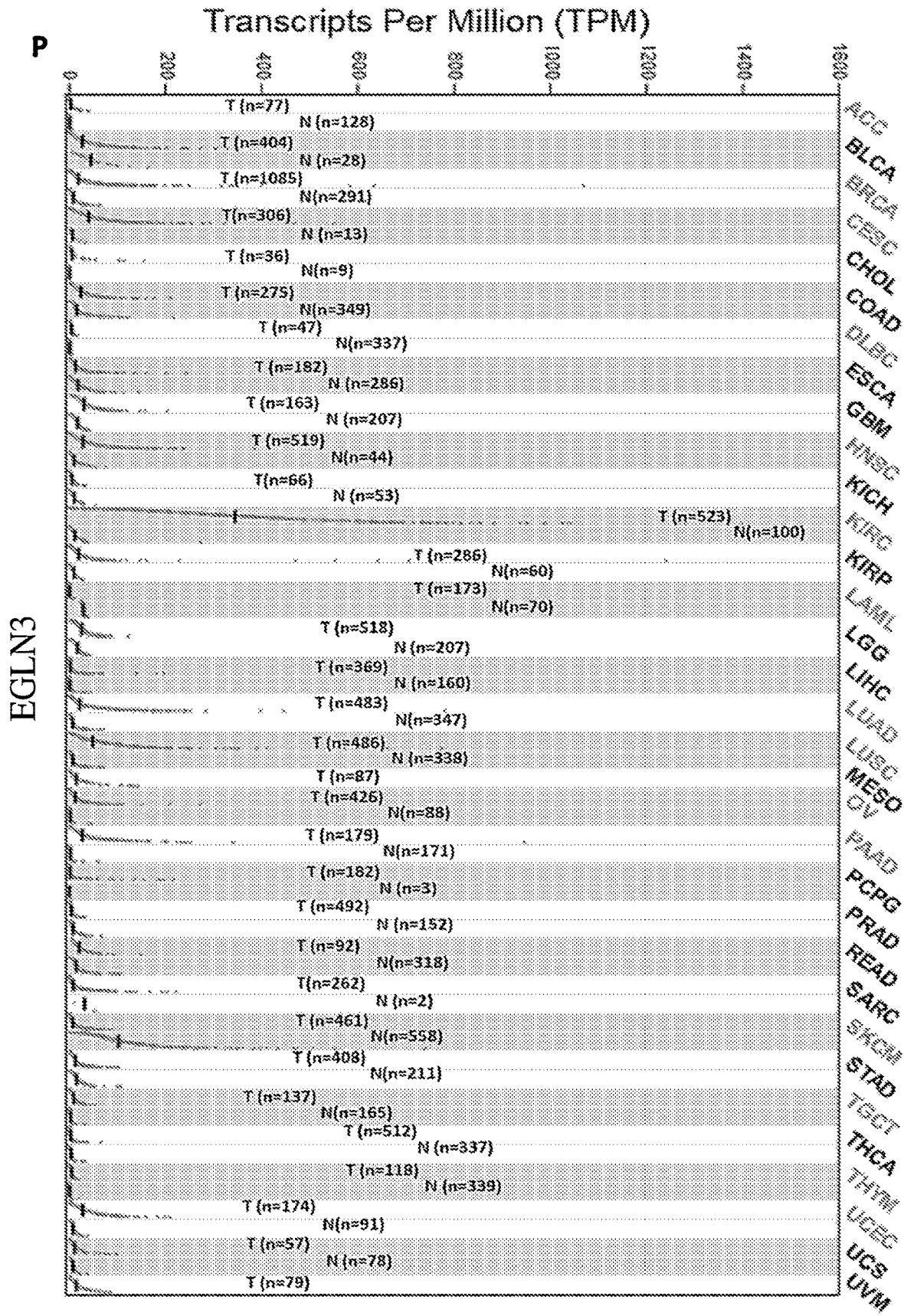
Figure 3Q:
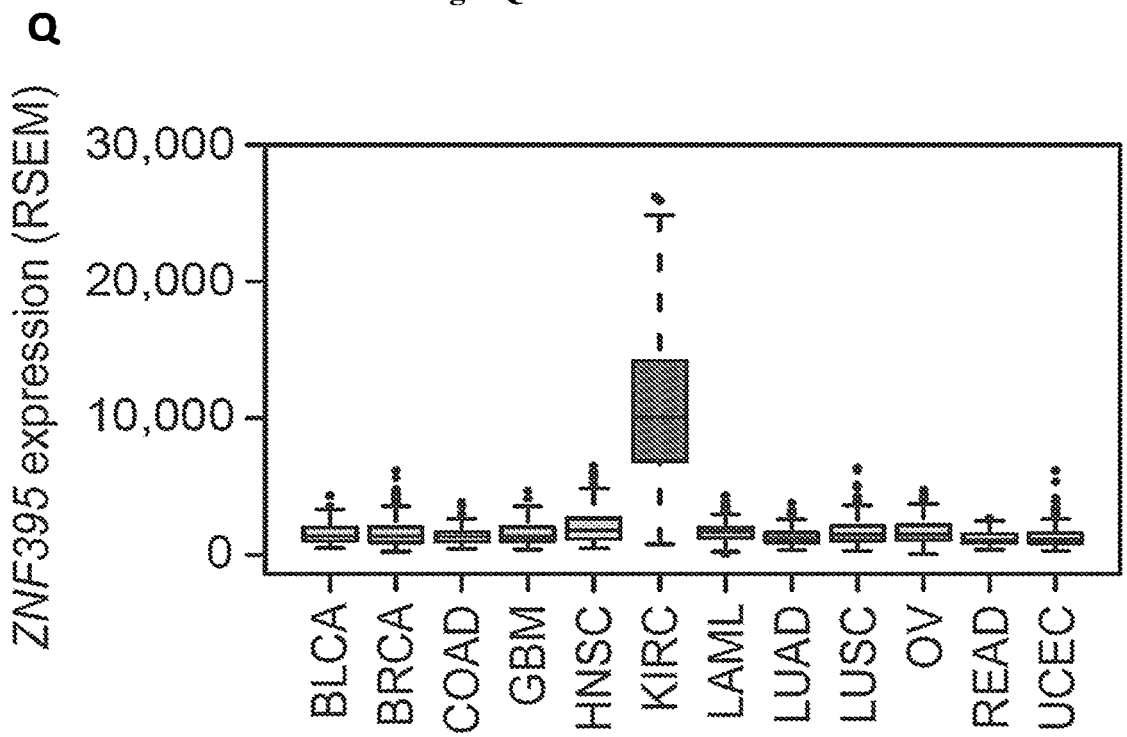
FIG. 3Q refers to a box plot with The Cancer Genome Atlas (TCGA) RNA-seq data that shows exclusive overexpression of ZNF395 amongst 12 cancer types.

Quantitative PCR (FIG. 3E) and immunoblotting (FIG. 3F) confirmed that A-498 and 786-O clear cell renal cell carcinoma cells exhibited high expression of ZNF395 and SMPDL3A, whereas normal kidney proximal tubule cells, PCS-400 and HK2, exhibited low expression of both genes. siRNA mediated knockdown of SMPDL3A had a cell line-dependent effect on colony formation, inhibiting the growth of A-498 cells but having no observable effect on 786-O cells (FIG. 3G). On the other hand, ZNF395 consistently inhibited colony formation in both 786-O and A-498 cells but had minimal effect on normal kidney cells (FIG. 3G, FIG. 3H). Consistent with this phenotypic observation, the ZNF395 super-enhancer was active only in clear cell renal cell carcinoma cells (786-O and A-498) but silent in normal kidney cells (HK2 and PCS-400; FIG. 3I). SMPDL3A and SLC28A1 (FIG. 3J) are also shown to be associated with a clear cell renal cell carcinoma-specific super-enhancer. SLC6A3, EGLN3 and VEGFA shows gain in promoters and enhancers in the tumour sample as compared to the normal (non-diseased) sample (FIGS. 3Ki, 3Kii and 3Kiii). Furthermore, among the 33 types of cancer profiled by The Cancer Genome Atlas (TCGA), SMPDL3A (FIG. 3L), SLC28A1 (FIG. 3M), SLC6A3 (FIG. 3N), VEGFA (FIG. 3O), EGLN3 (FIG. 3P), ZNF395 (FIG. 3Q—only 12 cancer types profiled) are also shown to be highly expressed in clear cell renal cell carcinoma tumours (KIRC) from The Cancer Genome Atlas (TCGA) data.

Figure 3R:
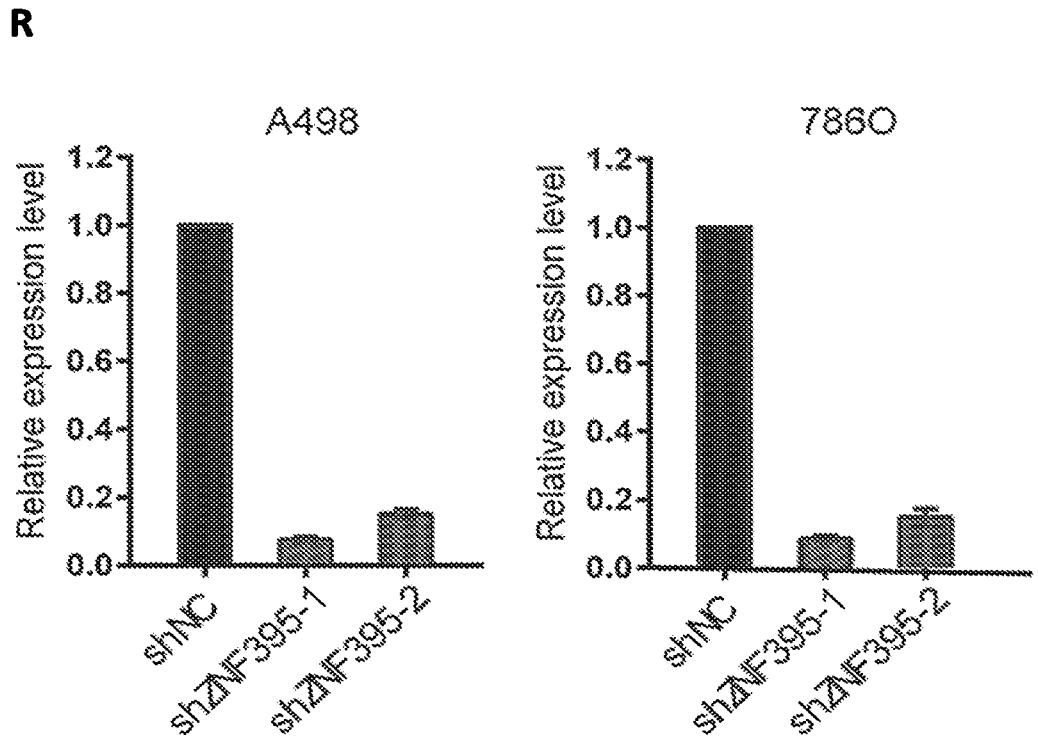
FIG. 3R shows a graph referring to shRNA knockdown efficiency of ZNF395 levels measured by reverse transcription polymerase chain reaction (RT-PCR) in 786-O and A-498 cells.
Figure 3S:
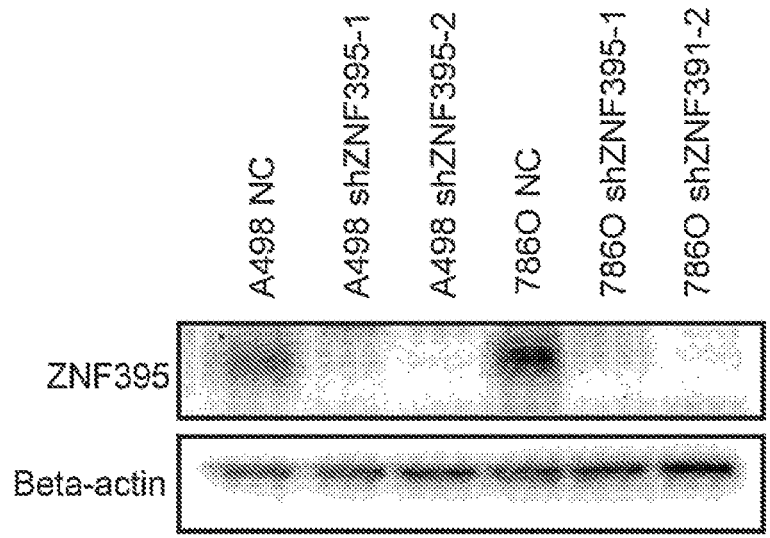
FIG. 3S illustrates an immunoblot referring to shRNA knockdown efficiency of ZNF395 levels measured by immunoblotting in 786-O and A-498 cells.
Figure 3T:
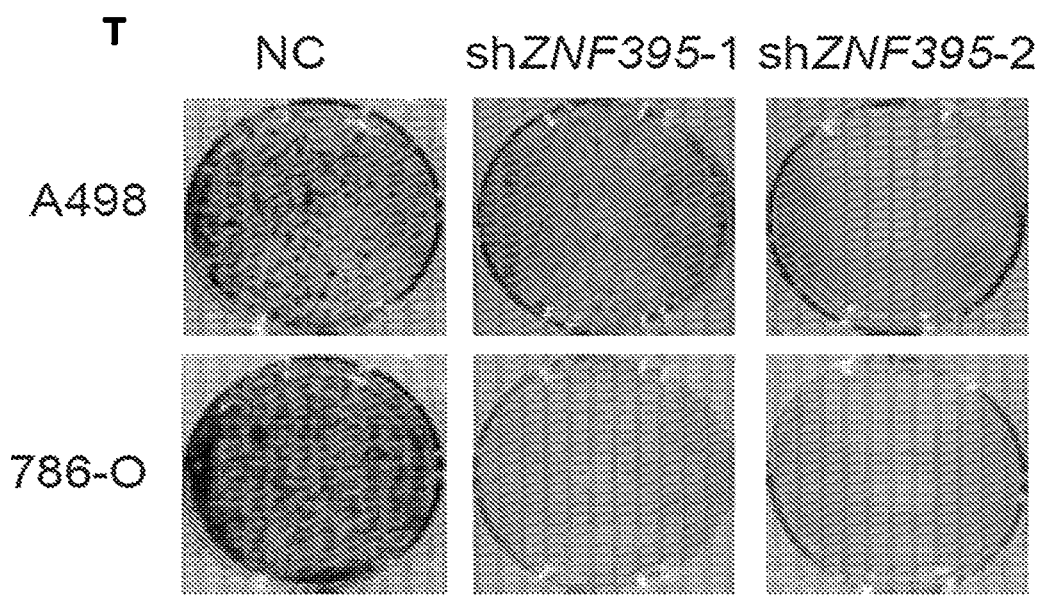
FIG. 3T shows images of ZNF395 inhibition by two shRNA clones that decrease colony formation in 786-O and A-498 cells.
Figure 3U:
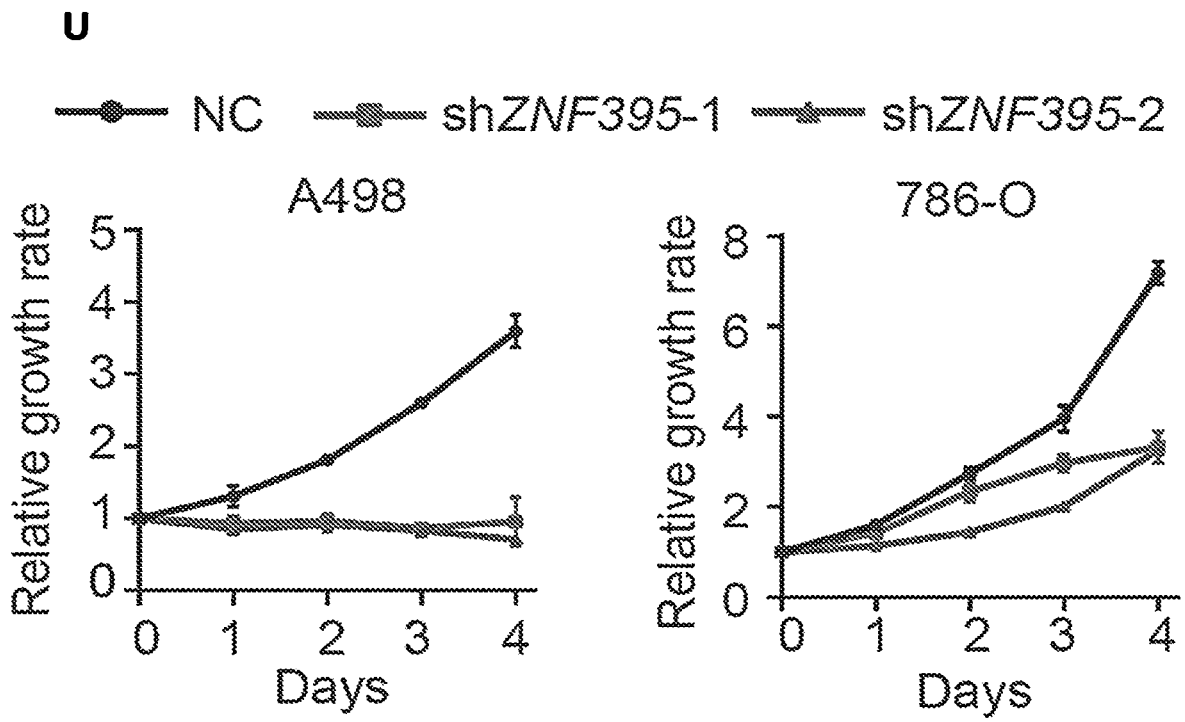
FIG. 3U refers to graphs of ZNF395 inhibition by two shRNA clones that decrease in vitro proliferation.
Figure 3V:
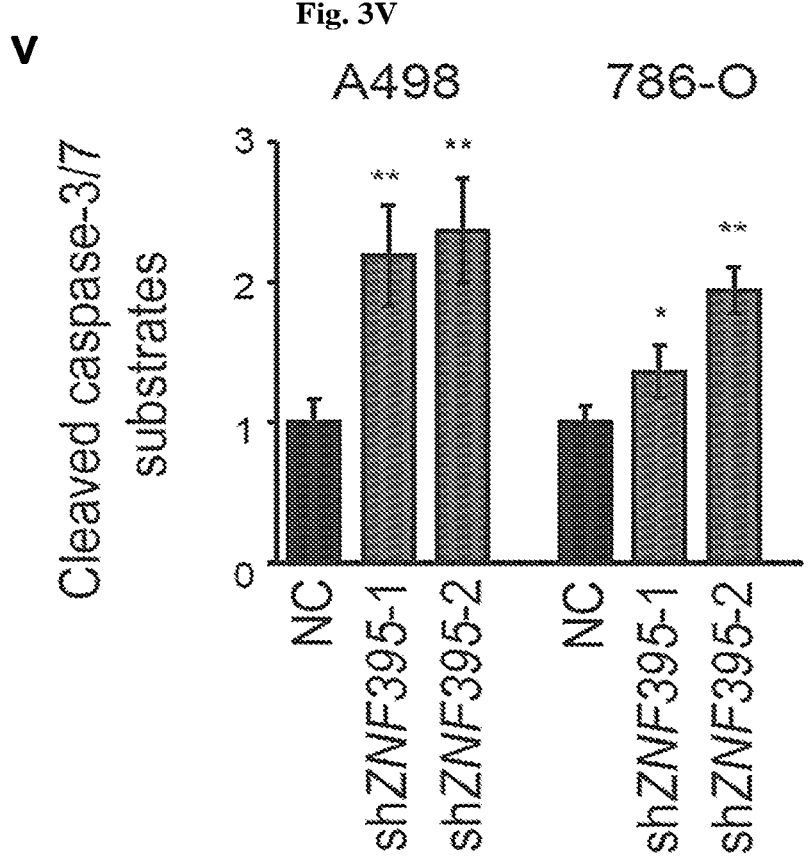
FIG. 3V shows a graph of ZNF395 inhibition by two shRNA clones that increases apoptosis measured by cleavage of Caspase3/7 substrate. *p-value <0.05, two-sided t-test.
Figure 3W:
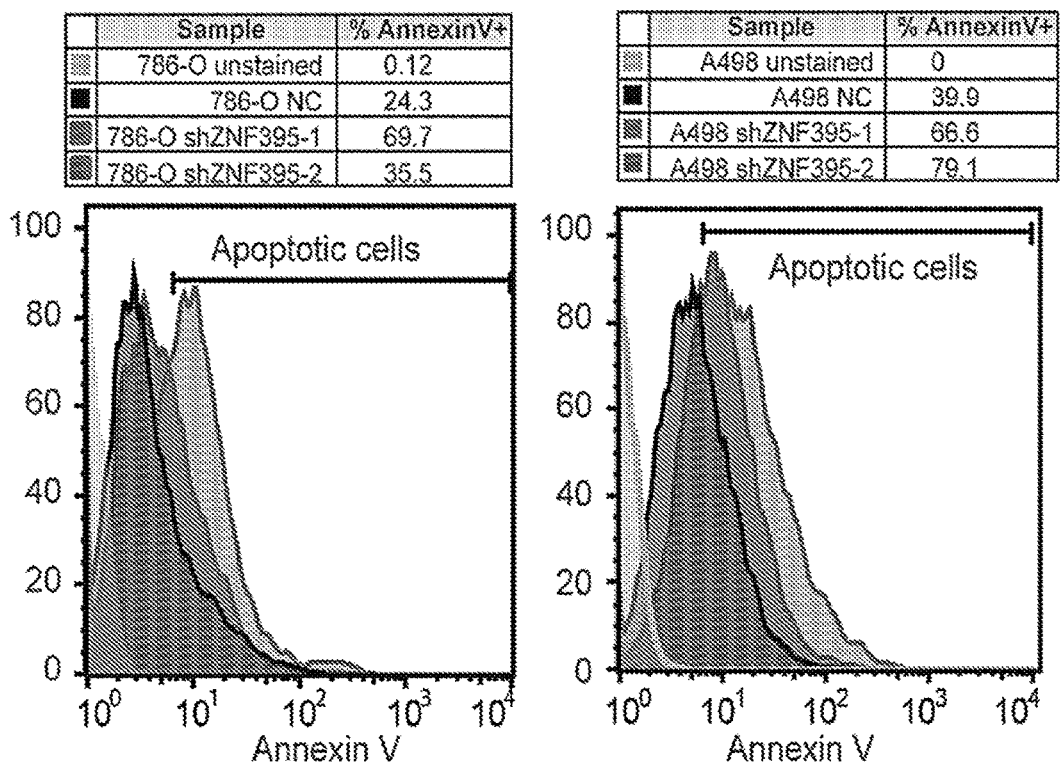
FIG. 3W shows histograms of Annexin V staining analyzed by flow cytometry after ZNF395 shRNA knockdown in 786-O and A-498 cells.
Figure 3X:
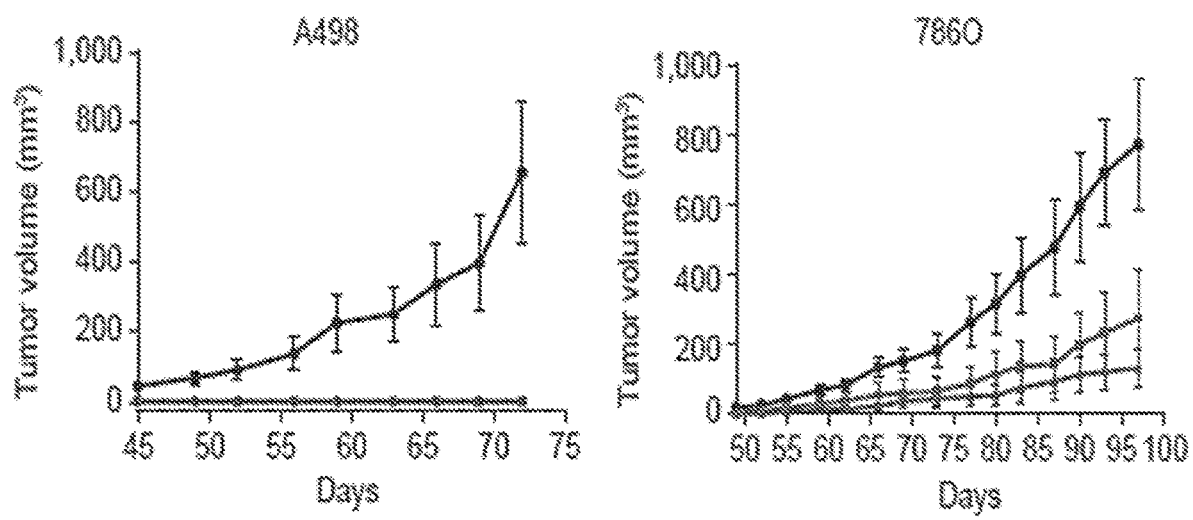
FIG. 3X refers to line graphs showing ZNF395 inhibition by shRNA that leads to total elimination of A-498 tumours in vivo and delayed tumour growth in 786-O cells. Negative control (NC): n=7, shZNF395-1: n=7, shZNF395-2: n=6

No study to date has functionally tested the tumourigenic requirement of ZNF395 in clear cell renal cell carcinoma or any other cancer type. ZNF395's tumour-promoting effect using individual shRNA clones was validated (FIG. 3R, FIG. 3S). Two independent ZNF395 shRNA clones drastically decreased in vitro colony formation (FIG. 3T) and cell viability (FIG. 3U) in both A-498 and 786-O cells. ZNF395 knockdown also resulted in increased apoptosis measured by cleavage of caspase 3/7 substrates (FIG. 3V) and Annexin V staining (FIG. 3W). In vivo, tumour formation studies in mouse xenograft models revealed marked tumour suppression by ZNF395 depletion (FIG. 3X). Knockdown of ZNF395 led to elimination of A-498 tumours up to day 74, when tumours in the control group began to exceed the size limits imposed by institutional animal protocols. Similarly, ZNF395 depletion significantly slowed in vivo tumour growth of 786-O cells (FIG. 3X). Taken together, the role ZNF395 plays in clear cell renal cell carcinoma tumourigenesis was shown.

Example 5—Von Hippel-Lindau (VHL) Deficiency Remodels Clear Cell Renal Cell Carcinoma Enhancer Landscapes To explore the extent to which epigenetic changes observed in primary clear cell renal cell carcinomas (FIG. 1) are directly driven by von Hippel-Lindau (VHL) loss, chromatin changes in isogenic cell lines were examined with and without VHL restoration. Consistent with earlier functional studies of VHL, VHL restoration in 786-O, A-498, and 12364284 cells had negligible effects on proliferation, colony formation, and apoptosis in vitro, but profoundly delayed tumour growth in vivo (FIGS. 4A, 4B, 4C and 4D), suggesting the importance of VHL in modulating processes required for in vivo tumourigenesis, including tumour-stroma cross-talk, angiogenesis, cell-matrix interactions, or tumour metabolism.

Figure 4A:
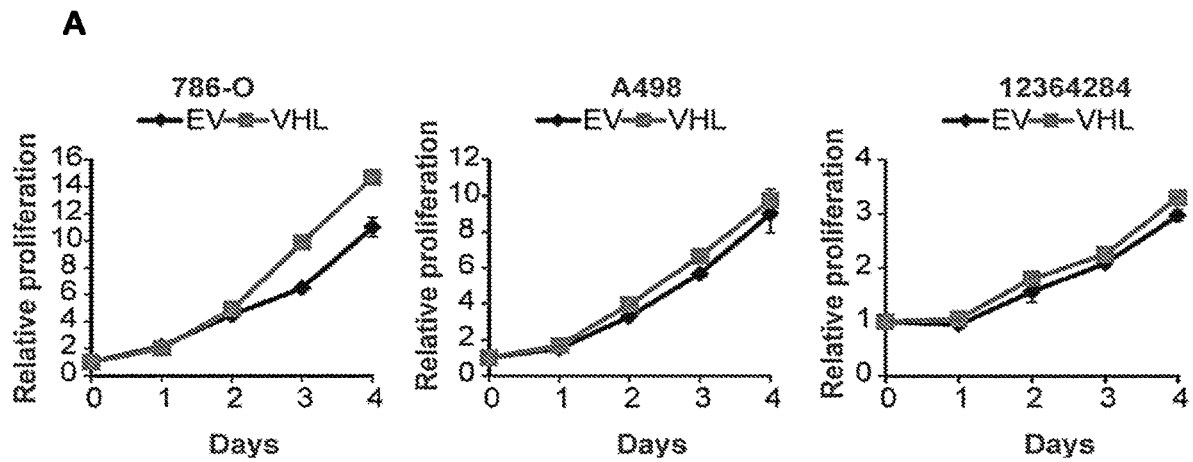
FIG. 4A show graphs referring to in vitro proliferation of 786-O, A-498 and 12364284 cell lines with and without VHL restoration. Proliferation rates were measured with CellTiterGlo, and normalized to day of seeding. EV refers to empty vector control and VHL refers to wild-type VHL restored.
Figure 4B:
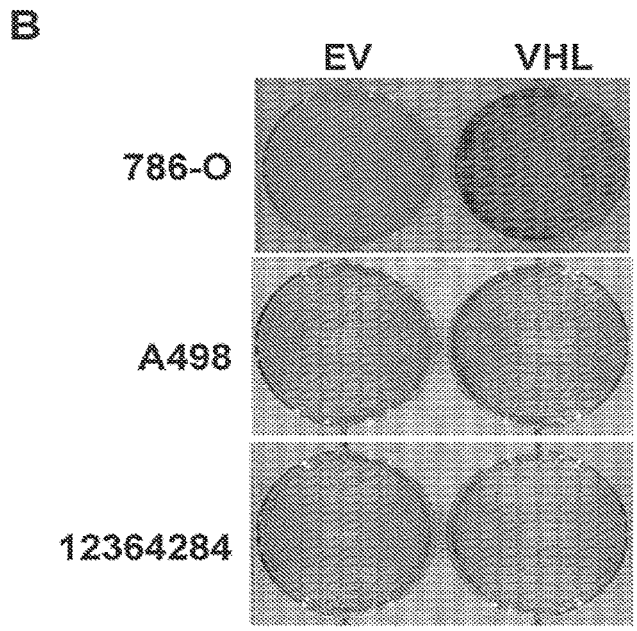
FIG. 4B refers to images of in vitro colony formation of 786-O, A-498 and 12364284 cell lines with and without VHL restoration. Rates of colony formation were measured by seeding 10,000 cells in the well and allowing colonies to form until the wells are confluent. EV refers to empty vector control and VHL refers to wild-type VHL restored.
Figure 4C:
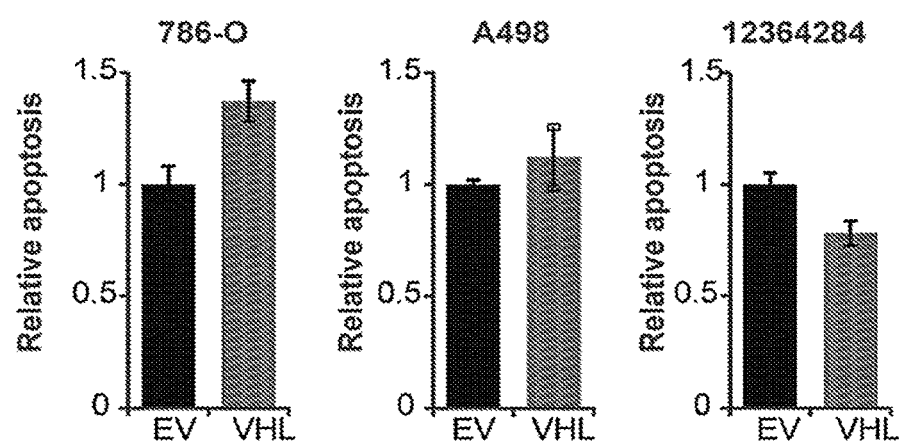
FIG. 4C shows graphs referring to apoptosis measured by cleavage of caspase3/7 substrates and normalized to empty vector controls of 786-O, A-498 and 12364284 cell lines, with and without VHL restoration. EV refers to empty vector control and VHL refers to wild-type VHL restored.
Figure 4D:
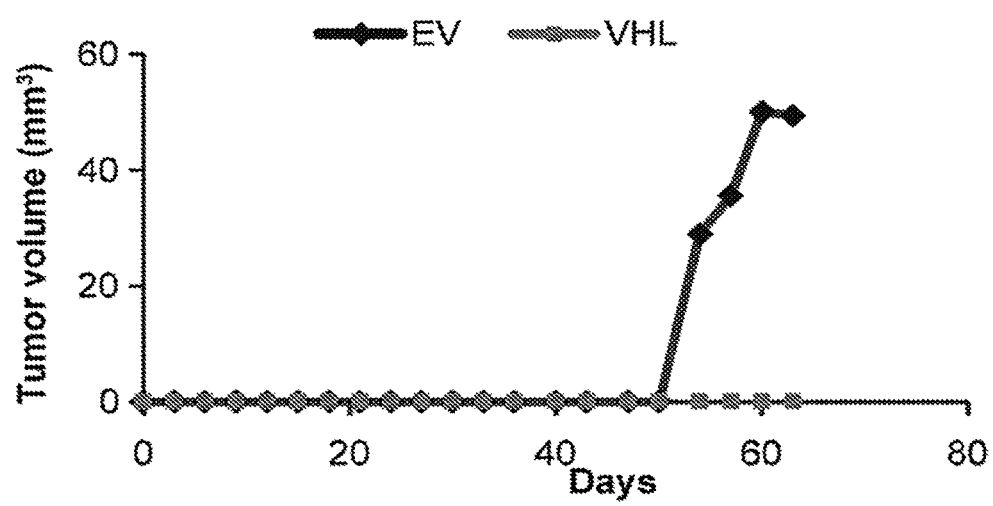
FIG. 4D illustrates a graph where in vivo growth of 786-O subcutaneous tumours in nude mice is compared for isogenic cells with and without VHL restoration. EV refers to empty vector control and VHL refers to wild-type VHL restored.
Figure 4E:
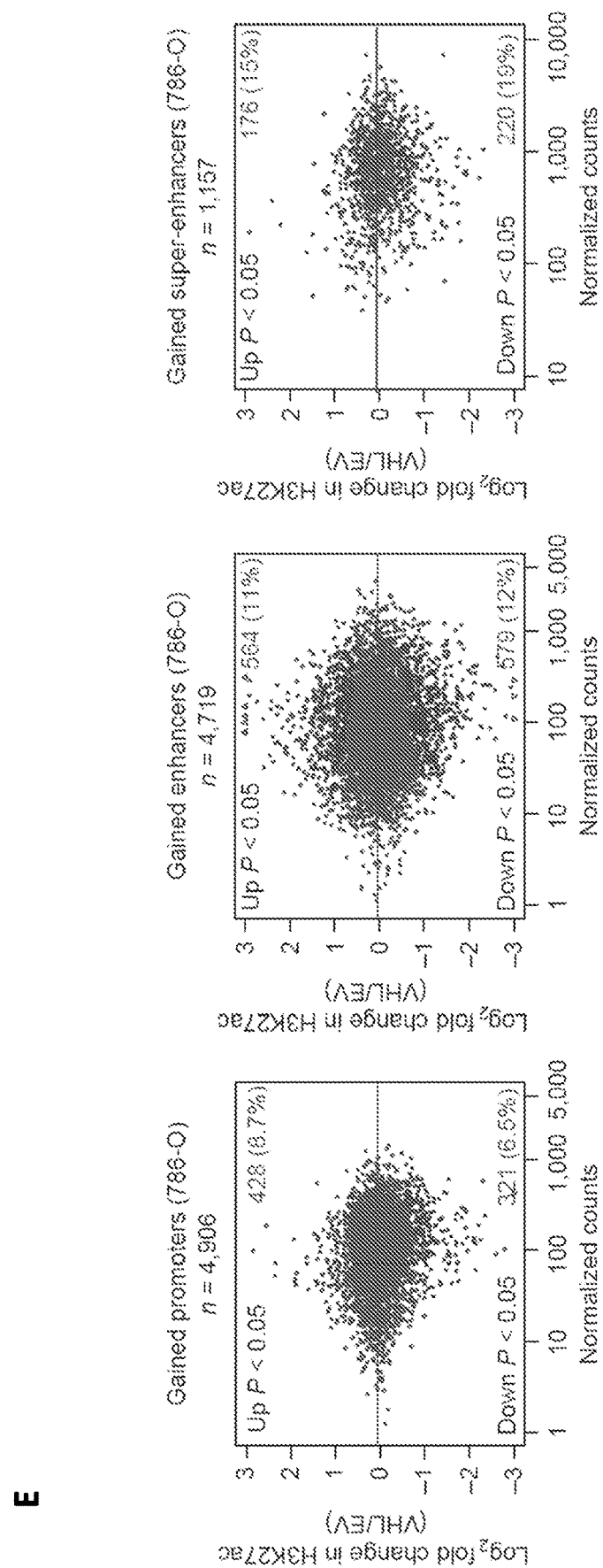
FIG. 4E shows dot plots with log fold changes of H3K27ac chromatin immunoprecipitation sequencing (ChIP-seq) signals at gained promoters, gained enhancers and gained super-enhancers as defined in the primary clear cell renal cell carcinoma dataset after VHL restoration in 786-O cells. Dots represent cis-regulatory elements with significant changes (p-value <0.05, negative binomial) in H3K27ac levels after VHL restoration. The number and percentage of altered regions (p-value <0.05, negative binomial) are shown at the upper and lower right corners.
Figure 4F:
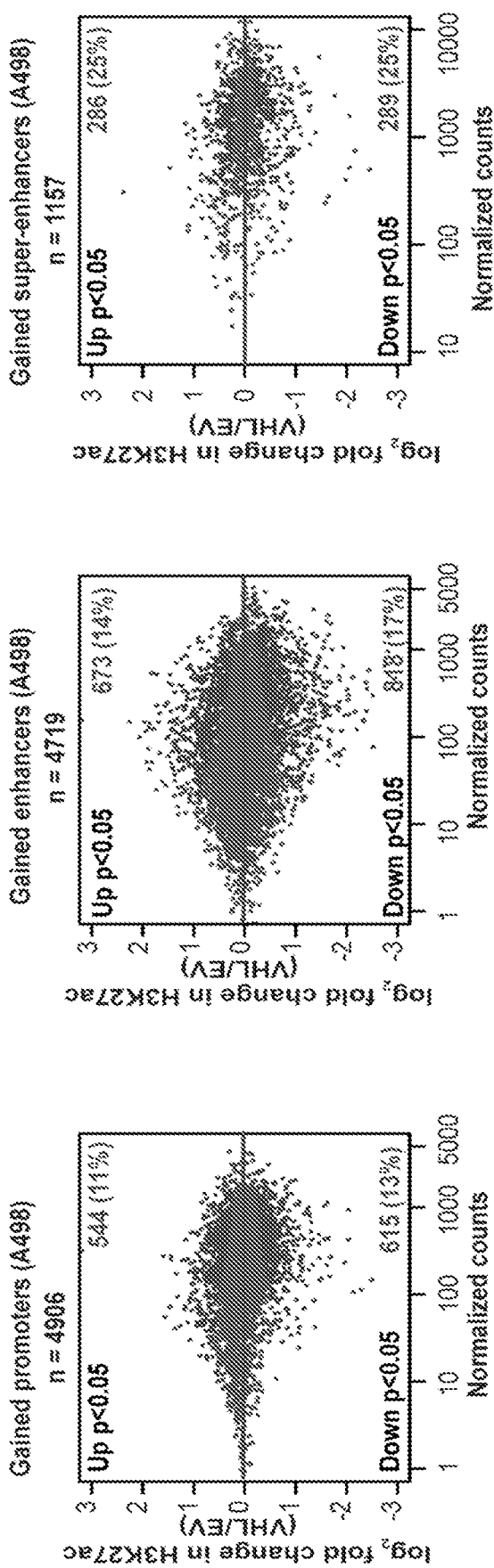
FIG. 4F, FIG. 4G and FIG. 4H shows dot plots with log fold changes of H3K27ac ChIP-seq signals at gained promoters, gained enhancers and gained super-enhancers after VHL restoration in (FIG. 4F) A-498 cells, (FIG. 4G) 12364284 cells and (FIG. 4H) 40911432 cells. Dots represent p-value<0.05. The number and percentage of altered regions are shown at the upper and lower right corners. EV refers to empty vector control and VHL refers to wild-type VHL restored.
Figure 4G:
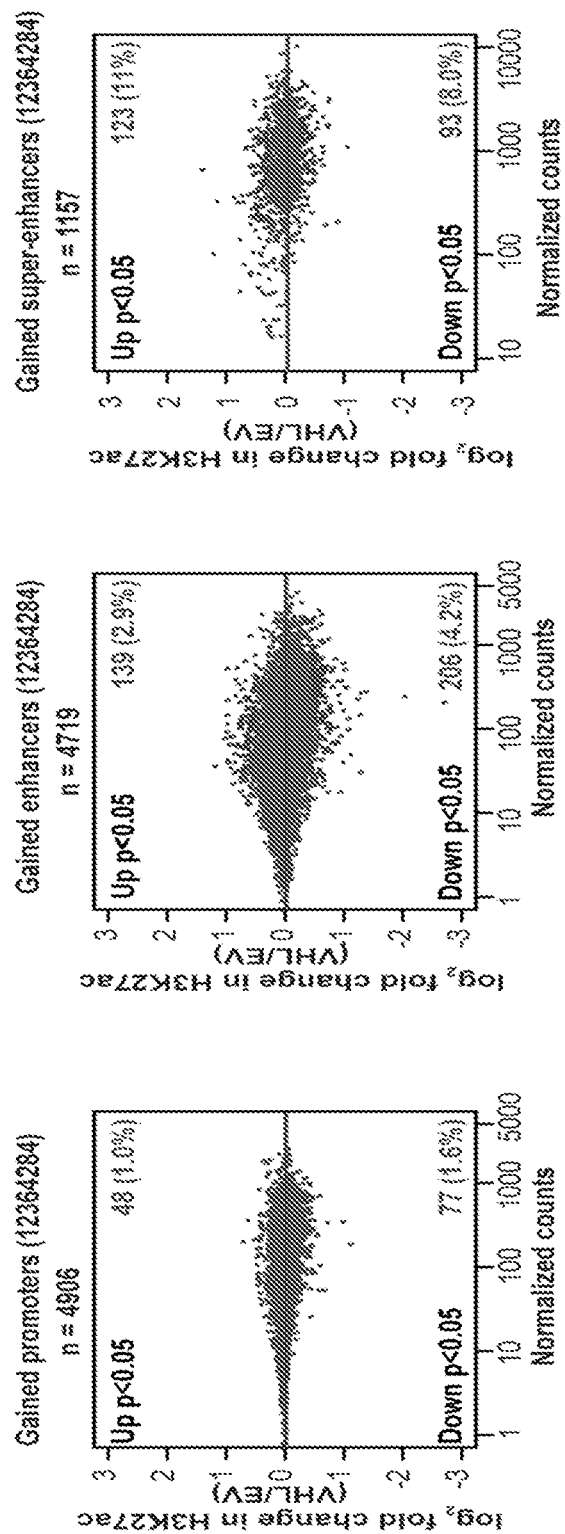
Figure 4H:
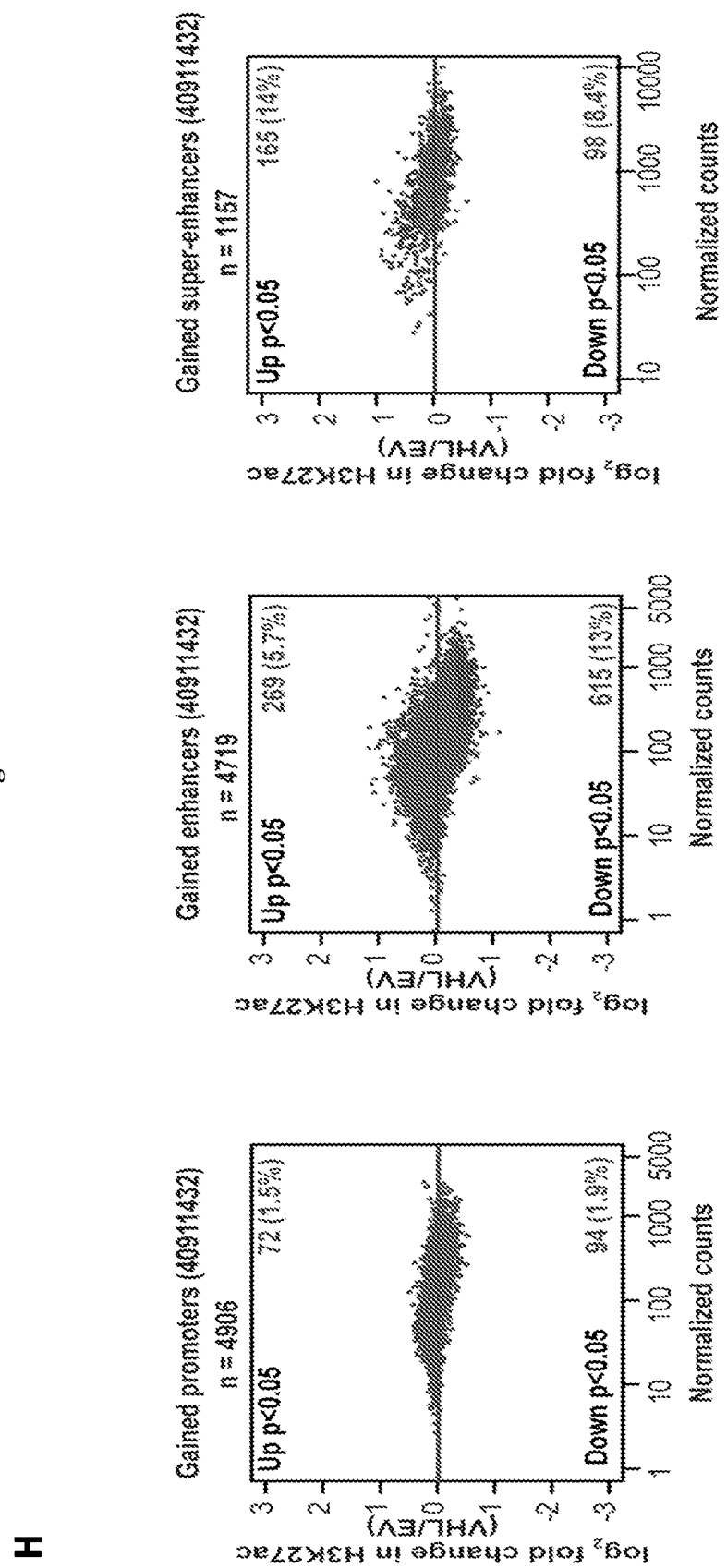

Focusing on the same regions defined in the primary tumours (4,719 gained promoters, 4,906 gained enhancers, and 1,157 gained super-enhancers; FIG. 1C), von Hippel-Lindau (VHL)-driven H3K27ac changes in four different cell lines (two commercial cell lines: 786-O and A-498; and two patient-derived cell lines: 12364284 and 40911432) was examined. Consistently across all four cell lines, VHL restoration induced more pronounced changes on enhancers and super-enhancers than on promoters (FIGS. 4E, 4F, 4G and 4H). For example, in 786-O cells, after VHL restoration 12% of enhancers (549 enhancers) were significantly depleted, compared with 6.5% of promoters (321 promoters; FIG. 4E). This confirmed that a greater fraction of enhancers were significantly altered by VHL restoration than promoters ($P<2.2\times10^{-16}$, proportions test), and an even higher proportion involved gained superenhancers ($P<2.2\times10^{-16}$, proportions test).

Figure 4I:
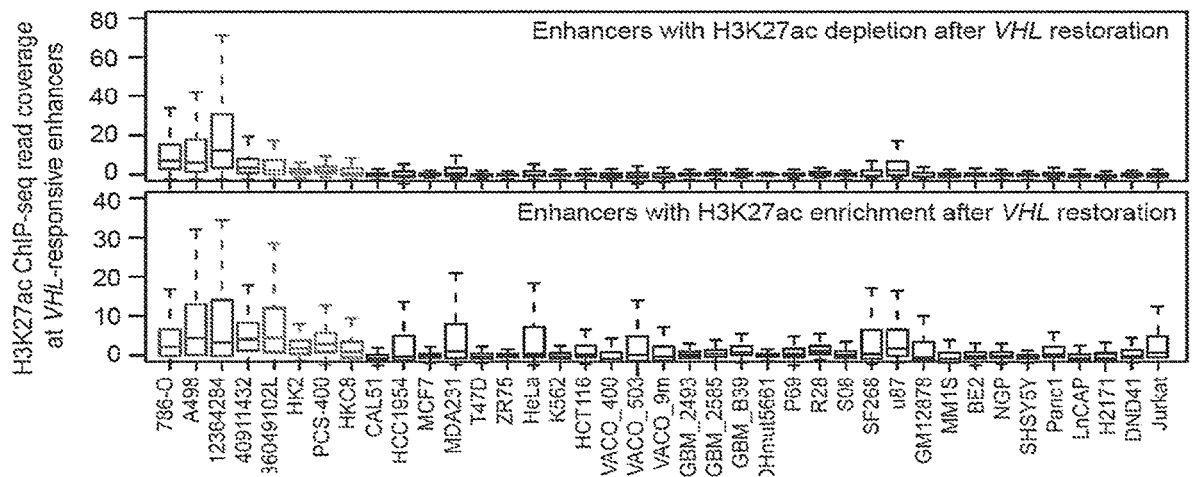
FIG. 4I shows box plots with read coverage of H3K27ac ChIP-seq at VHL-responsive enhancers in VHL-mutant clear cell renal cell carcinoma cell lines compared to VHL-wild-type clear cell renal cell carcinoma, normal kidney cell lines and 31 other cancer cell lines. Enhancers with H3K27ac depletion or enrichment after VHL restoration are shown.
Figure 4I:
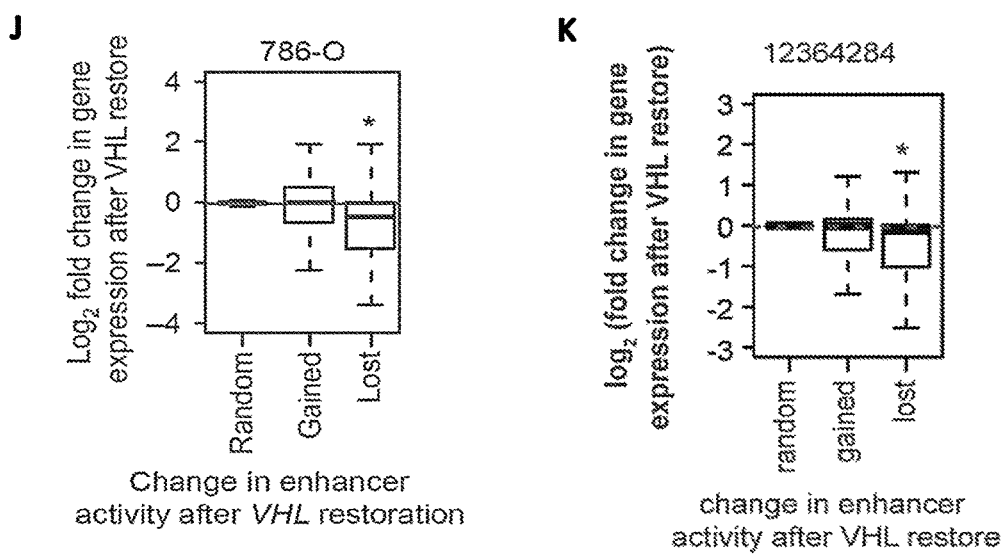

Even though gained enhancers were expected to show only depletion after von Hippel-Lindau (VHL) restoration, changes in H3K27ac levels were bidirectional (FIG. 4E). However, only gained enhancers with H3K27ac depletion were uniquely active in VHL-mutated clear cell renal cell carcinoma cell lines (786-O, A-498, and 12364284) compared with VHL-wild-type clear cell renal cell carcinoma cells (86049102L), normal kidney cell lines (PCS-400, HK2, and HKC-8), and 31 other cell lines of various cancer types (FIG. 4I). The lack of H3K27ac signals in normal kidney cell lines argues against tissue lineage as the dominant contributor to the high H3K27ac chromatin immuno-precipitation sequencing (ChIP-seq) signals seen in clear cell renal cell carcinoma cell lines. On the other hand, gained enhancers with H3K27ac enrichment after VHL restoration showed high activity across multiple cancer types, suggesting that these enhancers are not unique to clear cell renal cell carcinoma (FIG. 4I).

Figure 4L:
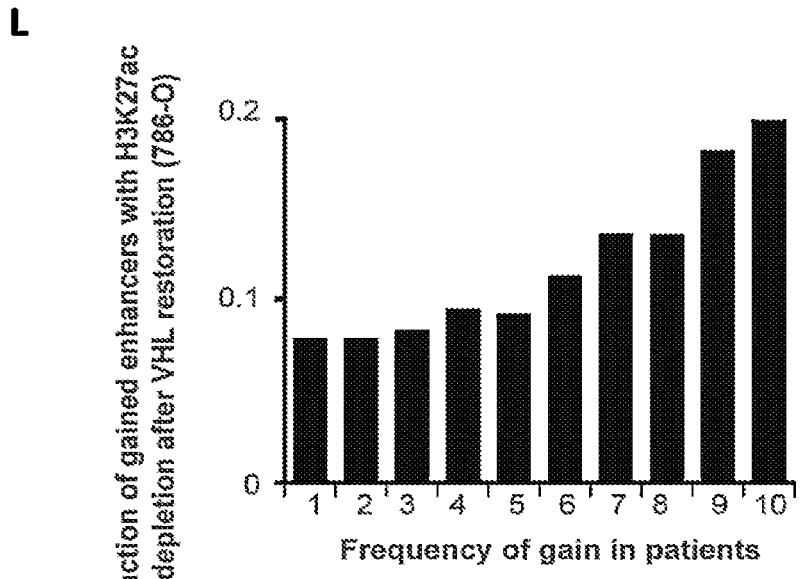
FIG. 4L refers to a bar graph with frequency of gained enhancers showing H3K27ac depletion after VHL restoration in patients.
Figure 4M:
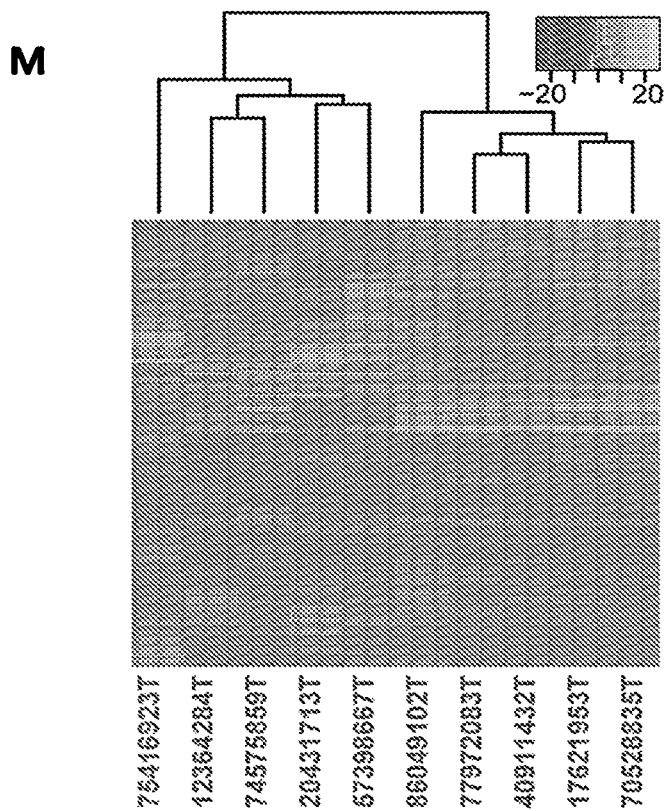
FIG. 4M shows a heatmap with unsupervised hierarchal clustering of differential H3K27ac ChIP-seq signals at gained enhancers showing H3K27ac depletion after VHL restoration.
Figure 4N:
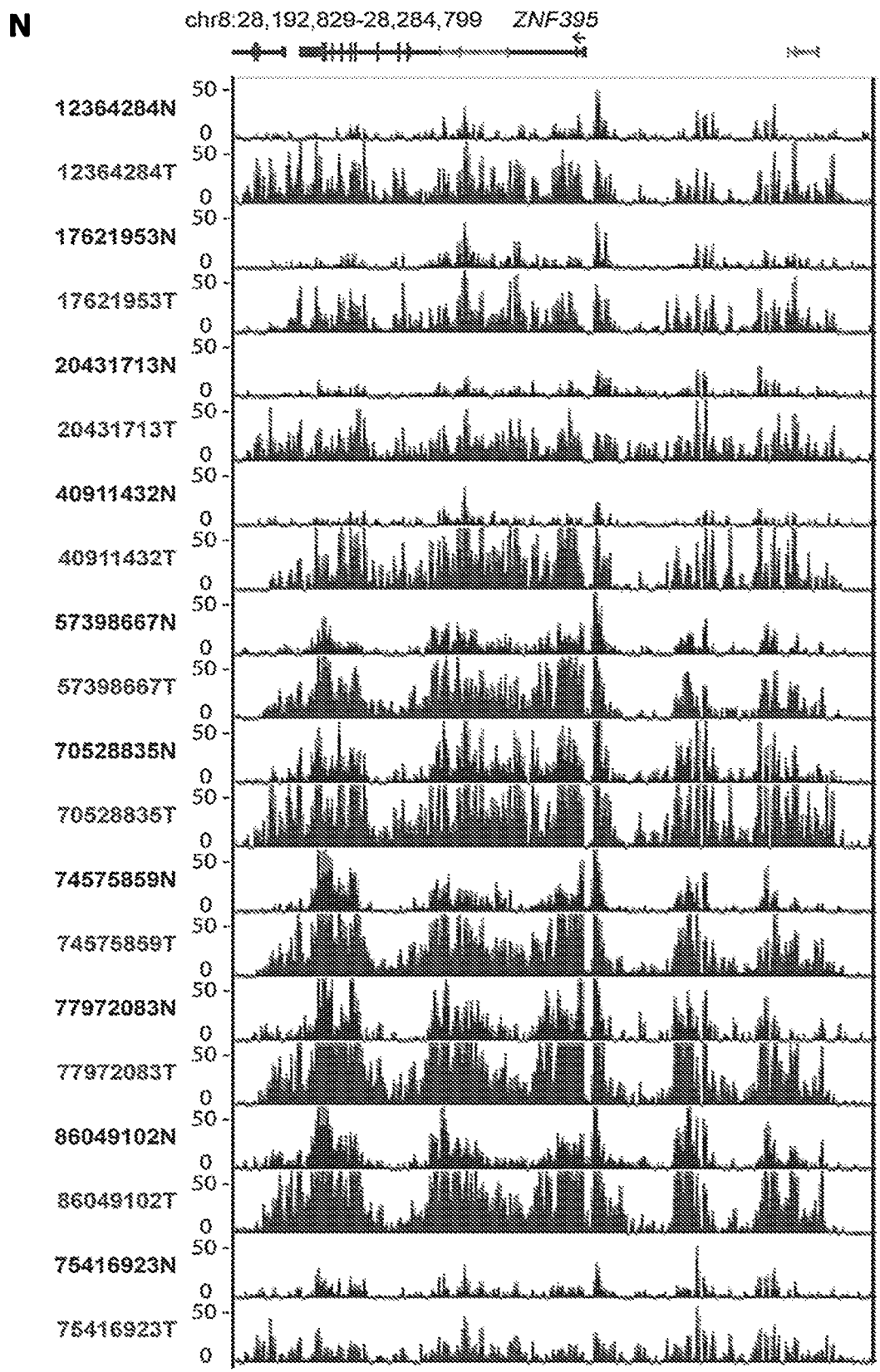
FIG. 4N shows a plot with H3K27ac ChIP-seq signals of all 10 tumour/normal pairs at the ZNF395 super-enhancer.
Figure 4O:
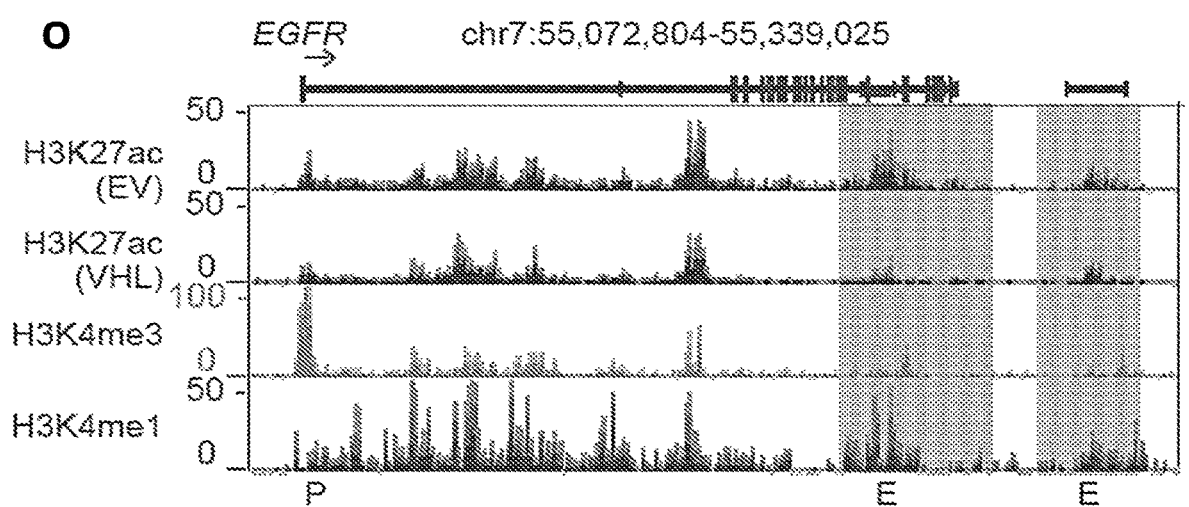
FIG. 4O, FIG. 4P and FIG. 4Q show plots of histone ChIP seq signals with examples of lost VHL-responsive enhancer/super-enhancers associated with EGFR (FIG. 4O), CCND1 (FIG. 4P) and ITGB3 (FIG. 4Q) in 786-O cells.
Figure 4P:
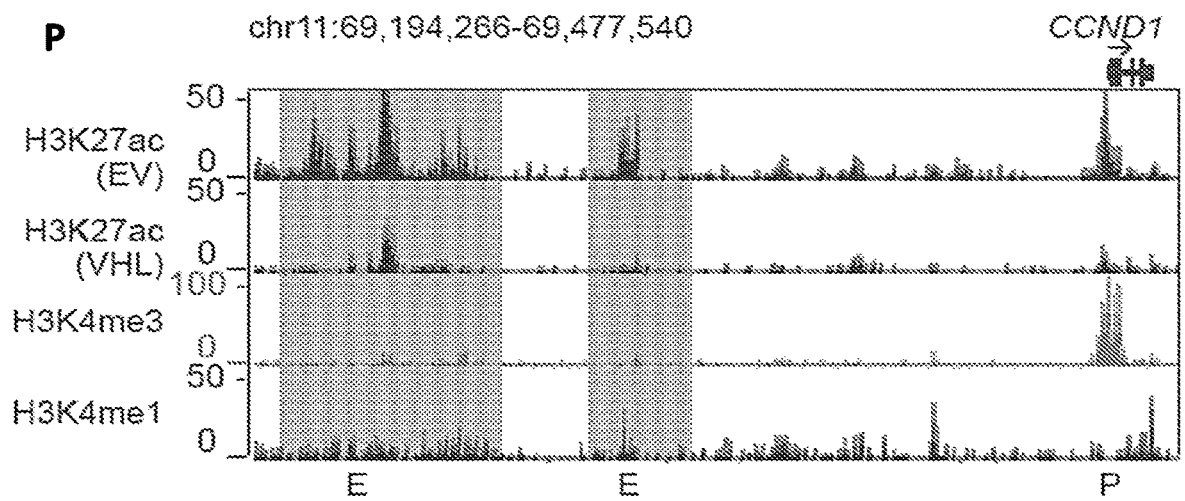
Figure 4Q:
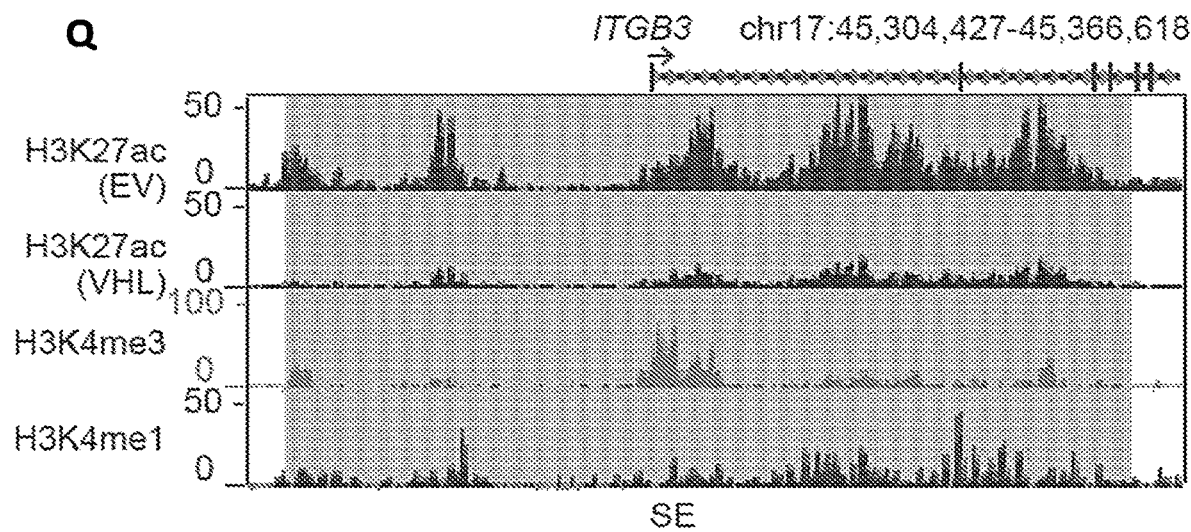
Figure 4R:
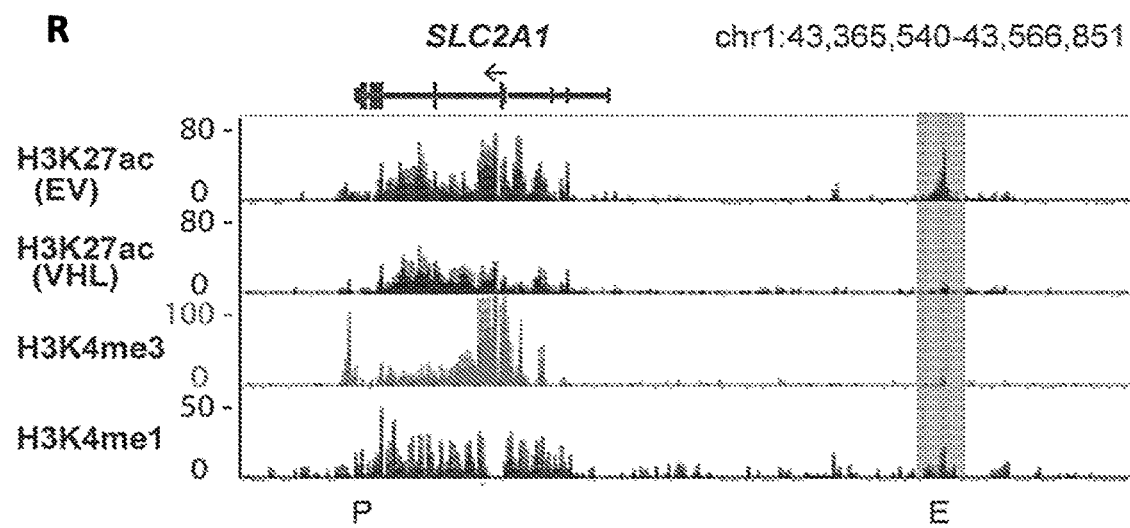
FIG. 4R show plot of histone ChIP signals with examples of lost VHL-responsive enhancer associated with SLC2A1 in 786-O cells.
Figure 4S:
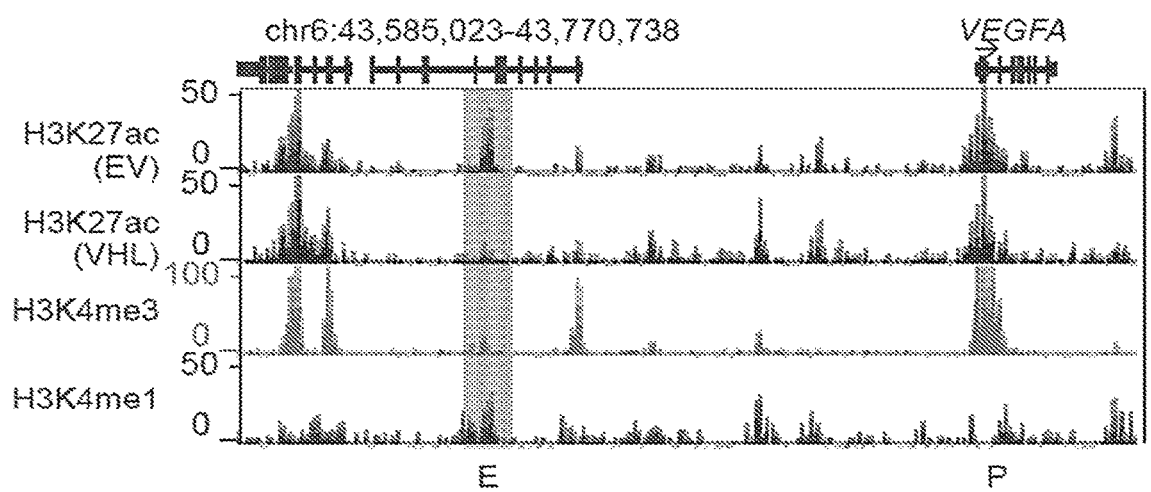
FIG. 4S show plot of histone ChIP seq signals with examples of lost VHL-responsive enhancer/super-enhancers associated with VEGFA in 786-O cells.
Figure 4T:
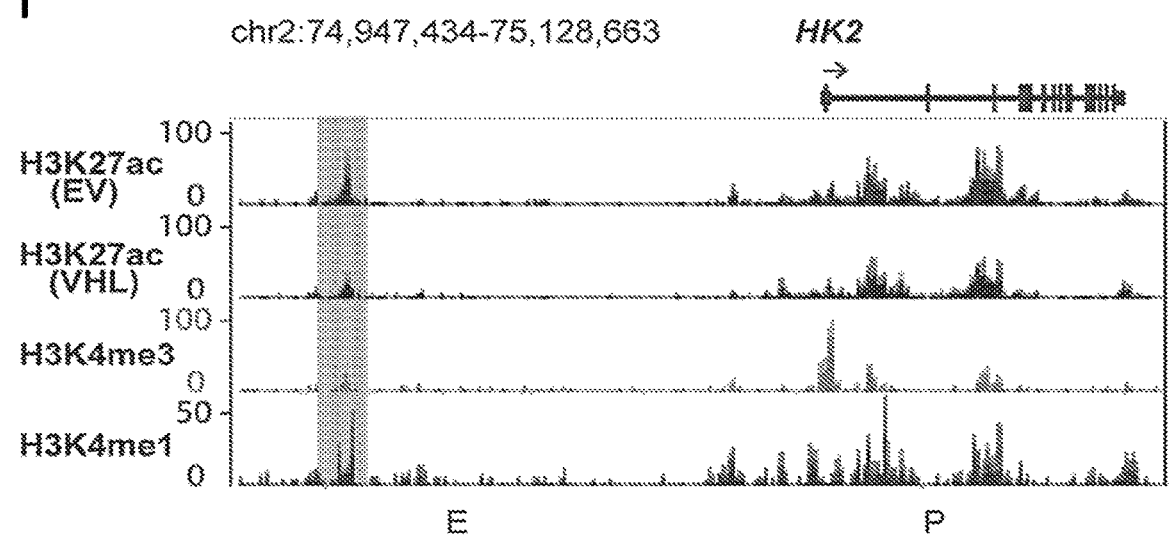
FIG. 4T show plot of histone ChIP signals with examples of lost VHL-responsive enhancer associated with HK2 in 786-O cells.

Furthermore, only gained enhancers showing H3K27ac depletion after von Hippel-Lindau (VHL) restoration were significantly associated with a concomitant downregulation of gene expression of their putative targets in both 786-O and 12364284 cells, whereas enhancers gained in primary clear cell renal cell carcinomas and further H3K27ac enriched after VHL restoration did not lead to significant gene upregulation on a global level (FIG. 4J, FIG. 4K). These results suggest that the former enhancers (H3K27ac depletion) are likely to represent clear cell renal cell carcinoma—and VHL specific epigenomic alterations, whereas the latter enhancers (H3K27ac enrichment) are likely to represent signify generic, compensatory mechanisms in response to VHL restoration. Combining data from multiple lines, a total of 1,564 enhancers were depleted by VHL restoration in cell line, representing almost a third (32%) of all gained enhancers identified in primary clear cell renal cell carcinoma tumours. The proportion of VHL responsive enhancers increased with the level of patient recurrence—only 7.8% of nonrecurrent gained enhancers (1/10 patients) showed von Hippel-Lindau (VHL)-mediated H3K27ac depletion, whereas 18% of enhancers recurrently gained in 9 of 10 patients and 20% of enhancers gained in 10 of 10 patients showed H3K27ac depletion in 786-O cells (FIG. 4L, P=0.0001, proportions test), consistent with the high prevalence of VHL mutations (9/10 patients) in the studies. Interestingly, unsupervised clustering using the 1,564 VHL-responsive gained enhancers segregated the single VHL-wild-type tumour (ID 75416923) away from the remaining 9 VHL-mutant tumours (FIG. 4M), with the VHL-wild-type tumour showing low H3K27ac signals at the ZNF395 super-enhancer comparable with its patient-matched normal (FIG. 4N). Collectively, pathway analysis of enhancers depleted in ≥2 cell lines highlighted direct p53 effectors, integrin-linked kinase signaling, and HIF1α transcription factor networks as the top five pathways, covering genes such as EGFR (FIG. 4O), CCND1 (FIG. 4P), ITGB3 (FIG. 4Q), VEGFA (FIG. 4S), SLC2A1 (FIG. 4R), and HK2 (FIG. 4T). These results support a role for VHL loss in clear cell renal cell carcinoma enhancer malfunction, even in the presence of other driver mutations.

Figure 4U:
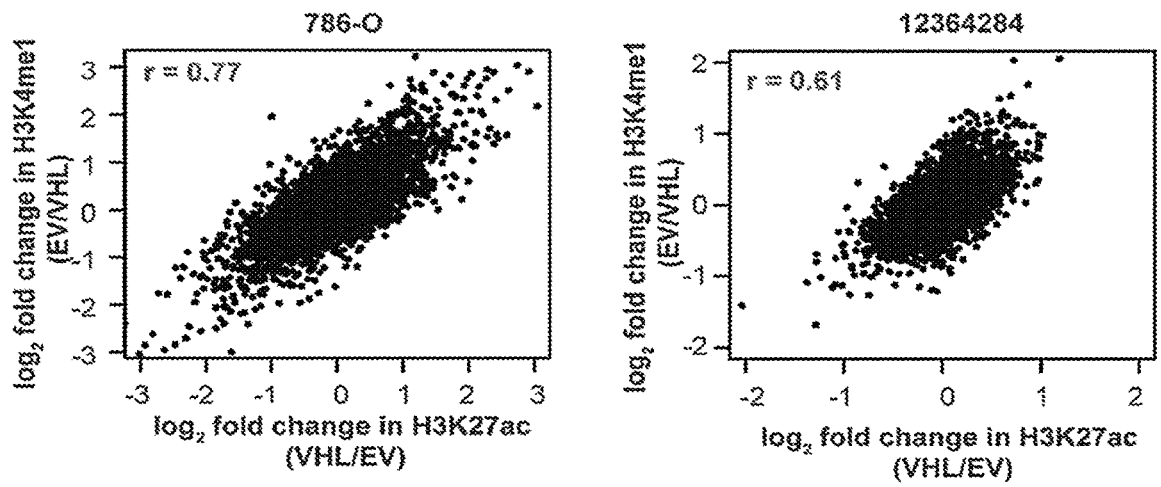
FIG. 4U shows dot plot of Pearson's correlation of log fold changes of H3K27ac and H3K4me1 in 786-O and 12364284 after VHL restoration. (removed as there is no colour in figure)
Figure 4V:
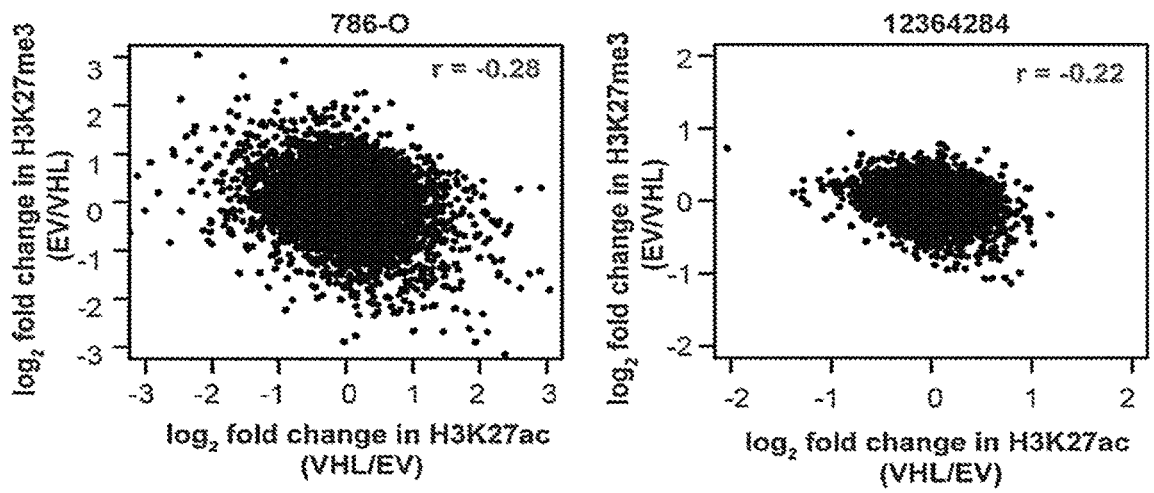
FIG. 4V shows dot plot of Pearson's correlation of log fold changes of H3K27ac and H3K27me3 in 786-O and 12364284 after VHL restoration.
Figure 4W:
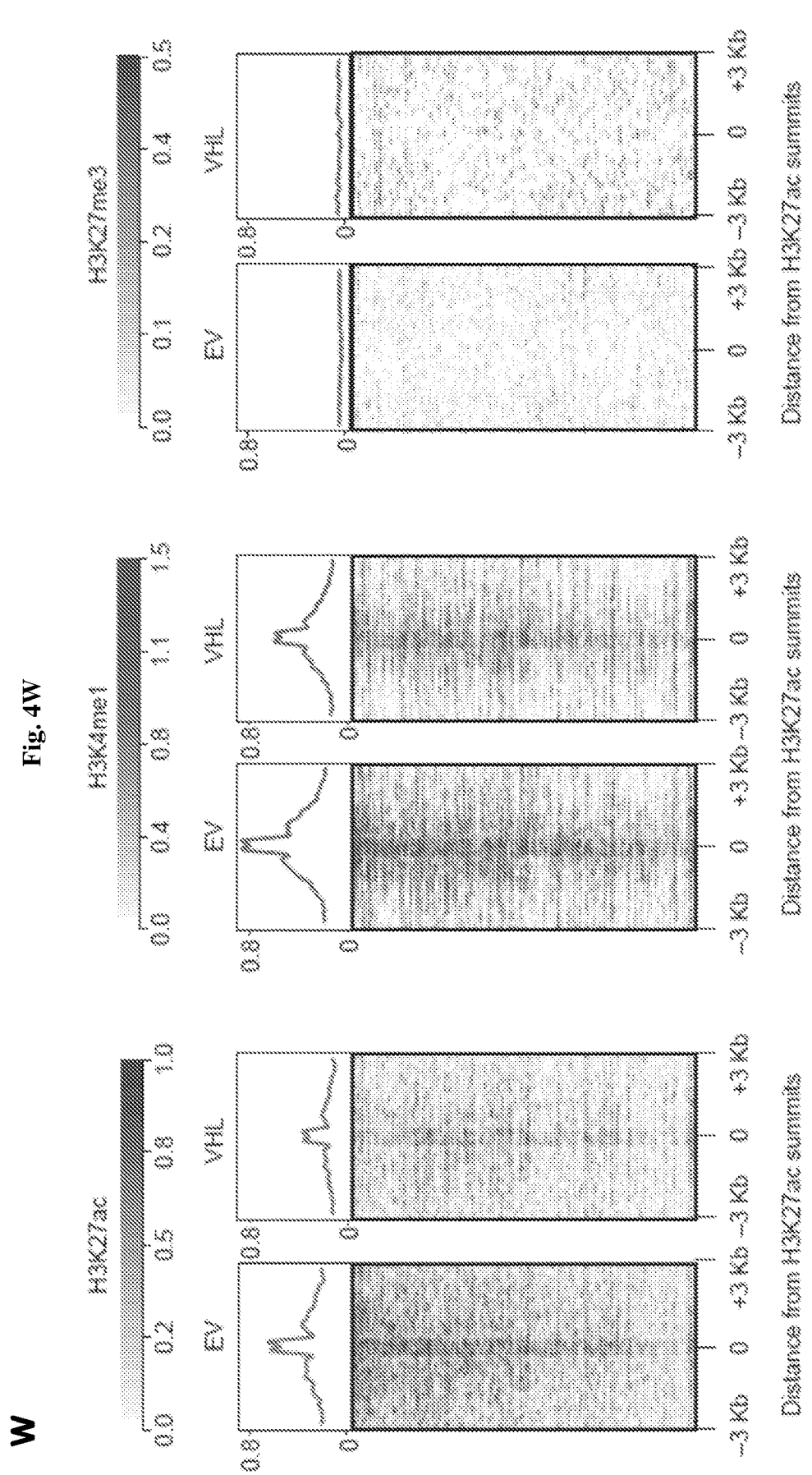
FIG. 4W refers to heatmap with log fold changes of H3K27ac, H3K4me1 and H3K27me3 signals at gained enhancers showing H3K27ac depletion after VHL restoration in 786-O cells.

It was also examined whether other histone marks were concomitantly altered with H3K27ac marks. A high degree of correlation was found between H3K27ac and H3K4me1 in response to von Hippel-Lindau (VHL) restoration in both 786-O cells (r=0.77, Pearson correlation) and 12364284 cells (r=0.61, Pearson correlation) in FIG. 4U. Globally, enhancers exhibiting H3K27ac depletion also experienced concomitant H3K4me1 depletion (FIG. 4W). It was next examined whether VHL restoration led to acquisition of the H3K27me3 repressive mark. Despite a moderate anticorrelation of H3K27ac and H3K27me3 (786-O cells: r=−0.28, Pearson correlation; 12364284 cells: r=−0.22, Pearson correlation, FIG. 4V), H3K27me3 levels remained low at gained enhancers even after VHL restoration (FIG. 4W). These findings suggest that VHL restoration may result in a loss of enhancer identity by codepletion of H3K27ac and H3K4me1, but not a formal transition to a poised enhancer state that would have retained H3K4me1 but acquired H3K27me3.

Figures 5A, 5B:
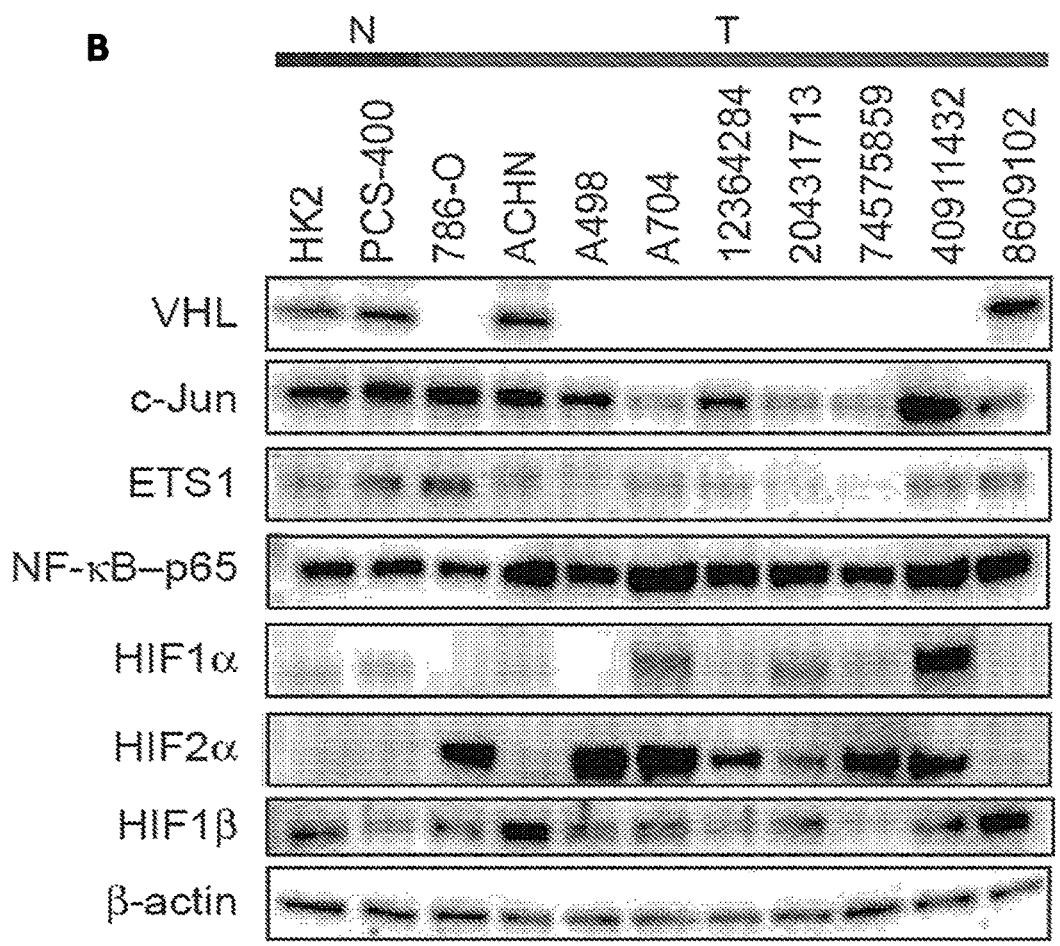
FIG. 5A refers to a table with motif analysis of gained enhancers using HOMER, revealing significant enrichment of AP-1 family, ETS family, NFκB and HIF1α/2α (hypergeometric test). Lost enhancers were used as background in the motif search to identify tumour-specific transcription factors.
FIG. 5B shows an immunoblot with protein expressions of putative transcription factors enriched at gained enhancers in 9 tumour cell lines (4 commercial cell lines and 5 patient-derived cell lines) and 2 normal cell lines. ACHN is a papillary renal cell carcinoma cell line.

Example 6—HIF2α-HIF1β Heterodimer is Enriched at Von Hippel-Lindau (VHL)-Responsive Enhancers It was investigated which transcription factors might mediate von Hippel-Lindau (VHL)-dependent chromatin remodeling at gained enhancers. Using the primary clear cell renal cell carcinoma dataset, enrichment of trans-regulators in gained enhancers over lost enhancers was examined. Using HOMER, it was found that the top enriched motifs were the AP1 family, ETS family, and NF-κB-p65-Rel and HIF1α/2α motifs (FIG. 5A). For subsequent in vitro validation, c-Jun was chosen as a representative AP1 family member because of its activation in clear cell renal cell carcinoma and ETS1 as an ETS family representative because of its known interaction with HIF2a, but acknowledge that other family AP1 and ETS family members may play a role in clear cell renal cell carcinoma. Immunoblotting of c-Jun, ETS1, and NF-κB-p65 showed variable protein expression in both normal and tumour cell lines, but expression of HIF1α and HIF2α restricted to tumour cells only (FIG. 5B). HIF2α was expressed in a higher proportion of clear cell renal cell carcinoma cell lines than HIF1α (FIG. 5B). Gene expression of these transcription factors was further examined in the The Cancer Genome Atlas (TCGA) cohort and found that ETS1, RELA (subunit of NF-κB-p65), and HIF2α were significantly overexpressed in tumours compared with normal tissues, with a range of tumour-association expression patterns similar to variations in clear cell renal cell carcinoma lines (FIG. 5C).

Figure 5D:
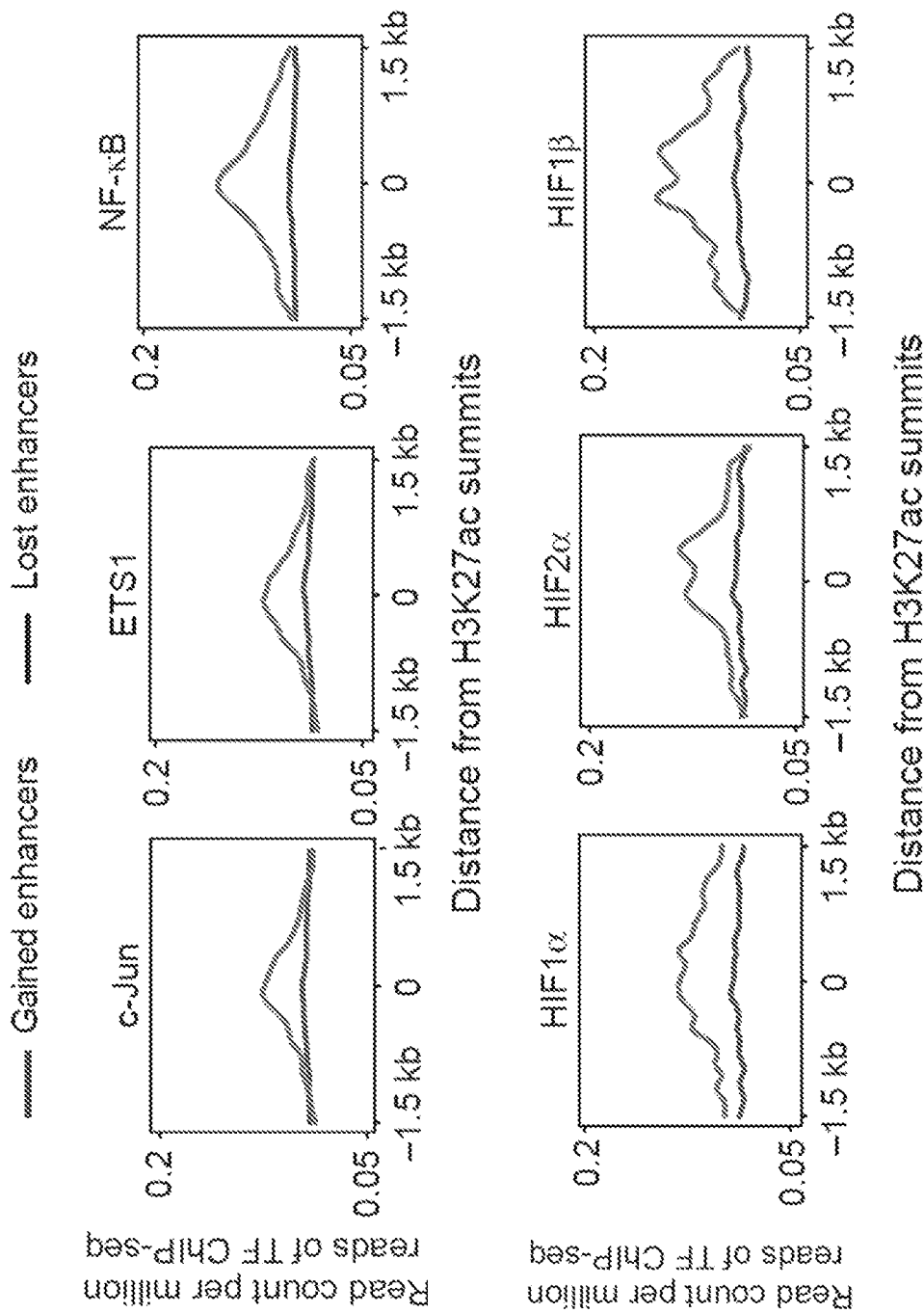
FIG. 5D illustrates graphs showing that chromatin immunoprecipitation sequencing (ChIP-seq) validated the enrichment of transcription factors in gained enhancers over lost enhancers.

To further investigate chromatin occupancy of these factors, chromatin immunoprecipitation sequencing (ChIP-seq) binding profiles of c-Jun, ETS1, and NF-κB cells were generated and HIF2α, HIF1α, and HIF1β binding profiles from the previous literature were examined in 786-O cells. As 786-O cells contain lost endogenous HIF1α expression through genomic deletion, the HIF1α ChIP-seq was performed on 786-O cells genetically manipulated to reexpress HIF1α protein. ChIP-seq results showed that all six transcription factors exhibited increased occupancy at gained enhancers compared with lost enhancers, validating the HOMER predictions (FIG. 5D).

Figure 5E:
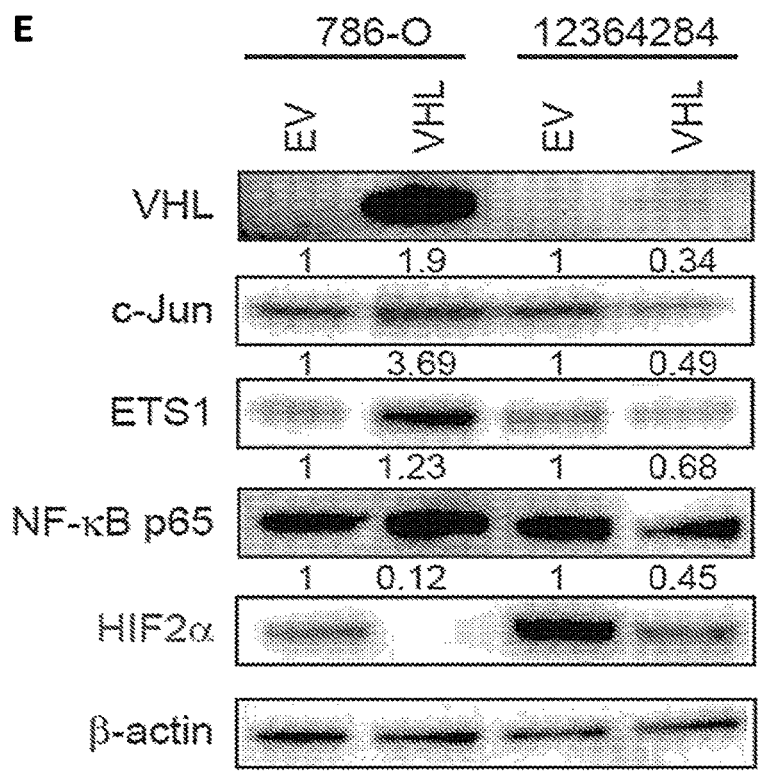
FIG. 5E refers to an immunoblot with protein expression of transcription factors shown in 786-O and 12364284 cells with and without wild-type VHL.
Figure 5F:
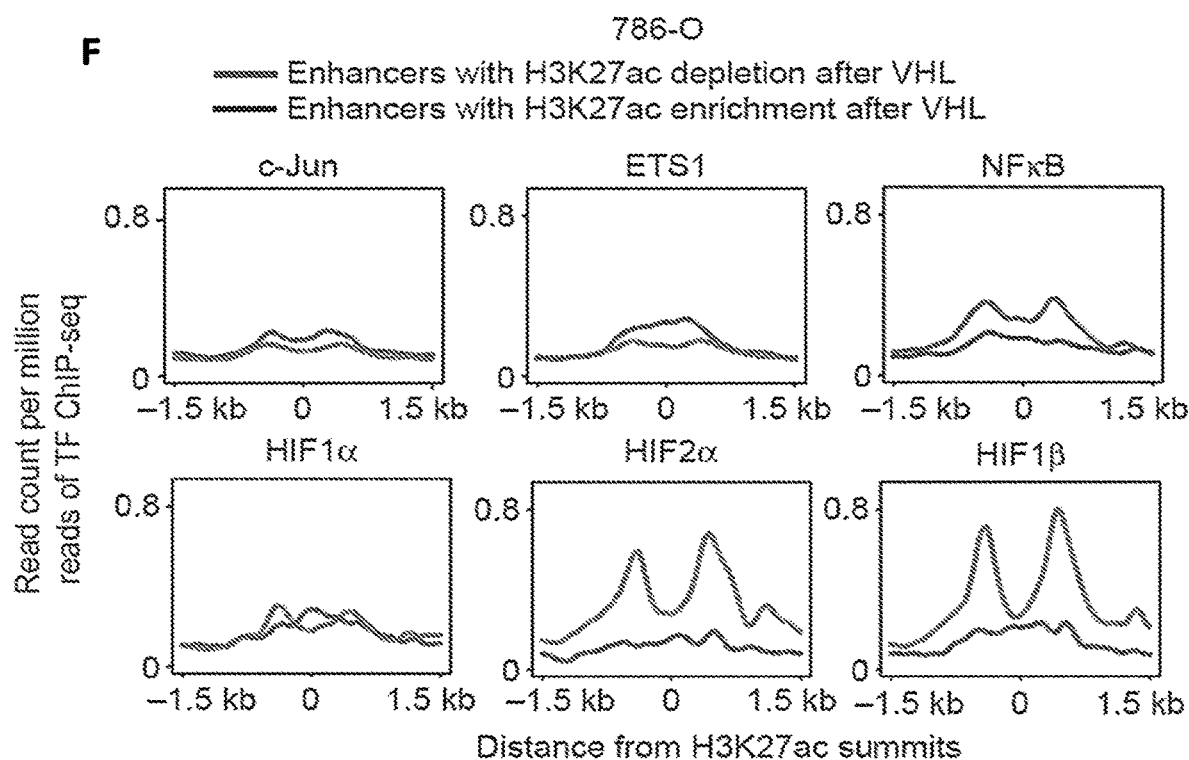
FIG. 5F illustrates line graphs of transcription factor binding at VHL-responsive gained enhancers that shows enrichment of HIF2α and HIF1β at enhancers with H3K27ac depletion over regions with H3K27ac enrichment after VHL restoration.
Figure 5G:
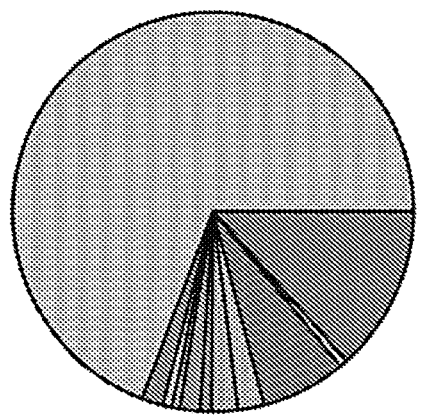
FIG. 5G refers to pie charts with distribution of exogenous HIF1α and endogenous HIF2α ChIP-seq binding sites in 786-O cells annotated using ChIPseeker.
Figure 5G:
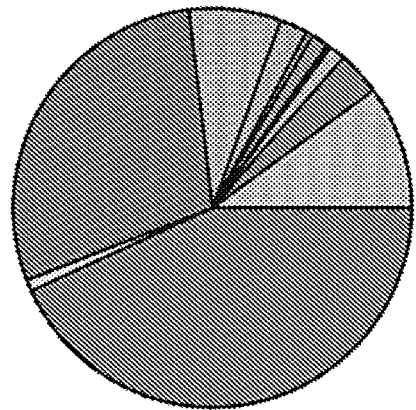
Figure 5H:
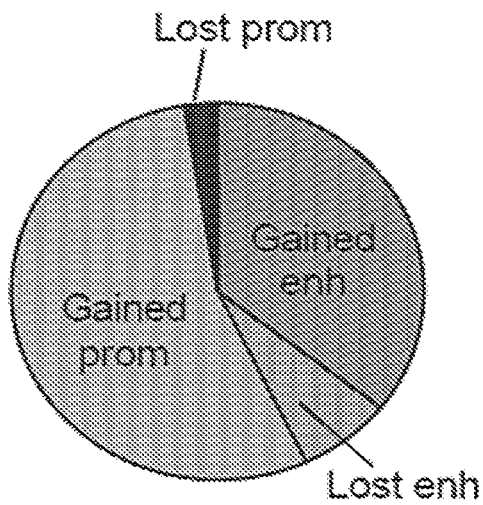
FIG. 5H shows pie charts of ChIP-Seq data that shows distribution of exogenous HIF1α and endogenous HIF2α binding at altered promoters and enhancers in 786-O cells that have been genetically engineered to overexpress HIF1α.
Figure 5H:
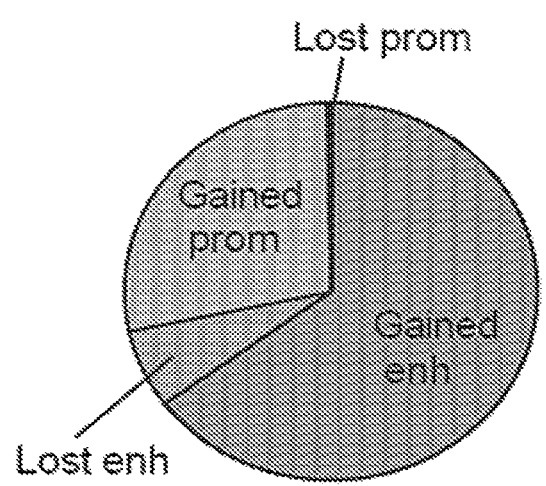

To determine which of these transcription factors might be directly dependent on von Hippel-Lindau (VHL), their protein expression was then compared in VHL-mutated isogenic cell lines with and without wild-type-VHL restoration. As shown in FIG. 5E, VHL restoration consistently downregulated HIF2α expression in both 786-O and 12364284 cell lines, but protein levels of other factors displayed contrasting trends between the two cell lines, implying that among the six factors examined, HIF2α protein expression was the most VHL-dependent. Indeed, supporting an important role for HIF2α in VHL-dependent enhancer remodeling, only HIF2α and HIF1β were significantly enriched at enhancers showing VHL-dependent H3K27ac depletion (FIG. 5F). Moreover, among all known motifs in the HOMER database, HIF2α was the most enriched motif at VHL-responsive enhancers exhibiting H3K27ac depletion ($P=1\times10^{-11}$). In contrast, HIF1α was not enriched at enhancers showing H3K27ac depletion (FIG. 5F). Despite sharing many binding sites with HIF2α, HIF1α predominantly localized to promoter-proximal regions, whereas HIF2α frequently occupied introns and intergenic regions in 786-O cells (FIG. 5G), consistent with a promoter-centric occupancy of HIF1a and an enhancer-centric occupancy of HIF2α (FIG. 5H). Gained enhancers displayed a HIF2α occupancy twice that of tumour-specific promoters ($P<1\times10^{-16}$, proportions test) in 786-O cells, suggesting that HIF2α may play a greater role in regulating enhancers than promoters.

Figure 5I:
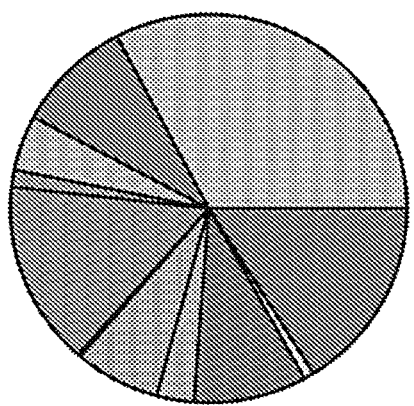
FIG. 5I shows pie charts of distribution of endogenous HIF1α and HIF2α ChIP-seq binding sites in 40911432 cells annotated using ChIPseeker.
Figure 5I:
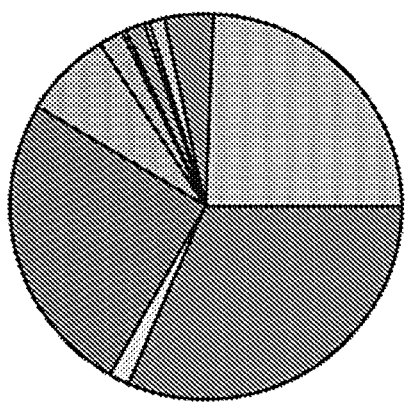
Figure 5J:
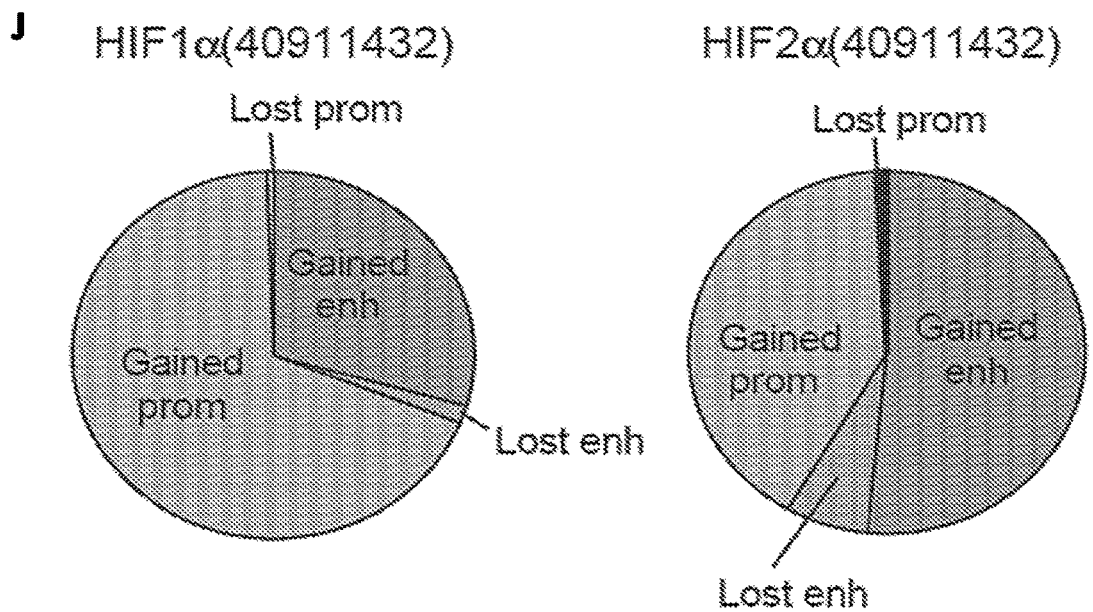
FIG. 5J shows pie chart of ChIP-Seq that shows distribution of endogenous HIF1α and HIF2α binding at altered promoters and enhancers in 40911432 cells.
Figure 5K:
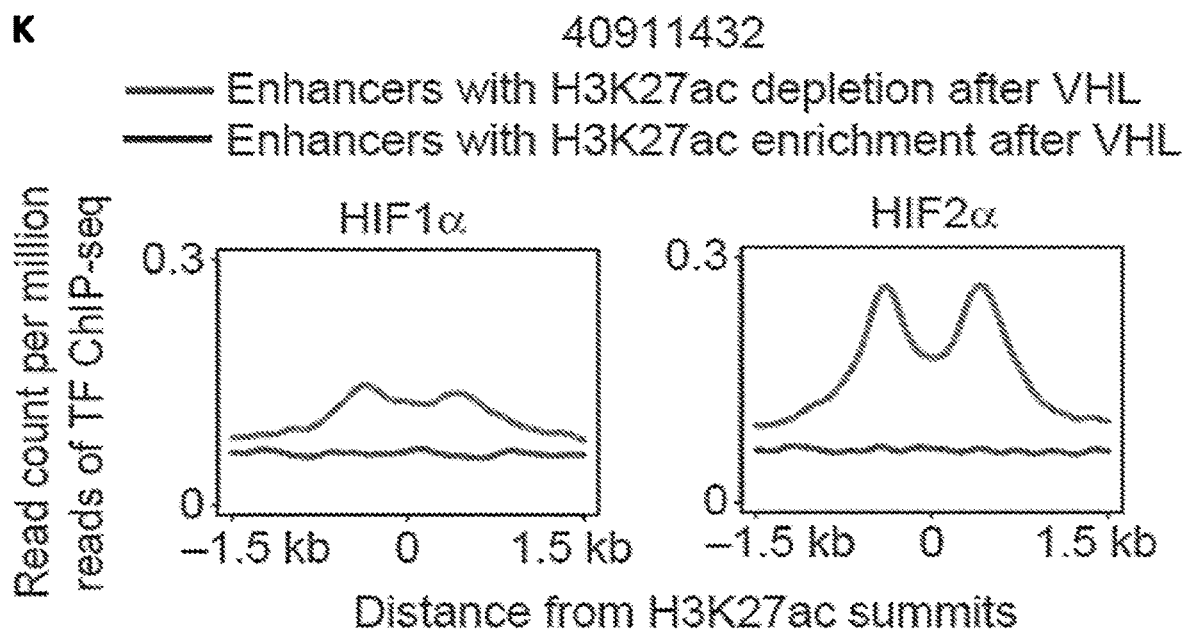
FIG. 5K refers to graph that shows transcription factor binding at VHL-responsive enhancers showing higher enrichment of HIF2α than HIF1α at enhancers with H3K27ac depletion after VHL restoration over regions with H3K27ac enrichment after VHL restoration.
Figure 5L:
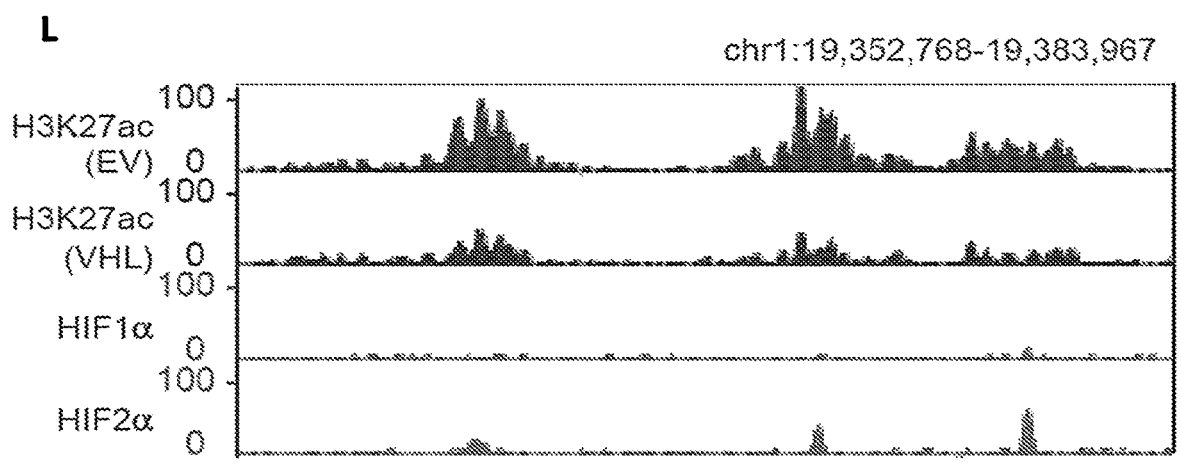
FIG. 5L refers to plot of ChIP Seq with example of a VHL-responsive enhancer near UBR4 with only HIF2α binding but not HIF1α binding.
Figure 5M:
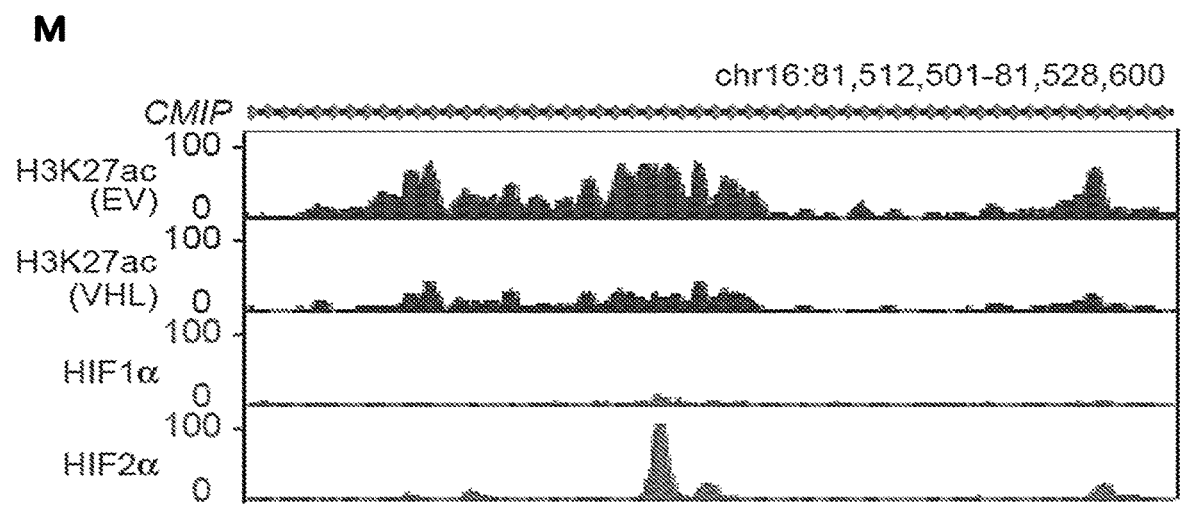
FIG. 5M refers to plot of ChIP Seq with example of a VHL-responsive super-enhancer near CM/P with only HIF2α binding but not HIF1α binding.

To extend these HIF1α and HIF2α occupancy-pattern findings to a system that expresses endogenous levels of both factors, HIF1α and HIF2α chromatin immunoprecipitation sequencing (ChIP-seq) was performed in 40911432 clear cell renal cell carcinoma cells, which abundantly coexpress both HIFα subunits (FIG. 5B). Similar to 786-O, in 40911432 cells, HIF1α showed a preferential occupancy at promoter-proximal regions, whereas a large proportion of HIF2α was found in distal regions (introns and distal intergenic regions; FIG. 5I). A higher proportion of HIF1α binding sites overlapped with gained promoters than HIF2α (68% of HIF1α vs. 41% of HIF2α, P=0.002, proportions test; FIG. 5J). Conversely, a higher proportion of HIF2α binding sites overlapped with gained enhancers than HIF1α (29% of HIF1α vs. 51% of HIF2α, $P<2.2\times10^{-16}$, proportions test). HIF2α's preferential occupancy at enhancers was further substantiated by its higher enrichment at enhancers showing H3K27ac depletion after von Hippel-Lindau (VHL) restoration than HIF1α (FIG. 5K). Specific examples of VHL-responsive enhancers bound exclusively by HIF2α but not HIF1α included an enhancer near UBR4 (FIG. 5L) and a superenhancer near CM/P (FIG. 5M). Therefore, even in HIF1α/HIF2α coexpressing clear cell renal cell carcinoma cells, these results suggest that HIF2α plays a greater role in VHL-mediated enhancer remodeling than HIF1α.

Example 7—HIF2α-HIF1β Bound Enhancers Modulate Gene Expression

Figure 6A:
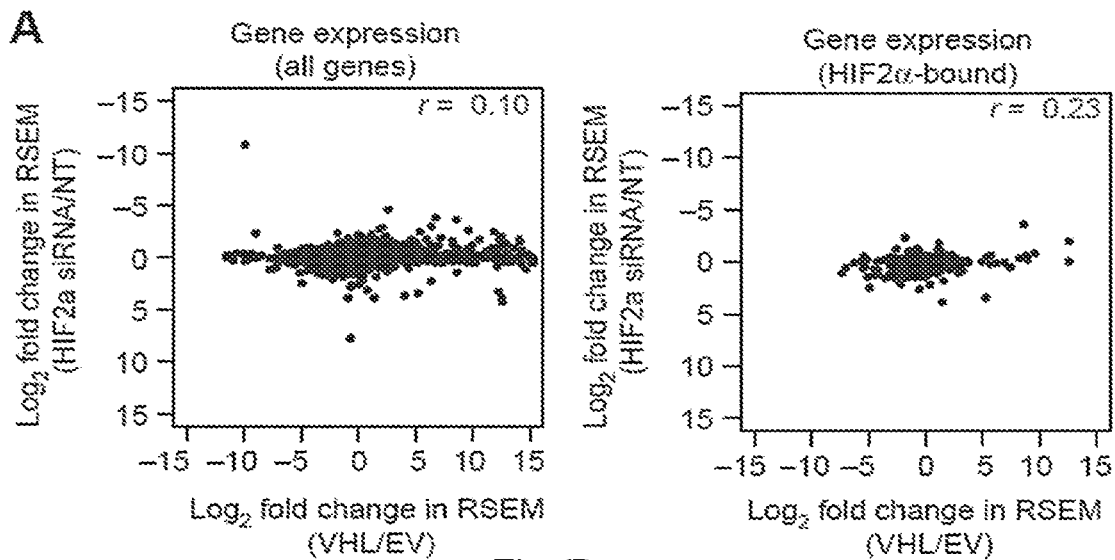
FIG. 6A refers to dot plots with Pearson's correlation of gene expression changes after either VHL restoration or HIF2α siRNA knockdown at all genes or genes adjacent to HIF2α binding sites.
Figure 6B:
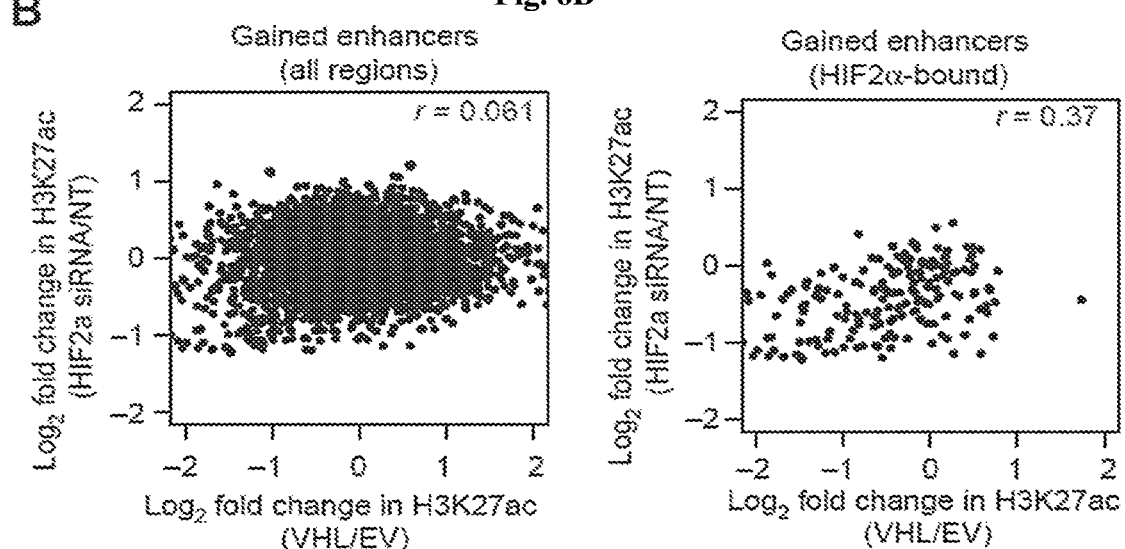
FIG. 6B refers to dot plots with Pearson's correlation of H3K27ac changes after VHL restoration and HIF2α siRNA knockdown at either all gained enhancers or HIF2α-bound enhancers adjacent to binding sites.
Figure 6C:
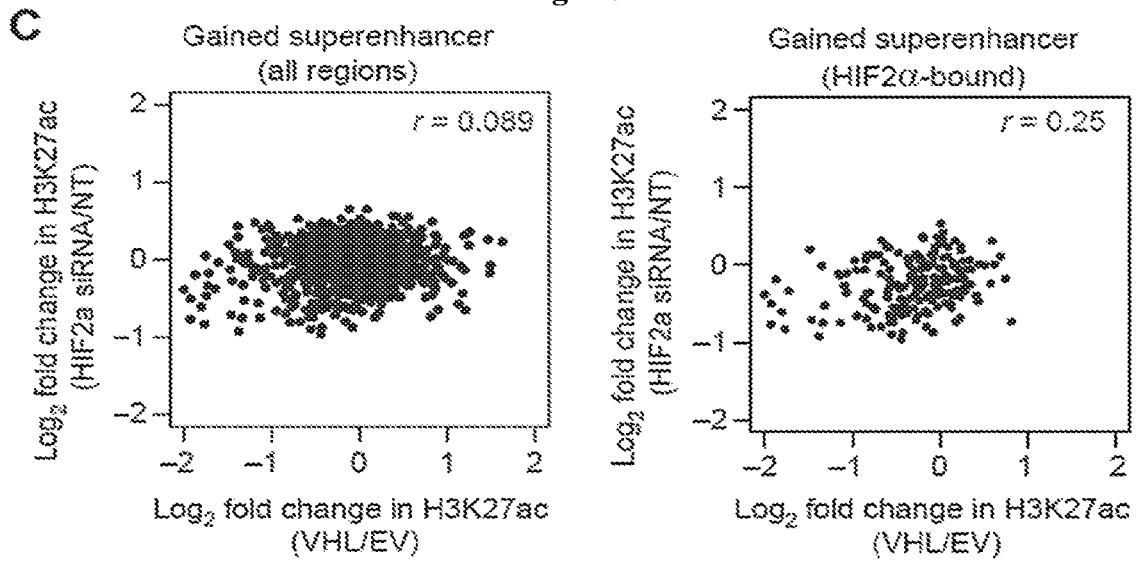
FIG. 6C refers to dot plots with Pearson's correlation of H3K27ac changes after VHL restoration and HIF2α siRNA knockdown at either all gained super-enhancers or HIF2α-bound super-enhancers adjacent to binding sites.
Figure 6D:
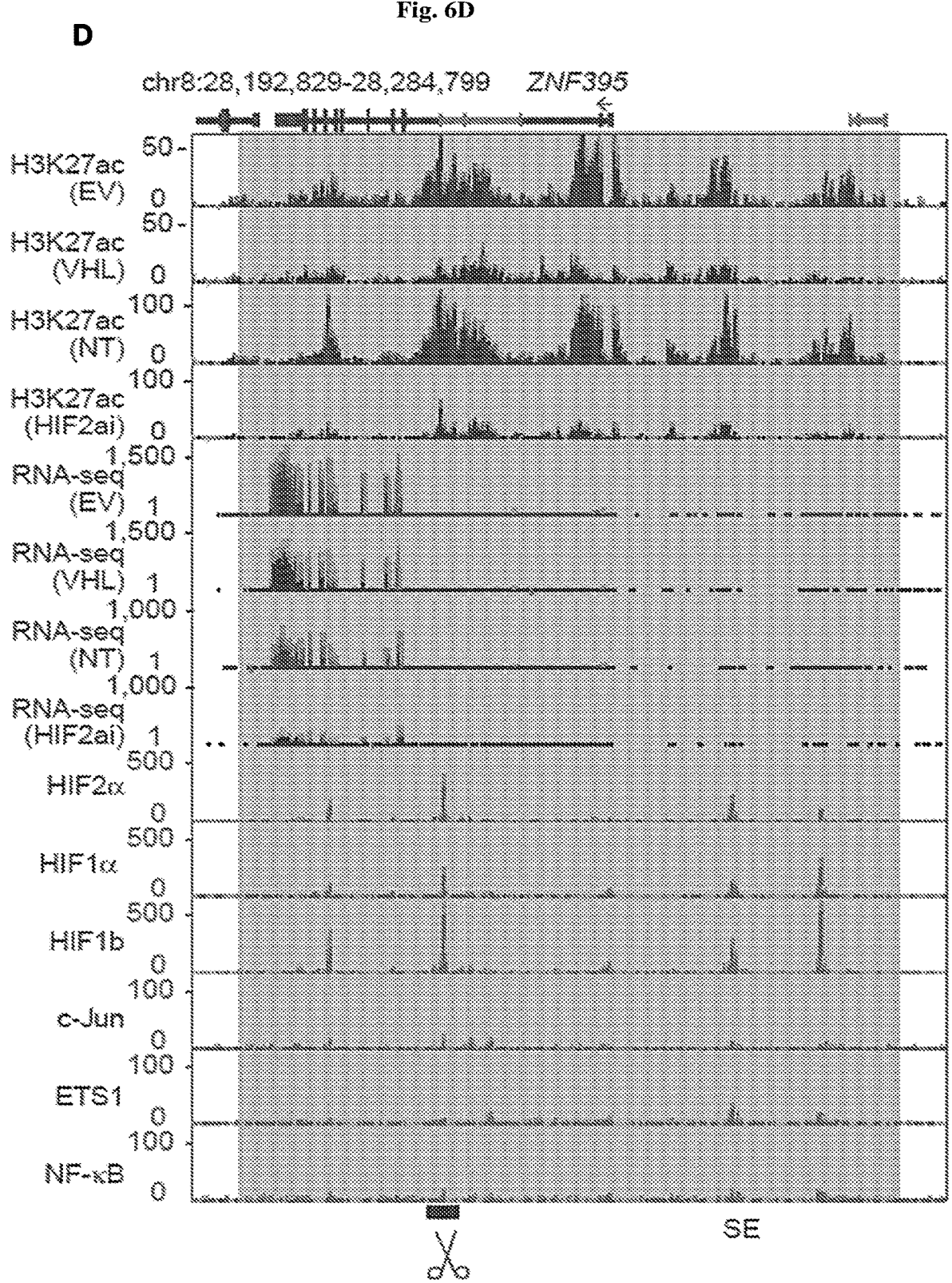
FIG. 6D refers to plots of histone chromatin immunoprecipitation sequencing (ChIP-Seq) profiles showing changes in RNAseq and H3K27ac ChIP-Seq signals after VHL restoration or HIF2α siRNA knockdown at ZNF395 super-enhancer (SE), together with binding profiles of transcription factors enriched at enhancers.
Figure 6E:
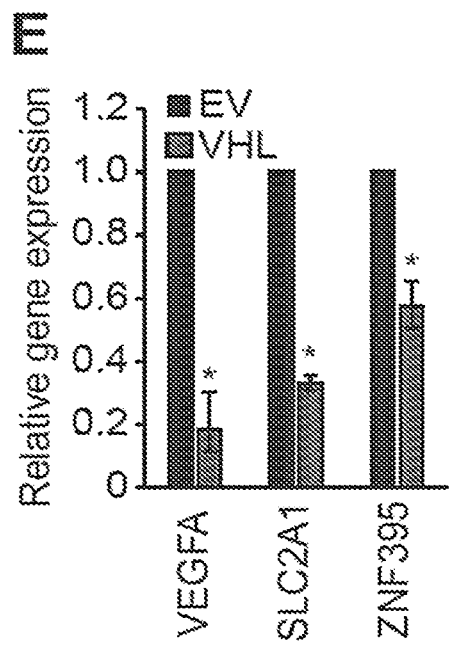
FIG. 6E refers to graphs showing both VHL restoration and HIF2α siRNA knockdown decreases expression of genes with HIF2α-bound enhancers in 786-O cells. *p-value <0.05, two-sided t-test.
Figure 6E:
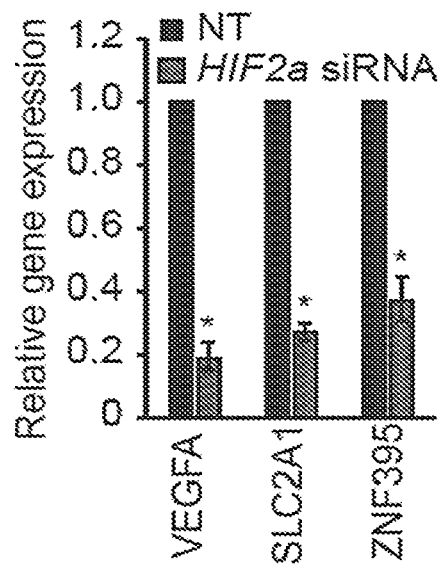
Figure 6F:
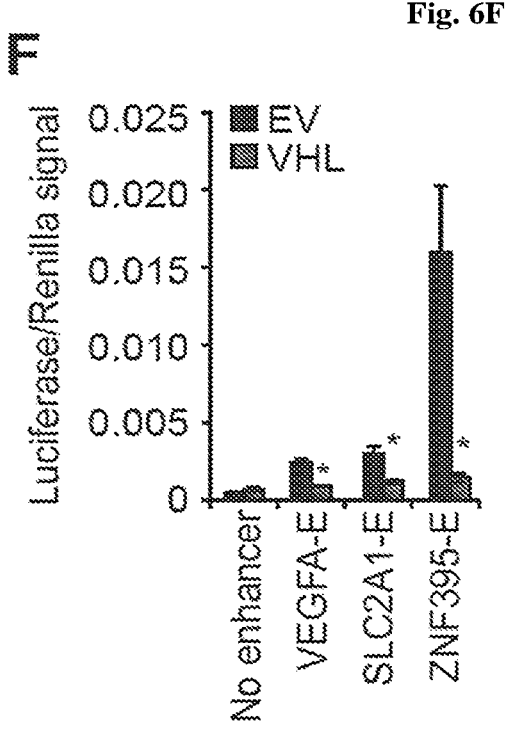
FIG. 6F refers to graphs showing both VHL restoration and HIF2α siRNA knockdown decrease enhancer activities measured by luciferase reporter assay in 786-O cells. *p-value <0.05, two-sided t-test.
Figure 6F:
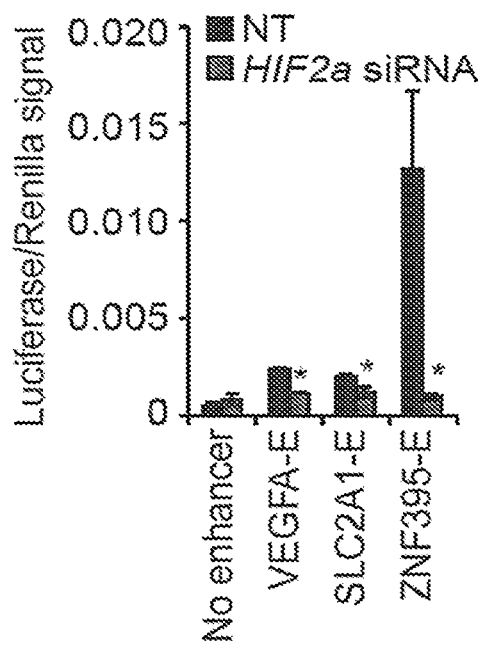

To investigate the extent to which HIF2α silencing is sufficient to recapitulate the effects of von Hippel-Lindau (VHL) restoration, H3K27ac chromatin immunoprecipitation sequencing (ChIP-seq) and RNA sequencing (RNA-seq) was performed in 786-O cells with HIF2α siRNA-mediated knockdown and analyzed correlations between HIF2α siRNA knockdown and VHL restoration. When assessed against all genes, there was a low correlation ($r=0.1$, $P=5.2\times10^{-31}$) between HIF2α knockdown and VHL restoration. Importantly, however, this correlation increased to 0.23 ($P=5.8\times10^{-14}$) for genes near HIF2α binding sites (FIG. 6A). Similar results were obtained at the epigenomic level, where for gained enhancers the correlation was low at 0.06 across all gained enhancers ($P=1.9\times10^{-5}$) but increased substantially to 0.37 ($P=9.5\times10^{-8}$) at HIF2α-bound enhancers (FIG. 6B) and at super-enhancers increased from 0.089 ($P=0.0025$) to 0.25 ($P=0.00054$) at HIF2α-bound super-enhancers (FIG. 6C). As a visual example, H3K27ac signals at the ZNF395 super-enhancer were diminished after VHL restoration or HIF2α knockdown, concomitant with decreased ZNF395 gene expression (FIG. 6D). Validation by RT-qPCR showed that HIF2α siRNA knockdown downregulated VEGFA, SLC2A1, and ZNF395 expression to a comparable degree as VHL restoration (FIG. 6E). Decreases in luciferase reporter activity of enhancer elements were also consistent between HIF2α siRNA knockdown and VHL restoration (FIG. 6F).

Figure 6G:
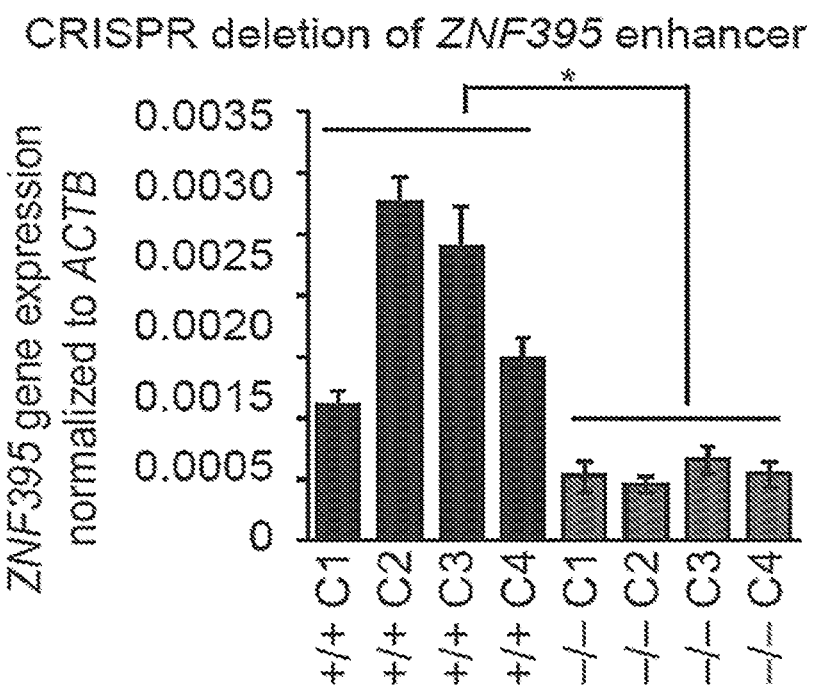
FIG. 6G refers to a column graph showing RT-qPCR measurement of ZNF395 expression in four wild-type clones and four clones with ZNF395 enhancer depleted by CRISPR. Depleted region has the highest HIF2α binding at ZNF395 super-enhancer in 786-O cells indicated by the back bar above the scissors (deleted region indicated in FIG. 6D). *p-value <0.05, two-sided t-test.

It was aimed to establish a causal link between HIF2α-bound enhancers and control of gene expression. CRISPR-mediated genomic depletion of the ZNF395 enhancer region with the highest HIF2α peak was performed (FIG. 6G). All four clones with the homozygous deleted ZNF395 enhancer consistently downregulated their ZNF395 expression compared with clones with the intact enhancer ($P<0.05$), providing evidence that ZNF395 expression is epigenetically controlled by this HIF2α—HIF1β-bound enhancer (FIG. 6G). Taken together, these results indicate that that HIF2α is an important mediator of von Hippel-Lindau (VHL)-driven enhancer remodeling.

Figure 7A:
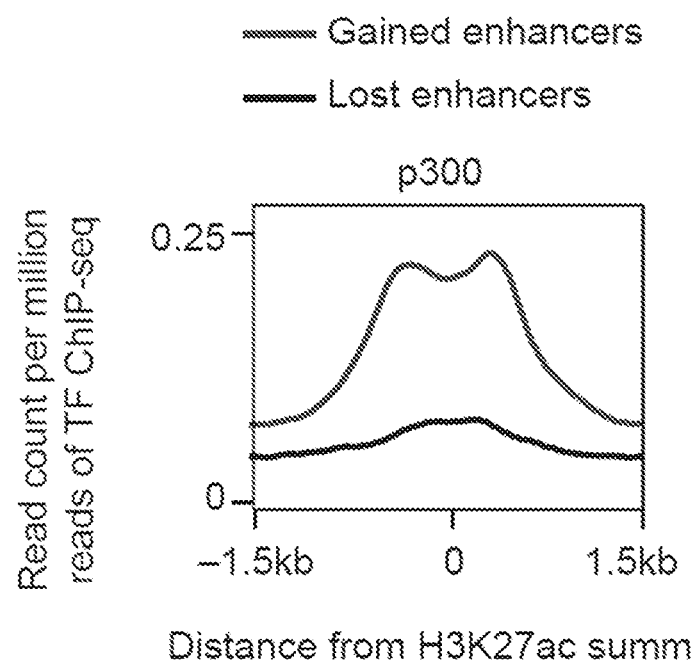
FIG. 7A shows a line graph of the enrichment of p300 binding at gained and lost enhancers based on chromatin immunoprecipitation sequencing (ChIP-Seq).
Figure 7B:
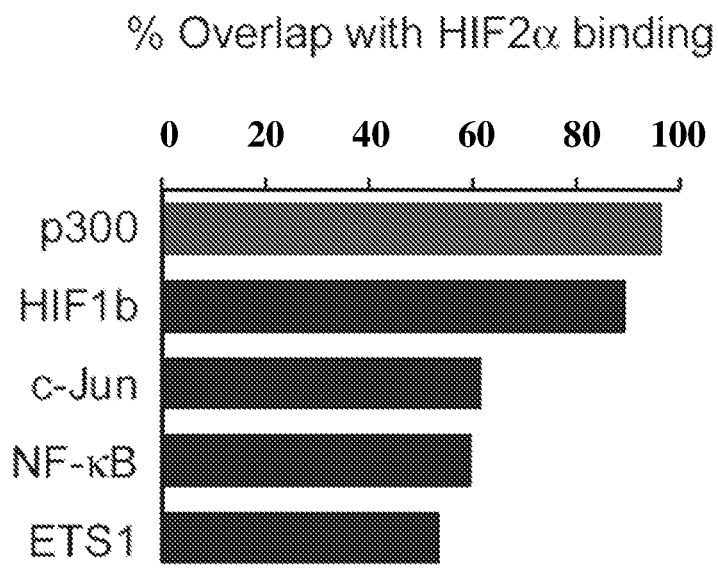
FIG. 7B refers to a column graph showing the percentage of overlap between HIF2α and other transcription factors.
Figure 7C:
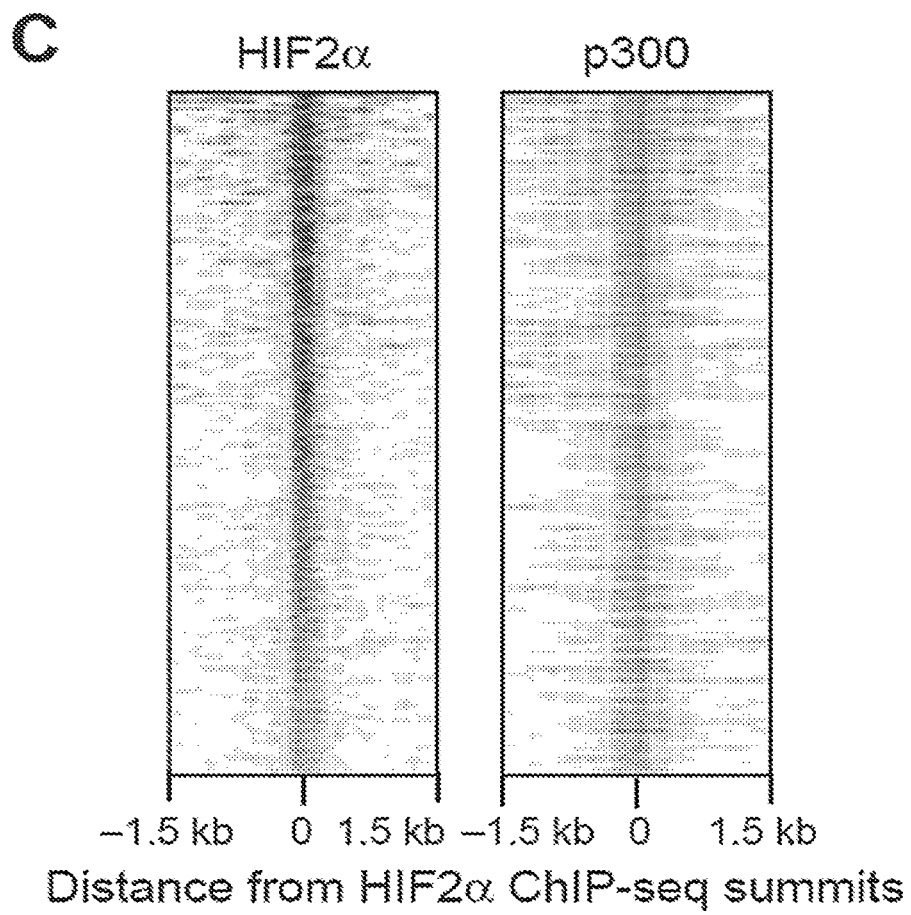
FIG. 7C refers to a heatmap of ChIP-Seq binding profiles of HIF2α and p300.
Figure 7D:
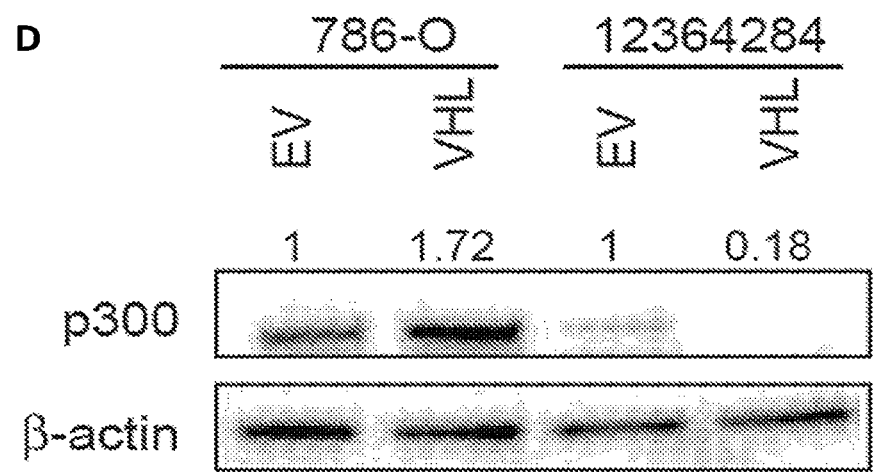
FIG. 7D shows an immunoblot of the protein expression of p300 with and without VHL in 786-O and 12364284 cells as measured by immunoblotting.
Figure 7E:
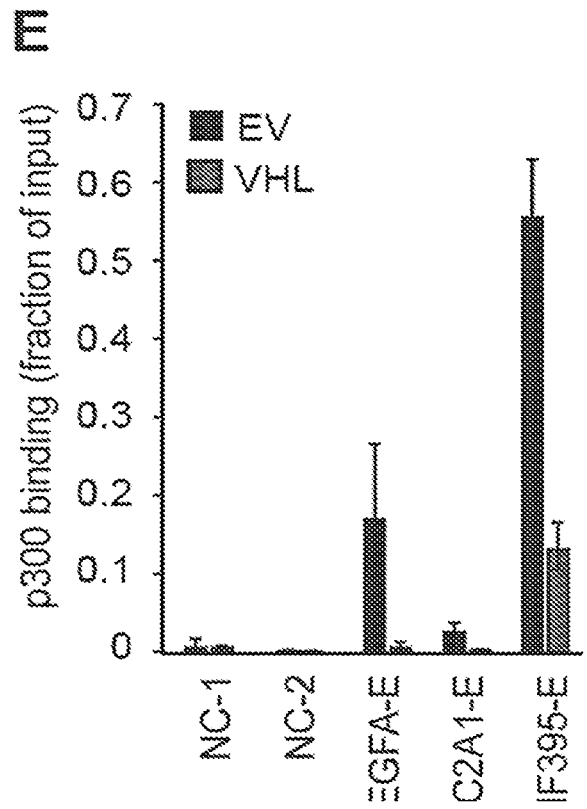
FIG. 7E shows a graph referring to ChIP-qPCR of p300 binding at enhancers with and without VHL restoration in 786-O cells. NC refers to negative control regions.
Figure 7F:
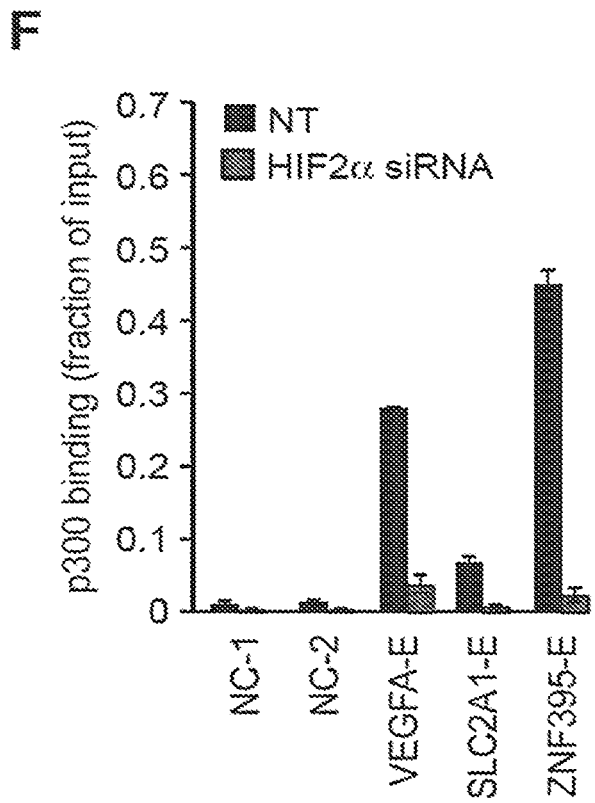
FIG. 7F refers to a graph showing the ChIP-qPCR of p300 binding at enhancers with and without HIF2α siRNA knockdown in 786-O cells. NC refers to negative control regions.

Example 8—Von Hippel-Lindau (VHL) Restoration Reduced P300 Recruitment but Preserved Promoter-Enhancer Interactions Finally, this study sought to investigate the reason von Hippel-Lindau (VHL) restoration caused a decrease in H3K27ac levels. Previous pulldown assays have reported that both HIF2α and HIF1β can interact with histone acetyltransferase p300. Indeed, p300 frequently marks enhancers and is thought to be recruited by tissue-specific transcription factors. However, chromatin profiles of p300 have not been previously established in kidney cancer cell lines, so the contribution of p300 in shaping enhancers in clear cell renal cell carcinoma remains unclear. Therefore, p300 chromatin immunoprecipitation sequencing (ChIP-seq) was performed in 786-O cells and confirmed its enrichment at gained enhancers over lost enhancers (FIG. 7A). Comparing p300 ChIP-seq with HIF2α ChIP-seq yielded a surprisingly high degree of overlap between HIF2α and p300 (96%), even more than that of HIF2α and HIF1β (89%; FIGS. 7B and 7C). In contrast, other transcription factors such as c-Jun, ETS1, and NF-κB did not exhibit such a high degree of overlap (60%; FIG. 7B).

p300 binding at tumour enhancers with and without VHL was compared. Despite increased p300 protein levels in 786-O cells after VHL restoration (FIG. 7D), binding of p300 decreased across all three enhancers examined (FIG. 7E). HIF2α depletion by siRNA knockdown also decreased p300 recruitment (FIG. 7F), suggesting that loss of HIF2α may interfere with p300 recruitment.

Figure 7G:
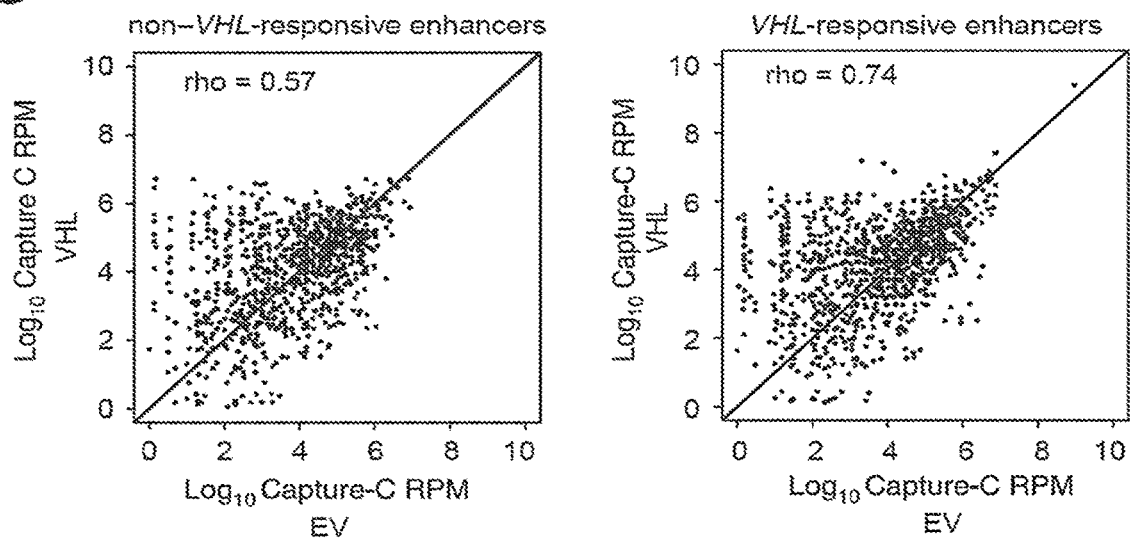
FIG. 7G shows scatter plots referring to correlation of enhancer interactions measured by Capture-C (RPM—reads per million) between 786-O cells with and without VHL restoration at both VHL-responsive and non-VHL-responsive enhancers.
Figure 7H:
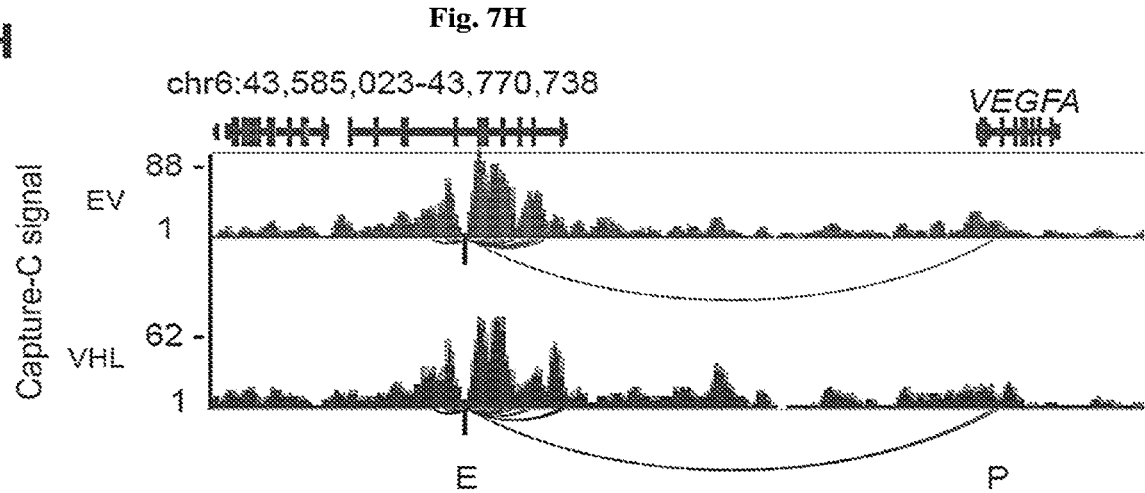
FIG. 7H shows a plot referring to Capture-C that shows that VEGFA enhancer-promoter interactions are maintained even after VHL restoration. E refers to enhancer and P refers to promoter.
Figure 7I:
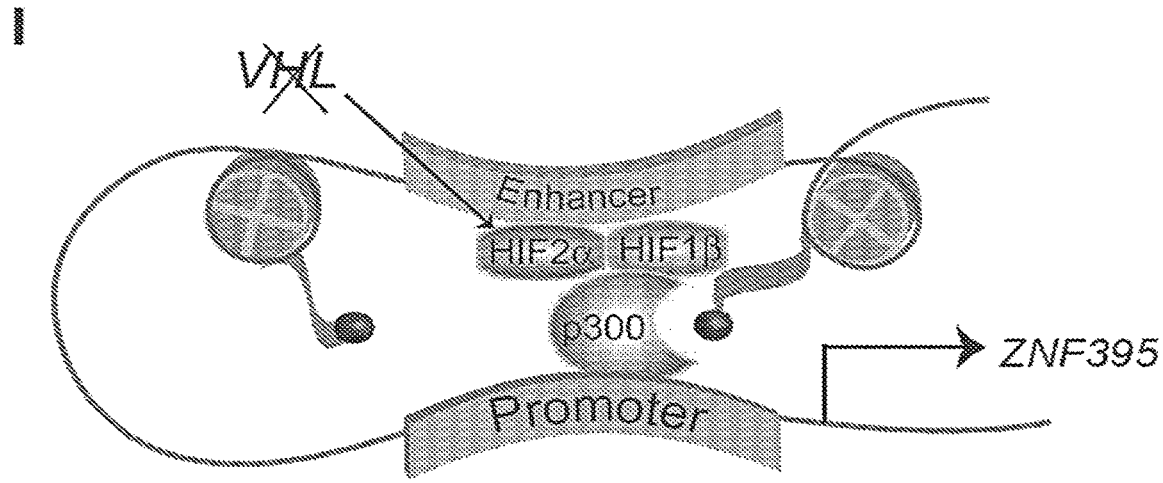
FIG. 7I shows a diagram with the schematics of VHL-driven enhancer aberration in clear cell renal cell carcinoma.
Figure 7J:
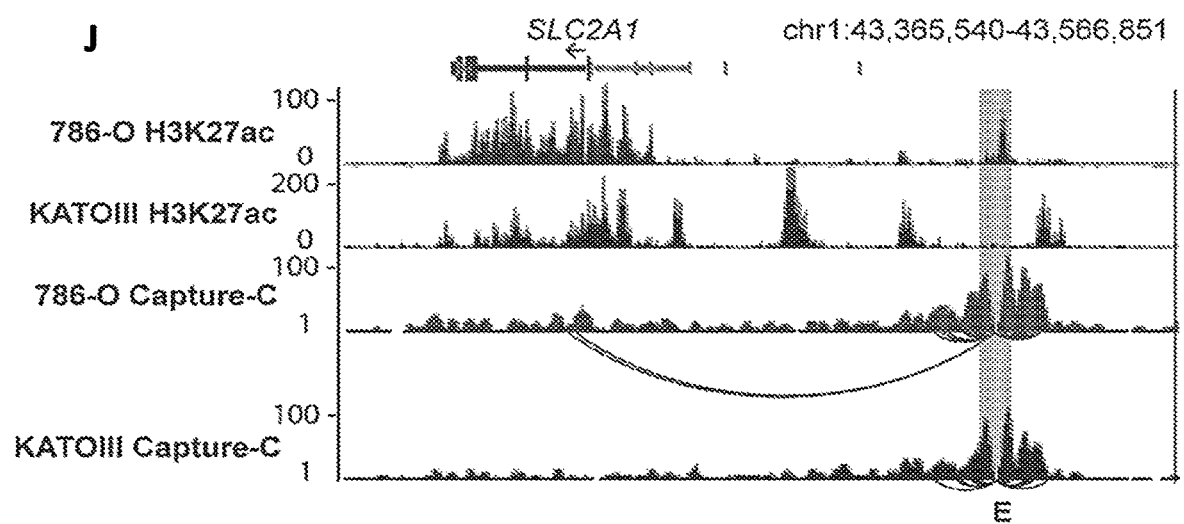
FIG. 7J refers to a plot with histone ChIP Seq profile of H3K27ac ChIP-seq and Capture C of 786-O (clear cell renal cell carcinoma cell line) and KATO III (gastric cancer cell line) showing that the SLC2A1 enhancer is specific to clear cell renal cell carcinoma.

It was investigated whether von Hippel-Lindau (VHL) restoration and the subsequent loss of p300 binding disrupted promoter-enhancer interactions. Capture-C of enhancer regions in paired 786-O cell lines with and without VHL restoration was performed. Capture-C interactions showed a relatively high correlation between VHL-deficient and VHL-restored 786-O cells at VHL-responsive regions ($r=0.74$, Pearson correlation), even higher than correlations observed at non-VHL-responsive regions ($r=0.57$, Pearson correlation; FIG. 7G). As a visual example, interactions between the VEGFA promoter and enhancer were intact even after VHL restoration (FIG. 7H), indicating that loss of enhancer activity is likely insufficient to dissociate promoter-enhancer interactions. Furthermore, many of these promoter-enhancers were lineage specific; for example, the interaction between SLC2A1 enhancer with its promoter was not detected in KATOIII, a gastric cancer cell line (FIG. 7J). Therefore, promoter-enhancer interactions often preexist in kidney cells, frequently in a tissue-specific manner.

Figure 8A:
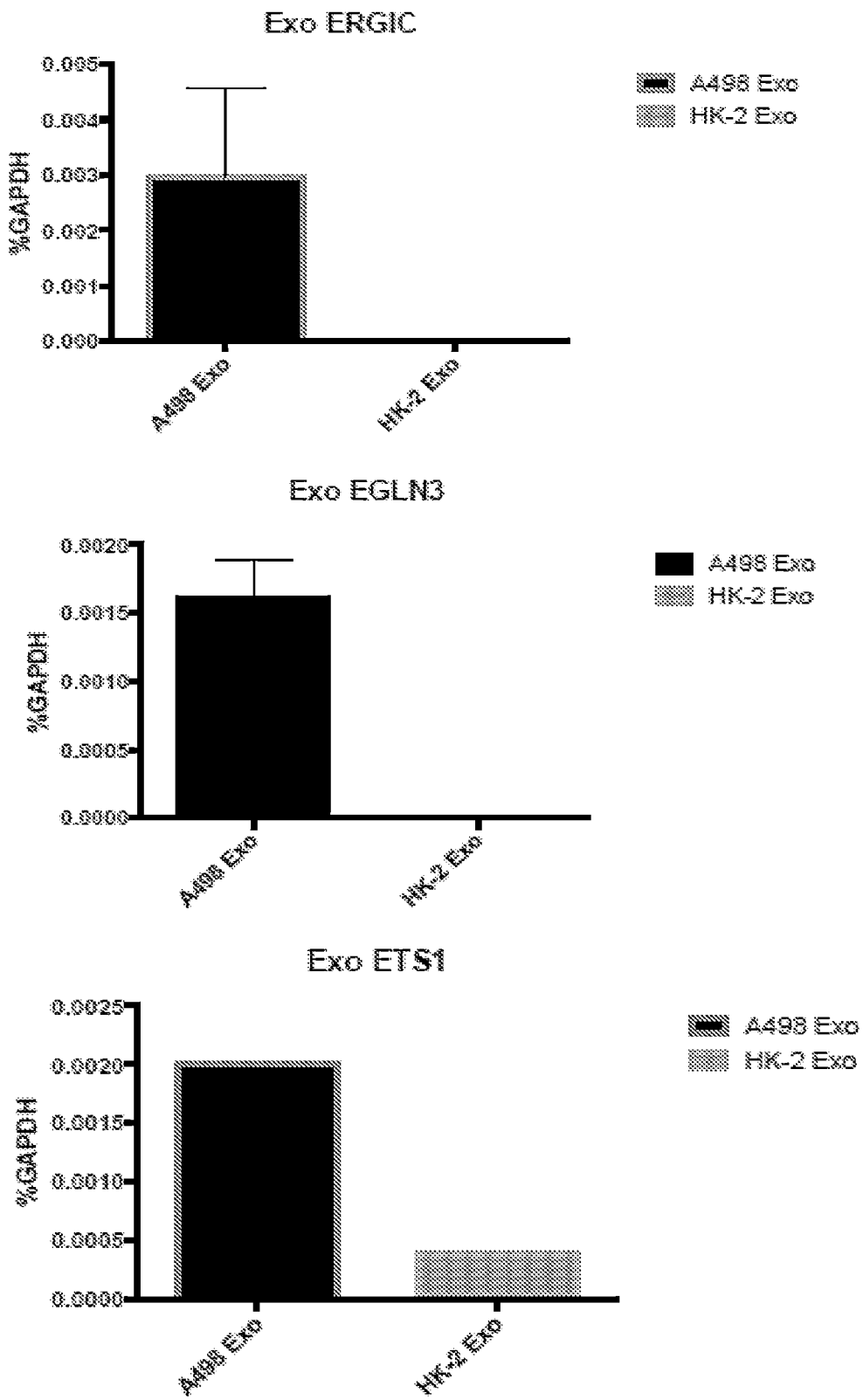
FIG. 8 (FIGS. 8A to 8C) shows graphs of analysis from exosomes obtained from A498 (clear cell renal cell carcinoma cell line) and HK-2 (normal kidney cell line). Each graph shows the level of the respective marker (as denoted by the title of each graph) that was detected based on exosomes secreted from the respective cell lines based on the graph legend. The y-axis of each graph shows gene expression of these markers as measured by quantitative polymerase chain reaction (qPCR).
Figure 8B:
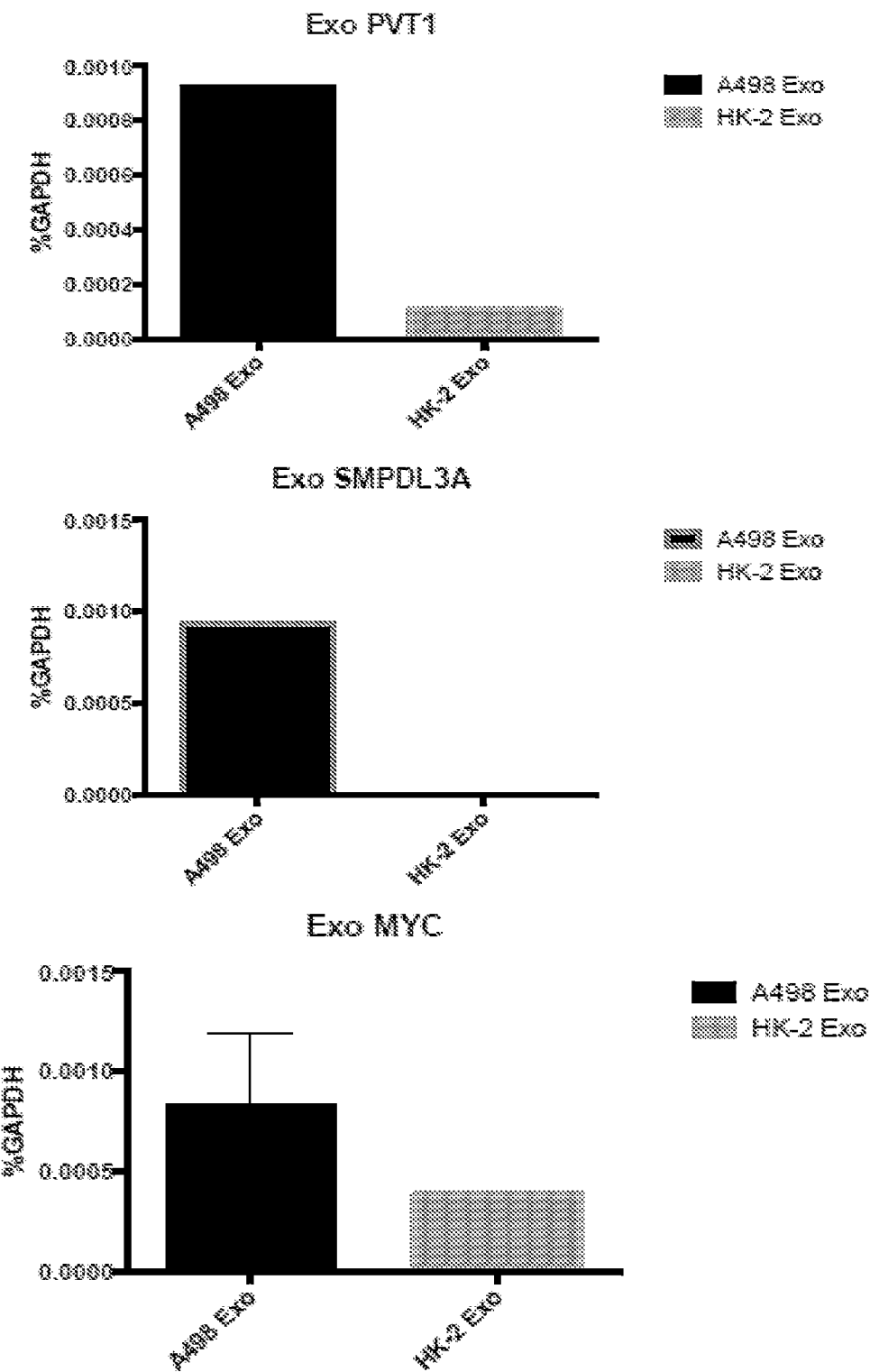
Figure 8C:
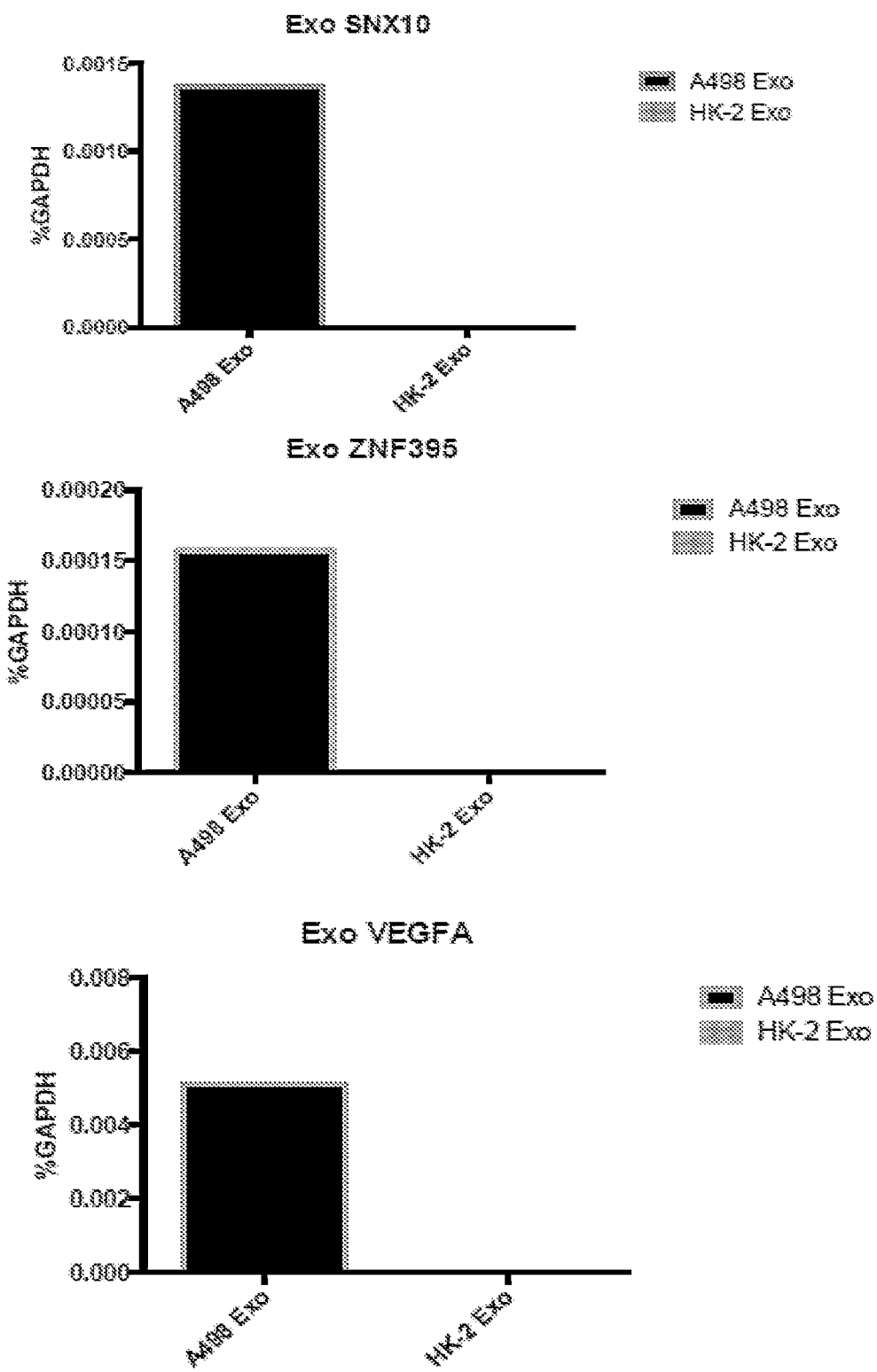

Clear cell renal cell carcinoma biomarkers were analysed from exosomes obtained from the culture medium of clear cell renal cell carcinoma cell line (A498) and normal kidney cell line (HK2), by measuring gene expression of the biomarkers by quantitative polymerase chain reaction (qPCR) (FIG. 8). ERGIC, EGLN3, ETS1, PVT1, MYC, SMPDL3A, SNX10, VEGFA and ZNF395 (FIGS. 8A, 8B and 8C) showed higher expression in clear cell renal cell carcinoma cell line compared to normal kidney cell line.

Figure 9:
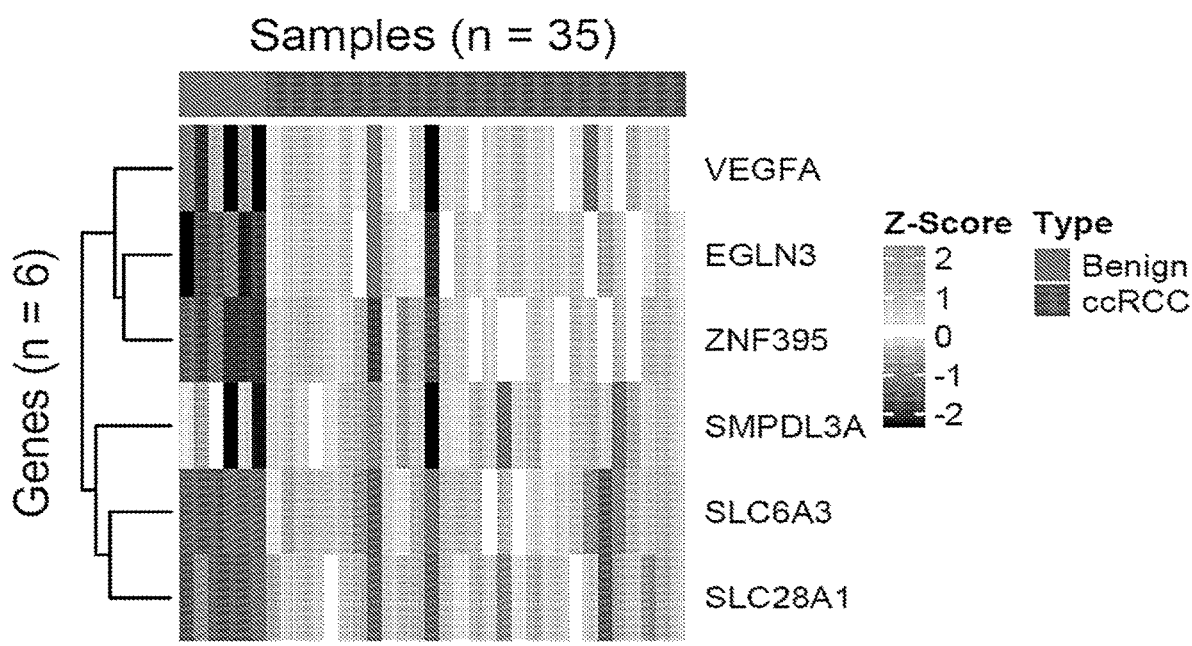
FIG. 9 shows a heatmap with microarray data analysis from patient cohorts with clear cell renal cell carcinoma (ccRCC) or benign oncocytoma (B). VEGFA, EGLN3, ZNF395, SMPDL3A, SLC6A3 and SLC28A1 expression levels were compared between benign oncocytoma and clear cell renal carcinoma. A higher Z score indicates higher expression levels.

Microarray data from patient cohorts with clear cell renal cell carcinoma or benign oncocytoma were compared. Expression levels of VEGFA. EGLN3, ZNF395, SLC6A3 and SLC28A1 are higher in clear cell renal cell carcinoma compared to benign oncocytoma as shown by higher Z score values (FIG. 9).

TABLE 5

A list of genes and proteins, and their accession numbers.

| | Accession number | Sequence |
|---|---|---|
| ZNF395 mRNA (SEQ ID NO: 43) | NM_018660.2 | aagtgcgcat gtgcgcgagg agtcgctcgg gcacttattg agcgccgact gtctacgggcggccgggggt gatgggcaga ggcttcagtg tcccctttcgc ctccgcagga gaggagaggcagcagcatgg cgagtgtcct gtcccgacgc cttggaaagc ggtccctcct gggagcccgggtgttgggac ccagtgcctc ggaggggccc tcggctgccc caccctcgga gccactgcta gaaggggccg ctccccagcc tttcaccacc tctgatgaca cccctgcca ggagcagccc aaggaagtcc ttaaggctcc cagcacctcg ggccttcagc aggtggcctt tcagcctggg cagaaggttt atgtgtggta cgggggtcaa gagtgcacag gactggtgga gcagcacagctggatggagg gtcaggtgac cgtctggctg ctggagcaga agctgcaggt ctgctgcaggtggaggagg tgtggctggc agagctgcag ggccctgtc cccaggcacc accctggagcccggagccc aggccctggc ctacaggccc gtctccagga acatcgatgt cccaaagag gaagtcggacg cagtggaaat ggatgagatg atggcggcca tggtgctgac gtccctgtcctgcagccctg ttgtacagag tcctcccggg accgaggcca |

TABLE 5-continued

A list of genes and proteins, and their accession numbers.

| Accession number | Sequence |
|---|---|
| | acttctctgc ttcccgtgcggcctgcgacc catggaagga gagtggtgac |
| | atctcggaca gcggcagcag cactaccagcggtcactgga gtgggagcag |
| | tggtgtctcc acccccctcgc ccccccaccc ccaggccagcccccaagtat |
| | tgggggatgc ttttggttct ccccaaactg atcatggctt tgagaccgat |
| | cctgacccct tcctgctgga cgaaccagct ccacgaaaaa gaaagaactc |
| | tgtgaaggtgatgtacaagt gcctgtggcc aaactgtggc aaagttctgc |
| | gctccattgt gggcatcaaa cgacacgtca aagccctcca tctgggggac |
| | acagtggact ctgatcagtt caagcgggag gaggatttct actacacaga |
| | ggtgcagctg aaggaggaat ctgctgctgc tgctgctgctgctgccgcag |
| | gcacccccagt ccctgggact cccacctccg agccagctcc cacccccagc |
| | atgactggcc tgcctctgtc tgctcttcca ccacctctgc acaaagccca |
| | gtcctccggc ccagaacatc ctggcccgga gtcctccctg ccctcagggg |
| | ctctcagcaa gtcagctcctgggtccttct ggcacattca ggcagatcat |
| | gcataccagg ctctgccatc cttccagatc ccagtctcac cacacatcta |
| | caccagtgtc agctgggctg ctgccccctc cgccgcctgc tctctctctc |
| | cggtccggag ccggtcgcta agcttcagcg agcccagca gccagcacct |
| | gcgatgaaat ctcatctgat cgtcacttct ccaccccggg cccagagtgg |
| | tgccaggaaa gcccgagggg aggctaagaa gtgccgcaag gtgtatggca |
| | tcgagcaccg ggaccagtgg tgcacggcct gccggtggaa gaaggcctgc |
| | cagcgctttc tggactgagc tgtgctgcag gttctactct gttcctggcc |
| | ctgccggcag ccactgacaa gaggccagtg tgtcaccagc cctcagcaga |
| | aaccgaaaga gaaagaacgg aaacacggag tttgggctct gttggctaag |
| | gtgtaacacttaaagcaattttctcccattgtgcgaacattttattttttaaaaa |
| | aaaga aacaaaaata ttttccccc taaaataggagagagccaaa |
| | actgaccaag gctattcagc agtgaaccag tgaccaaaga attaattacc |
| | ctccgttttcc cacatcccca ctctctaggg gattagcttg tgcgtgtcaa |
| | aagaaggaac agctcgttct gcttcctgct gagtcggtga attctttgct |
| | ttctaaactc ttccagaaag gactgtgagc aagatgaatt tacttttctt |
| | aaaaaaaaaa aaaaaaaaaa aaaaaaagag tttctggctg atgggtgact |
| | cagagtgcaggactgcctgg ccgtggggca gaggggtttg cccttctcgg |
| | agggtacctc ctgttccctg tctgagcatc ctgcatggaa gtcaaaggaa |
| | atccctttct tggtgacgac ttaaatctgg gttccctcag acattgggtt |
| | gcacccccaac aaatattaaa tggcttcttc ttaaagccca gagaaagagg |
| | tttttttaaaa gactgtcgcc aaatagctga gccaaaaggc tgatcagaat |
| | tcacttttttg gaatgtggca gttaaacact accttgatca ttctctcctc |
| | ttccctcgaggaactcctg agggtttgag cgtctggaaa ctctctgctc |
| | tgacccgagg aagcaccctc ctgacgccgc cttcctccgg ttattgaaag |
| | gacgcctcag aaatgctttg ttttctttta cgatgtattc agaagccttt |
| | actgattaaa gttttctttt atttgggtgg ccgggagaga cccagggagg |
| | ttctggaggt tccttctgt ctcctggccc caccaggat ttccccattt |
| | ctgtttgctg cctgaaagca ggatgaggaa ggccaaggag agtccttgca |
| | cccgtgagcg tcaggatgag gaaatgacag gaggaagacg tgggtttggg |
| | ttagtggctg ctggcgttttggcccttggt gtttctggag cctccaggga |
| | tctaggggag cctgggctgc gtgcatgtcg ataagcagag ctgttcttgg |
| | ggagaaggag ggaggtctcg ggagtgtagc accatgccaa ccagccctgc |
| | gcgaagacag agtgagccac gcccggatgg cagggcatgt ttctgttttg |
| | gtgtctcact ttcctcccag cgtgacttat ttggggattc ctcagggcct |
| | actggaatgt gactgcccac tgcccagctg cctcgggtac aagtcctggc |
| | cctatgtccc agctgtcagggggctcaggga atcctaccca gccacctgtc |
| | ctgggatgga gtgtcagcat ccacccctttg gttgtcatcg aggccgccct |
| | cccagtcctg ggtgaagata tttgggccac cagggctccc ttggcccctt |
| | cacgtaggaa atagacacgt gcttttttaat gcaggacact ttgagtgtta |
| | caaaatctgt agacctggca gtagggtcat gatgttggga agggtgtagt |
| | gccctaggtt ggtgacagaa gggacagaca cttgtgcaca ggtgtctttg |
| | gtgatgggt tttttttttt ataacttagt aaaaaaaaa aaatgtatgt |
| | ggaattctgt ctcttggtaa agctcaaagc caggctagcc tgaggtggcg |
| | cagggctctc cttcctgtcc cttcgatctc cttgagaatt aagagctggc |
| | agctgctgat ggtgtttccc aacccccctc acttcccaag acaacccccca |
| | gcttcaggtc ctcatgggga gggagggca cgttcttgac acatgggaac |
| | ttcgctcagg agggcctccc cttccctct ccctcagagt tttcactgcc |
| | gtctcgtctt tagaaagctg tttgaattcc cccgccccc agtttggacc |
| | gtgtagatat aactggatat acggattttt ctctttgtgc aggcttctta |
| | tgccgttggt atacagggca ggaaagagag gaataaaggg agagagcagt |
| | gtggaaacca cggtggtttt gctttgttct tactaggttt tggtgccacc |
| | ttccctgcct gcgcttgtgc cccctctcct ccttggcact ggcggcctcc |
| | ttgcctccct tccaccccgtg ctgccatccc gtgcctgtc tgttggttct |
| | tcacacgtgc tctgttctcg gggttgttcc attcatgcct tcttggaggg |
| | tgagggtggc ttgggaaccg acccagtgat catgcctact ttcttctttg |
| | tatctccctc cttcccagcc cacccgggca gcagactctg atggaaggaa |
| | ggtgccgtag gtgggcttt agaaactaac gggactggtt ttcaaagcag |
| | ttatcttggg aaactgttta ttccagcgat gtgacttttt tcagaatatt |
| | tcttggaatc atattcagag tctgggctg tgtgttgagc agccttaagg |
| | atgctagaca ctcatttagtgcccagggag tccagcgaat gacgtctgtg |
| | gccaagcgag gtctcaggtg caaagcaaaa ggaccatttta aagtaaaata |
| | gcttggattc aatcatgtga ctttttaaatt ggctcagaaa gcaatttttgt |

TABLE 5-continued

A list of genes and proteins, and their accession numbers.

| | Accession number | Sequence |
|---|---|---|
| | | aatttcagag agtgttttga gccatggcca cgttgtcatt gtgagtctat<br>agcttgactc cttggagaac aatattcatt tggttgtgga gactgatttg<br>ctgggagaaa tctgtcctgt tactttctgg tcatcccagg ttctgacttt<br>taccaggggc aaaaaaaaaaagcaagag ggagataaat cccatctgtg<br>agtttgtctt attggcgcct ttttcctcag ctgtcttcca agtattattt<br>ttactgttaa aaaattttt aaaaatgtga atgtaatgt tttacagca<br>acaatatgaa atatatttta taaggaataa atggtaccct tgtctgattt<br>aaaaaaa |
| ZNF395 protein (SEQ ID NO: 44) | NP_061130.1 | masvlsrrlg krsllgarvl gpsasegpsa appsepllleg aapqpfttsd<br>dtpcqeqpkevlkapstsgl qqvafqpgqk vyvwyggqec tglveqhswm<br>egqvtvwlle qklqvccrveevwlaelqgp cpqapplepg aqalayrpvs<br>rnidvpkrks davemdemma amvltslscspvvqsppgte anfsasraac<br>dpwkesgdis dsgssttsgh wsgsssgvstp spphpqaspkylgdafgspq<br>tdhgfetdpd pfllldepapr krknsvkvmy kelwpncgkv<br>lrsivgikrhvkalhlgdtv dsdqfkreed fyytevqlke esaaaaaaaa<br>agtpvpgtpt sepaptpsmtglplsalppp lhkaqssgpe hpgpesslps<br>galsksapgs fwhiqadhay qalpsfqipvsphiytsvsw aaapsaacsl<br>spvrsrslsf sepqqpapam kshlivtspp raqsgarkargeakkerkvy<br>giehrdqwet acrwkkacqr fld |
| SMPDL3A mRNA (isoform b) (SEQ ID NO: 45) | NM_001286138.1 | accagtatgt cagtgtttga catcaactgc accactgata cacgagtcgg<br>aatttgagcttctacaagta cattccttcc taggccaaac actgacgcta agaaatacga<br>gaacagatcatcgctaaaca gcagctgaag gtcaggcgaa ctgactcgct gcggaatctg<br>cctttgcacgtgatcagtcg gacgtctaca cccgcagccg tcttctgtct ccgcctcacc<br>ctcaggcctgacggtccgag tggagctgcg ggacagcccg aacctccagg tcagccccgc<br>ggccctccatggcgctggtg cgcgcactcg tctgctgcct gctgactgcc tggcactgcc<br>gctccggcctcgggctgccc gtgtgcgcccg caggcggcag gaatcctcct ccggcgatag<br>ggatagcccacctcatgttc ctgtacctga actctcaaca gacactgtta taaatgtgat<br>cactaatatgacaaccacca Tccagagtct Ctttccaaat ctccagtttt tccctgcgct<br>gggtaatcatgactattggc cacaggatca actgcctgta gtcaccagta aagtgtacaa<br>tgcagtagcaaacctctgga aaccatggct agatgaagaa gctattagta ctttaaggaa<br>aggtggttttattcacaga aagttacaac taatccaaac cttaggatca tcagtctaaa<br>catagcacatgttccagtgg gagacagcat tatggttctt aacatcacag caatgagaga<br>atactataatgagaaattga gactgttttca ggcgaatcta agtgatgtca ttgcaggaca<br>attttatggacacactcaca atctgacaga tcttcacag tcagataaaa aaggaagtcc<br>agtaaattcttttgtttgtgg ggtatctgcc tcaaaaatac aagagtgttt tagaaaaaca<br>gaccaacaatcctggtatca tagatatttt taccacagtg cgtgattata aattattgga<br>tatgttgcagtattacttga ctcctgctgt gtatgatcct aagggagagt ccatctggaa<br>cacaaacttgtactacggcc caaatataat gacactgaac aagactgacc cagccaacca<br>gtttgaatggctagaaagta cattgaacaa ctctcagcag aataaggaga aggtgtatat<br>gctggagtatatcctgaccc agacctacga cattgaagat ttgcagccgg aaagtttata<br>tggattagctaaacaattta caatcctaga cagtaagcag tttataaaat actacaatta<br>cttcttttgtgagttatgaca gcagtgtaac atgtgataag acatgtaagg cctttcagat<br>ttgtgcaattatgaatcttg ataatatttc ctatgcagat tgcctcaaac agctttatat<br>aaagcacaattactagtatt tcacagtttt tgctaataga aaatgctgat tctgattctg<br>agatcaatttgtgggaattt acataaaatc tttgttaatt actgagtggg caagtagact<br>gggtaatcatgactattggc cacaggatca actgcctgta gtcaccagta aagtgtacaa<br>cacaaacttgtactacggcc caaatataat gacactgaac aagactgacc cagccaacca<br>gtttgaatggctagaaagta cattgaacaa ctctcagcag aataaggaga aggtgtatat<br>ttgcagccgg aaagtttata |
| SMPDL3A protein (isoform b) (SEQ ID NO: 46) | NP_001273067.1 | mtttiqslfp nlqvfpalgn hdywpqdqlp vvtskvynav anlwkpwlde<br>eaistlrkggfysqkvttnp nlriislntn lyygpnimtl nktdpanqfe wlestlnnsq<br>qnkekvyiiahvpvgylpss qnitamreyy neklidifqk ysdviagqfy ghthrdsimv<br>lsdkkgspvnslfvapavtp vksvlekqtn npgirlfqyd prdyklldml qyylnltean<br>lkgesiwkleyiltqtydie dlqpeslygl akqftildsk qfikyynyff vsydssvtcd<br>ktckafqicaimnldnisya delkqlyikh ny |
| SMPDL3A protein (isoform a) (SEQ ID NO: 47) | NM_006714.4 | accagtatgt cagtgtttga catcaactgc accactgata cacgagtcgg<br>aatttgagcttctacaagta cattccttcc taggccaaac actgacgcta agaaatacga<br>gaacagatcatcgctaaaca gcagctgaag gtcaggcgaa ctgactcgct gcggaatctg<br>cctttgcacgtgatcagtcg gacgtctaca cccgcagccg tcttctgtct ccgcctcacc<br>ctcaggcctgacggtccgag tggagctgcg ggacagcccg aacctccagg tcagccccgc<br>ggccctccatggcgctggtg cgcgcactcg tctgctgcct gctgactgcc tggcactgcc<br>gctccggcctcgggctgccc gtgtgcgcccg caggcggcag gaatcctcct ccggcgatag<br>gacagttttggcatgtgact gacttacact tagaccctac ttaccacatc acagatgacc<br>acacaaaagtgtgtgcttca tctaaaggtg caaatgcctc caaccctggc cctttggag<br>atgttctgtgtgattctccatatcaacttattttgtcagcatttgatttattaaaaattctgg<br>acaagaagcat<br>ctttc atgatatgga caggggatag cccacctcat gttcctgtac<br>ctgaactctcaacagacact gttataaatg<br>tgatcactaa tatgacaacc accatccaga gtctctttcc aaatctccag ttttccctg<br>cgctgggtaa tcatgactat tggccacagg atcaactgcct gtagtcacc agtaaagtgt<br>acaatgcagt agcaaacctc tggaaaccat ggctagatga agaagctatt agtactttaa |

TABLE 5-continued

A list of genes and proteins, and their accession numbers.

| | Accession number | Sequence |
|---|---|---|
| | | ggaaaggtgg tttttattca cagaaagtta caactaatcc aaaccttagg atcatcagtc taaacacaaa cttgtactac ggcccaaata taatgacact gaacaagact gacccagcca accagtttga atggctagaa agtacattga acaactctca gcagaataag gagaaggtgt atatccatagc acatgttcca gtggggtatc tgccatcttc acagaacatc acagcaatga gagaatacta taatgagaaa ttgatagata tttttcaaaaa tacagtgat gtcattgcag gacaatttta tggacacact cacagagaca gcattatggt tcttttcgat aaaaaaggaa gtccagtaaa ttctttgttt gtggctcctg ctgttacacc agtgaagagt gttttagaaa aacagaccaa caatcctggt atcagactgt ttcagtatga tcctcgtgat tataaattat tggatatgtt gcagtattac ttgaatctga cagaggcgaa tctaaaggga gagtccatct ggaagctgga gtatatcctg acccagacct acgacattga agatttgcag ccggaaagtt tatatggatt agctaaacaa tttacaatcc tagacagtaa gcagtttata aatactaca attacttctt tgtgagttat gacagcagtg taacatgtga taagacatgt aaggcctttc agatttgtgc aattatga atcttgataa tatttcctat gcagattgcc tcaaacagct ttatataaag cacaattact agtatttc acagttttgc taatagaaaa tgctgattct gattctgagat caattgtggga atttttacata aatctttgtt aattactgagt gggcaagtag acttcctgtc tttgctttct ttttttt tttctttttga tgccttaatg tagatatctt tatcattctg aattgtatta tataattta aagtgctcat taataaatga tgatgatgta att ggatgtaaat attcagttta tataattata tcaatttgta ccccttgttg aaattgtcat ttatacaata aagcgaattc tttatctcta aaaaaaaaaa aaaaaaaaa |
| SMPDL3A protein (isoform a) (SEQ ID NO: 48) | NP_006705.1 | malvralvcc lltawhersg lglpvapagg rnpppaigqf whvtdlhldp tyhitddhtk vcasskgana snpgpfgdvl cdspyqlils afdfiknsgq easfmiwtgd spphvpvpel stdtvinvit nmttttiqslf pnlqvfpalg nhdywpqdql pvvtskvyna vanlwkpwld eeaistlrkg gfysqkvttn pnlriisslnt nlyygpnimt lnktdpanqf ewlestlnns qqnkekvyii ahvpvgylps sqnitamrey yneklidifq kysdviagqf yghthrdsim vlsdkkgspv nslfvapavt pvksvlekqt nnpgirlfqy dprdyklldm lqyylnltea nlkgesiwkl eyiltqtydi edlqpeslyg lakqftilds kqfikyynyf fvsydssvtc dktckafqic aimnldnisy adclkqlyik hny |
| SLC28A1 mRNA (SEQ ID NO: 49) | NM_001287761.1 | acaacgatgt gaaggttata agctgcactg catggttgct gctggatgtg ttgtgtgttcctggcttccctc tggatgctga cagaaacaag gctggaaggt ctgggacatg gagaacgacc cctcgagacg aagagagtcc atctctctca cacctgtggc caaggtctg gagaacatgg gggctgattt cttggaaagc ctggaggaag gccagctccc taggagtgac ttgagcccg cagagatcag gagcagctgg agcgaggcgg cgccgaagcc cttctccaga tggaggaacc tgcagccagc cctgagagcc agaagcttct gcagggagca catgcagctg tttcgatgga tcggcacagg cctgctctgc actgggctct ctgccttcct gctggtggcc tgcctcctgg atttccagag ggccctggct ctgtttgtcc tcacctgtgt ggtcctcacc ttcctgggcc accgctgct gaaacggctt ctggggccaa agctgaggag gtttctcaag cctcagggcc atccccgcct gctgctctgg tttaagaggg gtctagctct tgctgctttc ctgggcctgg tcctgtggct gtctctggac acctcccagc ggcctgagca actggtgtcc ttcgcaggaa tctgcgtgtt cgtcgctctc ctcttttgct gctcaaagca tcattgcgca cacgtgggcc tcatgcagtg ggtgatcctg aagattgcct ggctgatgca agtcaccatg ggcaccacag ccactgagac cctgagtgtg gctggaaaca tctttgtgag ccagaccgag gctccattac tgatccggcc ctacttggca gacatgacac tctctgaagt ccacgttgtc atgaccggag gttacgccac cattgctggc agctgctgg gtgcctacat ctccttttggg gtcagagctg aagtcctcac gacgtttgcc ctctgtggat ttgcaatttt cagctccatt gggatcatgc tgggaggctt gacctccatg gtcccccaac ggaagagcga cttctcccag atagtgctcc gggcgctctt cacgggagcc tgtgtgtccc tggtgaacgc ctgtatggca gggatcctct acatgcccag gggggctgaa gttgactgca tgtccctctt gaacacgacc ctcagcagca gtagctttga gatttaccag tgctgccgtg aggccttcca gagcgtcaat ccagagttca gcccagaggc cctggacaac tgctgcggt tttacaacca cacgatctgt gcacagtgag gacagaaacat gcttgtgctt ctgcgcttct gagggctgtt ctccccgggg aaccatctgt ccccacctcc cctttcccag agccctcttc agggaagcca caggacttag acccagctca atcccacaat tgggaagggt tcatggagtg agtgtgcaga gagtgagtga ggacataagg aaggacatgt cccactccat ccccttcct gctccccat ttcctaactc ccccagtgtg aattctcagg gtcacttctg cctcctcccg tttcccctcc acatccaaac agcaccctgg tcctctctat ccccccctc tgggtgtccc tcacatgccc cttcccttct gttgtgggct gcacaccaaa gcctcctccc ctccccactt cctaggcact aggatctctc tgtggcttcc cctgctgggt ggtgtcacct cttttctctgc tttcagaaa accctccccg ccttttcctca gagtgcttcc caaactgagg tcccatggca cactgtcctg gagggcgttc agagggttcc atgatggact aggtttggaa ccactgggtt aaataaactt agagagggct gttta |
| SLC28A1 protein (SEQ ID NO: 50) | NP_001274690.1 | mendpsrrre sisltpvakg lenmgadfle sleegqlprs dlspaeirss wseaapkpfs rwrnlqpalr arsfcrehmq lfrwigtgll ctglsafllv aclldfqral alfvltcvvl tflghrllkr llgpklrrfl kpqghprlll wfkrglalaa flglvlwlsl dtsqrpeqlv sfagicvfva llfacskhhc avswravswg lglqfvlgll virtepgfia fewlestlns flsytkagss fvfgealvkd vfafqvlpii vffscvisvl yhvglmqwvi lkiawlmqvt mgttatetls vagnifvsqt eapllirpyl admtlsevhv vmtggyatia gsllgayisf gvraevlttf alcgfanfss igimlgglts mvpqrksdfs qivlralftg acvslvnacm agilymprga evdcmsllnt tlssssfeiy qccreafqsv npefspeald nccrfynhti caq |

TABLE 5-continued

A list of genes and proteins, and their accession numbers.

| | Accession number | Sequence |
|---|---|---|
| VEGFA mRNA (SEQ ID NO: 51) | NM_001025366.2 | tcgcggaggc ttggggcagc cgggtagctc ggaggtcgtg gcgctggggg ctagcaccag cgctctgtcg ggaggcgcag cggttaggtg gaccggtcag cggactcacc ggccagggcg ctcggtgctg gaatttgata ttcattgatc cgggttttat ccctcttctt ttttcttaaa cattttttt taaaactgta ttgtttctcg ttttaattta ttttgcttg ccattcccca cttgaatcgg gccgacgct tggggagatt gctctacttc cccaaatcac tgtggatttt ggaaaccagc agaaagagga aagaggtagc aagagctcca gagagaagtc gaggaagaga gagacgggt cagagagagc gcgcgggcgt gcgagcagcg aaagcgacag gggcaaagtgagtgacctgc ttttgggggt gaccgccgga gcgcggcgtg agccctcccc cttgggatcccgcagctgac cagtcgcgct gacggacaga cagacagaca ccgcccccag ccccagctaccacctcctcc ccggccgcg gccgacagtg gacgcggcgg cgagccgcgg gcaggggccggagcccgcgc ccggaggcgg ggtggagggg gtcggggctc gcggcgtcgc actgaaacttttcgtccaac ttctgggctg ttctcgcttc ggaggagccg tggtccgcgc gggggaagccgagccgagcg gagccgcgag aagtgctagc tcgggccggg aggagccgca gccggaggaggggaggagg aagaagagaa ggaagaggag aggggccgc agtggcgact cggcgctcggaagccgggct catggcgggg tgaggcggcg gtgtgcgcag acagtgctcc agccgcgcgcgctccccagg ccctggcccg gcggaggaa gagtagctcg ccgaggcgccgaggagagcg ggccgcccca cagcccgagc cggagaggga gcgcgagccg cgccggcccggtcgggcct ccgaaaccat gaactttctg ctgtcttggg tgcattggag ccttgccttgctgctctacc tccaccatgc caagtggtcc caggctgcac catggcagaa ggaggagggcagaatcatc acgaagtggt gaagttcatg gatgtctatc agcgcagcta ctgccatccaatcgagaccc tggtggacat cttccaggag taccctgatg aaatcgagta catcttcaagccatcctgtg tgcccctgat gcgatgcggg gctgctgca atgacgaggg cctggagtgtgtgcccactg aggagtccaa catcaccatg cagattatgc ggatcaaacc tcaccaaggccagcacatag gagagatgag cttcctacag cacaacaaat gtgaatgcag accaagaaaagatagagcaa gacaagaaaa aaatcagtt cgaggaaagg gaagggggca aaaacgaaagcaagaaat cccggtataa gtcctggagc gtgtacgttg gtgccccgctg ctgtctaatgccctggagcc tccctggccc catcccgt gggccttgct cagacggag aaagcattttttgtacaag atccgcagac gtgtaaatgt tcctgcaaaa acacagactc gcgttgcaaggcgaggcagc ttgagttaaa cgaacgtact tgcagatgtg acaagccgag gcggtgagccgggcaggagg aaggagcctc cctcaggtt tcgggaacca gatctctcac caggaaagactgatacagaa cgatcgatac agaaaccagc ctgccgccac cacaccatca ccatcgacagaacagtcctt aatccagaaa cctgaaatga aggaagagga gactctgcgc agagcactttgggtccggag ggcgagactc cggcggaagc attcccgggc gggtgaccca gcacggtccctcttggaatt ggattcgcca ttttatttt cttgctgcta aatccgag cccggaagattagagagtt tatttctggg attcctgtag acacaccac ccacatacat acatttatatatatatat tatatatata tatctatatt ttatatatat aaaatatatatattctttt ttaaatttaac agtgctaatg ttattggtgt cttcactggatgtatttgac tgctgtggac ttgagttggg aggggaatgt tcccactcag atcctgacagggaagaggaggagatgagag actctggcat gatctttttt ttgtcccact tggtggggccagggtcctctcccctgccca ggaatgtgca aggccagggc atggggcaa atatgacccagttttgggaacaccgacaaa cccagccctg gcgctgagcc tctctacccc aggtcagacggacagaaagacagatcacag gtacagggat gaggacaccg gctctgacca ggagtttgggggagcttcaggacattgctgt gctttgggga ttccctccac atgctgcacg cgcatctcgcccccaggggcactgctggaa agattcagga gcctgggcgg ccttcgctta ctctcacctgcttctgagttgccccaggaga ccactggcag atgtcccggc gaagagaaga gacacattgttggaagaagcagccccatgac agctccccctt cctgggactc gccctcatcc tcttcctgctccccttcctggggtgcagcc taaaaggacc tatgtcctca caccattgaa accactagttctgtcccccaggagacctg gttgtgtgtg tgtgagtggt tgaccttcct ccatcccctggtccttccttcccttcccg aggcacagag acagggca ggatccacgt gccattgtggaggcagagaaaagagaaag tgtttatat acggtactta tttaatatcc ctttttaatt agaaattaaaacagttaatt taattaaaga gtagggtttt ttttcagtat tcttgttaa tatttaatttcaactatttatgagatgtat cttttgctct ctcttgctct cttatttgta cggttttgtatataaaat tcatgtttccaatctctctc tccctgatcg gtgacagtca ctagcttatctgaacagat atttaatttt gctaacactcagctctgccc tccccgatcc cctggctcccagcacacat tcctttgaaa taaggtttcaatatacatct acatactata tatatatttggcaacttgta tttgtgtgta tatatatata tatgtttatgtatatatg tgattctgataaaatagaca ttgctattct gttttttata tgtaaaaaca aaacaagaaaaatagagaattctacatac taaatctctc tccttttta attttaatat ttgttatcatttatttattggtgctactgt ttatccgtaa taattgtggg gaaaagatat taacatcacgtcttttgtctctagtgcagtt tttcgagata ttccgtagta catatttatt tttaaacaacgacaaagaaatacagatata tcttaaaaaa aaaaagcat tttgtattaa agaatttaattctgatctcaaaaaaaaaaa aaaaaa |
| VEGFA protein (SEQ ID NO: 52) | NP_001020537.2 | mtdrqtdtap spsyhllpgr rrtvdaaasr gqgpepapgg gvegvgargv alklfvqllg csrfggavvr ageaepsgaa rsassgreep qpeegeeeee keeergpqwr lgarkpgswt geaavcadsa paarapqala rasgrggrva rrgacesgpp hspsrrgsas ragpgraset mnfllswvhw slalllylhh akwsqaapma egggqnhhev vkfmdvyqrs ychpietlvdifqeypdeie yifkpscvpl mreggcende glecvptees nitmqimrik phqgqhigemsflqhnkec rpkkdrarqe kksvrgkgkg qkrkrkksry kswsvyvgar cclmpwslpgphpcgpcser rkhlfvqdpq tckcscktnd srckarqlel nertcredkp rr |

TABLE 5-continued

A list of genes and proteins, and their accession numbers.

| | Accession number | Sequence |
|---|---|---|
| EGLN3 mRNA (isoform 1) (SEQ ID NO: 53) | NM_001308103.1 | ggcttcgcgc tcgtgtagat cgttccctct ctggttgcac gctggggatc ccggacctcg attctgcggg cgagatgccc ctgggacaca tcatgaggct ggacctggag aaaattgccc tggagtacat cgtgccctgt ctgcacgagg caatggtggc ttgctatccg ggaaatggaa caggttatgt tcgccacgtg gacaaccccc acggtgatgg tcgctgcatc acctgcatct actatctgaa caagaattgg gatgccaagc tacatggtgg gatcctgcgg atatttccag agggaaatc attcatagca gatgtggagc ccatttttga cagactcctg ttcttctggt cagatcgtag gaacccacac gaagtgcagc cctcttacgc aaccagatat gctatgactg tctggtactt tgatgctgaa gaaagggcag aagccaaaaa gaaattcagg aatttaacta ggaaaactga atctgccctc actgaagact gaccgtgctc tgaaatctgc tggccttgtt cattttagta acgttcctg aattctctta aattctttga gatccaaaga tggcctcttc agtgacaaca atctccctgc tacttcttgc atccttcaca tccctgtctt gtgtgtggta cttcatgttt tcttgccaag actgtgttga tcttcagata ctctctttgc cagatgaagt tacttgctaa ctccagaaat tcctgcagac atcctactcg gccagcggtt tacctgatag attcggtaat actatcaaga aagagccta ggagcacagc gagggaatga accttacttg cactttatgt atacttcctg atttgaaagg aggaggtttg aaaagaaaaa aatggaggtg gtagatgcca cagagaggca tcacggaagc cttaacagca ggaaacagag aaatttgtgt catctgaaca atttccagat gttcttaatc cagggctgtt ggggtttctg gagaattatc acaacctaat gacattaata cctctagaaa gggctgctgt catagtgaac aatttataag tgtcccatgg ggcagacact cctttttccc cagtcctgca acctggattt tctgcctcag cccccatttg ctgaaaataa tgactttctg aataaagatg gcaacacaat tttttctcca ttttcagttc ttacctggga acctaattcc ccagaagcta aaaaactaga cattagttgt tttggttgct tgttggaat ggattaaa tttaatgaa aggaaaaaata tatccctggg agttttgtgt taaccactga taacttgga aagagctagg tctactgata tacaataaac atgtgtgcat cttgaacaat ttgagagggg aggtggagtt ggaaatgtgg gtgttcctgt ttttttttttt tttttttttt tagttttcct ttttaatgag ctcaccctt aacacaaaaa aagcaaggtg atgtatttta aaaaaggaag tggaaataaa aaaatctcaa agctatttga gttctcgtct gtccctagca gtctttcttc agctcacttg gctctctaga tccactgtgg ttggcagtat gaccagaatc atggaattgt ctagaactgt ggaagcttct actcctgcag taagcacaga tcgcactgcc tcaataactt ggtattgagc acgtattttg caaaagctac ttttcctagt tttcagtatt actttcatgt tttaaaatc cctttaattt cttgcttgaa aatcccatga acattaaaga gccagaaata ttttcctttg ttatgtacgg atatatatat atatagtctt ccaagataga agtttacttt ttcctcttct ggttttggaa aatttccaga taagacatgt caccattaat tctcaacgac tgctctattt tgttgtacgg taatagttat caccttctaa attactatgt aatttattca cttattatgt ttattgtctt gtatcctttc tctggagtgt aagcacaatg aagacaggaa ttttgtatat ttttaaccaa tgcaacatac tctcagcacc taaaatagtg ccgggaacat agtaagggct cagtaaatac ttgttgaata aactcagtct cctacattag cattctaaaa aaaaaaaaa |
| EGLN3 protein (isoform 1) (SEQ ID NO: 54) | NP_001295032.1 | mplghimrld lekialeyiv pclheamvac ypgngtgyvr hvdnpngdgr citciyylnk nwdaklhggi lrifpegksf iadvepifdr llffwsdrrn phevqpsyat ryamtvwyfd aeeracakkk frnltrktes alted |
| EGLN3 mRNA (isoform 2) (SEQ ID NO: 55) | NM_022073.3 | gagtctggcc gcagtcgcgg cagtggtggc ttcccatccc caaaaggcgc cctccgactc cttgcgccgc actgctcgcc gggccagtcc ggaaacgggt cgtggagctc cgcaccactc ccgctggttc ccgaaggcag atcccttctc ccgagagttg cgagaaactt tcccttgtcc ccgacgctgc agcggctcgg gtaccgtggc agccgcaggt ttctgaaccc cgggccacgc tccccgcgcc tcggcttcgc gctcgtgtag atcgttccct ctctggttgc acgctgggga tcccggacct cgattctgcg ggcgagatgc ccctgggaca catcatgagg ctggacctgg agaaaattgc cctggagtac atcgtgccct gtctgcacga ggtgggcttc tgctacctgg acaacttcct gggcgaggtg gtgggcgact gcgtcctgga gcgcgtcaag cagctgcact gcaccggggc cctgcggcag gccagctggg ccggcgcg cgccgcgtc tccaagcgac acctgcgggg cgaccagatc acgtggatcg ggggcaacga ggagggctgc gaggccatca gcttcctcct gtccctcatc gacaggctgg tcctctactg cgggagccgg ctgggcaaat actacgtcaa ggagaggtct aaggcaatgg tggcttgcta tccgggaaat ggaacaggtt atgttcgcca cgtggacaac cccaacggtg atggtcgctg catcacctgc atctactatc tgaacaagaa ttgggatgcc aagctacatg gtgggatcct gcggatattt ccagagggaa atcattcat agcagatgtg gagcccattt tgacagact cctgttcttc tggtcagatc gtaggaaccc acacgaagtg cagccctctt acgcaaccag atatgctatg actgtctggt actttgatgc tgaagaaagg gcagaagcca aaaagaaatt caggaattta actaggaaaa ctgaatctgc cctcactgaa gactgaccgt gctctgaaat ctgctggcct tgttcatttt agtaacggtt cctgaattct cttaaattct ttgagatcca agatggcct cttcagtgac aacaatctcc ctgctacttc ttgcatcctt cacatccctg tcttgtgtgt ggtacttcat gttttcttgc caagactgtg ttgatcttca gatactctct ttgccagatg aagttacttg ctaactccag aaattcctgc agacatccta ctcggccagc ggtttacctg atagattcgg taatactatc aagagaagag cctaggagca cagcgaggga atgaacctta cttgcacttt atgtatactt cctgatttga aaggaggagg tttgaaaaga aaaaaatgga ggtggtagat gccacagaga ggcatcacgg aagccttaac agcaggaaac agagaaattt gtgtcatctg aacaatttcc agatgttctt aatccagggc tgttggggtt tctggagaat tatcacaacc taatgacatt aatacctcta gaaagggctg ctgtcatagt gaacaattta agtgtccc atggggcaga cactccttt tccccagtcc tgcaacctgg attttctgcc tcagcccccat tttgctgaaa ataatgactt tctgaataaa gatggcaaca caattttttc tccatttttca gttcttacct gggaacctaa ttccccagaa gctaaaaaac tagacattag ttgttttggt |

TABLE 5-continued

A list of genes and proteins, and their accession numbers.

| | Accession number | Sequence |
|---|---|---|
| | | tgctttgttg gaatggaatt taaatttaaa tgaaaggaaa aatatatccc tggtagtttt<br>gtgttaacca ctgataactg tggaaagagc taggtctact gatatacaat aaacatgtgt<br>gcatcttgaa caatttgaga ggggaggtgg agttggaaat gtgggtgttc ctgttttttt<br>ttttttttt ttttttagttt tccttttaa tgagctcacc ctttaacaca aaaaaagcaa<br>ggtgatgtat tttaaaaaag gaagtggaaa taaaaaaatc tcaaagctat ttgagttctc<br>gtctgtccct agcagtcttt cttcagctca cttggctctc tagatccact gtggttggca<br>gtatgaccag aatcatggaa tttgctagaa ctgtggaagc ttctactcct gcagtaagca<br>cagatcgcac tgcctcaata acttggtatt gagcacgtat tttgcaaaag ctactttttcc<br>tagttttcag tattactttc atgttttaaa aatccctta atttcttgct tgaaaatccc<br>atgaacatta aagagccaga aatattttcc tttgttatgt acggatatat atatatatag<br>tcttccaaga tagaagttta cttttcctc ttctggtttt ggaaaatttc cagataagac<br>atgtcaccat taattctcaa cgactgctct attttgttgt acggtaatag ttatcacctt<br>ctaaattact atgtaattta ttcacttatt atgtttattg tcttgtatcc tttctctgga<br>gtgtaagcac aatgaagaca ggaatttttgt atatttttaa ccaatgcaac atactctcag<br>cacctaaaat agtgccggga acatagtaag ggctcagtaa atacttgttg aataaactca<br>gtctcctaca ttagcattct aa |
| EGLN3 protein (isoform 2) (SEQ ID NO: 56) | NP_071356.1 | mplghimrld lekialeyiv pclhevgfcy ldnflgevvg dcvlervkql hctgalrdgq<br>lagpragvsk rhlrgdqitw iggneegcea isfllslidr lvlycgsrlg kyyvkerska<br>mvacypgngt gyvrhvdnpn gdgrcitciy ylnknwdakl hggilrifpe gksfiadvep<br>ifdrllffws drrnphevqp syatryamtv wyfdacerae akkkfrnltr ktesalted |
| SLC6A3 mRNA (SEQ ID NO: 57) | NM_001044.4 | cgctgcggag cgggagggga ggcttcgcgg aacgctctcg gcgccaggac tcgcgtgcaa<br>agcccaggcc cgggcggcca gaccaagagg gaagaagcac agaattcctc aactcccagt<br>gtgcccatga gtaagagcaa atgctccgtg ggactcatgt cttccgtggt ggccccggct<br>aaggagccca atgccgtggg cccgaaggag gtggagctca tccttgtcaa ggagcagaac<br>ggagtgcagc tcaccagctc cacccctcac aacccgcggc agagcccgt ggaggcccag<br>gatcgggaga cctggggcaa gaagatcgac tttctcctgt ccgtcattgg ctttgctgtg<br>gacctggcca acgtctggcg gttccccac ctgtgctaca aaaatggtgg cggtgccttc<br>ctggtcccct acctgctctt catggtcatt gctgggatgc cacttttcta catggagctg<br>gccctcggcc agttcaacag ggaaggggcc gctggtgtct ggaagatctg ccccatactg<br>aaaggtgtgg gcttcacggt catcctcatc tcactggtag tcggcttctt ctacaacgtc<br>atcatcgcct gggcgctgca ctatctcttc tcctccttca ccacggagct ccctggatc<br>cactgcaaca actcctggaa cagccccaac tgctcggatg cccatcctgg tgactccagt<br>ggagacagct cgggcctcaa cgacactttt ggaccacac ctgctgccga gtactttgaa<br>cgtggcgtgc tgcacctcca ccagagccat ggcatcgacg acctggggcc tccgcggtgg<br>cagctcacag cctgcctggt gctggtcatc gtgctgctct acttcagcct ctggaagggc<br>gtgaagacct cagggaaggt ggtatggatc acagccacca tgccatacgt ggtcctcact<br>gccctgctcc tgcgtgggt caccctccct ggagcctag acggcatcag agcatacctg<br>agcgttgact tctaccggct ctgcgaggcg tctgtttgga ttgacgcggc cacccaggtg<br>tgcttctccc tgggcgtggg gttcggggtg ctgatcgcct tctccagcta caacaagttc<br>accaacaact gctacaggga cgcgattgtc accacctcca tcaactccct gacgagcttc<br>tcctccggct tcgtcgtctt ctccttcctg ggtacatgg cacagaagca cagtgtgccc<br>atcgggagg tggccaagga cgggcagg ctgatcttca tcatctaccc ggaagccatc<br>gccacgctcc ctctgtcctc agcctggggc gtggtcttct tcatcatgct gctcacccty<br>ggtatcgaca cgccatggg tggtatggag tcagtgatca ccgggctcat cgatgagttc<br>cagctgctgc acagacaccg tgagctcttc acgtcttca tcgtcctggc gaccttcctc<br>ctgtccctgt tctgcgtcac caacggtggc atctacgtct tcacgctcct ggaccatttt<br>gcagccggca cgtccatcct ctttggagtg ctcatcgaag ccatcggagt ggcctggttc<br>tatggtgttg gcagttcag cgacgacatc cagcagatga ccgggcagcg gcccagcctg<br>tactggcggc tgtgctggaa gctggtcagc ccctgctttc tcctgttcgt ggtcgtggtc<br>agcattgtga ccttcagacc ccccactac ggagcctaca tctcccccga ctgggccaac<br>gcgctgggct gggtcatcgc cacatcctcc atggccatgg tgccatcta tgccgcctac<br>aagttctgca gcctgctgg gtcctttcga gagaaactgg cctacgccat tgcacccgag<br>aaggaccgtg agctggtgga cagaggggag gtgcgccagt tcacgctccg ccactggctc<br>aaggtgtaga gggagcagag acgaagaccc caggaagtca tcctgcaatg ggagagacac<br>gaacaaacca aggaaatcta agtttcgaga gaaaggaggg caacttctac tcttcaacct<br>ctactgaaaa cacaaacaac aaagcagaag actcctctct tctgactgtt tacacctttc<br>cgtgccggga gcgcacctcg ccgtgtcttg tgttgctgta ataacgacgt agatctgtgc<br>agcgaggtcc accccgttgt tgtccctgca gggcagaaaa acgtctaact tcatgctgtc<br>tgtgtgaggc tccctccctc cctgctccct gctcccgct ctgaggctgc ccagggggca<br>ctgtgttctc aggcggggat cacgatcctt ctagacgcac ctgctgagaa tccccgtgct<br>cacagtagct tcctagacca tttactttgc ccatattaaa aagccaagtg tcctgcttgg<br>tttagctgtg cagaaggtga aatggaggaa accacaaatt catgcaaagt cctttcccga<br>tgcgtggctc ccagcagagg ccgtaaattg agcgttcagt tgacacattg cacacacagt<br>ctgttcagag gcattggagg atgggggtcc tggtatgtct caccaggaaa ttctgtttat<br>gttcttgcag cagagagaaa taaaactcct tgaaaccagc tcaggctact gccactcagg<br>cagcctgtgg gtccttgcgg tgtagggaac ggcctgagag gagcgtgtcc tatccccgga<br>cgcatgcagg gccccacag gagcgtgtac taccccgga cgcatgcagg gcccccacag<br>gagcatgtac tatccctgga cgcatgcagg gccccacag gagcgtgtac taccccagaa<br>cgcatgcagg gccccacag gagcgtgtac taccccagga cgcatgcagg gccccactg<br>gagcgtgtac taccccagga cgcatgcagg gccccacag gagcgtgtcc tatccccgga<br>ccggacgcat gcagggcccc cacaggagcg tgtactaccc caggacgcat gcagggcccc<br>cacaggagcg tgtactaccc caggatgcat gcagggcccc cacaggagcg tgtactaccc |

TABLE 5-continued

A list of genes and proteins, and their accession numbers.

| | Accession number | Sequence |
|---|---|---|
| | | caggacgcat gcagggcccc catgcaggca gcctgcagac cacactctgc ctggccttga<br>gccgtgacct ccaggaaggg accccactgg aatttttattt ctctcaggtg cgtgccacat<br>caataacaac agtttttatg tttgcgaatg gcttttttaaa atcatattta cctgtgaatc<br>aaaacaaatt caagaatgca gtatccgcga gcctgcttgc tgatattgca gttttttgttt<br>acaagaataa ttagcaatac tgagtgaagg atgttggcca aaagctgctt tccatggcac<br>actgccctct gccactgaca ggaaagtgga tgccatagtt tgaattcatg cctcaagtcg<br>gtgggcctgc ctacgtgctg cccgagggca ggggccgtgc agggccagtc atggctgtcc<br>cctgcaagtg gacgtgggct ccagggactg gagtgtaatg ctcggtggga gccgtcagcc<br>tgtgaactgc caggcagctg cagttagcac agaggatggc ttccccattg ccttctgggg<br>agggacacag aggacggctt ccccatcgcc ttctggccgc tgcagtcagc acagagagcg<br>gcttccccat tgccttctgg ggagggacac agaggacagc ttccccatcg ccttctggct<br>gctgcagtca gcacagagag cggcttcccc atcgccttct ggggagggggc tccgtgtagc<br>aacccaggtg ttgtccgtgt ctgttgacca atctctattc agcatcgtgt gggtccctaa<br>gcacaataaa agacatccac aatggaaaaa ctgcaaaaaa aaaaaaaaaa aa |
| SLC6A3 protein (SEQ ID NO: 58) | NP_001035.1 | mskskcsvgl mssvvapake pnavgpkeve lilvkeqngv qltsstltnp rqspveaqdr<br>gqfnregaag vwkicpilkg vgftvilisl yvgffynvii awalhylfss fttelpwihc<br>nnswnspncs dahpgdssgd ssglndtfgt tpaacyferg vlhlhqshgi ddlgpprwql<br>taclvlvivl lyfslwkgvk tsgkvvwita tmpyvvltal llrgvtlpga idgiraylsv<br>dfyrlceasv widaatqvcf slgvgfgvli afssynkftn ncyrdaivtt sinsltsfss<br>etwgkkidfl lsvigfavdl anvwrfpylc yknggggaflv pyllfmviag mplfymelal<br>gfvvfsflgy maqkhsvpig dvakdgpgli fiiypeaiat lplssawavv ffimlltlgi<br>dsamggmesv itglidefql lhrhrelftl fivlatflls lfcvtnggiy vftlldhfaa<br>gtsilfgvli eaigvawfyg vgqfsddiqq mtgqrpslyw rlcwklvspc flllfvvvvsi<br>vtfrpphyga yifpdwanal gwviatssma mvpiyaaykf cslpgsfrek layaiapekd<br>relvdrgevr qftlrhwlkv |

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method of treating clear cell renal cell carcinoma (ccRCC) in a subject, comprising:
    obtaining a renal sample from the subject;
    screening the renal sample for the upregulation of a clear cell renal cell carcinoma (ccRCC) biomarker set compared with a control group, wherein the biomarker set comprises at least two biomarkers selected from the group consisting of ZNF395, SMPDL3A, SLC28A1, SLC6A3, VEGFA, and EGLN3, wherein one of the at least two biomarkers is SMPDL3A or SLC28A1, wherein the biomarkers are nucleic acids encoding the same proteins, or variants thereof, and wherein the variants are allelic variants, splice variants, species-specific homologs, paralogs, and/or orthologs;
    identifying a subject as having ccRCC based on the upregulation of the biomarker set in the sample compared with the control group; and
    treating the subject identified as having ccRCC with an effective amount of an anti-ccRCC compound and/or treatment.

2. The method of claim 1, wherein the at least two biomarkers selected from the group consisting of ZNF395, SMPDL3A, SLC28A1, SLC6A3, VEGFA, and EGLN3 comprises at least three biomarkers.

3. The method of claim 1, wherein the biomarker set consists of ZNF395, SMPDL3A, and SLC28A1.

4. The method of claim 1, wherein screening the renal sample for the upregulation of a clear cell renal cell carcinoma (ccRCC) biomarker set is carried out using one or more molecular biological methods.

5. The method of claim 4, wherein the one or more molecular biological methods is or are selected from the group consisting of polymerase chain reaction (PCR), quantitative polymerase chain reaction (qPCR), mass spectrometry, and nucleic acid sequencing.

6. The method of claim 1, wherein the control group comprises one or more samples obtained from disease-free subjects and/or samples from non-diseased areas of the same or different subjects suffering from clear cell renal cell carcinoma.

7. The method of claim 1, wherein the renal sample is a solid sample or a fluid sample.

8. The method of claim 7, wherein the solid sample is solid tumour biopsy, optionally wherein the fluid sample is liquid tumour biopsy, urine sample, or cell culture medium.

9. The method of claim 7, wherein the fluid sample contains exosomes suspected to comprise the biomarker set, optionally wherein the exosomes are detected using quantitative polymerase chain reaction (qPCR).

10. The method of claim 1, wherein the clear cell renal cell carcinoma (ccRCC) is a recurrent ccRCC.

11. A method of detecting response of a subject with clear cell renal cell carcinoma (ccRCC) to a systemic treatment for ccRCC, the method comprising:
    a) obtaining a renal sample from the subject who is receiving or who has received systemic treatment for ccRCC;

b) determining the levels of a biomarker set in the renal sample, wherein the biomarker set comprises at least two biomarkers selected from the group consisting of ZNF395, SMPDL3A, SLC28A1, SLC6A3, VEGFA, and EGLN3,
wherein one of the at least two biomarkers is SMPDL3A or SLC28A1,
wherein the biomarkers are nucleic acids encoding proteins, or variants thereof, and wherein the variants are allelic variants, splice variants, species-specific homologs, paralogs, and/or orthologs, and
wherein an increase in levels or presence of the biomarker set in the sample relative to a renal sample obtained from the subject prior to receiving said systemic treatment identifies the subject as not responsive to said systemic treatment; and
   c) treating the subject identified as not responsive to said systemic treatment for ccRCC with an effective amount of a different systemic treatment for ccRCC.

12. The method of claim 11, wherein the at least two biomarkers selected from the group consisting of ZNF395, SMPDL3A, SLC28A1, SLC6A3, VEGFA, and EGLN3 comprises at least three biomarkers.

13. The method of claim 11, wherein the biomarker set consists of ZNF395, SMPDL3A, and SLC28A1.

14. The method of claim 11, wherein determining the levels of the biomarker set in the renal sample is carried out using one or more molecular biological methods.

15. The method of claim 14, wherein the one or more molecular biological methods is or are selected from the group consisting of polymerase chain reaction (PCR), quantitative polymerase chain reaction (qPCR), mass spectrometry, and nucleic acid sequencing.

16. The method of claim 11, wherein the renal sample is a solid sample or a fluid sample.

17. The method of claim 16, wherein the solid sample is solid tumour biopsy, optionally wherein the fluid sample is liquid tumour biopsy, urine sample, or cell culture medium.

18. The method of claim 16, wherein the fluid sample contains exosomes suspected to comprise the biomarker set, optionally wherein the exosomes are detected using quantitative polymerase chain reaction (qPCR).

\* \* \* \* \*